US011266693B2

(12) United States Patent
Nicholson et al.

(10) Patent No.: US 11,266,693 B2
(45) Date of Patent: Mar. 8, 2022

(54) NUCLEIC ACIDS ENCODING ENGINEERED MEGANUCLEASES WITH RECOGNITION SEQUENCES FOUND IN THE HUMAN T CELL RECEPTOR ALPHA CONSTANT REGION GENE

(71) Applicant: Precision BioSciences, Inc., Durham, NC (US)

(72) Inventors: Michael G. Nicholson, Chapel Hill, NC (US); James Jefferson Smith, Morrisville, NC (US); Derek Jantz, Durham, NC (US); Victor Bartsevich, Durham, NC (US); Daniel T. MacLeod, Durham, NC (US); Jeyaraj Antony, Chapel Hill, NC (US)

(73) Assignee: Precision BioSciences, Inc., Durham, NC (US)

( * ) Notice: Subject to any disclaimer, the term of this patent is extended or adjusted under 35 U.S.C. 154(b) by 0 days.

(21) Appl. No.: 17/016,056

(22) Filed: Sep. 9, 2020

(65) Prior Publication Data
US 2021/0052650 A1 Feb. 25, 2021

Related U.S. Application Data

(62) Division of application No. 15/766,290, filed as application No. PCT/US2016/055472 on Oct. 5, 2016, now Pat. No. 10,799,535.

(60) Provisional application No. 62/297,445, filed on Feb. 19, 2016, provisional application No. 62/237,382, filed on Oct. 5, 2015.

(51) Int. Cl.
| | | |
|---|---|---|
| *C12N 9/22* | (2006.01) | |
| *A61K 35/17* | (2015.01) | |
| *A61K 47/66* | (2017.01) | |
| *A61K 47/65* | (2017.01) | |
| *A61P 35/00* | (2006.01) | |
| *A61K 47/42* | (2017.01) | |
| *A61K 38/00* | (2006.01) | |

(52) U.S. Cl.
CPC .............. *A61K 35/17* (2013.01); *A61K 47/42* (2013.01); *A61K 47/65* (2017.08); *A61K 47/67* (2017.08); *A61P 35/00* (2018.01); *C12N 9/22* (2013.01); *A61K 38/00* (2013.01)

(58) Field of Classification Search
CPC ........ A61K 35/17; A61K 47/67; A61K 47/65; A61K 47/42; A61K 38/00; A61K 39/0011; A61K 2039/5156; A61K 2039/5158; C12N 9/22; A61P 35/00; C07K 2319/03; C07K 14/7051
See application file for complete search history.

(56) References Cited

U.S. PATENT DOCUMENTS

| | | |
|---|---|---|
| 4,873,192 A | 10/1989 | Kunkel |
| 6,015,832 A | 1/2000 | Baker, Jr. et al. |
| 6,506,803 B1 | 1/2003 | Baker, Jr. et al. |
| 6,559,189 B2 | 5/2003 | Baker, Jr. et al. |
| 6,635,676 B2 | 10/2003 | Baker, Jr. et al. |
| 8,021,867 B2 | 9/2011 | Smith et al. |
| 8,445,251 B2 | 5/2013 | Smith et al. |
| 8,697,359 B1 | 4/2014 | Zhang |
| 8,822,647 B2 | 9/2014 | Jensen et al. |
| 8,956,828 B2 | 2/2015 | Bonini et al. |
| 9,434,931 B2 | 9/2016 | Smith et al. |
| 9,889,160 B2 | 2/2018 | Jantz et al. |
| 9,889,161 B2 | 2/2018 | Jantz et al. |
| 9,950,010 B1 | 4/2018 | Jantz et al. |
| 9,950,011 B1 | 4/2018 | Jantz et al. |
| 9,969,975 B1 | 5/2018 | Jantz et al. |
| 9,993,501 B2 | 6/2018 | Jantz et al. |
| 9,993,502 B1 | 6/2018 | Jantz et al. |
| 10,093,899 B1 | 10/2018 | Jantz et al. |
| 10,093,900 B2 | 10/2018 | Jantz et al. |
| 10,799,535 B2 | 10/2020 | Nicholson et al. |
| 11,053,484 B2 | 7/2021 | Jantz et al. |
| 2002/0045667 A1 | 4/2002 | Baker et al. |
| 2004/0043041 A1 | 3/2004 | Baker et al. |
| 2007/0036773 A1 | 2/2007 | Cooper et al. |
| 2010/0151556 A1 | 6/2010 | Arnould et al. |
| 2012/0321667 A1 | 12/2012 | Sentman |
| 2013/0315884 A1 | 11/2013 | Galetto et al. |
| 2014/0034902 A1 | 2/2014 | Hwang et al. |
| 2014/0301990 A1 | 10/2014 | Gregory et al. |
| 2014/0349402 A1 | 11/2014 | Cooper et al. |
| 2015/0376650 A1 | 12/2015 | Auerbach et al. |
| 2016/0081314 A1 | 3/2016 | Thurston et al. |
| 2016/0120906 A1 | 5/2016 | Galetto et al. |
| 2016/0208243 A1 | 7/2016 | Zhang et al. |

(Continued)

FOREIGN PATENT DOCUMENTS

| | | |
|---|---|---|
| EP | 3 004 337 B1 | 8/2017 |
| JP | 2009-511085 A | 3/2009 |

(Continued)

OTHER PUBLICATIONS

U.S. Appl. No. 16/150,179, filed Oct. 2, 2018, Jantz et al.
U.S. Appl. No. 16/065,756, filed Jun. 22, 2018, Bartsevich et al.
EP 19212310.7, Jun. 15, 2020, Extended European Search Report.
PCT/US2016/055472, Dec. 19, 2016, International Search Report and Written Opinion.

(Continued)

*Primary Examiner* — Delia M Ramirez
(74) *Attorney, Agent, or Firm* — Wolf, Greenfield & Sacks, P.C.

(57) ABSTRACT

Disclosed herein are recombinant meganucleases engineered to recognize and cleave a recognition sequence present in the human T cell receptor alpha constant region gene. The present disclosure further relates to the use of such recombinant meganucleases in methods for producing genetically-modified eukaryotic cells.

9 Claims, 62 Drawing Sheets

Specification includes a Sequence Listing.

(56) References Cited

U.S. PATENT DOCUMENTS

| | | |
|---|---|---|
| 2017/0016027 A1 | 1/2017 | Lee et al. |
| 2017/0333481 A1 | 11/2017 | Jantz et al. |
| 2017/0335010 A1 | 11/2017 | Jantz et al. |
| 2018/0289741 A1 | 10/2018 | Nicholson et al. |
| 2018/0360883 A1 | 12/2018 | Galetto et al. |
| 2019/0017075 A1 | 1/2019 | Bartsevich et al. |
| 2019/0194616 A1 | 6/2019 | Jantz et al. |
| 2020/0123516 A1 | 4/2020 | Jantz et al. |
| 2021/0113616 A1 | 4/2021 | Smith et al. |
| 2021/0207093 A1 | 7/2021 | Jantz et al. |
| 2021/0277373 A1 | 9/2021 | Jantz et al. |

FOREIGN PATENT DOCUMENTS

| | | |
|---|---|---|
| JP | 2011-501971 A | 1/2011 |
| JP | 2013-538562 A | 10/2013 |
| WO | WO 2002/012514 A2 | 2/2002 |
| WO | WO 2007/047859 A2 | 4/2007 |
| WO | WO 2008/102199 A1 | 8/2008 |
| WO | WO 2008/102274 A2 | 8/2008 |
| WO | WO 2009/059195 A2 | 5/2009 |
| WO | WO 2010/015899 A2 | 2/2010 |
| WO | WO 2012/167192 A2 | 12/2012 |
| WO | WO 2013/074916 A1 | 5/2013 |
| WO | WO 2013/153391 A1 | 10/2013 |
| WO | WO 2013/176915 A1 | 11/2013 |
| WO | WO 2014/153470 A2 | 9/2014 |
| WO | WO 2014/165707 A2 | 10/2014 |
| WO | WO 2014/191128 A1 | 12/2014 |
| WO | WO 2014/191525 A1 | 12/2014 |
| WO | WO 2014/191527 A1 | 12/2014 |
| WO | WO 2015/057980 A1 | 4/2015 |
| WO | WO 2015/121454 A1 | 8/2015 |
| WO | WO 2015/136001 A1 | 9/2015 |
| WO | WO 2015/138739 A2 | 9/2015 |
| WO | WO 2015/167766 A1 | 11/2015 |
| WO | WO 2016/069282 A1 | 5/2016 |
| WO | WO 2016/069283 A1 | 5/2016 |
| WO | WO 2016/160721 A1 | 10/2016 |
| WO | WO 2017/011519 A1 | 1/2017 |
| WO | WO 2017/023801 A1 | 2/2017 |
| WO | WO 2017/062439 A1 | 4/2017 |
| WO | WO 2017/062451 A1 | 4/2017 |
| WO | WO 2017/070429 A1 | 4/2017 |
| WO | WO 2017/112859 A1 | 6/2017 |
| WO | WO 2017/156484 A1 | 9/2017 |
| WO | WO 2017/180989 A2 | 10/2017 |

OTHER PUBLICATIONS

PCT/US2016/055472, Apr. 19, 2018, International Preliminary Report on Patentability.
PCT/US2016/055492, Feb. 3, 2017, International Search Report and Written Opinion.
PCT/US2016/055492, Apr. 19, 2018, International Preliminary Report on Patentability.
PCT/US2016/068289, Jun. 8, 2017, International Search Report and Written Opinion.
PCT/US2016/068289, Jul. 5, 2018, International Preliminary Report on Patentability.
Extended European Search Report dated Jun. 6, 2020 in connection with Application No. EP 19212310.7.
International Search Report and Written Opinion for Application No. PCT/US2016/068289 dated Jun. 8, 2017.
International Preliminary Report on Patentability for Application No. PCT/US2016/068289 dated Jul. 5, 2018.
International Search Report and Written Opinion dated Dec. 19, 2016 for Application No. PCT/US2016/055472.
International Preliminary Report on Patentability dated Apr. 19, 2018 for Application No. PCT/US2016/055472.
International Search Report and Written Opinion for Application No. PCT/US2016/055492 dated Feb. 3, 2017.
International Preliminary Report on Patentability dated Apr. 19, 2018 for Application No. PCT/US2016/055492.
Airenne et al., "Baculovirus: an insect-derived vector for diverse gene transfer applications," Mol. Ther. 21(4), 739-749 (2013).
Altschul et al., "Basic local alignment search tool," J. Mol. Biol. 215, pp. 403-410 (1990).
Altschul et al., "Gapped BLAST and PSI-BLAST: a new generation of protein database search programs," Nucleic Acids Res. 25, pp. 3389-3402 (1997).
Arnould et al., "Engineering of large numbers of highly specific homing endonucleases that induce recombination on novel DNA targets," J. Mol. Biol. 355, pp. 443-458 (2006).
Baxter et al., "Engineering domain fusion chimeras from I-OnuI family LAGLIDADG homing endonucleases," Nucleic Acids Research, 40(16), pp. 7985-8000 (2012).
Benoist et al., "In vivo sequence requirements of the SV40 early promotor region," Nature 290(5804), pp. 304-310 (1981).
Beurdeley et al., "Compact designer TALENs for efficient genome engineering," Nat. Commun. 4, p. 1762 (2013).
Boissel et al., "megaTALs: a rare-cleaving nuclease architecture for therapeutic genome engineering," Nucleic Acid Research 42(4), pp. 2591-2601 (2014).
Cahill et al., "Mechanisms of eukaryotic DNA double strand break repair," Front. Biosci. 11, pp. 1958-1976 (2006).
Cartellieri et al., Chimeric antigen receptor-engineered T cells for immunotherapy of cancer. J Biomed Biotechnol. 2010;2010:956304. doi: 10.1155/2010/956304. Epub May 5, 2010.
Chames et al., "In vivo selection of engineered homing endonucleases using double-strand break induced homologous recombination," Nucleic Acids Res. 33, p. e178 (2005).
Chang et al., "Inducible retroviral vectors regulated by lac repressor in mammalian cells," Gene 183, pp. 137-142 (1996).
Chen et al., "A novel adenoviral vector carrying an all-in-one Tet-On system with an autoregulatory loop for tight, inducible transgene expression," BMC Biotechnol. 15, 8 pages (2015).
Chen, "Exploiting the Intron-splicing Mechanism of Insect Cells to Produce Viral Vectors Harboring Toxic Genes for Suicide Gene Therapy," Mol. Ther. Nucleic Acids 1, e57; pp. 1-10 (2012).
Cheng et al., "Dendrimers as drug carriers: applications in different routes of drug administration," J. Pharm. Sci. 97(1): 123-143 (2008).
Chevalier and Stoddard, "Homing endonucleases: structural and functional insight into the catalysts of intron/intein mobility," Nucleic Acids Res. 29(18), pp. 3757-3774 (2001).
Cots et al., "Helper dependent adenovirus vectors: progress and future prospects," Curr. Gene Ther. 13(5) pp. 370-381 (2013).
Deshayes et al., "Cell-penetrating peptides: tools for intracellular delivery of therapeutics," Cell Mol. Life Sci. 62, pp. 1839-1849 (2005).
Deshayes et al., "Primary amphipathic cell-penetrating peptides: structural requirements and interactions with model membranes," Biochemistry 43, pp. 7698-7706 (2004).
Dinda et al., "Nanobiotechnology-based drug delivery in brain targeting," Curr. Pharm. Biotechnol. 14, pp. 1264-1274 (2013).
Dingermann et al., "Establishment of a system for conditional gene expression using an inducible tRNA suppressor gene," Mol. Cell Biol. 12(9), pp. 4038-4045 (1992).
Durai et al., "Zinc finger nucleases: custom-designed molecular scissors for genome engineering of plant and mammalian cells," Nucleic Acids Res. 33, pp. 5978-5990 (2005).
Ellebrecht et al., "Reengineering chimeric antigen receptor T cells for targeted therapy of autoimmune disease," Science. Jul. 8, 2016;353(6295):179-84. doi: 10.1126/science.aaf6756. Epub Jun. 30, 2016. Author manuscript.
Fu et al., "High-frequency off-target mutagenesis induced by CRISPR-Cas nucleases in human cells," Nat. Biotechnol. 31, pp. 822-826 (2013).
Gao et al., "Efficient gene delivery into mammalian cells mediated by a recombinant baculovirus containing a whispovirus iel promoter, a novel shuttle promoter between insect cells and mammalian cells," J. Biotechnol. 131(2), pp. 138-143 (2007).
Gish et al., "Identification of protein coding regions by database similarity search," Nature Genet. 3, pp. 266-272 (1993).

(56) References Cited

OTHER PUBLICATIONS

Grizot et al., "Efficient targeting of a SCID gene by an engineered single-chain homing endonuclease," Nucleic Acids Res. 37, pp. 5405-5419 (2009).
Haase, et al., "Generation of a tumor- and tissue-specific episomal non-viral vector system," BMC Biotechnol. 13, pp. 49-54 (2013).
Hale et al., "Homology-Directed Recombination for Enhanced Engineering of Chimeric Antigen Receptor T Cells," Molecular Therapy 4, pp. 192-203 (2017).
Hegde et al., "Current status of chimeric antigen receptor engineered T cell-based and immune checkpoint blockade-based cancer immunotherapies," Cancer Immunol Immunother 66, pp. 1113-1121 (2017).
Hudecz et al., "Medium-sized peptides as built in carriers for biologically active compounds," Med. Res. Rev. 25, pp. 679-736 (2005).
Ibarra et al., "Efficient Targeted Gene Modification in Primary Human Hematopoietic Cells Using Co-Delivery of Nuclease mRNA and AAV Donors," Mol. Ther., 23(suppl. 1), p. S273 (2015).
Imai et al., Chimeric receptors with 4-1BB signaling capacity provoke potent cytotoxicity against acute lymphoblastic leukemia. Leukemia. Apr. 2004;18(4):676-84.
Jacox et al., "Tissue-specific and ubiquitous expression patterns from alternative promoters of human genes," PLoS One 5(8), p. e12274 (2010).
Jearawiriyapaisam et al., "Sustained dystrophin expression induced by peptide-conjugated morpholino oligomers in the muscles of mdx mice," Mol. Ther. 16, pp. 1624-1629 (2008).
Jiang et al., "Cationic core-shell liponanoparticles for ocular gene delivery," Biomaterials. 33(30), pp. 7621-7630 (2012).
Kang et al., "Harnessing the capacity of cell-penetrating peptides for drug delivery to the central nervous system," Curr. Pharm. Biotechnol. 15(3), pp. 220-230 (2014).
Karlin et al., "Applications and statistics for multiple high-scoring segments in molecular sequences," Proc Natl Acad Sci U S A. Jun. 15, 1993;90(12):5873-7.
Kramer et al., "In vitro and in vivo comparative study of chimeric liver-specific promoters," Mol. Ther. 7, pp. 375-385 (2003).
Kunkel, "Rapid and efficient site-specific mutagenesis without phenotypic selection," Proc Natl Acad Sci U S A. Jan. 1985;82(2):488-92.
Lee et al., "Efficient Generation of CART Cells by Homology Directed Transgene Integration into the TCR-Alpha Locus," Molecular Therapy, vol. 24, Supplement 1, S130 (May 2016).
Lentz, et al., "Viral vectors for gene delivery to the central nervous system," Neurobiol. Dis. 48, pp. 179-188 (2012).
Li et al., "Generation of single-chain LAGLIDADG homing endonucleases from native homodimeric precursor proteins," Nucleic Acids• Res. 37, pp. 1650-1662 (2009).
Liu et al., "Therapeutic levels of factor IX expression using a muscle-specific promoter and adeno-associated virus serotype 1 vector," Hum. Gene Ther. 15, pp. 783-792 (2004).
MacLeod et al., Generation of a Novel Allogeneic CAR T Cell Platform Utilizing an Engineered Meganuclease and AAV Donor Template to Achieve Efficient Disruption of T Cell Receptor Expression and Simultaneous Homology-Directed Insertion of a CD19 CAR. Mol Ther. May 1, 2016;24(S1):S156. Abstract.
MacLeod et al., Integration of a CD19 CAR into the TCR Alpha Chain Locus Streamlines Production of Allogeneic Gene-Edited CAR T Cells. Molecular Therapy. Apr. 2017;25(4):949-961.
Madden et al., "Applications of network BLAST server," Meth. Enzymol. 266, pp. 131-141 (1996).
Mak et al., "TAL effectors: function, structure, engineering and applications," Curr. Opin. Struct. Biol. 23, pp. 93-99 (2013).
Mali et al., "Cas9 as a versatile tool for engineering biology," Nat. Methods 10, pp. 957-963 (2013).
Mao et al., "Comparison of nonhomologous end joining and homologous recombination in human cells," DNA Repair 7(10), pp. 1765-1771 (2008). Author's manuscript.

Martin et al., "Gene delivery to the eye using adeno-associated viral vectors," Methods 28, pp. 267-275 (2002).
Mastorakos et al., "Hydroxyl PAMAM dendrimer-based gene vectors for transgene delivery to human retinal pigment epithelial cells," Nanoscale 7(9), pp. 3845-3856 (2015).
McCall et al., "Pathogen-inspired drug delivery to the central nervous system," Tissue Barriers. 2(4), e944449; 12 pages (2014).
McCarty et al., "Self-complementary recombinant adeno-associated virus (scAAV) vectors promote efficient transduction independently of DNA synthesis," Gene Ther. 8, pp. 1248-1254 (2001).
Mishra et al., "Recent applications of liposomes in ophthalmic drug delivery," J. Drug Deliv. 2011, pp. 1-14 (2011).
Mombaerts et al., Mutations in T-cell antigen receptor genes alpha and beta block thymocyte development at different stages. Nature. Nov. 19, 1992;360(6401):225-31. Erratum in Nature Dec. 3, 1992;360(6403):491.
Morgan et al., "Genetic Modification of T Cells," Biomedicines 4, pp. 1-14 (2016).
Papapetrou et al., "Gene Insertion Into Genomic Safe Harbors for Human Gene Therapy," Molecular Therapy 24(4), pp. 678-684 (2016).
Pham et al., "Generation of CAR-T Cells Lacking T Cell Receptor and Human Leukocyte Antigen Using Engineered Meganucleases" Molecular Therapy, 24(suppl. 1), p. S78 (2016).
Poirot et al., "Multiplex Genome-Edited T-cell Manufacturing Platform for "Off-the-Shelf" Adoptive T-cell Immunotherapies," Cancer Research, 75(18), pp. 3853-3864 (2015).
Qasim et al., "First Clinical Application of Talen Engineered Universal CAR19 T Cells in B-ALL," Blood 126(2046), pp. 1-3 (2015). Abstract only.
Qian et al., "Improved brain uptake of peptide-based CNS drugs via alternative routes of administrations of its nanocarrier delivery systems: a promising strategy for CNS targeting delivery of peptides," Expert Opin. Drug Metab. Toxicol. 10(11), (2014) 1491-1508.
Ran et al., "Genome engineering using the CRISPR-Cas9 system," Nat. Protoc. 8, pp. 2281-2308 (2013).
Reyon et al., "FLASH assembly of TALENs for high-throughput genome editing," Nat Biotechnol. May 2012;30(5):460-5. doi: 10.1038/nbt.2170. Author manuscript.
Sadowski et al., The sequence-structure relationship and protein function prediction. Curr Opin Struct Biol. Jun. 2009;19(3):357-62. doi: 10.1016/j.sbi.2009.03.008. Epub May 4, 2009.
Sather et al., "Efficient modification of CCR5 in primary human hematopoietic cells using a megaTAL nuclease and AAV donor template," Science Translation Medicine. 7(307), pp. 1-14 (2015).
Seffernick et al., Melamine deaminase and atrazine chlorohydrolase: 98 percent identical but functionally different. J Bacteriol. Apr. 2001;183(8):2405-10.
Seligman et al., "Mutations altering the cleavage specificity of a homing endonuclease," Nucleic Acids Res. 30, pp. 3870-3879 (2002).
Sha et al., "Chimaeric antigen receptor T-cell therapy for tumour immunotherapy," Bioscience Reports 37, pp. 1-12 (2017).
Sharma et al., "Formulation and optimization of polymeric nanoparticles for intranasal delivery of lorazepam using Box-Behnken design: in vitro and in vivo evaluation," Biomed Res Int. 2014;2014:156010. doi: 10.1155/2014/156010. Epub Jul. 14, 2014.
Sharma et al., "Next generation delivery system for proteins and genes of therapeutic purpose: why and how?" Biomed Res Int. 2014;2014:327950. doi: 10.1155/2014/327950. Epub Jul. 15, 2014.
Simeoni et al., "Insight into the mechanism of the peptide-based gene delivery system MPG: implications for delivery of siRNA into mammalian cells," Nucleic Acids Res. 31, pp. 2717-2724 (2003).
Smith et al., A combinatorial approach to create artificial homing endonucleases cleaving chosen sequences. Nucleic Acids Res. 2006;34(22):e149. Epub Nov. 27, 2006.
Sowa et al., "In vitro and in vivo testing of a novel regulatory system for gene therapy for intervertebral disc degeneration," Spine, 36(10), pp. E623-E628 (2011).
Spear et al., "Strategies to genetically engineer T cells for cancer immunotherapy," Cancer Immunol Immunother. Jun. 2016;65(6):631-49. doi: 10.1007/s00262-016-1842-5. Epub May 2, 2016. Author manuscript.

(56) References Cited

OTHER PUBLICATIONS

Stoddard, Homing endonuclease structure and function. Q Rev Biophys. Feb. 2005;38(1):49-95. Epub Dec. 9, 2005.
Sussman et al., "Isolation and characterization of new homing endonuclease specificities at individual target site positions," J. Mol. Biol. 342, pp. 31-41 (2004).
Tamboli et al. Polymeric vectors for ocular gene delivery. Ther Deliv. Apr. 2011;2(4):523-36. doi: 10.4155/tde.11.20. Author manuscript.
Tammana et al., 4-1BB and CD28 signaling plays a synergistic role in redirecting umbilical cord blood T cells against B-cell malignancies. Hum Gene Ther. Jan. 2010;21(1):75-86. doi: 10.1089/hum. 2009.122.
Tang et al., Identification of Dehalobacter reductive dehalogenases that catalyse dechlorination of chloroform, 1,1,1-trichloroethane and 1,1-dichloroethane. Philos Trans R Soc Lond B Biol Sci. Mar. 11, 2013;368(1616):20120318. doi: 10.1098/rstb.2012.0318.
Thomsen et al., "Promoter-regulatory region of the major immediate early gene of human cytomegalovirus," Proc. Natl. Acad. Sci. USA 81(3), pp. 659-663 (1984).
Tong et al., "Eye drop delivery of nano-polymeric micelle formulated genes with cornea-specific promoters," J. Gene Med. 9(11), pp. 956-966 (2007).
Torikai et al., "A foundation for universal T-cell based immunotherapy: T cells engineered to express a CD19-specific chimeric-antigen-receptor and eliminate expression of endogenous TCR," Blood 119(24), pp. 5697-5705 (2012).
Torikai et al., Toward eliminating HLA class I expression to generate universal cells from allogeneic donors. Blood. Aug. 22, 2013;122(8):1341-9. doi: 10.1182/blood-2013-03-478255. Epub Jun. 5, 2013.
Vannucci et al., "Viral vectors: a look back and ahead on gene transfer technology," New Microbiol. 36, pp. 1-22 (2013).
Witkowski et al., Conversion of a beta-ketoacyl synthase to a malonyl decarboxylase by replacement of the active-site cysteine with glutamine. Biochemistry. Sep. 7, 1999;38(36):11643-50.
Yoshikai et al., "Organization and sequences of the variable joining and constant region genes of the human t cell receptor alpha-chain," Nature, 316(6031), pp. 837-840 (1985).
Yuasa et al., "Adeno-associated virus vector-mediated gene transfer into dystrophin-deficient skeletal muscles evokes enhanced immune response against the transgene product," Gene Ther. 9, pp. 1576-1588 (2002).
Zhang et al., "A greedy algorithm for aligning DNA sequences," J. Comput. Biol. 7(1-2), pp. 203-214 (2000).
Zhang et al., "Engineering CAR-T cells," Biomarker Research 5(22), pp. 1-6 (2017).
Zuris et al., "Efficient Delivery of Genome-Editing Proteins In Vitro and In Vivo," Nat. Biotechnol. 33, pp. 73-80 (2015). Author manuscript. Published online Oct. 30, 2014. doi: 10.1038/nbt.3081.
U.S. Appl. No. 17/189,243, filed Mar. 1, 2021, Jantz et al.
U.S. Appl. No. 17/330,365, filed May 25, 2021, Jantz et al.
U.S. Appl. No. 17/046,761, filed Oct. 9, 2020, Smith et al.
EP 16782371.5, Nov. 8, 2019, EPO Communication.
EP 20172471.3, Nov. 26, 2020, Extended European Search Report.
PCT/US2018/039740, Sep. 24, 2018, International Search Report and Written Opinion.
PCT/US2018/039740, Jan. 9, 2020, International Preliminary Report on Patentability.
PCT/US2019/027019, Jun. 27, 2019, International Search Report and Written Opinion.
PCT/US2019/027019, Oct. 22, 2020, International Preliminary Report on Patentability.
EPO Communication for Application No. EP 16782371.5 dated Nov. 8, 2019. 6 pages.
Extended European Search Report dated Nov. 26, 2020 in connection with Application No. EP 20172471.3.
International Search Report and Written Opinion for Application No. PCT/US2018/039740 dated Sep. 24, 2018.

International Preliminary Report on Patentability for Application No. PCT/US2018/039740 dated Jan. 9, 2020.
International Search Report and Written Opinion for Application No. PCT/US2019/027019 dated Jun. 27, 2019.
International Preliminary Report on Patentability for Application No. PCT/US2019/027019 dated Oct. 22, 2020.
[No Author Listed], Decision—Motions—37 C.F.R. § 41.125. *Jantz v. Galetto*. Patent Interference No. 106,117. USPTO Before the Patent Trial and Appeal Board. Oct. 13, 2020:35 pages.
[No Author Listed], Decision—Motions—37 C.F.R. § 41.125. *Jantz v. Galetto*. Patent Interference No. 106,118. USPTO Before the Patent Trial and Appeal Board. Sep. 30, 2020:33 pages.
[No Author Listed], Genbank Accession No. BDV42890. TRC 1-2x.87 EE meganuclease, SEQ ID 8. Jun. 1, 2017; 1 page.
[No Author Listed], Genbank Accession No. BDV42894. TRC 1-2x.6 meganuclease, SEQ ID 12. Jun. 1, 2017; 1 page.
[No Author Listed], Genbank Accession No. BDV42944. TRC 1-2x.6 meganuclease 7-153, SEQ ID 62. Jun. 1, 2017; 1 page.
[No Author Listed], Genbank Accession No. BDV43178. Chlamydomonas reinhardtii CreI meganuclease, SEQ ID 8. Jun. 15, 2017; 1 page.
[No Author Listed], Genbank Accession No. BDV43182. Chlamydomonas reinhardtii CreI meganuclease, SEQ ID 12. Jun. 15, 2017; 1 page.
[No Author Listed], Genbank Accession No. BDV43232. Chlamydomonas reinhardtii CreI meganuclease, SEQ ID 62. Jun. 15, 2017; 1 page.
[No Author Listed], Genbank Accession No. BEA51599. TRC 1-2x.87 EE meganuclease, SEQ ID 131. Aug. 10, 2017; 1 page.
[No Author Listed], Genbank M94081.1. Human TCR-c-DELTA GENEM EXONS 1-4; Tcr-V-delta gene, exons 1-2; T-cell receptor alpha (Tcr-alpha) gene, J1-J61 segments; and Tcr-C-alpha gene, exons 1-4.. Jul. 24, 2016; Last Accessed Apr. 27, 2021; 27 pages.
Brickman et al., A wider context for gene trap mutagenesis. Methods Enzymol. 2010;477:271-95. doi: 10.1016/S0076-6879(10)77014-2.
Eyquem et al., Targeting a CAR to theTRAC locus with CRISPR/CAS9 enhances tumour rejection. Nature. Mar. 2, 2017;543(7643):113-117. doi: 10.1037/nature21405. Epub Feb. 22, 2017.
Galetto et al., Targeted approaches for gene therapy and the emergence of engineered meganucleases. Expert Opin Biol Ther. Oct. 2009;9(10):1289-303. doi: 10.1517/14712590903213669.
Handel et al., Versatile and efficient genome editing in human cells by combining zinc-finger nucleases with adeno-associated viral vectors. Hum Gene Ther. Mar. 2012;23(3):321-9. doi: 10.1089/hum. 2011.140. Epub Dec. 14, 2011.
Koonin et al., Diversity, classification and evolution of CRISPR-Cas systems. Curr Opin Microbiol. Jun. 2017;37:67-78. doi: 10.1016/j.mib.2017.05.008. Epub Jun. 9, 2017.
Kunkel et al., Rapid and efficient site-specific mutagenesis without phenotypic selection. Methods Enzymol. 1987;154:367-82. doi: 10.1016/0076-6879(87)54085-x.
Lange et al., Classical nuclear localization signals: definition, function, and interaction with importin alpha. J Biol Chem. Feb. 23, 2007;282(8):5101-5. doi: 10.1074/jbc.R600026200. Epub Dec. 14, 2006.
Osborn et al., Evaluation of TCR Gene Editing Achieved by TALENs, CRISPR/Cas9, and megaTAL Nucleases. Mol Ther. Mar. 2016;24(3):570-81. doi: 10.1038/mt.2015.197. Epub Oct. 27, 2015.
Provasi et al., Editing T cell specificity towards leukemia by zinc finger nucleases and lentiviral gene transfer. Nat Med. May 2012;18(5):807-815. doi: 10.1038/nm.2700.
Rosenberg et al., Use of tumor-infiltrating lymphocytes and interleukin-2 in the immunotherapy of patients with metastatic melanoma. A preliminary report. N Engl J Med. Dec. 22, 1988;319(25):1676-80.
Shao et al., Mechanisms for U2AF to define 3' splice sites and regulate alternative splicing in the human genome. Nat Struct Mol Biol. Nov. 2014;21(11):997-1005. doi: 10.1038/nsmb.2906. Epub Oct. 19, 2014.
Taylor et al., Apoptosis: controlled demolition at the cellular level. Nat Rev Mol Cell Biol. Mar. 2008;9(3):231-41. doi: 10.1038/nrm2312.

(56) References Cited

OTHER PUBLICATIONS

Van De Loo et al., An oleate 12-hydroxylase from *Ricinus communis* L. is a fatty acyl desaturase homolog. Proc Natl Acad Sci U S A. Jul. 18, 1995;92(15):6743-7. doi: 10.1073/pnas.92.15.6743.
Wieczorek et al., Genetically modified T cells for the treatment of malignant disease. Transfus Med Hemother. Dec. 2013;40(6):388-402. doi: 10.1159/000357163. Epub Nov. 29, 2013.

A.

```
                            TRC1          TRC2
                          Half-Site     Half-Site
TRC 1-2               TGGCCTGGAGCAA CAAATCTGA     (SEQ ID NO:3)
Recognition Sequence  ACCGGACCT CGTTGTTTAGACT     (SEQ ID NO:83)

TRC3          TRC4
                          Half-Site     Half-Site
TRC 3-4               ACAAATGTGTCAC AAAGTAAGG     (SEQ ID NO:4)
Recognition Sequence  TGTTTACAC AGTGTTTCATTCC     (SEQ ID NO:84)

TRC7          TRC8
                          Half-Site     Half-Site
TRC 7-8               CTGATGTGTATAT CACAGACAA     (SEQ ID NO:5)
Recognition Sequence  GACTACACA TATAGTGTCTGTT     (SEQ ID NO:85)
```

B.

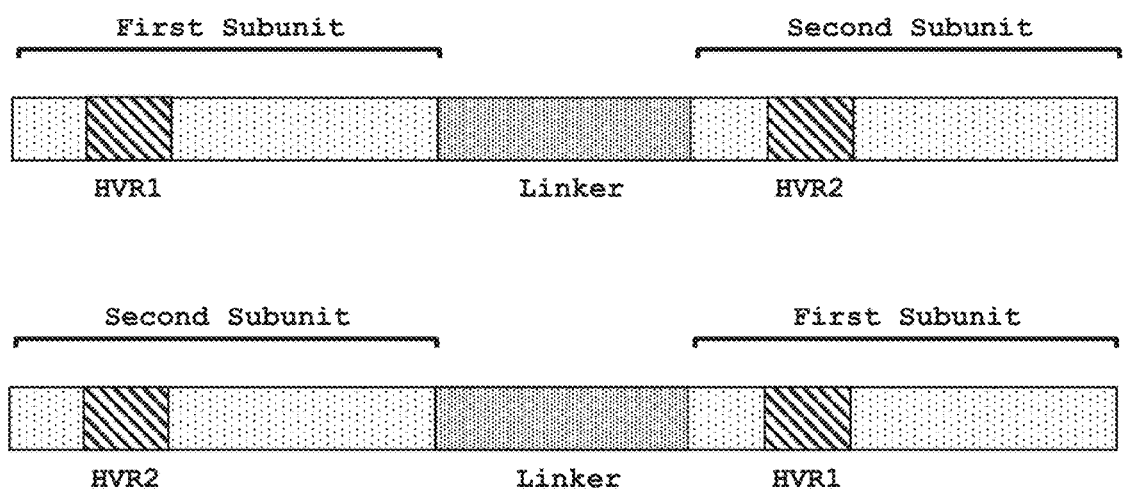

| SEQ ID NO: | | 198 | | Hypervariable Region 1 (HVR1) | 271 |
|---|---|---|---|---|---|
| 33 | TRC 1-2x.87_EE | KEFLLYLAGFVDGDGS | IYACIAPRQGSKFKHRLKLGFAVGQKTQRRWFLDKLVDEIGVGYVDRGSVSEYVLSE |
| 34 | TRC 1-2x.87_QE | KEFLLYLAGFVDGDGS | IYACIAPRQGSKFKHRLKLGFAVGQKTQRRWFLDKLVDEIGVGYVDRGSVSEYVLSQ |
| 35 | TRC 1-2x.87_EQ | KEFLLYLAGFVDGDGS | IYACIAPRQGSKFKHRLKLGFAVGQKTQRRWFLDKLVDEIGVGYVDRGSVSEYVLSQ |
| 36 | TRC 1-2x.87 | KEFLLYLAGFVDGDGS | IYACIAPRQGSKFKHRLKLGFAVGQKTQRRWFLDKLVDEIGVGYVDRGSVSEYVLSQ |
| 37 | TRC 1-2x.6 | KEFLLYLAGFVDGDGS | IYACIAPRQGSKFKHRLKLGFAVGQKTQRRWFLDKLVDEIGVGYVDRGSVSEYVLSQ |
| 38 | TRC 1-2x.20 | KEFLLYLAGFVDGDGS | IYACIAPRQGRAKFKHRLKLGFAVGQKTQRRWFLDKLVDEIGVGYVDRGSVSEYVLSE |
| 39 | TRC 1-2x.55 | KEFLLYLAGFVDGDGS | IYATIAPCQRAKFKHRLLLAFTVSQKTQRRWFLDKLVDEIGVGHVDRGSVSEYILSE |
| 40 | TRC 1-2x.60 | KEFLLYLAGFVDGDGS | IYAQIKPQRAKFKHRLLLAFTVSQKTQRRWFLDKLVDEIGVGYVDRGSVSEYVLSQ |
| 41 | TRC 1-2x.105 | KEFLLYLAGFVDGDGS | IYASIRPSQRSKFKHRMLGLGFAVGQKTQRRWFLDKLVDEIGVGYVDRGSVSEYVLSQ |
| 42 | TRC 1-2x.163 | KEFLLYLAGFVDGDGS | IYACIAPRQGSKFKHRLKLGFAVGQKTQREWFLDKLVDEIGVGYVDRGSVSEYVLSQ |
| 43 | TRC 1-2x.113_3 | KEFLLYLAGFVDGDGS | IYACIAPRQGSKFKHRLKLGFAVGQKTQRRWFLDKLVDEIGVGYVDRGSVSEYVLSQ |

| SEQ ID NO: | | 7 | | Hypervariable Region 1 (HVR1) | 80 |
|---|---|---|---|---|---|
| 44 | TRC 1-2x.5 | KEFLLYLAGFVDGDGS | IYACIAPRQGSKFKHRLKLGFAVGQKTQRRWFLDKLVDEIGVGYVDRGSVSEYVLSQ |
| 45 | TRC 1-2x.8 | KEFLLYLAGFVDGDGS | IYATIRPAQRAKFKHRLVLGFAVGQKTQRRWFLDKLVDEIGVGYVDGGSVSEYRLSQ |
| 46 | TRC 1-2x.25 | KEFLLYLAGFVDGDGS | IYACIAPRQGSKFKHRLKLGFAVGQKTQRRWFLDKLVDEIGVGYVDRGSVSEYVLSQ |
| 47 | TRC 1-2x.72 | KEFLLYLAGFVDGDGS | IYACIAPRQGSKFKHRLKLGFAVGQKTQRRWFLDKLVDEIGVGYVDRGSVSEYVLSQ |
| 48 | TRC 1-2x.80 | KEFLLYLAGFVDGDGS | IYACIAPRQGRAKFKHRLKLGFTVGQKTQRRWFLDKLVDEIGVGYVDRGSVSEYVLSQ |
| 49 | TRC 1-2x.84 | KEFLLYLAGFVDGDGS | IYATIAPCQRAKFKHRLKLGFAVGQKTQRRWFLDKLVDEIGVGHVDRGSVSEYVLSE |
| 50 | TRC 1-2x.120 | KEFLLYLAGFVDGDGS | IYACIAPRQGSKFKHRLKLGFAVGQKTQRRWFLDKLVDEIGVGYVDRGSVSEYVLSQ |
| 51 | TRC 1-2x.113_1 | KEFLLYLAGFVDGDGS | IYACIAPRQGSKFKHRLKLGFAVGQKTQRRWFLDKLVDEIGVGYVDRGSVSEYVLSE |
| 52 | TRC 1-2x.113_2 | KEFLLYLAGFVDGDGS | IYACIAGQGSKFKHRLKLGFAVGQKTQRRWFLDKLVDEIGVGYVDRGSVSEYVLSE |

| SEQ ID NO: | | 7 | Hypervariable Region 1 (HVR1) | 80 |
|---|---|---|---|---|
| 53 | TRC 3-4x.3 | KEFLLYLAGFVDGDGSI | KATICFQQTKFKHYLTLSFSVYQKTQRRWFLDKLVDEIGVGYVY | DQGSVSCYRLSQ |
| 54 | TRC 3-4x.19 | KEFLLYLAGFVDGDGSI | KATICFPDQALKFKHYLSLTFAVYQKTQRRWFLDKLVDEIGVGYVY | DQGSVSCYRLSQ |

| | | 81 | | 153 |
|---|---|---|---|---|
| | TRC 3-4x.3 | IKPLHNFLTQLQPFLKLKQKQANLVLKIIEQLPSAKESPDKFLEVCTWVDQIAALNDSKTRKTTSETVRAVLD |
| | TRC 3-4x.19 | IKPLHNFLTQLQPFLKLKQKQANLVLKIIEQLPSAKESPDKFLEVCTWVDQIAALNDSKTRKTTSETVRAVLD |

FIGURE 4

```
SEQ ID                                                                      Hypervariable Region 2 (HVR2)
NO:            198                                                                                                            271
78  TRC 3-4x.3    KEFLLYLAGFVDGDGSIHACIQFPQDYKFKHQLHLRFTVHQKTQRRWFLDKLVDEIGVGYVVDAGSVSTYCLSQ
79  TRC 3-4x.19   KEFLLYLAGFVDGDGSIHACIQFMQSMKFKHHLHLRFTVHQKTQRRWFLDKLVDETGVGYVVDAGSVSTYCLSQ 272                                                                          344
TRC 3-4x.3    IKPLHNFLTQLQPFLKLKQKQANLVLKIIEQLPSAKESPDKFLEVCTWVDQIAALNDSKTRKKTTSETVRAVLD
TRC 3-4x.19   IKPLHNFLTQLQPFLKLKQKQANLVLKIIEQLPSAKESPDKFLEVCTWVDQIAALNDSKTRKKTTSETVRAVLD
```

FIGURE 5

| SEQ ID NO: | | | | Hypervariable Region 1 (HVR1) | |
|---|---|---|---|---|---|
| 55 | TRC 7-8x.7 | 7 | KEFLLYLAGFVDGDGSI | YACITPQQDMKFKHRLQLRFCVTQKTQRRWFLDKLVDEIGVGYVQDCGSVSEYRLSE | 80 |

| SEQ ID NO: | | | | Hypervariable Region 1 (HVR1) | |
|---|---|---|---|---|---|
| 56 | TRC 7-8x.9 | 198 | KEFLLYLAGFVDGDGSI | YACITPQQDMKFKHRLQLRFCVTQKTQRRWFLDKLVDEIGVGYVQDHGGASEYRLSE | 271 |
| 57 | TRC 7-8x.14 | | KEFLLYLAGFVDGDGSI | YACITPQQDMKFKHRLQLRFCVTQKTQRRWFLDKLVDEIGVGYVQDKGSASEYRLSE | |

FIGURE 6A

```
TRC 7-8x.7    81  IKPLENFLTQLQPFLKLKQKQANLVLKIIEQLPSAKESPDKFLEVCTWVDQIAALNDSKIRKTTSETVRAVLD  153

TRC 7-8x.9   272  IKPLENFLTQLQPFLKLKQKQANLVLKIIEQLPSAKESPDKFLEVCTWVDQIAALNDSKIRKTTSETVRAVLD  344
TRC 7-8x.14       IKPLENFLTQLQPFLKLKQKQANLVLKIIEQLPSAKESPDKFLEVCTWVDQIAALNDSKIRKTTSETVRAVLD
```

FIGURE 6B

```
SEQ ID                198                                       Hypervariable Region 2 (HVR2)                      271
NO:
 80    TRC 7-8x.7     KEFLLYLAGFVDGDGSI WASIKPRQVAKFKHRLMLEFTVVQKTQRRWFLDKLVDEIGVGYV IDLGQASRYDLS Q SEQ ID                7                                         Hypervariable Region 2 (HVR2)                      80
NO:
 81    TRC 7-8x.9     KEFLLYLAGFVDGDGSI KASIKPDQAAKFKHRLLLEFTVQKTQRRWFLDKLVDEIGVGYV DQGSVSEYRLS Q
 82    TRC 7-8x.14    KEFLLYLAGFVDGDGSI WASIRPTQIAKFKHALWLGFAVVQKTQRRWFLDKLVDEIGVGYV DSGSVSKYELSE
```

FIGURE 7A

```
TRC 7-8x.7    272  IKPLHNFLTQLQPFLKLKQKQANLVLKIIEQLPSAKESPDKFLEVCTWVDQIAALNDSKTRKTTSETVRAVLD  344

TRC 7-8x.9     81  IKPLHNFLTQLQPFLKLKQKQANLVLKIIEQLPSAKESPDKFLEVCTWVDQIAALNDSKTRKTTSETVRAVLD  153
TRC 7-8x.14        IKPLHNFLTQLQPFLKLKQKQANLVLKIIEQLPSAKESPDKFLEVCTWVDQIAALNDSKTRKTTSETVRAVLD
```

FIGURE 7B

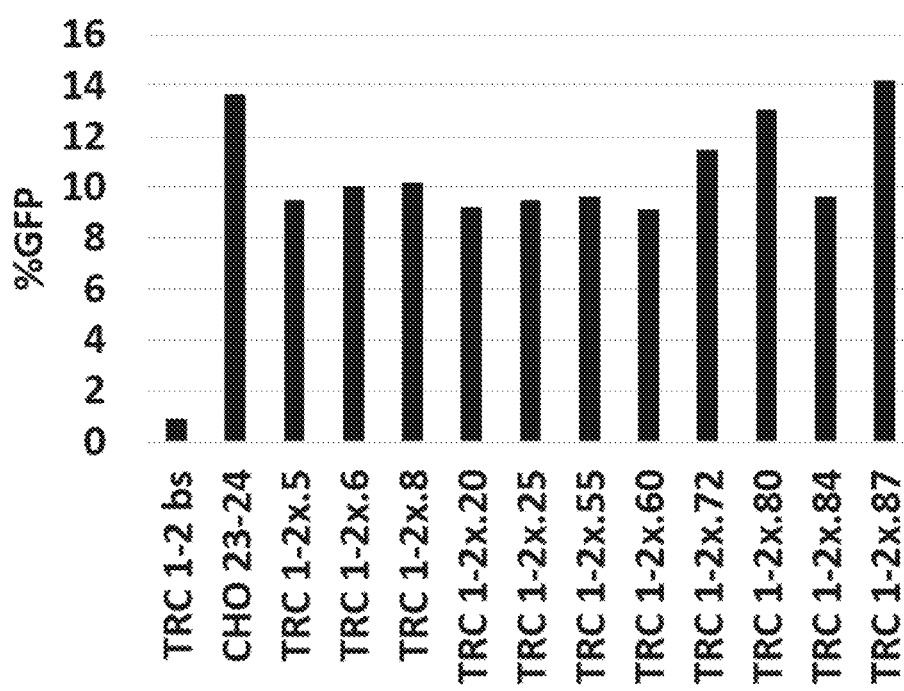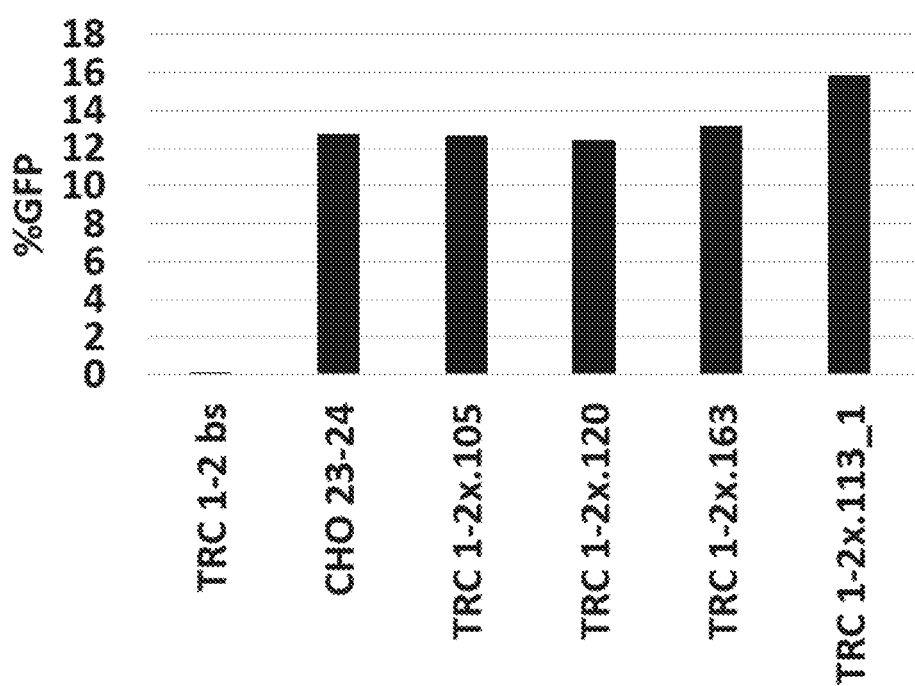
FIGURE 9

C.
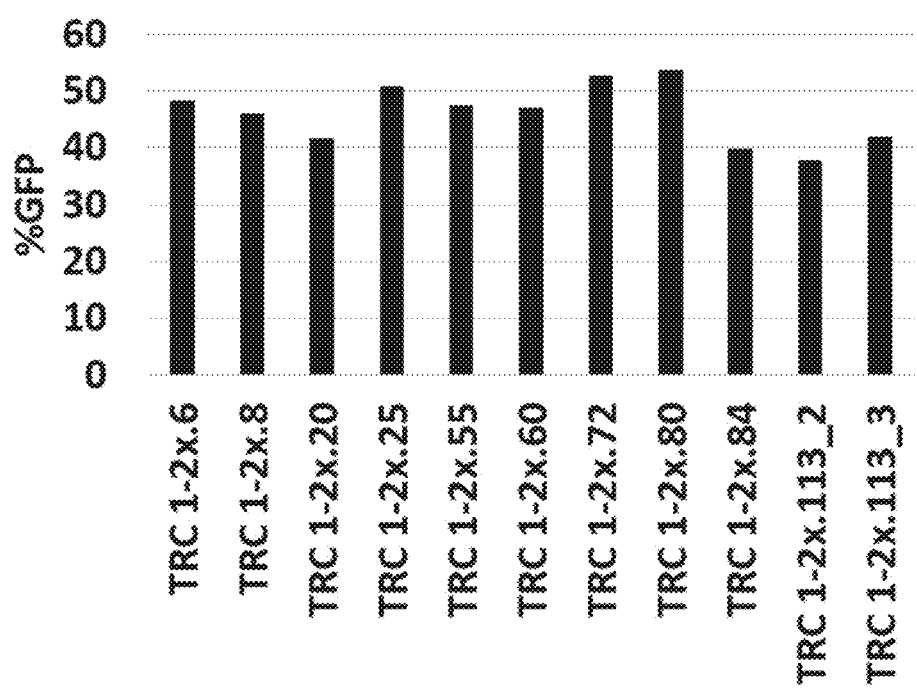
D.
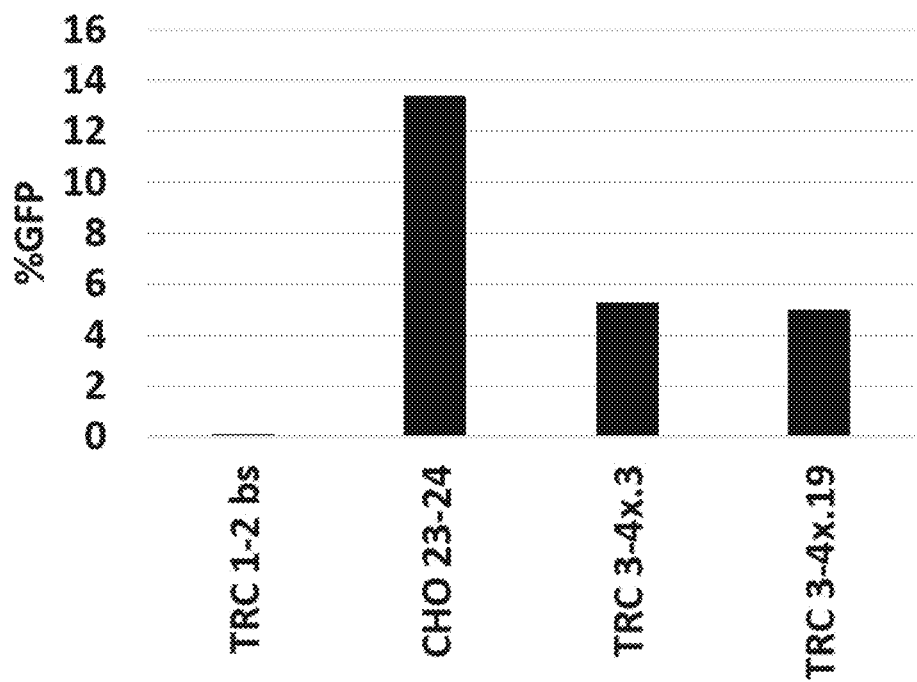
FIGURE 9 (cont.)

E.
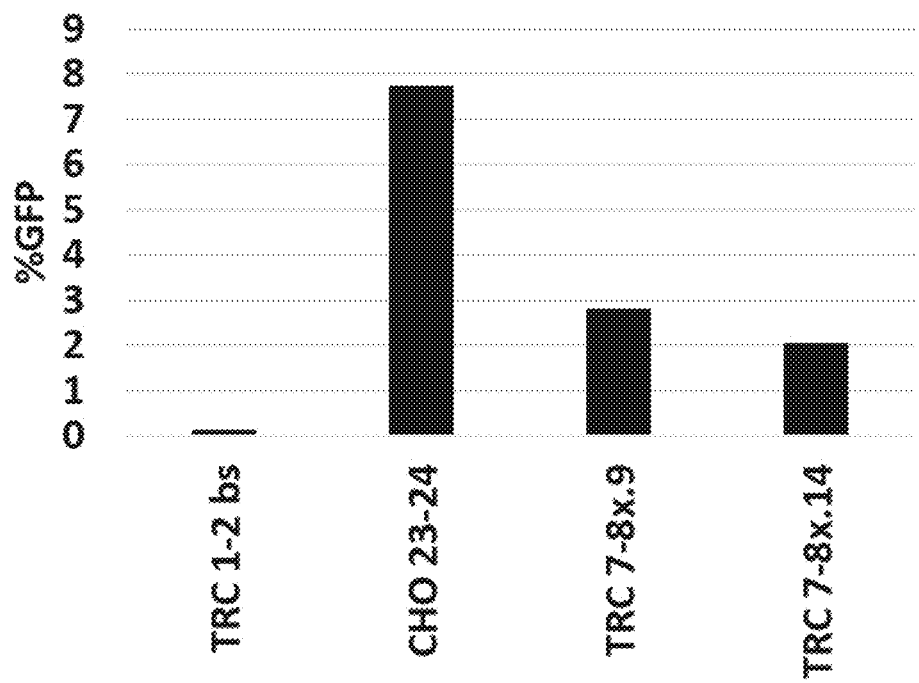
F.
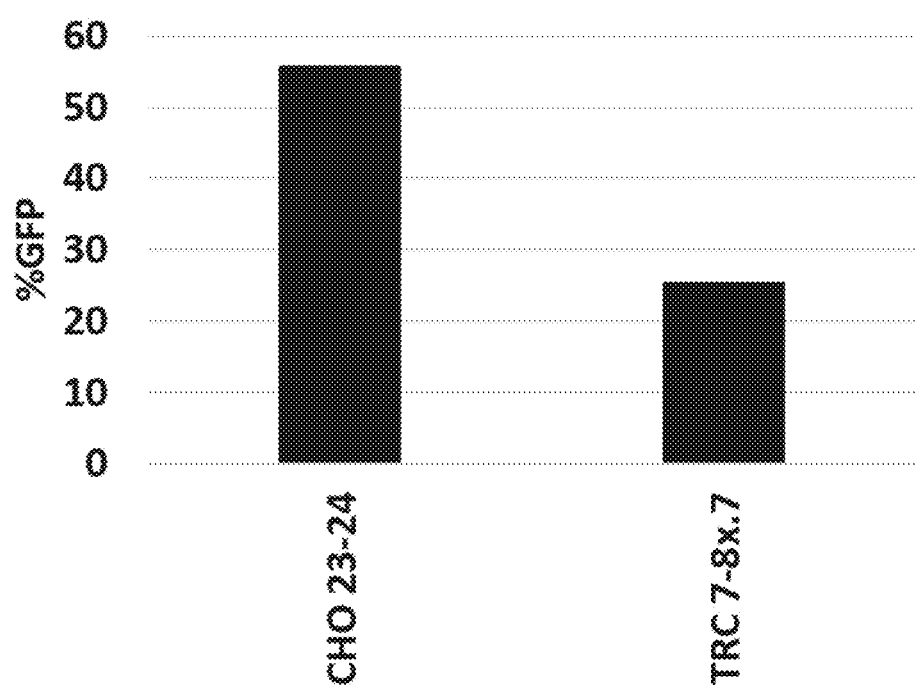
FIGURE 9 (cont.)

G.

| SEQ ID NO: | | 162 | | 233 |
|---|---|---|---|---|
| 86 | Wild-Type | ATGGACTTCAAGAGCAACAGTGCTGCTGCTGGCCTGGAGCAACAAATCTGA | CTTTGCATGTGCAAACGCCCTTCAAC |
| 87 | Indel | ATGGACTTCAAGAGCAACAGTGCTGCTGTGGCCTGGAG---CAAATCTGA | CTTTGCATGTGCAAACGCCCTTCAAC |
| 88 | Indel | ATGGACTTCAAGAGCAACAGCAACA-------------AACAAATCTGA | CTTTGCATGTGCAAACGCCCTTCAAC |
| 89 | Indel | ATGGACTTCAAGAGCAACAGTGCTGCTGTGGCCTGGAG--------AATCTGA | CTTTGCATGTGCAAACGCCCTTCAAC |
| 90 | Indel | ATGGACTTCAAGAGCAACAGTGCTGCTGTGGCCTGGAG-------------- | CTTTGCATGTGCAAACGCCCTTCAAC |
| 91 | Indel | ATGGACTTCAAGAGCAACAA--------------TCTGAAATCTGA | CTTTGCATGTGCAAACGCCCTTCAAC |
| 92 | Indel | ATGGACTTCAAGAGCAACAGTGCTGCTGTGGCCTGGAG-------ACAAATCTGA | CTTTGCATGTGCAAACGCCCTTCAAC |
| 93 | Indel | ATGGACTTCAAGAGCAACAGTGCTGCTGTGGCCTGGAG-------ACAAATCTGA | CTTTGCATGTGCAAACGCCCTTCAAC |
| 94 | Indel | ATGGACTTCAAGAGCAACAGTGCTGCTGTGGCCTGGAGCAA------TCTGACTTTGCAAATCTGACTTTGCAAACGCCCTTCAAC | |
| 95 | Indel | ATGGACTTCAAGAGCAACAGTGCTGCTGTGGCCTGGAGCAACAAATCTGACTTTGCAAATCTGCATGTGCAAACGCCTTCAAC | |

FIGURE 14

A.
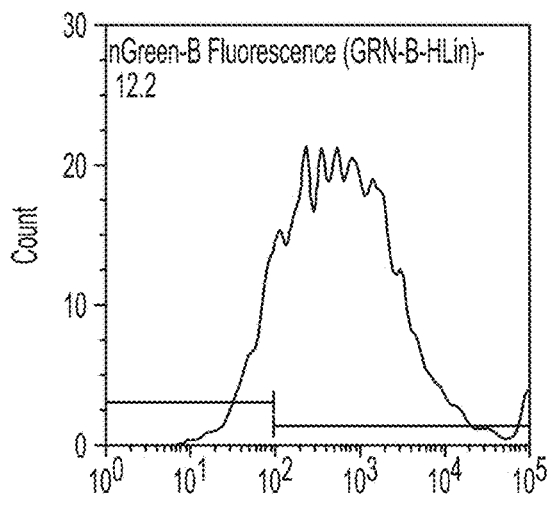
B.
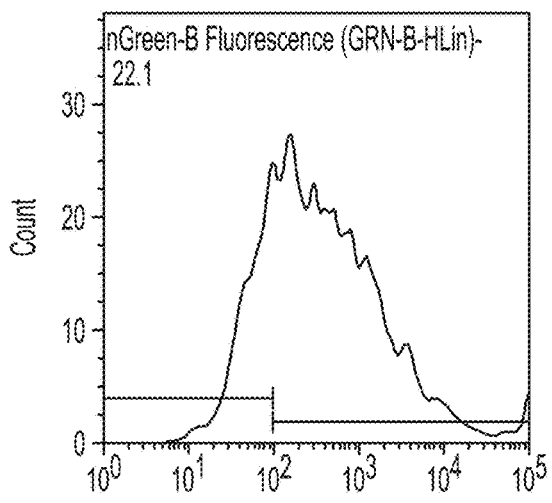
C.
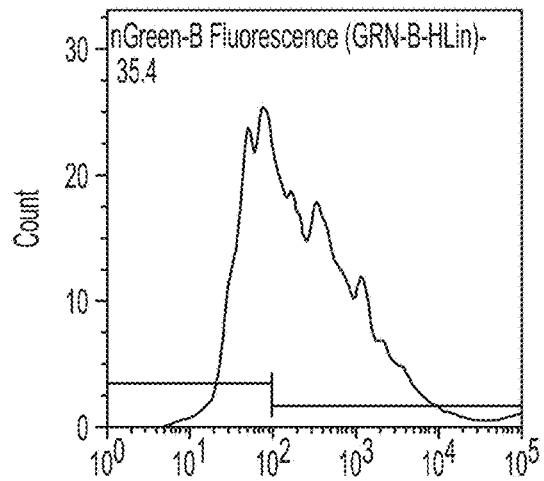
FIGURE 18

A.
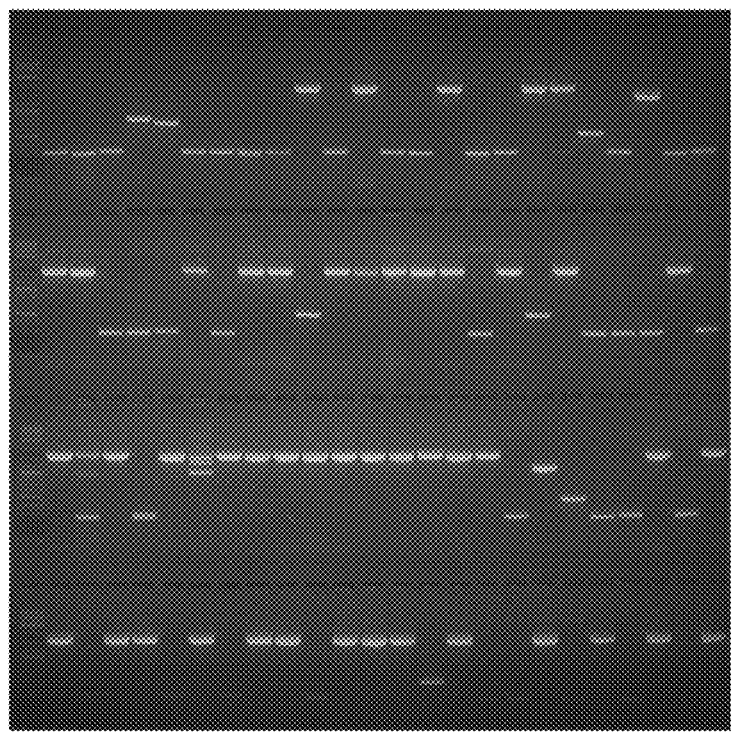
B.
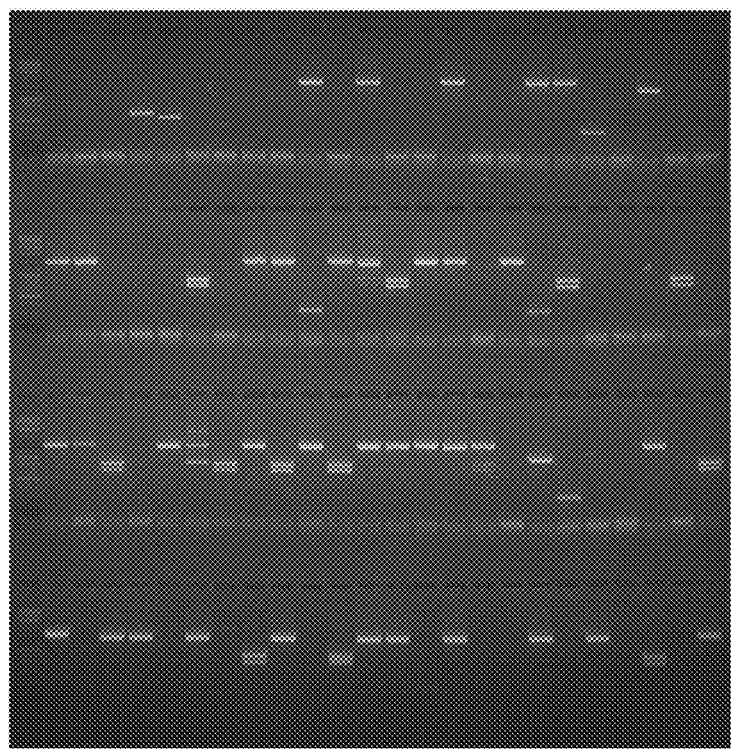
FIGURE 20

A.
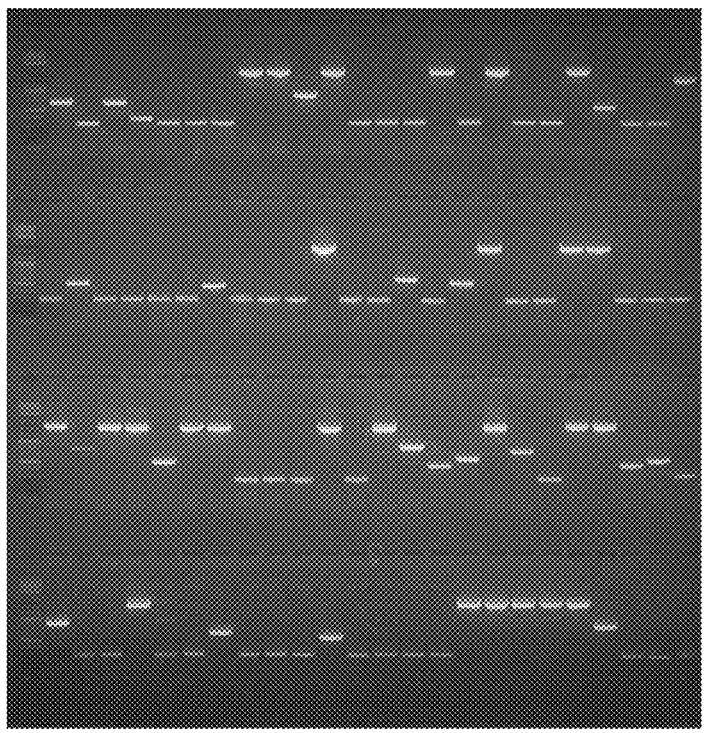
B.
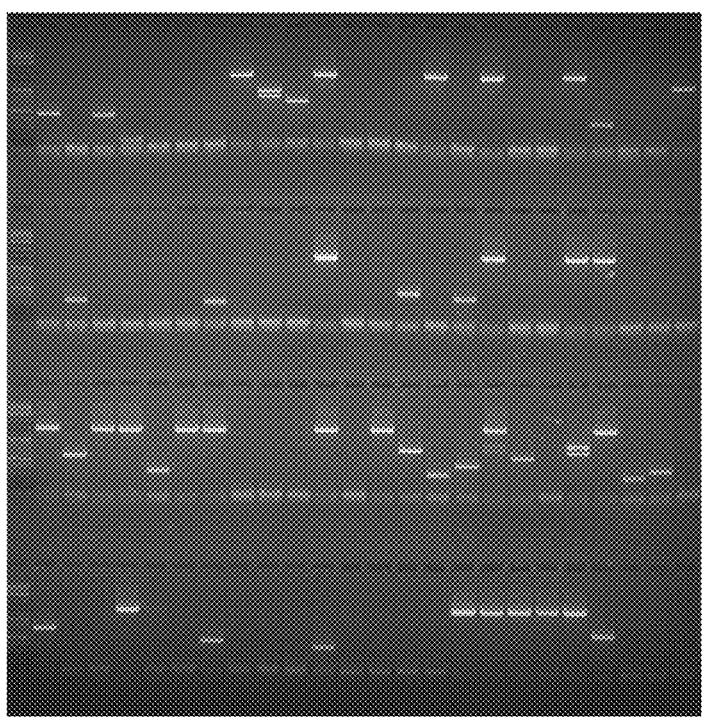
FIGURE 21

A.

| SEQ ID NO: | | 162 | | 233 |
|---|---|---|---|---|
| 92 | Wild-Type | ATGGACTTCAAGAGCAACAGTGCTG | TGGCCTGGAGCAACAAATCTGA | CTTTGCATGTGCAAACGCCTTCAAC |
| 102 | Indel | ATGGACTTCAAGAGCAACAGTGCTGCTGGCCTGTGGCCTGG---- | --CAACAAATCTGACTTTGCATGTGCAAACGCCTTCAAC |
| 103 | Indel | ATGGACTTCAAGAGCAACAGTGCTGCTGGCCTGCTGTGGC------ | --AAAATCTGACTTTGCATGTGCAAACGCCTTCAAC |
| 104 | Indel | ATGGACTTCAAGAGCAACAGTGCTGCTGGCCTGCTGTGTGGCCTGGA---- | --CAAATCTGACTTTGCATGTGCAAACGCCTTCAAC |
| 105 | Indel | ATGGACTTCAAGAGCAACAGTGCTGCTGGCCTGCTGTGTGGCCTGGCCTGGA---- | --ATCTGACTTTGCATGTGCAAACGCCTTCAAC |
| 106 | Indel | ATGGACTTCAAGAGCAACAGTGCTGCTGGCCTGCTGTGTGGCCTGGGGCCTGGAGCAA----- | ---TGTGCAAACGCCTTCAAC |
| 107 | Indel | ATGGACTTCAAGAGCAACAGTGCTGCTGGCCTGCTGTGTGGCCTGGGGCCTGGAGCAA-----ACAAATCTGACTTTGCATGTGCAAACGCCTTCAAC |
| 108 | Indel | ATGGACTTCAAGAGCAACAGTGCTGCTGGCCTGCTGTGTGGCCTGCTGGAGCAA-CAAATCTGACTTTGCATGTGCAAACGCCTTCAAC |
| 109 | Indel | ATGGACTTCAAGAGCAACAGTGCTGCTGGCCTGCTGCTGTGGCCTGCTGGAGCA-CAAATCTGACTTTGCATGTGCAAACGCCTTCAAC |
| 110 | Indel | AT------ | --CAAATCTGACTTTGCATGTGCAAACGCCTTCAAC |

B.

| SEQ ID NO: | | 181 | | 214 |
|---|---|---|---|---|
| 111 | Wild-Type | GTGCTGCTGGCCTGCCTGTGGCCA---- | ------CAAATCTGACTTTGC |
| 112 | Insertion | GTGCTGCTGGCCTGCCTGTGGCCGCGGGCCTGGAATTCATCGGCCGGCAATCGAGCCAA | AAACCGACTTTGC |

Eag1 Site

FIGURE 22

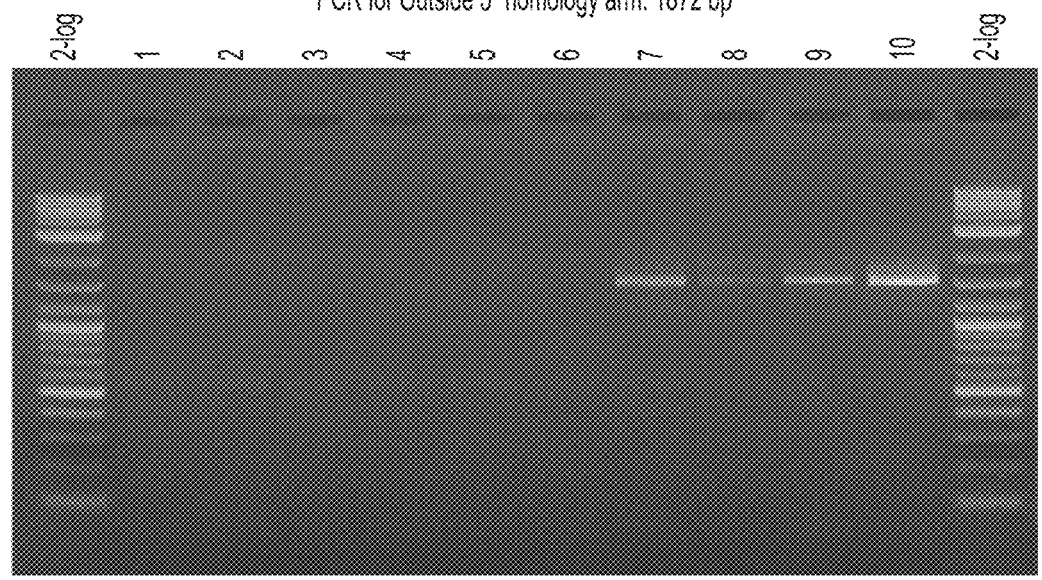
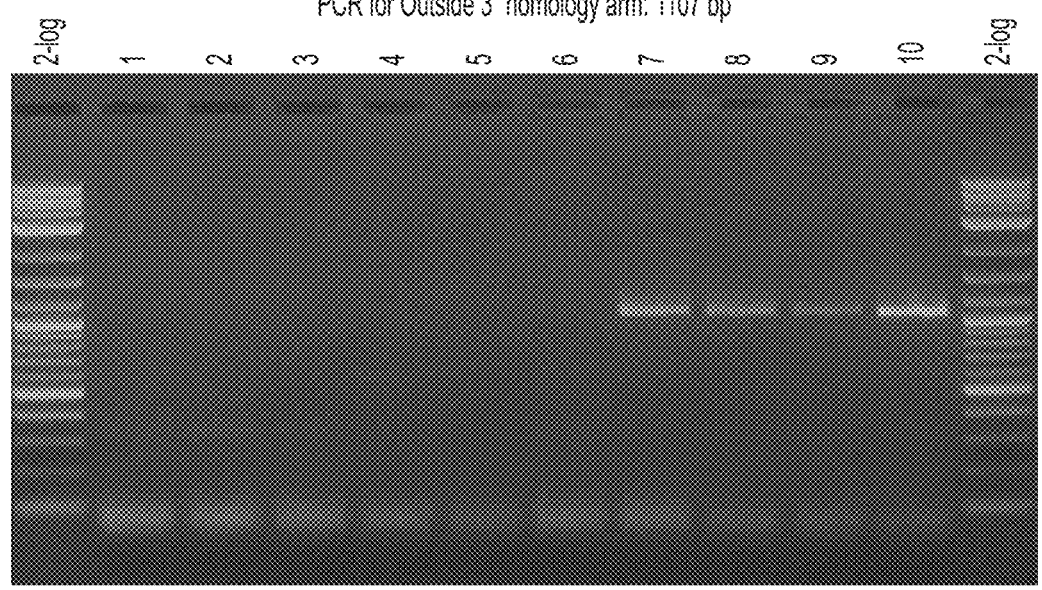
FIGURE 27

A.
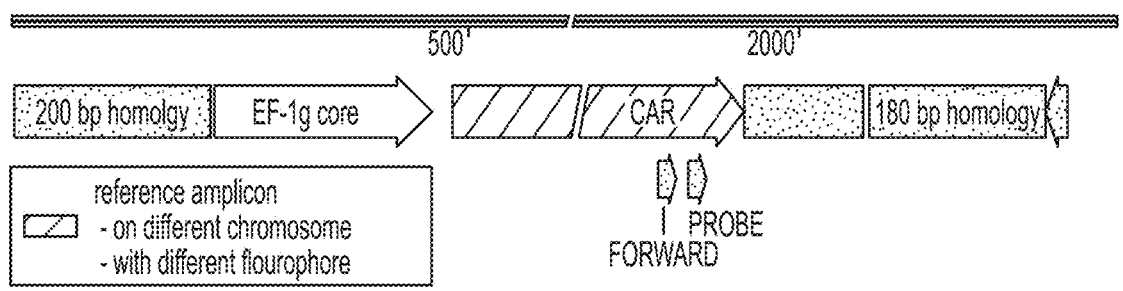
B.
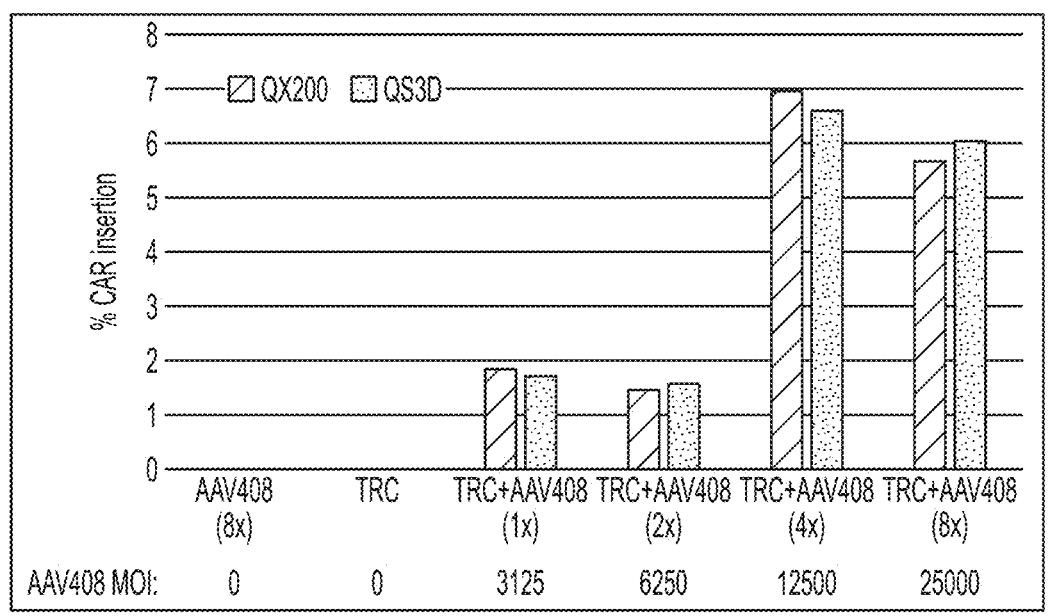
FIGURE 28

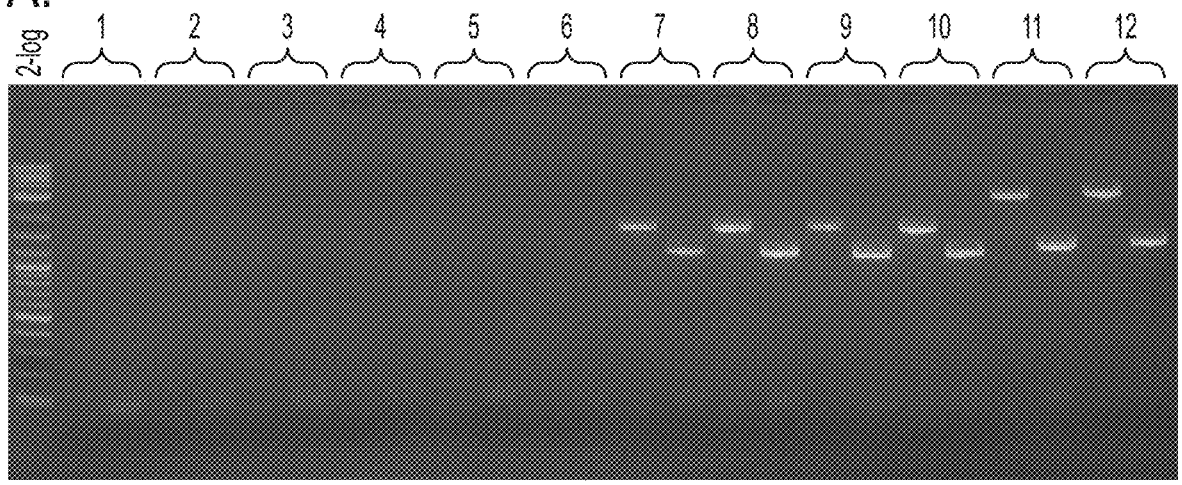
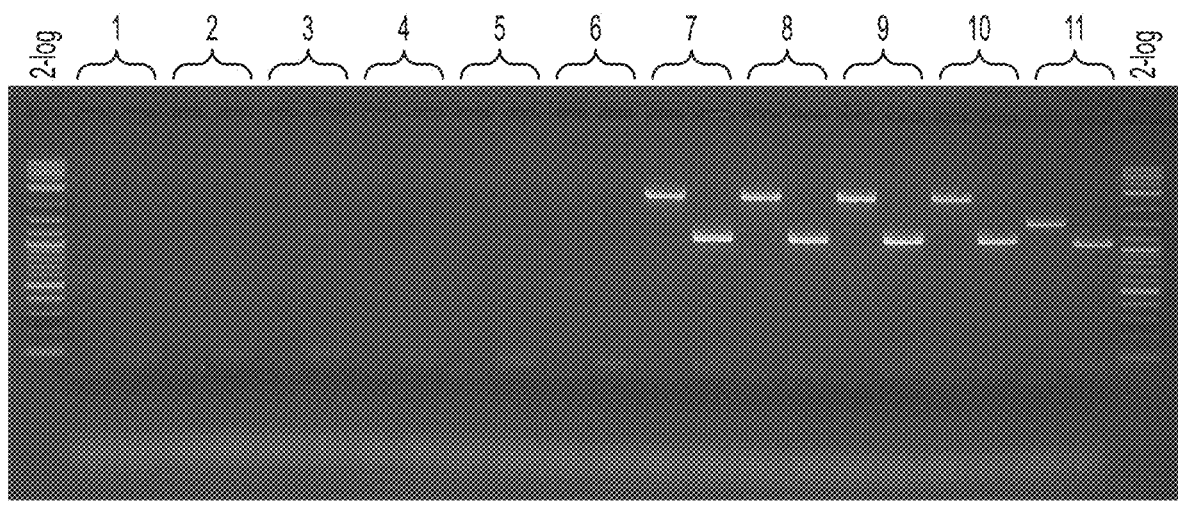
FIGURE 32

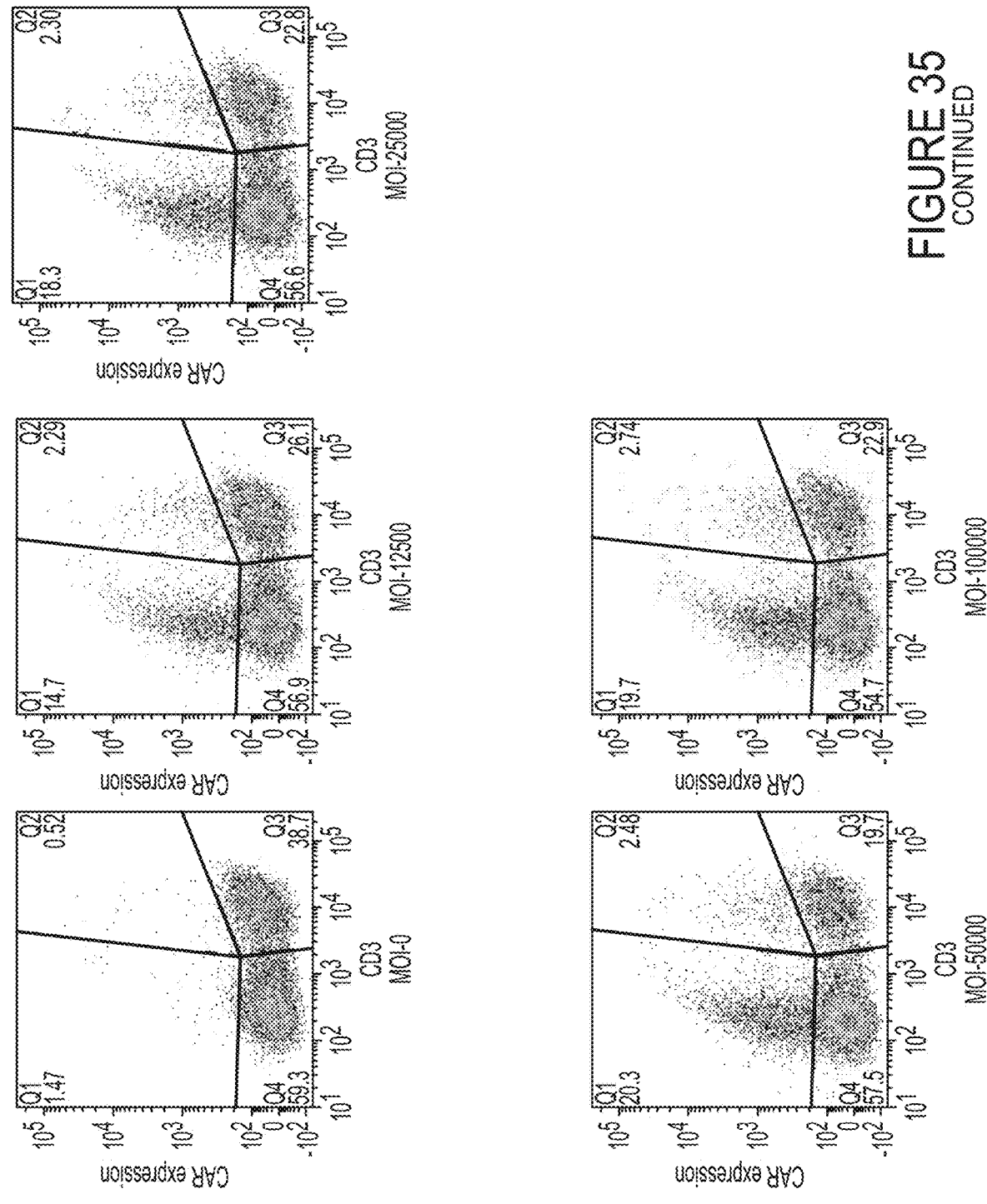

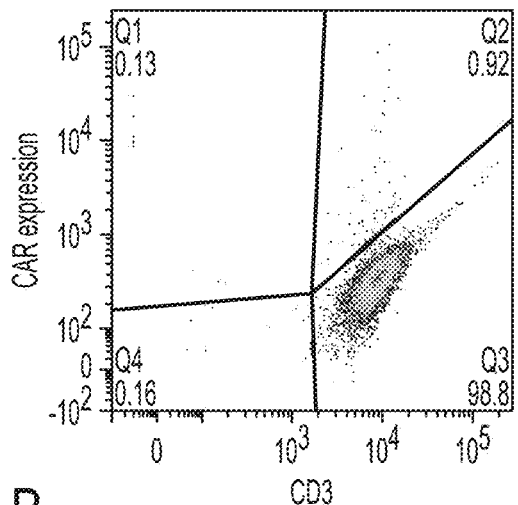
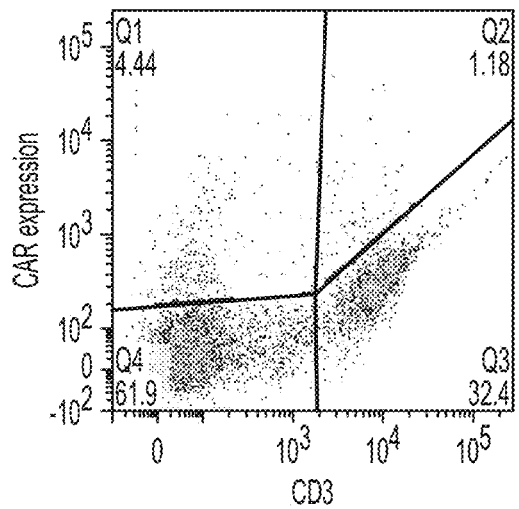
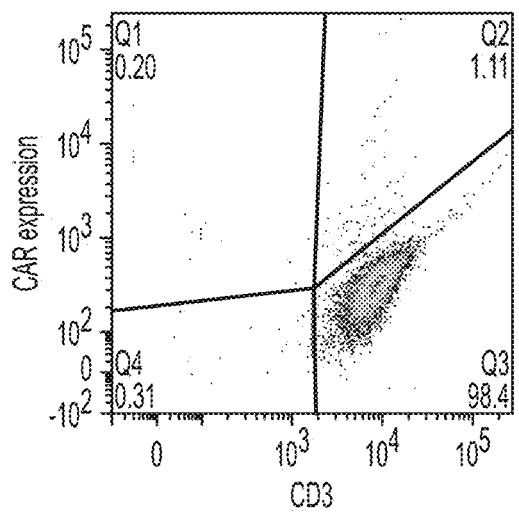
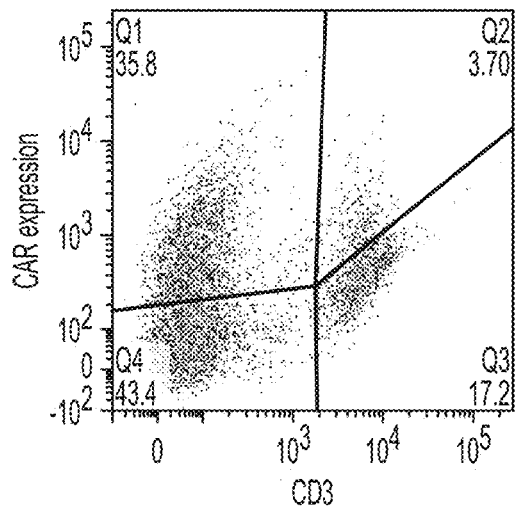
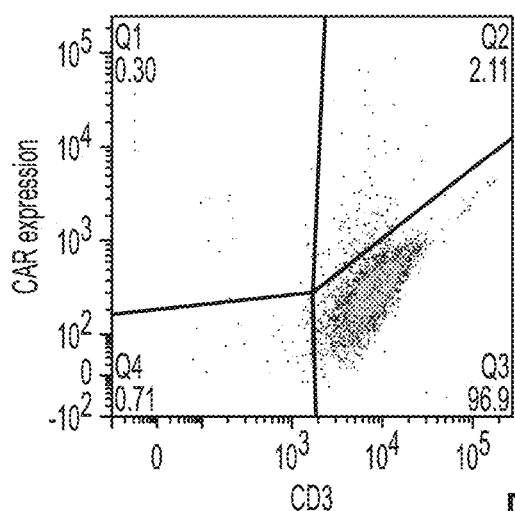
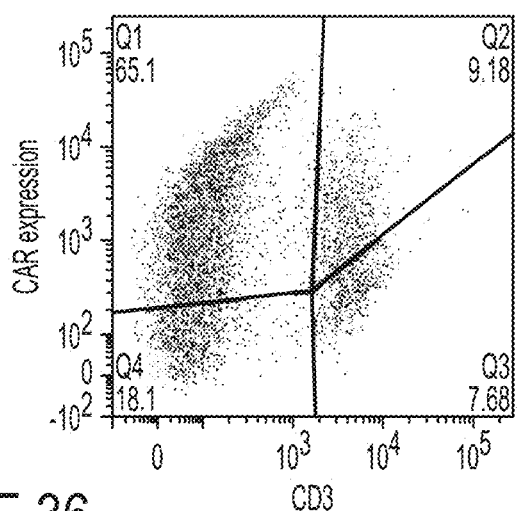
FIGURE 36

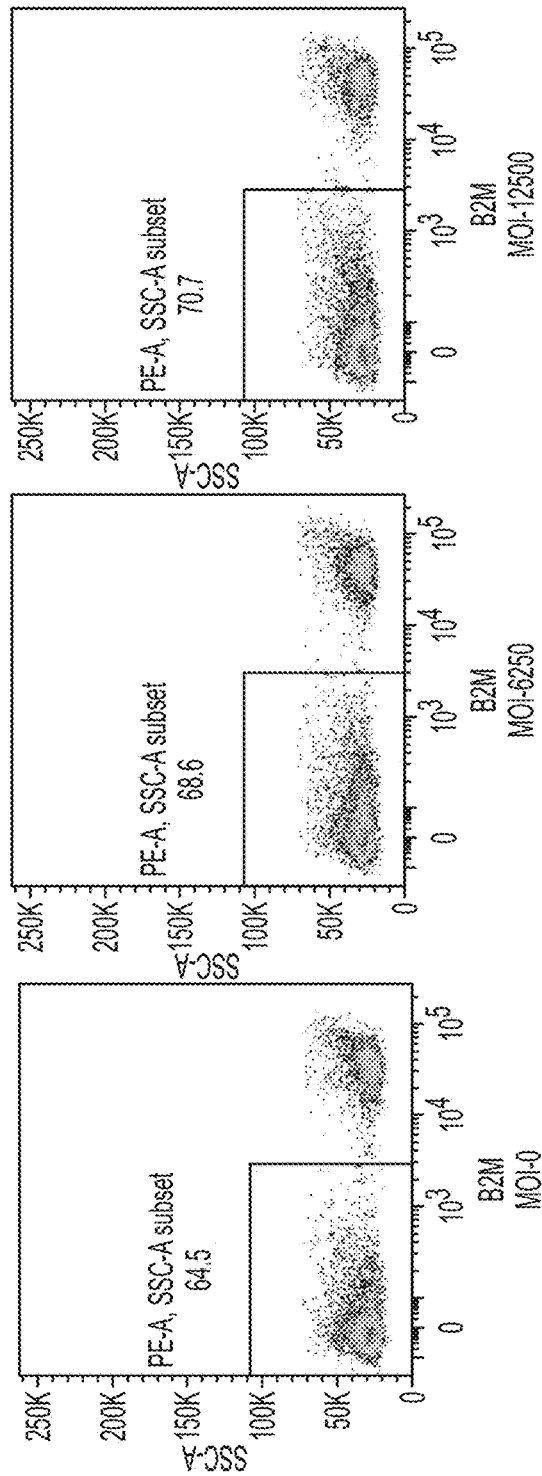
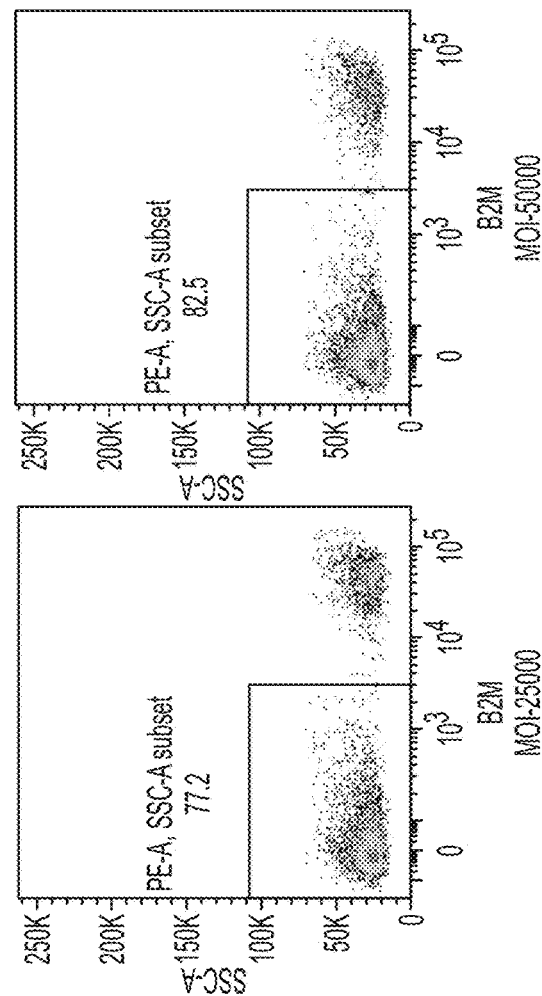
FIGURE 37
CONTINUED

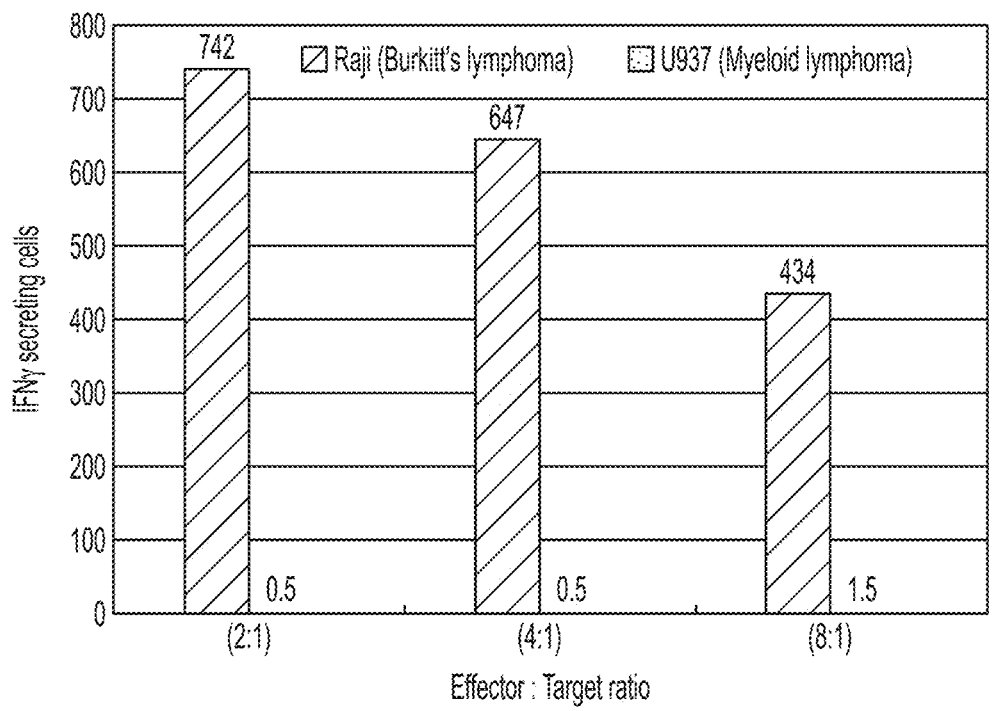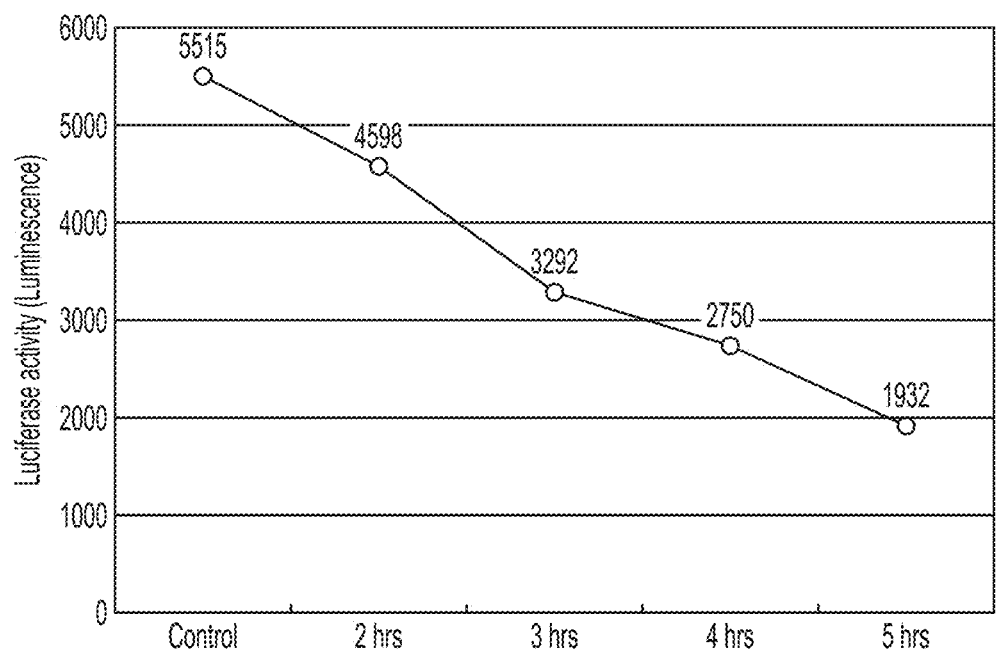
FIGURE 38

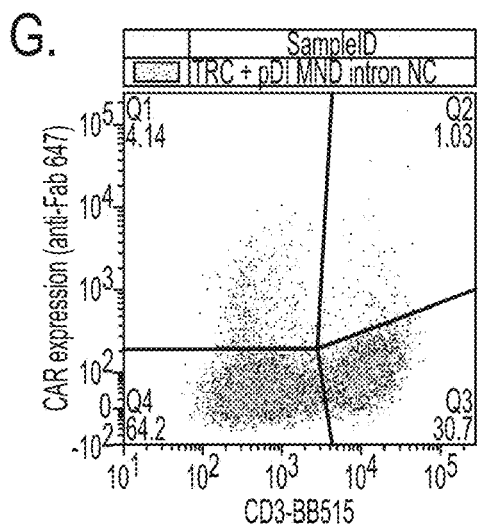
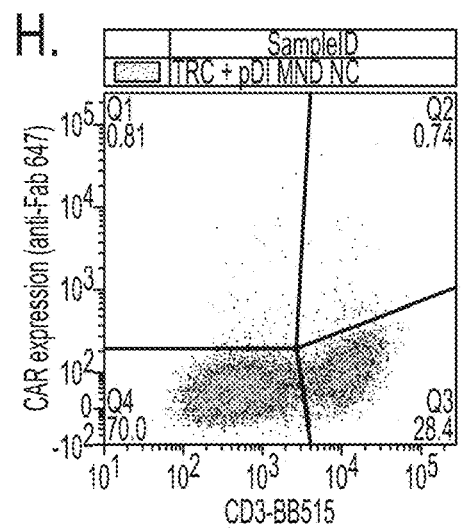
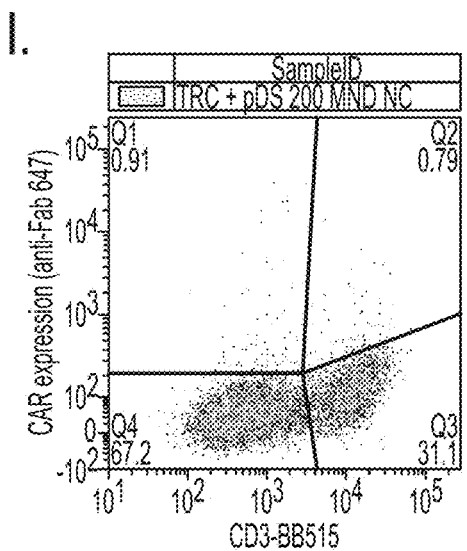
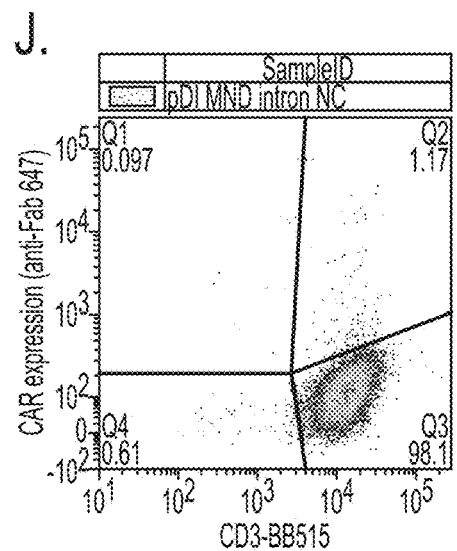
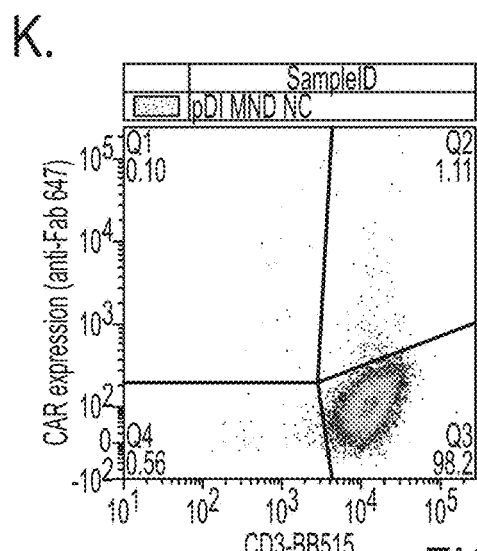
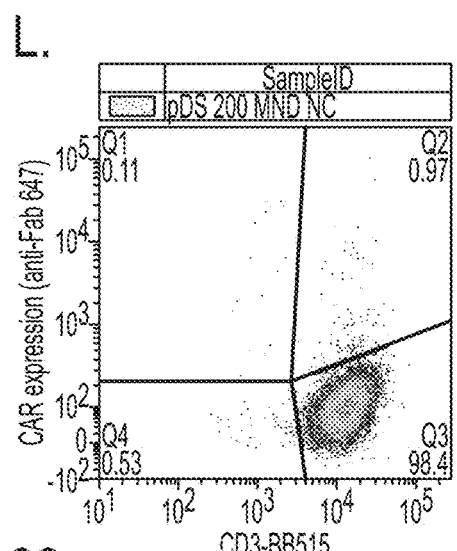
FIGURE 39
CONTINUED

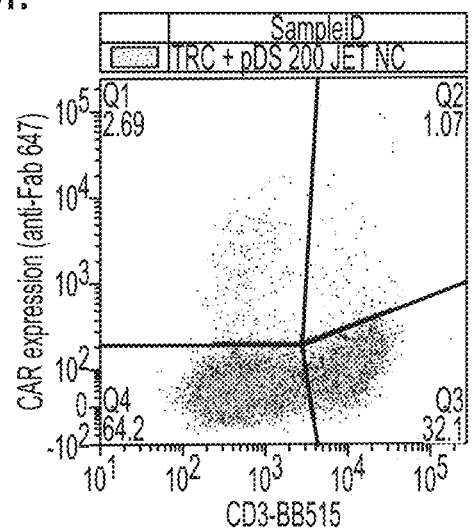
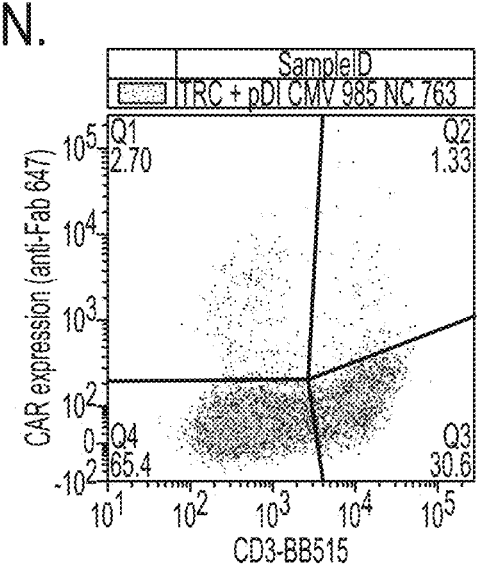
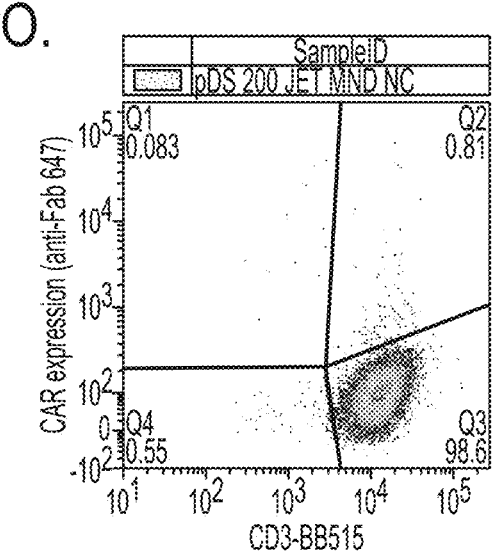
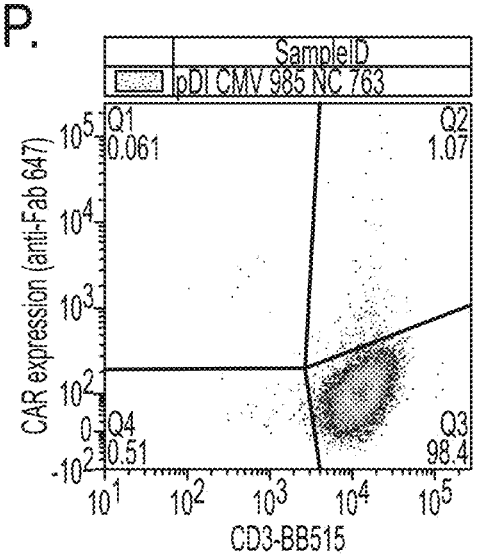
FIGURE 39
CONTINUED

SEQUENCE LISTING

```
<160> NUMBER OF SEQ ID NOS: 125

<210> SEQ ID NO 1
<211> LENGTH: 4627
<212> TYPE: DNA
<213> ORGANISM: Homo sapiens

<400> SEQUENCE: 1
atatccagaa ccctgaccct gccgtgtacc agctgagaga ctctaaatcc agtgacaagt      60
ctgtctgcct attcaccgat tttgattctc aaacaaatgt gtcacaaagt aaggattctg     120
atgtgtatat cacagacaaa actgtgctag acatgaggtc tatggacttc aagagcaaca     180
gtgctgtggc ctggagcaac aaatctgact ttgcatgtgc aaacgccttc aacaacagca     240
ttattccaga agacaccttc ttccccagcc caggtaaggg cagctttggt gccttcgcag     300
gctgtttcct tgcttcagga atggccaggt tctgcccaga gctctggtca atgatgtcta     360
aaactcctct gattggtggt ctcggcctta tccattgcca ccaaaaccct cttttttacta    420 agaaacagtg agccttgttc tggcagtcca gagaatgaca cgggaaaaaa gcagatgaag     480
agaaggtggc aggagagggc acgtggccca gcctcagtct ctccaactga gttcctgcct     540
gcctgccttt gctcagactg tttgccctt actgctcttc taggcctcat tctaagcccc     600
ttctccaagt tgcctctcct tatttctccc tgtctgccaa aaaatctttc ccagctcact     660
aagtcagtct cacgcagtca ctcattaacc caccaatcac tgattgtgcc ggcacatgaa     720
tgcaccaggt gttgaagtgg aggaattaaa aagtcagatg aggggtgtgc ccagaggaag     780
caccattcta gttgggggag cccatctgtc agctgggaaa agtccaaata acttcagatt     840
ggaatgtgtt ttaactcagg gttgagaaaa cagctacctt caggacaaaa gtcagggaag     900
ggctctctga agaaatgcta cttgaagata ccagccctac caagggcagg gagaggaccc     960
tatagaggcc tgggacagga gctcaatgag aaaggagaag agcagcaggc atgagttgaa    1020
tgaaggaggc agggccgggt cacagggcct tctaggccat gagagggtag acagtattct    1080
aaggacgcca gaaagctgtt gatcggcttc aagcagggga gggacaccta atttgctttt    1140
cttttttttt tttttttttt tttttttttt tgagatggag ttttgctctt gttgcccagg    1200
ctggagtgca atggtgcatc ttggctcact gcaacctccg cctcccaggt tcaagtgatt    1260
ctcctgcctc agcctcccga gtagctgaga ttacaggcac ccgccaccat gcctggctaa    1320 tttttttgtat tttagtaga cagggtttt cactatgttg gccaggctgg tctcgaactc    1380
ctgacctcag gtgatccacc cgcttcagcc tcccaaagtg ctgggattac aggcgtgagc    1440
caccacaccc ggcctgcttt tcttaaagat caatctgagt gctgtacgga gagtgggttg    1500
taagccaaga gtagaagcag aaagggagca gttgcagcag agagatgatg gaggcctggg    1560
cagggtggtg gcagggaggt aaccaacacc attcaggttt caaaggtaga accatgcagg    1620
gatgagaaag caaagagggg atcaaggaag gcagctggat tttggcctga gcagctgagt    1680
```

```
caatgatagt gccgtttact aagaagaaac caaggaaaaa atttggggtg cagggatcaa    1740 aacttttttgg aacatatgaa agtacgtgtt tatactcttt atggcccttg tcactatgta    1800
tgcctcgctg cctccattgg actctagaat gaagccaggc aagagcaggg tctatgtgtg    1860
atggcacatg tggccagggt catgcaacat gtactttgta caaacagtgt atattgagta    1920
aatagaaatg gtgtccagga gccgaggtat cggtcctgcc agggccaggg gctctcccta    1980
gcaggtgctc atatgctgta agttccctcc agatctctcc acaaggaggc atggaaaggc    2040
tgtagttgtt cacctgccca agaactagga ggtctggggt gggagagtca gcctgctctg    2100
gatgctgaaa gaatgtctgt ttttcctttt agaaagttcc tgtgatgtca gctggtcga    2160 gaaaagcttt gaaacaggta agacaggggt ctagcctggg tttgcacagg attgcggaag    2220
tgatgaaccc gcaataaccc tgcctggatg agggagtggg aagaaattag tagatgtggg    2280
aatgaatgat gaggaatgga aacagcggtt caagacctgc ccagagctgg gtggggtctc    2340
tcctgaatcc ctctcaccat ctctgacttt ccattctaag cactttgagg atgagtttct    2400
agcttcaata gaccaaggac tctctcctag gcctctgtat tcctttcaac agctccactg    2460
tcaagagagc cagagagagc ttctgggtgg cccagctgtg aaatttctga gtcccttagg    2520
gatagcccta aacgaaccag atcatcctga ggacagccaa gaggttttgc cttctttcaa    2580
gacaagcaac agtactcaca taggctgtgg gcaatggtcc tgtctctcaa gaatcccctg    2640
ccactcctca cacccaccct gggcccatat tcatttccat ttgagttgtt cttattgagt    2700
catccttcct gtggtagcgg aactcactaa ggggcccatc tggacccgag gtattgtgat    2760
gataaattct gagcacctac cccatcccca aagggctca gaaataaaat aagagccaag    2820
tctagtcggt gtttcctgtc ttgaaacaca atactgttgg ccctggaaga atgcacagaa    2880
tctgtttgta aggggatatg cacagaagct gcaaggaca ggaggtgcag gagctgcagg    2940
cctcccccac ccagcctgct ctgccttggg gaaaaccgtg ggtgtgtcct gcaggccatg    3000
caggcctggg acatgcaagc ccataaccgc tgtggcctct tggttttaca gatacgaacc    3060
taaactttca aaacctgtca gtgattgggt tccgaatcct cctcctgaaa gtggccgggt    3120
ttaatctgct catgacgctg cggctgtggt ccagctgagg tgaggggcct tgaagctggg    3180
agtgggggtt agggacgcgg gtctctgggt gcatcctaag ctctgagagc aaacctccct    3240
gcagggtctt gcttttaagt ccaaagcctg agcccaccaa actctcctac ttcttcctgt    3300
tacaaattcc tcttgtgcaa taataatggc ctgaaacgct gtaaaatatc ctcatttcag    3360
ccgcctcagt tgcacttctc ccctatgagg taggaagaac agttgtttag aaacgaagaa    3420
actgaggccc cacagctaat gagtggagga agagagacac ttgtgtacac cacatgcctt    3480
gtgttgtact tctctcaccg tgtaacctcc tcatgtcctc tctccccagt acggctctct    3540
tagctcagta gaaagaagac attacactca tattacaccc caatcctggc tagagtctcc    3600
gcaccctcct cccccagggt ccccagtcgt cttgctgaca actgcatcct gttccatcac    3660
catcaaaaaa aaactccagg ctgggtgcgg ggctcacac ctgtaatccc agcactttgg    3720
gaggcagagg caggaggagc acaggagctg gagaccagcc tgggcaacac agggagaccc    3780
cgcctctaca aaaagtgaaa aaattaacca ggtgtggtgc tgcacacctg tagtcccagc    3840
tacttaagag gctgagatgg gaggatcgct tgagccctgg aatgttgagg ctacaatgag    3900
ctgtgattgc gtcactgcac tccagcctgg aagacaaagc aagatcctgt ctcaaataat    3960
aaaaaaaata gaactccag ggtacatttg ctcctgaaac tctaccacat agccccaaac    4020
agagccatca ccatcacatc cctaacagtc ctgggtcttc ctcagtgtcc agcctgactt    4080
```

-continued

```
ctgttcttcc tcattccaga tctgcaagat tgtaagacag cctgtgctcc ctcgctcctt    4140
cctctgcatt gccctcttc tccctctcca aacagaggga actctcctac ccccaaggag    4200
gtgaaagctg ctaccacctc tgtgcccccc cggcaatgcc accaactgga tcctacccga    4260
atttatgatt aagattgctg aagagctgcc aaacactgct gccacccct ctgttccctt    4320 attgctgctt gtcactgcct gacattcacg gcagaggcaa ggctgctgca gcctcccctg    4380
gctgtgcaca ttcctcctg ctccccagag actgcctccg ccatcccaca gatgatggat    4440
cttcagtggg ttctcttggg ctctaggtcc tgcagaatgt tgtgagggg ttattttttt    4500 ttaatagtgt tcataaagaa atacatagta ttcttcttct caagacgtgg ggggaaatta    4560
tctcattatc gaggccctgc tatgctgtgt atctgggcgt gttgtatgtc ctgctgccga    4620
tgccttc                                                              4627
```

<210> SEQ ID NO 2
<211> LENGTH: 142
<212> TYPE: PRT
<213> ORGANISM: Homo sapiens

<400> SEQUENCE: 2

```
Pro Asn Ile Gln Asn Pro Asp Pro Ala Val Tyr Gln Leu Arg Asp Ser
1               5                  10                  15

Lys Ser Ser Asp Lys Ser Val Cys Leu Phe Thr Asp Phe Asp Ser Gln
            20                  25                  30

Thr Asn Val Ser Gln Ser Lys Asp Ser Asp Val Tyr Ile Thr Asp Lys
        35                  40                  45

Thr Val Leu Asp Met Arg Ser Met Asp Phe Lys Ser Asn Ser Ala Val
    50                  55                  60

Ala Trp Ser Asn Lys Ser Asp Phe Ala Cys Ala Asn Ala Phe Asn Asn
65                  70                  75                  80

Ser Ile Ile Pro Glu Asp Thr Phe Phe Pro Ser Pro Glu Ser Ser Cys
                85                  90                  95

Asp Val Lys Leu Val Glu Lys Ser Phe Glu Thr Asp Thr Asn Leu Asn
            100                 105                 110

Phe Gln Asn Leu Ser Val Ile Gly Phe Arg Ile Leu Leu Leu Lys Val
        115                 120                 125

Ala Gly Phe Asn Leu Leu Met Thr Leu Arg Leu Trp Ser Ser
    130                 135                 140
```

<210> SEQ ID NO 3
<211> LENGTH: 22
<212> TYPE: DNA
<213> ORGANISM: Homo sapiens

<400> SEQUENCE: 3
tggcctggag caacaaatct ga                                             22

<210> SEQ ID NO 4
<211> LENGTH: 22
<212> TYPE: DNA
<213> ORGANISM: Homo sapiens

<400> SEQUENCE: 4
acaaatgtgt cacaaagtaa gg                                             22

<210> SEQ ID NO 5
<211> LENGTH: 22

<212> TYPE: DNA
<213> ORGANISM: Homo sapiens

<400> SEQUENCE: 5
ctgatgtgta tatcacagac aa                                                22

<210> SEQ ID NO 6
<211> LENGTH: 163
<212> TYPE: PRT
<213> ORGANISM: Chlamydomonas reinhardtii

<400> SEQUENCE: 6

Met Asn Thr Lys Tyr Asn Lys Glu Phe Leu Leu Tyr Leu Ala Gly Phe
1               5                   10                  15

Val Asp Gly Asp Gly Ser Ile Ile Ala Gln Ile Lys Pro Asn Gln Ser
            20                  25                  30

Tyr Lys Phe Lys His Gln Leu Ser Leu Ala Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Arg Gly Ser Val Ser Asp Tyr Ile Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Trp Arg Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Ser Glu Lys Lys Lys
145                 150                 155                 160

Ser Ser Pro

<210> SEQ ID NO 7
<211> LENGTH: 9
<212> TYPE: PRT
<213> ORGANISM: Chlamydomonas reinhardtii

<400> SEQUENCE: 7

Leu Ala Gly Leu Ile Asp Ala Asp Gly
1               5

<210> SEQ ID NO 8
<211> LENGTH: 354
<212> TYPE: PRT
<213> ORGANISM: Artificial Sequence
<220> FEATURE:
<223> OTHER INFORMATION: Synthesized

<400> SEQUENCE: 8

Met Asn Thr Lys Tyr Asn Lys Glu Phe Leu Leu Tyr Leu Ala Gly Phe
1               5                   10                  15

Val Asp Gly Asp Gly Ser Ile Phe Ala Ser Ile Tyr Pro His Gln Arg
            20                  25                  30

Ala Lys Phe Lys His Phe Leu Lys Leu Thr Phe Ala Val Tyr Gln Lys
        35                  40                  45

Thr Gln Arg Arg Trp Phe Leu Asp Lys Leu Val Asp Glu Ile Gly Val
    50                  55                  60

```
Gly Tyr Val Tyr Asp Ser Gly Ser Val Ser Glu Tyr Arg Leu Ser Glu
 65                  70                  75                  80

Ile Lys Pro Leu His Asn Phe Leu Thr Gln Leu Gln Pro Phe Leu Lys
                 85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Arg Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
            195                 200                 205

Asp Gly Asp Gly Ser Ile Tyr Ala Cys Ile Ala Pro Arg Gln Gly Ser
210                 215                 220

Lys Phe Lys His Arg Leu Lys Leu Gly Phe Ala Val Gly Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Arg Gly Ser Val Ser Glu Tyr Val Leu Ser Glu Ile
                260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 9
<211> LENGTH: 354
<212> TYPE: PRT
<213> ORGANISM: Artificial Sequence
<220> FEATURE:
<223> OTHER INFORMATION: Synthesized

<400> SEQUENCE: 9

Met Asn Thr Lys Tyr Asn Lys Glu Phe Leu Leu Tyr Leu Ala Gly Phe
 1               5                  10                  15

Val Asp Gly Asp Gly Ser Ile Phe Ala Ser Ile Tyr Pro His Gln Arg
                20                  25                  30

Ala Lys Phe Lys His Phe Leu Lys Leu Thr Phe Ala Val Tyr Gln Lys
            35                  40                  45

Thr Gln Arg Arg Trp Phe Leu Asp Lys Leu Val Asp Glu Ile Gly Val
50                  55                  60
```

Gly Tyr Val Tyr Asp Ser Gly Ser Val Ser Glu Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
            115                 120                 125

Val Asp Gln Ile Ala Ala Leu Asn Asp Ser Arg Thr Arg Lys Thr Thr
            130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
            195                 200                 205

Asp Gly Asp Gly Ser Ile Tyr Ala Cys Ile Ala Pro Arg Gln Gly Ser
            210                 215                 220

Lys Phe Lys His Arg Leu Lys Leu Gly Phe Ala Val Gly Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Arg Gly Ser Val Ser Glu Tyr Val Leu Ser Glu Ile
                260                 265                 270

Lys Pro Leu His Asn Phe Leu Thr Gln Leu Gln Pro Phe Leu Lys Leu
                275                 280                 285

Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 10
<211> LENGTH: 354
<212> TYPE: PRT
<213> ORGANISM: Artificial Sequence
<220> FEATURE:
<223> OTHER INFORMATION: Synthesized

<400> SEQUENCE: 10

Met Asn Thr Lys Tyr Asn Lys Glu Phe Leu Leu Tyr Leu Ala Gly Phe
1               5                   10                  15

Val Asp Gly Asp Gly Ser Ile Phe Ala Ser Ile Tyr Pro His Gln Arg
            20                  25                  30

Ala Lys Phe Lys His Phe Leu Lys Leu Thr Phe Ala Val Tyr Gln Lys
            35                  40                  45

Thr Gln Arg Arg Trp Phe Leu Asp Lys Leu Val Asp Glu Ile Gly Val
        50                  55                  60

Gly Tyr Val Tyr Asp Ser Gly Ser Val Ser Glu Tyr Arg Leu Ser Glu

```
                65                  70                  75                  80
Ile Lys Pro Leu His Asn Phe Leu Thr Gln Leu Gln Pro Phe Leu Lys
                85                  90                  95
Leu Lys Gln Lys Gln Ala Asn Leu Val Leu Lys Ile Ile Glu Gln Leu
            100                 105                 110
Pro Ser Ala Lys Glu Ser Pro Asp Lys Phe Leu Glu Val Cys Thr Trp
        115                 120                 125
Val Asp Gln Ile Ala Ala Leu Asn Asp Ser Arg Thr Arg Lys Thr Thr
    130                 135                 140
Ser Glu Thr Val Arg Ala Val Leu Asp Ser Leu Pro Gly Ser Val Gly
145                 150                 155                 160
Gly Leu Ser Pro Ser Gln Ala Ser Ser Ala Ala Ser Ser Ala Ser Ser
                165                 170                 175
Ser Pro Gly Ser Gly Ile Ser Glu Ala Leu Arg Ala Gly Ala Gly Ser
            180                 185                 190
Gly Thr Gly Tyr Asn Lys Glu Phe Leu Leu Tyr Leu Ala Gly Phe Val
        195                 200                 205
Asp Gly Asp Gly Ser Ile Tyr Ala Cys Ile Ala Pro Arg Gln Gly Ser
    210                 215                 220
Lys Phe Lys His Arg Leu Lys Leu Gly Phe Ala Val Gly Gln Lys Thr
225                 230                 235                 240
Gln Arg Arg Trp Phe Leu Asp Lys Leu Val Asp Glu Ile Gly Val Gly
                245                 250                 255
Tyr Val Tyr Asp Arg Gly Ser Val Ser Glu Tyr Val Leu Ser Gln Ile
            260                 265                 270
Lys Pro Leu His Asn Phe Leu Thr Gln Leu Gln Pro Phe Leu Lys Leu
        275                 280                 285
Lys Gln Lys Gln Ala Asn Leu Val Leu Lys Ile Ile Glu Gln Leu Pro
    290                 295                 300
Ser Ala Lys Glu Ser Pro Asp Lys Phe Leu Glu Val Cys Thr Trp Val
305                 310                 315                 320
Asp Gln Ile Ala Ala Leu Asn Asp Ser Lys Thr Arg Lys Thr Thr Ser
                325                 330                 335
Glu Thr Val Arg Ala Val Leu Asp Ser Leu Ser Glu Lys Lys Lys Ser
            340                 345                 350
Ser Pro

<210> SEQ ID NO 11
<211> LENGTH: 354
<212> TYPE: PRT
<213> ORGANISM: Artificial Sequence
<220> FEATURE:
<223> OTHER INFORMATION: Synthesized

<400> SEQUENCE: 11

Met Asn Thr Lys Tyr Asn Lys Glu Phe Leu Leu Tyr Leu Ala Gly Phe
1               5                   10                  15
Val Asp Gly Asp Gly Ser Ile Phe Ala Ser Ile Tyr Pro His Gln Arg
            20                  25                  30
Ala Lys Phe Lys His Phe Leu Lys Leu Thr Phe Ala Val Tyr Gln Lys
        35                  40                  45
Thr Gln Arg Arg Trp Phe Leu Asp Lys Leu Val Asp Glu Ile Gly Val
    50                  55                  60
Gly Tyr Val Tyr Asp Ser Gly Ser Val Ser Glu Tyr Arg Leu Ser Gln
65                  70                  75                  80
```

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Arg Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
        180                 185                 190

Gly Thr Gly Tyr Asn Lys Glu Phe Leu Leu Tyr Leu Ala Gly Phe Val
            195                 200                 205

Asp Gly Asp Gly Ser Ile Tyr Ala Cys Ile Ala Pro Arg Gln Gly Ser
        210                 215                 220

Lys Phe Lys His Arg Leu Lys Leu Gly Phe Ala Val Gly Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Arg Gly Ser Val Ser Glu Tyr Val Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 12
<211> LENGTH: 354
<212> TYPE: PRT
<213> ORGANISM: Artificial Sequence
<220> FEATURE:
<223> OTHER INFORMATION: Synthesized

<400> SEQUENCE: 12

Met Asn Thr Lys Tyr Asn Lys Glu Phe Leu Leu Tyr Leu Ala Gly Phe
1               5                   10                  15

Val Asp Gly Asp Gly Ser Ile Tyr Ala Cys Ile Tyr Pro His Gln Arg
            20                  25                  30

Ala Lys Phe Lys His Leu Leu Lys Leu Val Phe Ala Val His Gln Lys
        35                  40                  45

Thr Gln Arg Arg Trp Phe Leu Asp Lys Leu Val Asp Glu Ile Gly Val
    50                  55                  60

Gly Tyr Val Tyr Asp Ala Gly Ser Val Ser Glu Tyr Arg Leu Ser Gln
65                  70                  75                  80

-continued

```
Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Cys Ile Ala Pro Arg Gln Gly Ser
    210                 215                 220

Lys Phe Lys His Arg Leu Lys Leu Gly Phe Ala Val Gly Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Arg Gly Ser Val Ser Glu Tyr Val Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro
```

<210> SEQ ID NO 13
<211> LENGTH: 354
<212> TYPE: PRT
<213> ORGANISM: Artificial Sequence
<220> FEATURE:
<223> OTHER INFORMATION: Synthesized

<400> SEQUENCE: 13

```
Met Asn Thr Lys Tyr Asn Lys Glu Phe Leu Leu Tyr Leu Ala Gly Phe
1               5                   10                  15

Val Asp Gly Asp Gly Ser Ile Tyr Ala Cys Ile Tyr Pro Asp Gln Arg
            20                  25                  30

Thr Lys Phe Lys His Gly Leu Arg Leu Asn Phe Ser Val Phe Gln Lys
        35                  40                  45

Thr Gln Arg Arg Trp Phe Leu Asp Lys Leu Val Asp Glu Ile Gly Val
    50                  55                  60

Gly Tyr Val Phe Asp Ala Gly Ser Val Ser Glu Tyr Arg Leu Ser Gln
65                  70                  75                  80

Ile Lys Pro Leu His Asn Phe Leu Thr Gln Leu Gln Pro Phe Leu Lys
```

```
                         85                  90                  95
Leu Lys Gln Lys Gln Ala Asn Leu Val Leu Lys Ile Ile Glu Gln Leu
                100                 105                 110

Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
                195                 200                 205

Asp Gly Asp Gly Ser Ile Tyr Ala Cys Ile Ala Pro Arg Gln Gly Ser
    210                 215                 220

Lys Phe Lys His Arg Leu Lys Leu Gly Phe Ala Val Gly Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Arg Gly Ser Val Ser Glu Tyr Val Leu Ser Gln Ile
            260                 265                 270

Lys Pro Leu His Asn Phe Leu Thr Gln Leu Gln Pro Phe Leu Lys Leu
                275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 14
<211> LENGTH: 354
<212> TYPE: PRT
<213> ORGANISM: Artificial Sequence
<220> FEATURE:
<223> OTHER INFORMATION: Synthesized

<400> SEQUENCE: 14

Met Asn Thr Lys Tyr Asn Lys Glu Phe Leu Leu Tyr Leu Ala Gly Phe
1               5                   10                  15

Val Asp Gly Asp Gly Ser Ile Phe Ala Thr Ile His Pro Asp Gln Arg
            20                  25                  30

Ser Lys Phe Lys His Tyr Leu Arg Leu Phe Ser Val Phe Gln Lys
        35                  40                  45

Thr Gln Arg Arg Trp Phe Leu Asp Lys Leu Val Asp Glu Ile Gly Val
    50                  55                  60

Gly Tyr Val Tyr Asp Ala Gly Ser Val Ser Glu Tyr Arg Leu Ser Gln
65                  70                  75                  80

Ile Lys Pro Leu His Asn Phe Leu Thr Gln Leu Gln Pro Phe Leu Lys
                85                  90                  95
```

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
            195                 200                 205

Asp Gly Asp Gly Ser Ile Tyr Ala Thr Ile Ala Pro Cys Gln Arg Ala
            210                 215                 220

Lys Phe Lys His Arg Leu Lys Leu Gly Phe Thr Val Gly Gln Lys Thr
225                 230                 235                 240

Gln Arg Arg Trp Phe Leu Asp Lys Leu Val Asp Glu Ile Gly Val Gly
                245                 250                 255

His Val Tyr Asp Arg Gly Ser Val Ser Glu Tyr Val Leu Ser Glu Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 15
<211> LENGTH: 354
<212> TYPE: PRT
<213> ORGANISM: Artificial Sequence
<220> FEATURE:
<223> OTHER INFORMATION: Synthesized

<400> SEQUENCE: 15

Met Asn Thr Lys Tyr Asn Lys Glu Phe Leu Leu Tyr Leu Ala Gly Phe
1               5                   10                  15

Val Asp Gly Asp Gly Ser Ile Phe Ala Gln Ile Lys Pro Asp Gln Lys
            20                  25                  30

Met Lys Phe Lys His Tyr Leu Ser Leu His Phe Ser Val Phe Gln Lys
        35                  40                  45

Thr Gln Arg Arg Trp Phe Leu Asp Lys Leu Val Asp Glu Ile Gly Val
    50                  55                  60

Gly Tyr Val Tyr Asp Gly Gly Ser Val Ser Glu Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
            165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
            195                 200                 205

Asp Gly Asp Gly Ser Ile Tyr Ala Gln Ile Lys Pro Gln Gln Arg Ala
            210                 215                 220

Lys Phe Lys His Arg Leu Leu Leu Ala Phe Thr Val Ser Gln Lys Thr
225                 230                 235                 240

Gln Arg Arg Trp Phe Leu Asp Lys Leu Val Asp Glu Ile Gly Val Gly
            245                 250                 255

Tyr Val Ile Asp Arg Gly Gly Val Ser Glu Tyr Ile Leu Ser Glu Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
            325                 330                 335

Glu Thr Val Arg Ala Val Leu Asp Ser Leu Ser Glu Lys Lys Lys Ser
            340                 345                 350

Ser Pro

<210> SEQ ID NO 16
<211> LENGTH: 354
<212> TYPE: PRT
<213> ORGANISM: Artificial Sequence
<220> FEATURE:
<223> OTHER INFORMATION: Synthesized

<400> SEQUENCE: 16

Met Asn Thr Lys Tyr Asn Lys Glu Phe Leu Leu Tyr Leu Ala Gly Phe
1               5                   10                  15

Val Asp Gly Asp Gly Ser Ile Phe Ala Ser Ile Asn Pro Asp Gln Arg
            20                  25                  30

Ala Lys Phe Lys His Ser Leu Lys Leu Thr Phe Ser Val Tyr Gln Lys
            35                  40                  45

Thr Gln Arg Arg Trp Phe Leu Asp Lys Leu Val Asp Glu Ile Gly Val
        50                  55                  60

Gly Tyr Val Tyr Asp Thr Gly Ser Val Ser Glu Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu

```
            100                 105                 110
Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
                180                 185                 190

Gly Thr Gly Tyr Asn Lys Glu Phe Leu Leu Tyr Leu Ala Gly Phe Val
            195                 200                 205

Asp Gly Asp Gly Ser Ile Tyr Ala Ser Ile Arg Pro Ser Gln Arg Ser
    210                 215                 220

Lys Phe Lys His Lys Leu Gly Leu Gly Phe Ala Val Gly Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Arg Gly Ser Val Ser Glu Tyr Val Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 17
<211> LENGTH: 354
<212> TYPE: PRT
<213> ORGANISM: Artificial Sequence
<220> FEATURE:
<223> OTHER INFORMATION: Synthesized

<400> SEQUENCE: 17

Met Asn Thr Lys Tyr Asn Lys Glu Phe Leu Leu Tyr Leu Ala Gly Phe
1               5                   10                  15

Val Asp Gly Asp Gly Ser Ile Phe Ala Ser Ile Tyr Pro His Gln Arg
            20                  25                  30

Ala Lys Phe Lys His Phe Leu Lys Leu Thr Phe Ala Val Tyr Gln Lys
        35                  40                  45

Thr Gln Arg Arg Trp Phe Leu Asp Lys Leu Val Asp Glu Ile Gly Val
    50                  55                  60

Gly Tyr Val Tyr Asp Ser Gly Ser Val Ser Glu Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110
```

Pro Ser Ala Lys Glu Ser Pro Asp Lys Phe Leu Glu Val Cys Thr Trp
            115                 120                 125

Val Asp Gln Ile Ala Ala Leu Asn Asp Ser Arg Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
            195                 200                 205

Asp Gly Asp Gly Ser Ile Tyr Ala Cys Ile Ala Pro Arg Gln Gly Ser
            210                 215                 220

Lys Phe Lys His Arg Leu Lys Leu Gly Phe Ala Val Gly Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Arg Gly Ser Val Ser Glu Tyr Val Leu Ser Gln Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 18
<211> LENGTH: 354
<212> TYPE: PRT
<213> ORGANISM: Artificial Sequence
<220> FEATURE:
<223> OTHER INFORMATION: Synthesized

<400> SEQUENCE: 18

Met Asn Thr Lys Tyr Asn Lys Glu Phe Leu Leu Tyr Leu Ala Gly Phe
1               5                   10                  15

Val Asp Gly Asp Gly Ser Ile Tyr Ala Cys Ile Ala Pro Asp Gln Arg
            20                  25                  30

Ala Lys Phe Lys His Tyr Leu Arg Leu Gln Phe Ser Val Phe Gln Lys
            35                  40                  45

Thr Gln Arg Arg Trp Phe Leu Asp Lys Leu Val Asp Glu Ile Gly Val
        50                  55                  60

Gly Tyr Val Phe Asp Ala Gly Ser Val Ser Glu Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
            165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
            195                 200                 205

Asp Gly Asp Gly Ser Ile Tyr Ala Cys Ile Ala Pro Arg Gln Gly Ser
210                 215                 220

Lys Phe Lys His Arg Leu Lys Leu Gly Phe Ala Val Gly Gln Lys Thr
225                 230                 235                 240

Gln Arg Arg Trp Phe Leu Asp Lys Leu Val Asp Glu Ile Gly Val Gly
            245                 250                 255

Tyr Val Tyr Asp Arg Gly Ser Val Ser Glu Tyr Val Leu Ser Gln Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
            325                 330                 335

Glu Thr Val Arg Ala Val Leu Asp Ser Leu Ser Glu Lys Lys Lys Ser
            340                 345                 350

Ser Pro

<210> SEQ ID NO 19
<211> LENGTH: 354
<212> TYPE: PRT
<213> ORGANISM: Artificial Sequence
<220> FEATURE:
<223> OTHER INFORMATION: Synthesized

<400> SEQUENCE: 19

Met Asn Thr Lys Tyr Asn Lys Glu Phe Leu Leu Tyr Leu Ala Gly Phe
1               5                   10                  15

Val Asp Gly Asp Gly Ser Ile Tyr Ala Cys Ile Ala Pro Arg Gln Gly
            20                  25                  30

Ser Lys Phe Lys His Arg Leu Lys Leu Gly Phe Ala Val Gly Gln Lys
        35                  40                  45

Thr Gln Arg Arg Trp Phe Leu Asp Lys Leu Val Asp Glu Ile Gly Val
    50                  55                  60

Gly Tyr Val Tyr Asp Arg Gly Ser Val Ser Glu Tyr Val Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp

```
                115                 120                 125
Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Thr Ile Tyr Pro Asp Gln Arg Ala
    210                 215                 220

Lys Phe Lys His Ala Leu Lys Leu Ile Phe Ser Val Phe Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Gly Gly Ser Val Ser Glu Tyr Arg Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Ser
            340                 345                 350

Ser Pro

<210> SEQ ID NO 20
<211> LENGTH: 354
<212> TYPE: PRT
<213> ORGANISM: Artificial Sequence
<220> FEATURE:
<223> OTHER INFORMATION: Synthesized

<400> SEQUENCE: 20

Met Asn Thr Lys Tyr Asn Lys Glu Phe Leu Leu Tyr Leu Ala Gly Phe
1               5                   10                  15

Val Asp Gly Asp Gly Ser Ile Tyr Ala Thr Ile Arg Pro Ala Gln Arg
            20                  25                  30

Ala Lys Phe Lys His Arg Leu Val Leu Gly Phe Glu Val Gly Gln Lys
        35                  40                  45

Thr Gln Arg Arg Trp Phe Leu Asp Lys Leu Val Asp Glu Ile Gly Val
    50                  55                  60

Gly Tyr Val Tyr Asp Gly Gly Ser Val Ser Lys Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125
```

```
Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
                195                 200                 205

Asp Gly Asp Gly Ser Ile Phe Ala Thr Ile Ala Pro Asp Gln Arg Pro
    210                 215                 220

Lys Phe Lys His Gln Leu Arg Leu Ile Phe Asn Val Cys Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Thr Gly Ser Val Ser Glu Tyr Arg Leu Ser Glu Ile
                260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 21
<211> LENGTH: 354
<212> TYPE: PRT
<213> ORGANISM: Artificial Sequence
<220> FEATURE:
<223> OTHER INFORMATION: Synthesized

<400> SEQUENCE: 21

Met Asn Thr Lys Tyr Asn Lys Glu Phe Leu Leu Tyr Leu Ala Gly Phe
1               5                   10                  15

Val Asp Gly Asp Gly Ser Ile Tyr Ala Cys Ile Ala Pro Arg Gln Gly
                20                  25                  30

Ser Lys Phe Lys His Arg Leu Lys Leu Gly Phe Ala Val Gly Gln Lys
            35                  40                  45

Thr Gln Arg Arg Trp Phe Leu Asp Lys Leu Val Asp Glu Ile Gly Val
    50                  55                  60

Gly Tyr Val Tyr Asp Arg Gly Ser Val Ser Glu Tyr Val Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125
```

```
Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
                180                 185                 190

Gly Thr Gly Tyr Asn Lys Glu Phe Leu Tyr Leu Ala Gly Phe Val
                195                 200                 205

Asp Gly Asp Gly Ser Ile Phe Ala Ser Ile Tyr Pro His Gln Arg Ala
    210                 215                 220

Lys Phe Lys His Phe Leu Lys Leu Thr Phe Ala Val Tyr Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Ser Gly Ser Val Ser Glu Tyr Arg Leu Ser Gln Ile
                260                 265                 270

Lys Pro Leu His Asn Phe Leu Thr Gln Leu Gln Pro Phe Leu Lys Leu
                275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
                340                 345                 350

Ser Pro

<210> SEQ ID NO 22
<211> LENGTH: 354
<212> TYPE: PRT
<213> ORGANISM: Artificial Sequence
<220> FEATURE:
<223> OTHER INFORMATION: Synthesized

<400> SEQUENCE: 22

Met Asn Thr Lys Tyr Asn Lys Glu Phe Leu Leu Tyr Leu Ala Gly Phe
1               5                   10                  15

Val Asp Gly Asp Gly Ser Ile Tyr Ala Cys Ile Ala Pro Arg Gln Gly
                20                  25                  30

Ser Lys Phe Lys His Arg Leu Lys Leu Gly Phe Ala Val Gly Gln Lys
                35                  40                  45

Thr Gln Arg Arg Trp Phe Leu Asp Lys Leu Val Asp Glu Ile Gly Val
    50                  55                  60

Gly Tyr Val Tyr Asp Arg Gly Ser Val Ser Glu Tyr Val Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
                100                 105                 110

Pro Ser Ala Lys Glu Ser Pro Asp Lys Phe Leu Glu Val Cys Thr Trp
                115                 120                 125

Val Asp Gln Ile Ala Ala Leu Asn Asp Ser Lys Thr Arg Lys Thr Thr
```

```
                130               135               140
Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
                180                 185                 190

Gly Thr Gly Tyr Asn Lys Glu Phe Leu Leu Tyr Leu Ala Gly Phe Val
                195                 200                 205

Asp Gly Asp Gly Ser Ile Phe Ala Thr Ile Val Pro Glu Gln Arg Ser
                210                 215                 220

Lys Phe Lys His Tyr Leu Lys Leu Thr Phe Ser Val Phe Gln Lys Thr
225                 230                 235                 240

Gln Arg Arg Trp Phe Leu Asp Arg Leu Val Asp Glu Ile Gly Val Gly
                245                 250                 255

Tyr Val Tyr Asp Ala Gly Ser Val Ser Glu Tyr Arg Leu Ser Gln Ile
                260                 265                 270

Lys Pro Leu His Asn Phe Leu Thr Gln Leu Gln Pro Phe Leu Lys Leu
                275                 280                 285

Lys Gln Lys Gln Ala Asn Leu Val Leu Lys Ile Ile Glu Gln Leu Pro
                290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
                340                 345                 350

Ser Pro

<210> SEQ ID NO 23
<211> LENGTH: 354
<212> TYPE: PRT
<213> ORGANISM: Artificial Sequence
<220> FEATURE:
<223> OTHER INFORMATION: Synthesized

<400> SEQUENCE: 23

Met Asn Thr Lys Tyr Asn Lys Glu Phe Leu Leu Tyr Leu Ala Gly Phe
1               5                   10                  15

Val Asp Gly Asp Gly Ser Ile Tyr Ala Cys Ile Ala Pro Arg Gln Gly
                20                  25                  30

Ser Lys Phe Lys His Arg Leu Lys Leu Gly Phe Ala Val Gly Gln Lys
                35                  40                  45

Thr Gln Arg Arg Trp Phe Leu Asp Lys Leu Val Asp Glu Ile Gly Val
50                  55                  60

Gly Tyr Val Tyr Asp Arg Gly Ser Val Ser Glu Tyr Val Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
                100                 105                 110

Pro Ser Ala Lys Glu Ser Pro Asp Lys Phe Leu Glu Val Cys Thr Trp
                115                 120                 125

Val Asp Gln Ile Ala Ala Leu Asn Asp Ser Lys Thr Arg Lys Thr Thr
                130                 135                 140
```

```
Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
            165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
            195                 200                 205

Asp Gly Asp Gly Ser Ile Phe Ala Thr Ile Phe Pro Asp Gln Arg Met
            210                 215                 220

Lys Phe Lys His Gln Leu Arg Leu His Phe Cys Val His Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Ser Gly Ser Val Ser Glu Tyr Arg Leu Ser Gln Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 24
<211> LENGTH: 354
<212> TYPE: PRT
<213> ORGANISM: Artificial Sequence
<220> FEATURE:
<223> OTHER INFORMATION: Synthesized

<400> SEQUENCE: 24

Met Asn Thr Lys Tyr Asn Lys Glu Phe Leu Leu Tyr Leu Ala Gly Phe
1               5                   10                  15

Val Asp Gly Asp Gly Ser Ile Tyr Ala Thr Ile Ala Pro Cys Gln Arg
                20                  25                  30

Ala Lys Phe Lys His Arg Leu Lys Leu Gly Phe Thr Val Gly Gln Lys
            35                  40                  45

Thr Gln Arg Arg Trp Phe Leu Asp Lys Leu Val Asp Glu Ile Gly Val
    50                  55                  60

Gly His Val Tyr Asp Arg Gly Ser Val Ser Glu Tyr Val Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140
```

```
Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
            165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
            195                 200                 205

Asp Gly Asp Gly Ser Ile Phe Ala Ser Ile Tyr Pro His Gln Arg Ala
210                 215                 220

Lys Phe Lys His Phe Leu Lys Leu Thr Phe Ala Val Tyr Gln Lys Thr
225                 230                 235                 240

Gln Arg Arg Trp Phe Leu Asp Lys Leu Val Asp Glu Ile Gly Val Gly
            245                 250                 255

Tyr Val Tyr Asp Ser Gly Ser Val Ser Glu Tyr Arg Leu Ser Gln Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
            325                 330                 335

Glu Thr Val Arg Ala Val Leu Asp Ser Leu Ser Glu Lys Lys Lys Ser
            340                 345                 350

Ser Pro

<210> SEQ ID NO 25
<211> LENGTH: 354
<212> TYPE: PRT
<213> ORGANISM: Artificial Sequence
<220> FEATURE:
<223> OTHER INFORMATION: Synthesized

<400> SEQUENCE: 25

Met Asn Thr Lys Tyr Asn Lys Glu Phe Leu Leu Tyr Leu Ala Gly Phe
1               5                   10                  15

Val Asp Gly Asp Gly Ser Ile Tyr Ala Cys Ile Ala Pro Arg Gln Gly
            20                  25                  30

Ser Lys Phe Lys His Arg Leu Lys Leu Gly Phe Ala Val Gly Gln Lys
            35                  40                  45

Thr Gln Arg Arg Trp Phe Leu Asp Lys Leu Val Asp Glu Ile Gly Val
50                  55                  60

Gly Tyr Val Tyr Asp Arg Gly Ser Val Ser Glu Tyr Val Leu Ser Gln
65                  70                  75                  80

Ile Lys Pro Leu His Asn Phe Leu Thr Gln Leu Gln Pro Phe Leu Lys
            85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
```

```
                145                 150                 155                 160
Gly Leu Ser Pro Ser Gln Ala Ser Ser Ala Ser Ser Ala Ser Ser
                    165                 170                 175
Ser Pro Gly Ser Gly Ile Ser Glu Ala Leu Arg Ala Gly Ala Gly Ser
                180                 185                 190
Gly Thr Gly Tyr Asn Lys Glu Phe Leu Tyr Leu Ala Gly Phe Val
            195                 200                 205
Asp Gly Asp Gly Ser Ile Phe Ala Thr Ile Phe Pro Asp Gln Arg Met
        210                 215                 220
Lys Phe Lys His Gln Leu Arg Leu His Phe Cys Val His Gln Lys Thr
225                 230                 235                 240
Gln Arg Arg Trp Phe Leu Asp Lys Leu Val Asp Glu Ile Gly Val Gly
                245                 250                 255
Tyr Val Tyr Asp Ser Gly Ser Val Ser Glu Tyr Arg Leu Ser Gln Ile
            260                 265                 270
Lys Pro Leu His Asn Phe Leu Thr Gln Leu Gln Pro Phe Leu Lys Leu
        275                 280                 285
Lys Gln Lys Gln Ala Asn Leu Val Leu Lys Ile Ile Glu Gln Leu Pro
    290                 295                 300
Ser Ala Lys Glu Ser Pro Asp Lys Phe Leu Glu Val Cys Thr Trp Val
305                 310                 315                 320
Asp Gln Ile Ala Ala Leu Asn Asp Ser Lys Thr Arg Lys Thr Thr Ser
                325                 330                 335
Glu Thr Val Arg Ala Val Leu Asp Ser Leu Ser Glu Lys Lys Lys Ser
            340                 345                 350
Ser Pro

<210> SEQ ID NO 26
<211> LENGTH: 354
<212> TYPE: PRT
<213> ORGANISM: Artificial Sequence
<220> FEATURE:
<223> OTHER INFORMATION: Synthesized

<400> SEQUENCE: 26

Met Asn Thr Lys Tyr Asn Lys Glu Phe Leu Leu Tyr Leu Ala Gly Phe
1               5                   10                  15
Val Asp Gly Asp Gly Ser Ile Tyr Ala Cys Ile Ala Pro Arg Gln Gly
                20                  25                  30
Ser Lys Phe Lys His Arg Leu Lys Leu Gly Phe Ala Val Gly Gln Lys
            35                  40                  45
Thr Gln Arg Arg Trp Phe Leu Asp Lys Leu Val Asp Glu Ile Gly Val
        50                  55                  60
Gly Tyr Val Tyr Asp Arg Gly Ser Val Ser Glu Tyr Val Leu Ser Glu
65                  70                  75                  80
Ile Lys Pro Leu His Asn Phe Leu Thr Gln Leu Gln Pro Phe Leu Lys
                85                  90                  95
Leu Lys Gln Lys Gln Ala Asn Leu Val Leu Lys Ile Ile Glu Gln Leu
            100                 105                 110
Pro Ser Ala Lys Glu Ser Pro Asp Lys Phe Leu Glu Val Cys Thr Trp
        115                 120                 125
Val Asp Gln Ile Ala Ala Leu Asn Asp Ser Lys Thr Arg Lys Thr Thr
    130                 135                 140
Ser Glu Thr Val Arg Ala Val Leu Asp Ser Leu Pro Gly Ser Val Gly
145                 150                 155                 160
```

Gly Leu Ser Pro Ser Gln Ala Ser Ala Ala Ser Ser Ala Ser Ser
            165                 170                 175

Ser Pro Gly Ser Gly Ile Ser Glu Ala Leu Arg Ala Gly Ala Gly Ser
        180                 185                 190

Gly Thr Gly Tyr Asn Lys Glu Phe Leu Leu Tyr Leu Ala Gly Phe Val
            195                 200                 205

Asp Gly Asp Gly Ser Ile Phe Ala Thr Ile Phe Pro Asp Gln Arg Met
210                 215                 220

Lys Phe Lys His Gln Leu Arg Leu His Phe Cys Val His Gln Lys Thr
225                 230                 235                 240

Gln Arg Arg Trp Phe Leu Asp Lys Leu Val Asp Glu Ile Gly Val Gly
            245                 250                 255

Tyr Val Tyr Asp Ser Gly Ser Val Ser Glu Tyr Arg Leu Ser Gln Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 27
<211> LENGTH: 354
<212> TYPE: PRT
<213> ORGANISM: Artificial Sequence
<220> FEATURE:
<223> OTHER INFORMATION: Synthesized

<400> SEQUENCE: 27

Met Asn Thr Lys Tyr Asn Lys Glu Phe Leu Leu Tyr Leu Ala Gly Phe
1               5                   10                  15

Val Asp Gly Asp Gly Ser Ile Tyr Ala Cys Ile Ala Pro Gly Gln Gly
            20                  25                  30

Ser Lys Phe Lys His Arg Leu Lys Leu Gly Phe Ala Val Gly Gln Lys
        35                  40                  45

Thr Gln Arg Arg Trp Phe Leu Asp Lys Leu Val Asp Glu Ile Gly Val
50                  55                  60

Gly Tyr Val Tyr Asp Arg Gly Ser Val Ser Glu Tyr Val Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
            165                 170                 175

Ser Pro Gly Ser Gly Ile Ser Glu Ala Leu Arg Ala Gly Ala Gly Ser
        180                 185                 190

Gly Thr Gly Tyr Asn Lys Glu Phe Leu Leu Tyr Leu Ala Gly Phe Val
        195                 200                 205

Asp Gly Asp Gly Ser Ile Phe Ala Thr Ile Phe Pro Asp Gln Arg Met
        210                 215                 220

Lys Phe Lys His Gln Leu Arg Leu Gly Phe Ala Val His Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Arg Gly Ser Val Ser Glu Tyr Arg Leu Ser Gln Ile
                260                 265                 270

Lys Pro Leu His Asn Phe Leu Thr Gln Leu Gln Pro Phe Leu Lys Leu
                275                 280                 285

Lys Gln Lys Gln Ala Asn Leu Val Leu Lys Ile Ile Glu Gln Leu Pro
        290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
                340                 345                 350

Ser Pro

<210> SEQ ID NO 28
<211> LENGTH: 354
<212> TYPE: PRT
<213> ORGANISM: Artificial Sequence
<220> FEATURE:
<223> OTHER INFORMATION: Synthesized

<400> SEQUENCE: 28

Met Asn Thr Lys Tyr Asn Lys Glu Phe Leu Leu Tyr Leu Ala Gly Phe
1               5                   10                  15

Val Asp Gly Asp Gly Ser Ile Tyr Ala Thr Ile Cys Pro Cys Gln Thr
                20                  25                  30

Leu Lys Phe Lys His Tyr Leu Thr Leu Ser Phe Ser Val Tyr Gln Lys
            35                  40                  45

Thr Gln Arg Arg Trp Phe Leu Asp Lys Leu Val Asp Glu Ile Gly Val
    50                  55                  60

Gly Tyr Val Tyr Asp Gln Gly Ser Val Ser Cys Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser

```
                        165                 170                 175
Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile His Ala Cys Ile Gln Pro Gln Gln Asp Val
    210                 215                 220

Lys Phe Lys His Gln Leu His Leu Arg Phe Thr Val His Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Ala Gly Ser Val Ser Thr Tyr Cys Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 29
<211> LENGTH: 354
<212> TYPE: PRT
<213> ORGANISM: Artificial Sequence
<220> FEATURE:
<223> OTHER INFORMATION: Synthesized

<400> SEQUENCE: 29

Met Asn Thr Lys Tyr Asn Lys Glu Phe Leu Leu Tyr Leu Ala Gly Phe
1               5                   10                  15

Val Asp Gly Asp Gly Ser Ile Tyr Ala Thr Ile Cys Pro Asp Gln Ala
            20                  25                  30

Leu Lys Phe Lys His Tyr Leu Ser Leu Thr Phe Ala Val Tyr Gln Lys
        35                  40                  45

Thr Gln Arg Arg Trp Phe Leu Asp Lys Leu Val Asp Glu Ile Gly Val
    50                  55                  60

Gly Tyr Val Tyr Asp Gln Gly Ser Val Ser Cys Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175
```

```
Ser Pro Gly Ser Gly Ile Ser Glu Ala Leu Arg Ala Gly Ala Gly Ser
            180                 185                 190

Gly Thr Gly Tyr Asn Lys Glu Phe Leu Tyr Leu Ala Gly Phe Val
            195                 200                 205

Asp Gly Asp Gly Ser Ile His Ala Cys Ile Gln Pro Met Gln Ser Met
210                 215                 220

Lys Phe Lys His Tyr Leu His Leu Arg Phe Thr Val His Gln Lys Thr
225                 230                 235                 240

Gln Arg Arg Trp Phe Leu Asp Lys Leu Val Asp Glu Thr Gly Val Gly
            245                 250                 255

Tyr Val Tyr Asp Ala Gly Ser Val Ser Thr Tyr Cys Leu Ser Gln Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 30
<211> LENGTH: 354
<212> TYPE: PRT
<213> ORGANISM: Artificial Sequence
<220> FEATURE:
<223> OTHER INFORMATION: Synthesized

<400> SEQUENCE: 30

Met Asn Thr Lys Tyr Asn Lys Glu Phe Leu Leu Tyr Leu Ala Gly Phe
1               5                   10                  15

Val Asp Gly Asp Gly Ser Ile Tyr Ala Cys Ile Thr Pro Gln Gln Asp
            20                  25                  30

Met Lys Phe Lys His Arg Leu Gln Leu Arg Phe Cys Val Thr Gln Lys
        35                  40                  45

Thr Gln Arg Arg Trp Phe Leu Asp Lys Leu Val Asp Glu Ile Gly Val
    50                  55                  60

Gly Tyr Val Gln Asp Cys Gly Ser Val Ser Glu Tyr Arg Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175
```

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Val Ala Ser Ile Lys Pro Gln Gln Val Ala
    210                 215                 220

Lys Phe Lys His Arg Leu Met Leu Glu Phe Val Tyr Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Leu Gly Gly Ala Ser Arg Tyr Val Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 31
<211> LENGTH: 354
<212> TYPE: PRT
<213> ORGANISM: Artificial Sequence
<220> FEATURE:
<223> OTHER INFORMATION: Synthesized

<400> SEQUENCE: 31

Met Asn Thr Lys Tyr Asn Lys Glu Phe Leu Leu Tyr Leu Ala Gly Phe
1               5                   10                  15

Val Asp Gly Asp Gly Ser Ile Tyr Ala Cys Ile Lys Pro Asp Gln Ala
            20                  25                  30

Ala Lys Phe Lys His Arg Leu Leu Leu Glu Phe Thr Val Cys Gln Lys
        35                  40                  45

Thr Gln Arg Arg Trp Phe Leu Asp Lys Leu Val Asp Glu Ile Gly Val
    50                  55                  60

Gly Tyr Val Val Asp Gln Gly Ser Val Ser Glu Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser

```
                  180                 185                 190
Gly Thr Gly Tyr Asn Lys Glu Phe Leu Leu Tyr Leu Ala Gly Phe Val
            195                 200                 205

Asp Gly Asp Gly Ser Ile Tyr Ala Cys Ile Thr Pro Gln Gln Asp Met
            210                 215                 220

Lys Phe Lys His Arg Leu Gln Leu Arg Phe Cys Val Thr Gln Lys Thr
225                 230                 235                 240

Gln Arg Arg Trp Phe Leu Asp Lys Leu Val Asp Glu Ile Gly Val Gly
            245                 250                 255

Tyr Val Gln Asp His Gly Gly Ala Ser Glu Tyr Arg Leu Ser Glu Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
            325                 330                 335

Glu Thr Val Arg Ala Val Leu Asp Ser Leu Ser Glu Lys Lys Lys Ser
            340                 345                 350

Ser Pro

<210> SEQ ID NO 32
<211> LENGTH: 354
<212> TYPE: PRT
<213> ORGANISM: Artificial Sequence
<220> FEATURE:
<223> OTHER INFORMATION: Synthesized

<400> SEQUENCE: 32

Met Asn Thr Lys Tyr Asn Lys Glu Phe Leu Leu Tyr Leu Ala Gly Phe
1               5                   10                  15

Val Asp Gly Asp Gly Ser Ile Trp Ala Ser Ile Arg Pro Thr Gln Leu
            20                  25                  30

Ala Lys Phe Lys His Ala Leu Trp Leu Gly Phe Ala Val Tyr Gln Lys
            35                  40                  45

Thr Gln Arg Arg Trp Phe Leu Asp Lys Leu Val Asp Glu Ile Gly Val
            50                  55                  60

Gly Tyr Val Tyr Asp Ser Gly Ser Val Ser Lys Tyr Thr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
                100                 105                 110

Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190
```

Gly Thr Gly Tyr Asn Lys Glu Phe Leu Leu Tyr Leu Ala Gly Phe Val
            195                 200                 205

Asp Gly Asp Gly Ser Ile Tyr Ala Cys Ile Thr Pro Gln Gln Asp Met
210                 215                 220

Lys Phe Lys His Arg Leu Gln Leu Arg Phe Cys Val Thr Gln Lys Thr
225                 230                 235                 240

Gln Arg Arg Trp Phe Leu Asp Lys Leu Val Asp Glu Ile Gly Val Gly
            245                 250                 255

Tyr Val Gln Asp Lys Gly Ser Ala Ser Glu Tyr Arg Leu Ser Glu Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 33
<211> LENGTH: 147
<212> TYPE: PRT
<213> ORGANISM: Artificial Sequence
<220> FEATURE:
<223> OTHER INFORMATION: Synthesized

<400> SEQUENCE: 33

Lys Glu Phe Leu Leu Tyr Leu Ala Gly Phe Val Asp Gly Asp Gly Ser
1               5                   10                  15

Ile Tyr Ala Cys Ile Ala Pro Arg Gln Gly Ser Lys Phe Lys His Arg
            20                  25                  30

Leu Lys Leu Gly Phe Ala Val Gly Gln Lys Thr Gln Arg Arg Trp Phe
            35                  40                  45

Leu Asp Lys Leu Val Asp Glu Ile Gly Val Gly Tyr Val Tyr Asp Arg
        50                  55                  60

Gly Ser Val Ser Glu Tyr Val Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
        130                 135                 140

Val Leu Asp
145

<210> SEQ ID NO 34
<211> LENGTH: 147
<212> TYPE: PRT
<213> ORGANISM: Artificial Sequence
<220> FEATURE:

<223> OTHER INFORMATION: Synthesized

<400> SEQUENCE: 34

```
Lys Glu Phe Leu Leu Tyr Leu Ala Gly Phe Val Asp Gly Asp Gly Ser
1               5                   10                  15

Ile Tyr Ala Cys Ile Ala Pro Arg Gln Gly Ser Lys Phe Lys His Arg
            20                  25                  30

Leu Lys Leu Gly Phe Ala Val Gly Gln Lys Thr Gln Arg Arg Trp Phe
        35                  40                  45

Leu Asp Lys Leu Val Asp Glu Ile Gly Val Gly Tyr Val Tyr Asp Arg
    50                  55                  60

Gly Ser Val Ser Glu Tyr Val Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145
```

<210> SEQ ID NO 35
<211> LENGTH: 147
<212> TYPE: PRT
<213> ORGANISM: Artificial Sequence
<220> FEATURE:
<223> OTHER INFORMATION: Synthesized

<400> SEQUENCE: 35

```
Lys Glu Phe Leu Leu Tyr Leu Ala Gly Phe Val Asp Gly Asp Gly Ser
1               5                   10                  15

Ile Tyr Ala Cys Ile Ala Pro Arg Gln Gly Ser Lys Phe Lys His Arg
            20                  25                  30

Leu Lys Leu Gly Phe Ala Val Gly Gln Lys Thr Gln Arg Arg Trp Phe
        35                  40                  45

Leu Asp Lys Leu Val Asp Glu Ile Gly Val Gly Tyr Val Tyr Asp Arg
    50                  55                  60

Gly Ser Val Ser Glu Tyr Val Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145
```

<210> SEQ ID NO 36
<211> LENGTH: 147
<212> TYPE: PRT
<213> ORGANISM: Artificial Sequence
<220> FEATURE:
<223> OTHER INFORMATION: Synthesized

<400> SEQUENCE: 36

```
Lys Glu Phe Leu Leu Tyr Leu Ala Gly Phe Val Asp Gly Asp Gly Ser
1               5                   10                  15

Ile Tyr Ala Cys Ile Ala Pro Arg Gln Gly Ser Lys Phe Lys His Arg
            20                  25                  30

Leu Lys Leu Gly Phe Ala Val Gly Gln Lys Thr Gln Arg Arg Trp Phe
        35                  40                  45

Leu Asp Lys Leu Val Asp Glu Ile Gly Val Gly Tyr Val Tyr Asp Arg
    50                  55                  60

Gly Ser Val Ser Glu Tyr Val Leu Ser Gln Ile Lys Pro Leu His Asn
65              70                  75                  80

Phe Leu Thr Gln Leu Gln Pro Phe Leu Lys Leu Lys Gln Lys Gln Ala
            85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
    130                 135                 140

Val Leu Asp
145
```

<210> SEQ ID NO 37
<211> LENGTH: 147
<212> TYPE: PRT
<213> ORGANISM: Artificial Sequence
<220> FEATURE:
<223> OTHER INFORMATION: Synthesized

<400> SEQUENCE: 37

```
Lys Glu Phe Leu Leu Tyr Leu Ala Gly Phe Val Asp Gly Asp Gly Ser
1               5                   10                  15

Ile Tyr Ala Cys Ile Ala Pro Arg Gln Gly Ser Lys Phe Lys His Arg
            20                  25                  30

Leu Lys Leu Gly Phe Ala Val Gly Gln Lys Thr Gln Arg Arg Trp Phe
        35                  40                  45

Leu Asp Lys Leu Val Asp Glu Ile Gly Val Gly Tyr Val Tyr Asp Arg
    50                  55                  60

Gly Ser Val Ser Glu Tyr Val Leu Ser Gln Ile Lys Pro Leu His Asn
65              70                  75                  80

Phe Leu Thr Gln Leu Gln Pro Phe Leu Lys Leu Lys Gln Lys Gln Ala
            85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
    130                 135                 140

Val Leu Asp
145
```

<210> SEQ ID NO 38
<211> LENGTH: 147
<212> TYPE: PRT

<213> ORGANISM: Artificial Sequence
<220> FEATURE:
<223> OTHER INFORMATION: Synthesized

<400> SEQUENCE: 38

```
Lys Glu Phe Leu Leu Tyr Leu Ala Gly Phe Val Asp Gly Asp Gly Ser
1               5                   10                  15

Ile Tyr Ala Cys Ile Ala Pro Arg Gln Gly Ser Lys Phe Lys His Arg
            20                  25                  30

Leu Lys Leu Gly Phe Ala Val Gly Gln Lys Thr Gln Arg Arg Trp Phe
        35                  40                  45

Leu Asp Lys Leu Val Asp Glu Ile Gly Val Gly Tyr Val Tyr Asp Arg
    50                  55                  60

Gly Ser Val Ser Glu Tyr Val Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145
```

<210> SEQ ID NO 39
<211> LENGTH: 147
<212> TYPE: PRT
<213> ORGANISM: Artificial Sequence
<220> FEATURE:
<223> OTHER INFORMATION: Synthesized

<400> SEQUENCE: 39

```
Lys Glu Phe Leu Leu Tyr Leu Ala Gly Phe Val Asp Gly Asp Gly Ser
1               5                   10                  15

Ile Tyr Ala Thr Ile Ala Pro Cys Gln Arg Ala Lys Phe Lys His Arg
            20                  25                  30

Leu Lys Leu Gly Phe Thr Val Gly Gln Lys Thr Gln Arg Arg Trp Phe
        35                  40                  45

Leu Asp Lys Leu Val Asp Glu Ile Gly Val Gly His Val Tyr Asp Arg
    50                  55                  60

Gly Ser Val Ser Glu Tyr Val Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145
```

<210> SEQ ID NO 40
<211> LENGTH: 147

```
<212> TYPE: PRT
<213> ORGANISM: Artificial Sequence
<220> FEATURE:
<223> OTHER INFORMATION: Synthesized

<400> SEQUENCE: 40

Lys Glu Phe Leu Leu Tyr Leu Ala Gly Phe Val Asp Gly Asp Gly Ser
1               5                   10                  15

Ile Tyr Ala Gln Ile Lys Pro Gln Gln Arg Ala Lys Phe Lys His Arg
            20                  25                  30

Leu Leu Leu Ala Phe Thr Val Ser Gln Lys Thr Gln Arg Arg Trp Phe
        35                  40                  45

Leu Asp Lys Leu Val Asp Glu Ile Gly Val Gly Tyr Val Ile Asp Arg
    50                  55                  60

Gly Val Ser Glu Tyr Ile Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 41
<211> LENGTH: 147
<212> TYPE: PRT
<213> ORGANISM: Artificial Sequence
<220> FEATURE:
<223> OTHER INFORMATION: Synthesized

<400> SEQUENCE: 41

Lys Glu Phe Leu Leu Tyr Leu Ala Gly Phe Val Asp Gly Asp Gly Ser
1               5                   10                  15

Ile Tyr Ala Ser Ile Arg Pro Ser Gln Arg Ser Lys Phe Lys His Lys
            20                  25                  30

Leu Gly Leu Gly Phe Ala Val Gly Gln Lys Thr Gln Arg Arg Trp Phe
        35                  40                  45

Leu Asp Lys Leu Val Asp Glu Ile Gly Val Gly Tyr Val Tyr Asp Arg
    50                  55                  60

Gly Ser Val Ser Glu Tyr Val Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 42
```

```
<211> LENGTH: 147
<212> TYPE: PRT
<213> ORGANISM: Artificial Sequence
<220> FEATURE:
<223> OTHER INFORMATION: Synthesized

<400> SEQUENCE: 42

Lys Glu Phe Leu Leu Tyr Leu Ala Gly Phe Val Asp Gly Asp Gly Ser
1               5                   10                  15

Ile Tyr Ala Cys Ile Ala Pro Arg Gln Gly Ser Lys Phe Lys His Arg
            20                  25                  30

Leu Lys Leu Gly Phe Ala Val Gly Gln Lys Thr Gln Arg Arg Trp Phe
        35                  40                  45

Leu Asp Lys Leu Val Asp Glu Ile Gly Val Gly Tyr Val Tyr Asp Arg
    50                  55                  60

Gly Ser Val Ser Glu Tyr Val Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 43
<211> LENGTH: 147
<212> TYPE: PRT
<213> ORGANISM: Artificial Sequence
<220> FEATURE:
<223> OTHER INFORMATION: Synthesized

<400> SEQUENCE: 43

Lys Glu Phe Leu Leu Tyr Leu Ala Gly Phe Val Asp Gly Asp Gly Ser
1               5                   10                  15

Ile Tyr Ala Cys Ile Ala Pro Arg Gln Gly Ser Lys Phe Lys His Arg
            20                  25                  30

Leu Lys Leu Gly Phe Ala Val Gly Gln Lys Thr Gln Arg Arg Trp Phe
        35                  40                  45

Leu Asp Lys Leu Val Asp Glu Ile Gly Val Gly Tyr Val Tyr Asp Arg
    50                  55                  60

Gly Ser Val Ser Glu Tyr Val Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145
```

```
<210> SEQ ID NO 44
<211> LENGTH: 147
<212> TYPE: PRT
<213> ORGANISM: Artificial Sequence
<220> FEATURE:
<223> OTHER INFORMATION: Synthesized

<400> SEQUENCE: 44

Lys Glu Phe Leu Leu Tyr Leu Ala Gly Phe Val Asp Gly Asp Gly Ser
1               5                   10                  15

Ile Tyr Ala Cys Ile Ala Pro Arg Gln Gly Ser Lys Phe Lys His Arg
            20                  25                  30

Leu Lys Leu Gly Phe Ala Val Gly Gln Lys Thr Gln Arg Arg Trp Phe
        35                  40                  45

Leu Asp Lys Leu Val Asp Glu Ile Gly Val Gly Tyr Val Tyr Asp Arg
50                  55                  60

Gly Ser Val Ser Glu Tyr Val Leu Ser Gln Ile Lys Pro Leu His Asn
65                  70                  75                  80

Phe Leu Thr Gln Leu Gln Pro Phe Leu Lys Leu Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
        130                 135                 140

Val Leu Asp
145

<210> SEQ ID NO 45
<211> LENGTH: 147
<212> TYPE: PRT
<213> ORGANISM: Artificial Sequence
<220> FEATURE:
<223> OTHER INFORMATION: Synthesized

<400> SEQUENCE: 45

Lys Glu Phe Leu Leu Tyr Leu Ala Gly Phe Val Asp Gly Asp Gly Ser
1               5                   10                  15

Ile Tyr Ala Thr Ile Arg Pro Ala Gln Arg Ala Lys Phe Lys His Arg
            20                  25                  30

Leu Val Leu Gly Phe Glu Val Gly Gln Lys Thr Gln Arg Arg Trp Phe
        35                  40                  45

Leu Asp Lys Leu Val Asp Glu Ile Gly Val Gly Tyr Val Tyr Asp Gly
50                  55                  60

Gly Ser Val Ser Lys Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
        130                 135                 140

Val Leu Asp
145
```

```
<210> SEQ ID NO 46
<211> LENGTH: 147
<212> TYPE: PRT
<213> ORGANISM: Artificial Sequence
<220> FEATURE:
<223> OTHER INFORMATION: Synthesized

<400> SEQUENCE: 46

Lys Glu Phe Leu Leu Tyr Leu Ala Gly Phe Val Asp Gly Asp Gly Ser
1               5                   10                  15

Ile Tyr Ala Cys Ile Ala Pro Arg Gln Gly Ser Lys Phe Lys His Arg
            20                  25                  30

Leu Lys Leu Gly Phe Ala Val Gly Gln Lys Thr Gln Arg Arg Trp Phe
        35                  40                  45

Leu Asp Lys Leu Val Asp Glu Ile Gly Val Gly Tyr Val Tyr Asp Arg
    50                  55                  60

Gly Ser Val Ser Glu Tyr Val Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 47
<211> LENGTH: 147
<212> TYPE: PRT
<213> ORGANISM: Artificial Sequence
<220> FEATURE:
<223> OTHER INFORMATION: Synthesized

<400> SEQUENCE: 47

Lys Glu Phe Leu Leu Tyr Leu Ala Gly Phe Val Asp Gly Asp Gly Ser
1               5                   10                  15

Ile Tyr Ala Cys Ile Ala Pro Arg Gln Gly Ser Lys Phe Lys His Arg
            20                  25                  30

Leu Lys Leu Gly Phe Ala Val Gly Gln Lys Thr Gln Arg Arg Trp Phe
        35                  40                  45

Leu Asp Lys Leu Val Asp Glu Ile Gly Val Gly Tyr Val Tyr Asp Arg
    50                  55                  60

Gly Ser Val Ser Glu Tyr Val Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145
```

```
<210> SEQ ID NO 48
<211> LENGTH: 147
<212> TYPE: PRT
<213> ORGANISM: Artificial Sequence
<220> FEATURE:
<223> OTHER INFORMATION: Synthesized

<400> SEQUENCE: 48

Lys Glu Phe Leu Leu Tyr Leu Ala Gly Phe Val Asp Gly Asp Gly Ser
1               5                   10                  15

Ile Tyr Ala Cys Ile Ala Pro Arg Gln Gly Ser Lys Phe Lys His Arg
            20                  25                  30

Leu Lys Leu Gly Phe Ala Val Gly Gln Lys Thr Gln Arg Arg Trp Phe
        35                  40                  45

Leu Asp Lys Leu Val Asp Glu Ile Gly Val Gly Tyr Val Tyr Asp Arg
    50                  55                  60

Gly Ser Val Ser Glu Tyr Val Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 49
<211> LENGTH: 147
<212> TYPE: PRT
<213> ORGANISM: Artificial Sequence
<220> FEATURE:
<223> OTHER INFORMATION: Synthesized

<400> SEQUENCE: 49

Lys Glu Phe Leu Leu Tyr Leu Ala Gly Phe Val Asp Gly Asp Gly Ser
1               5                   10                  15

Ile Tyr Ala Thr Ile Ala Pro Cys Gln Arg Ala Lys Phe Lys His Arg
            20                  25                  30

Leu Lys Leu Gly Phe Thr Val Gly Gln Lys Thr Gln Arg Arg Trp Phe
        35                  40                  45

Leu Asp Lys Leu Val Asp Glu Ile Gly Val Gly His Val Tyr Asp Arg
    50                  55                  60

Gly Ser Val Ser Glu Tyr Val Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
```

<210> SEQ ID NO 50
<211> LENGTH: 147
<212> TYPE: PRT
<213> ORGANISM: Artificial Sequence
<220> FEATURE:
<223> OTHER INFORMATION: Synthesized

<400> SEQUENCE: 50

```
Lys Glu Phe Leu Leu Tyr Leu Ala Gly Phe Val Asp Gly Asp Gly Ser
1               5                   10                  15

Ile Tyr Ala Cys Ile Ala Pro Arg Gln Gly Ser Lys Phe Lys His Arg
            20                  25                  30

Leu Lys Leu Gly Phe Ala Val Gly Gln Lys Thr Gln Arg Arg Trp Phe
        35                  40                  45

Leu Asp Lys Leu Val Asp Glu Ile Gly Val Gly Tyr Val Tyr Asp Arg
    50                  55                  60

Gly Ser Val Ser Glu Tyr Val Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145
```

<210> SEQ ID NO 51
<211> LENGTH: 147
<212> TYPE: PRT
<213> ORGANISM: Artificial Sequence
<220> FEATURE:
<223> OTHER INFORMATION: Synthesized

<400> SEQUENCE: 51

```
Lys Glu Phe Leu Leu Tyr Leu Ala Gly Phe Val Asp Gly Asp Gly Ser
1               5                   10                  15

Ile Tyr Ala Cys Ile Ala Pro Arg Gln Gly Ser Lys Phe Lys His Arg
            20                  25                  30

Leu Lys Leu Gly Phe Ala Val Gly Gln Lys Thr Gln Arg Arg Trp Phe
        35                  40                  45

Leu Asp Lys Leu Val Asp Glu Ile Gly Val Gly Tyr Val Tyr Asp Arg
    50                  55                  60

Gly Ser Val Ser Glu Tyr Val Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140
```

Val Leu Asp
145

<210> SEQ ID NO 52
<211> LENGTH: 147
<212> TYPE: PRT
<213> ORGANISM: Artificial Sequence
<220> FEATURE:
<223> OTHER INFORMATION: Synthesized

<400> SEQUENCE: 52

Lys Glu Phe Leu Leu Tyr Leu Ala Gly Phe Val Asp Gly Asp Gly Ser
1               5                   10                  15

Ile Tyr Ala Cys Ile Ala Pro Gly Gln Gly Ser Lys Phe Lys His Arg
            20                  25                  30

Leu Lys Leu Gly Phe Ala Val Gly Gln Lys Thr Gln Arg Arg Trp Phe
        35                  40                  45

Leu Asp Lys Leu Val Asp Glu Ile Gly Val Gly Tyr Val Tyr Asp Arg
    50                  55                  60

Gly Ser Val Ser Glu Tyr Val Leu Ser Glu Ile Lys Pro Leu His Asn
65                  70                  75                  80

Phe Leu Thr Gln Leu Gln Pro Phe Leu Lys Leu Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 53
<211> LENGTH: 147
<212> TYPE: PRT
<213> ORGANISM: Artificial Sequence
<220> FEATURE:
<223> OTHER INFORMATION: Synthesized

<400> SEQUENCE: 53

Lys Glu Phe Leu Leu Tyr Leu Ala Gly Phe Val Asp Gly Asp Gly Ser
1               5                   10                  15

Ile Tyr Ala Thr Ile Cys Pro Cys Gln Thr Leu Lys Phe Lys His Tyr
            20                  25                  30

Leu Thr Leu Ser Phe Ser Val Tyr Gln Lys Thr Gln Arg Arg Trp Phe
        35                  40                  45

Leu Asp Lys Leu Val Asp Glu Ile Gly Val Gly Tyr Val Tyr Asp Gln
    50                  55                  60

Gly Ser Val Ser Cys Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 54
<211> LENGTH: 147
<212> TYPE: PRT
<213> ORGANISM: Artificial Sequence
<220> FEATURE:
<223> OTHER INFORMATION: Synthesized

<400> SEQUENCE: 54

Lys Glu Phe Leu Leu Tyr Leu Ala Gly Phe Val Asp Gly Asp Gly Ser
1               5                   10                  15

Ile Tyr Ala Thr Ile Cys Pro Asp Gln Ala Leu Lys Phe Lys His Tyr
            20                  25                  30

Leu Ser Leu Thr Phe Ala Val Tyr Gln Lys Thr Gln Arg Arg Trp Phe
        35                  40                  45

Leu Asp Lys Leu Val Asp Glu Ile Gly Val Gly Tyr Val Tyr Asp Gln
    50                  55                  60

Gly Ser Val Ser Cys Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 55
<211> LENGTH: 147
<212> TYPE: PRT
<213> ORGANISM: Artificial Sequence
<220> FEATURE:
<223> OTHER INFORMATION: Synthesized

<400> SEQUENCE: 55

Lys Glu Phe Leu Leu Tyr Leu Ala Gly Phe Val Asp Gly Asp Gly Ser
1               5                   10                  15

Ile Tyr Ala Cys Ile Thr Pro Gln Gln Asp Met Lys Phe Lys His Arg
            20                  25                  30

Leu Gln Leu Arg Phe Cys Val Thr Gln Lys Thr Gln Arg Arg Trp Phe
        35                  40                  45

Leu Asp Lys Leu Val Asp Glu Ile Gly Val Gly Tyr Val Gln Asp Cys
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala

Val Leu Asp
145

<210> SEQ ID NO 56
<211> LENGTH: 147
<212> TYPE: PRT
<213> ORGANISM: Artificial Sequence
<220> FEATURE:
<223> OTHER INFORMATION: Synthesized

<400> SEQUENCE: 56

Lys Glu Phe Leu Leu Tyr Leu Ala Gly Phe Val Asp Gly Asp Gly Ser
1               5                   10                  15

Ile Tyr Ala Cys Ile Thr Pro Gln Gln Asp Met Lys Phe Lys His Arg
            20                  25                  30

Leu Gln Leu Arg Phe Cys Val Thr Gln Lys Thr Gln Arg Arg Trp Phe
        35                  40                  45

Leu Asp Lys Leu Val Asp Glu Ile Gly Val Gly Tyr Val Gln Asp His
    50                  55                  60

Gly Gly Ala Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 57
<211> LENGTH: 147
<212> TYPE: PRT
<213> ORGANISM: Artificial Sequence
<220> FEATURE:
<223> OTHER INFORMATION: Synthesized

<400> SEQUENCE: 57

Lys Glu Phe Leu Leu Tyr Leu Ala Gly Phe Val Asp Gly Asp Gly Ser
1               5                   10                  15

Ile Tyr Ala Cys Ile Thr Pro Gln Gln Asp Met Lys Phe Lys His Arg
            20                  25                  30

Leu Gln Leu Arg Phe Cys Val Thr Gln Lys Thr Gln Arg Arg Trp Phe
        35                  40                  45

Leu Asp Lys Leu Val Asp Glu Ile Gly Val Gly Tyr Val Gln Asp Lys
    50                  55                  60

Gly Ser Ala Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
            130                 135                 140

Val Leu Asp
145

<210> SEQ ID NO 58
<211> LENGTH: 147
<212> TYPE: PRT
<213> ORGANISM: Artificial Sequence
<220> FEATURE:
<223> OTHER INFORMATION: Synthesized

<400> SEQUENCE: 58

Lys Glu Phe Leu Leu Tyr Leu Ala Gly Phe Val Asp Gly Asp Gly Ser
1               5                   10                  15

Ile Phe Ala Ser Ile Tyr Pro His Gln Arg Ala Lys Phe Lys His Phe
            20                  25                  30

Leu Lys Leu Thr Phe Ala Val Tyr Gln Lys Thr Gln Arg Arg Trp Phe
        35                  40                  45

Leu Asp Lys Leu Val Asp Glu Ile Gly Val Gly Tyr Val Tyr Asp Ser
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Arg Thr Arg Lys Thr Thr Ser Glu Thr Val Arg Ala
    130                 135                 140

Val Leu Asp
145

<210> SEQ ID NO 59
<211> LENGTH: 147
<212> TYPE: PRT
<213> ORGANISM: Artificial Sequence
<220> FEATURE:
<223> OTHER INFORMATION: Synthesized

<400> SEQUENCE: 59

Lys Glu Phe Leu Leu Tyr Leu Ala Gly Phe Val Asp Gly Asp Gly Ser
1               5                   10                  15

Ile Phe Ala Ser Ile Tyr Pro His Gln Arg Ala Lys Phe Lys His Phe
            20                  25                  30

Leu Lys Leu Thr Phe Ala Val Tyr Gln Lys Thr Gln Arg Arg Trp Phe
        35                  40                  45

Leu Asp Lys Leu Val Asp Glu Ile Gly Val Gly Tyr Val Tyr Asp Ser
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Arg Thr Arg Lys Thr Thr Ser Glu Thr Val Arg Ala
            130                 135                 140

Val Leu Asp
145

<210> SEQ ID NO 60
<211> LENGTH: 147
<212> TYPE: PRT
<213> ORGANISM: Artificial Sequence
<220> FEATURE:
<223> OTHER INFORMATION: Synthesized

<400> SEQUENCE: 60

Lys Glu Phe Leu Leu Tyr Leu Ala Gly Phe Val Asp Gly Asp Gly Ser
1               5                   10                  15

Ile Phe Ala Ser Ile Tyr Pro His Gln Arg Ala Lys Phe Lys His Phe
            20                  25                  30

Leu Lys Leu Thr Phe Ala Val Tyr Gln Lys Thr Gln Arg Arg Trp Phe
        35                  40                  45

Leu Asp Lys Leu Val Asp Glu Ile Gly Val Gly Tyr Val Tyr Asp Ser
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Arg Thr Arg Lys Thr Thr Ser Glu Thr Val Arg Ala
    130                 135                 140

Val Leu Asp
145

<210> SEQ ID NO 61
<211> LENGTH: 147
<212> TYPE: PRT
<213> ORGANISM: Artificial Sequence
<220> FEATURE:
<223> OTHER INFORMATION: Synthesized

<400> SEQUENCE: 61

Lys Glu Phe Leu Leu Tyr Leu Ala Gly Phe Val Asp Gly Asp Gly Ser
1               5                   10                  15

Ile Phe Ala Ser Ile Tyr Pro His Gln Arg Ala Lys Phe Lys His Phe
            20                  25                  30

Leu Lys Leu Thr Phe Ala Val Tyr Gln Lys Thr Gln Arg Arg Trp Phe
        35                  40                  45

Leu Asp Lys Leu Val Asp Glu Ile Gly Val Gly Tyr Val Tyr Asp Ser
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala

```
            115                 120                 125

Leu Asn Asp Ser Arg Thr Arg Lys Thr Thr Ser Glu Thr Val Arg Ala
        130                 135                 140

Val Leu Asp
145

<210> SEQ ID NO 62
<211> LENGTH: 147
<212> TYPE: PRT
<213> ORGANISM: Artificial Sequence
<220> FEATURE:
<223> OTHER INFORMATION: Synthesized

<400> SEQUENCE: 62

Lys Glu Phe Leu Leu Tyr Leu Ala Gly Phe Val Asp Gly Asp Gly Ser
1               5                   10                  15

Ile Tyr Ala Cys Ile Tyr Pro His Gln Arg Ala Lys Phe Lys His Leu
            20                  25                  30

Leu Lys Leu Val Phe Ala Val His Gln Lys Thr Gln Arg Arg Trp Phe
        35                  40                  45

Leu Asp Lys Leu Val Asp Glu Ile Gly Val Gly Tyr Val Tyr Asp Ala
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 63
<211> LENGTH: 147
<212> TYPE: PRT
<213> ORGANISM: Artificial Sequence
<220> FEATURE:
<223> OTHER INFORMATION: Synthesized

<400> SEQUENCE: 63

Lys Glu Phe Leu Leu Tyr Leu Ala Gly Phe Val Asp Gly Asp Gly Ser
1               5                   10                  15

Ile Tyr Ala Cys Ile Tyr Pro Asp Gln Arg Thr Lys Phe Lys His Gly
            20                  25                  30

Leu Arg Leu Asn Phe Ser Val Phe Gln Lys Thr Gln Arg Arg Trp Phe
        35                  40                  45

Leu Asp Lys Leu Val Asp Glu Ile Gly Val Gly Tyr Val Phe Asp Ala
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110
```

```
Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
    130                 135                 140

Val Leu Asp
145

<210> SEQ ID NO 64
<211> LENGTH: 147
<212> TYPE: PRT
<213> ORGANISM: Artificial Sequence
<220> FEATURE:
<223> OTHER INFORMATION: Synthesized

<400> SEQUENCE: 64

Lys Glu Phe Leu Leu Tyr Leu Ala Gly Phe Val Asp Gly Asp Gly Ser
1               5                   10                  15

Ile Phe Ala Thr Ile His Pro Asp Gln Arg Ser Lys Phe Lys His Tyr
            20                  25                  30

Leu Arg Leu Phe Phe Ser Val Phe Gln Lys Thr Gln Arg Arg Trp Phe
        35                  40                  45

Leu Asp Lys Leu Val Asp Glu Ile Gly Val Gly Tyr Val Tyr Asp Ala
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 65
<211> LENGTH: 147
<212> TYPE: PRT
<213> ORGANISM: Artificial Sequence
<220> FEATURE:
<223> OTHER INFORMATION: Synthesized

<400> SEQUENCE: 65

Lys Glu Phe Leu Leu Tyr Leu Ala Gly Phe Val Asp Gly Asp Gly Ser
1               5                   10                  15

Ile Phe Ala Gln Ile Lys Pro Asp Gln Lys Met Lys Phe Lys His Tyr
            20                  25                  30

Leu Ser Leu His Phe Ser Val Phe Gln Lys Thr Gln Arg Arg Trp Phe
        35                  40                  45

Leu Asp Lys Leu Val Asp Glu Ile Gly Val Gly Tyr Val Tyr Asp Gly
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110
```

-continued

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 66
<211> LENGTH: 147
<212> TYPE: PRT
<213> ORGANISM: Artificial Sequence
<220> FEATURE:
<223> OTHER INFORMATION: Synthesized

<400> SEQUENCE: 66

Lys Glu Phe Leu Leu Tyr Leu Ala Gly Phe Val Asp Gly Asp Gly Ser
1               5                   10                  15

Ile Phe Ala Ser Ile Asn Pro Asp Gln Arg Ala Lys Phe Lys His Ser
            20                  25                  30

Leu Lys Leu Thr Phe Ser Val Tyr Gln Lys Thr Gln Arg Arg Trp Phe
        35                  40                  45

Leu Asp Lys Leu Val Asp Glu Ile Gly Val Gly Tyr Val Tyr Asp Thr
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 67
<211> LENGTH: 147
<212> TYPE: PRT
<213> ORGANISM: Artificial Sequence
<220> FEATURE:
<223> OTHER INFORMATION: Synthesized

<400> SEQUENCE: 67

Lys Glu Phe Leu Leu Tyr Leu Ala Gly Phe Val Asp Gly Asp Gly Ser
1               5                   10                  15

Ile Phe Ala Ser Ile Tyr Pro His Gln Arg Ala Lys Phe Lys His Phe
            20                  25                  30

Leu Lys Leu Thr Phe Ala Val Tyr Gln Lys Thr Gln Arg Arg Trp Phe
        35                  40                  45

Leu Asp Lys Leu Val Asp Glu Ile Gly Val Gly Tyr Val Tyr Asp Ser
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser

```
                    100                 105                 110
Pro Asp Lys Phe Leu Glu Val Cys Thr Trp Val Asp Gln Ile Ala Ala
        115                 120                 125

Leu Asn Asp Ser Arg Thr Arg Lys Thr Thr Ser Glu Thr Val Arg Ala
    130                 135                 140

Val Leu Asp
145

<210> SEQ ID NO 68
<211> LENGTH: 147
<212> TYPE: PRT
<213> ORGANISM: Artificial Sequence
<220> FEATURE:
<223> OTHER INFORMATION: Synthesized

<400> SEQUENCE: 68

Lys Glu Phe Leu Leu Tyr Leu Ala Gly Phe Val Asp Gly Asp Gly Ser
1               5                   10                  15

Ile Tyr Ala Cys Ile Ala Pro Asp Gln Arg Ala Lys Phe Lys His Tyr
            20                  25                  30

Leu Arg Leu Gln Phe Ser Val Phe Gln Lys Thr Gln Arg Arg Trp Phe
        35                  40                  45

Leu Asp Lys Leu Val Asp Glu Ile Gly Val Gly Tyr Val Phe Asp Ala
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 69
<211> LENGTH: 147
<212> TYPE: PRT
<213> ORGANISM: Artificial Sequence
<220> FEATURE:
<223> OTHER INFORMATION: Synthesized

<400> SEQUENCE: 69

Lys Glu Phe Leu Leu Tyr Leu Ala Gly Phe Val Asp Gly Asp Gly Ser
1               5                   10                  15

Ile Tyr Ala Thr Ile Tyr Pro Asp Gln Arg Ala Lys Phe Lys His Ala
            20                  25                  30

Leu Lys Leu Ile Phe Ser Val Phe Gln Lys Thr Gln Arg Arg Trp Phe
        35                  40                  45

Leu Asp Lys Leu Val Asp Glu Ile Gly Val Gly Tyr Val Tyr Asp Gly
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95
```

```
Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
        130                 135                 140

Val Leu Asp
145

<210> SEQ ID NO 70
<211> LENGTH: 147
<212> TYPE: PRT
<213> ORGANISM: Artificial Sequence
<220> FEATURE:
<223> OTHER INFORMATION: Synthesized

<400> SEQUENCE: 70

Lys Glu Phe Leu Leu Tyr Leu Ala Gly Phe Val Asp Gly Asp Gly Ser
1               5                   10                  15

Ile Phe Ala Thr Ile Ala Pro Asp Gln Arg Pro Lys Phe Lys His Gln
            20                  25                  30

Leu Arg Leu Ile Phe Asn Val Cys Gln Lys Thr Gln Arg Arg Trp Phe
        35                  40                  45

Leu Asp Lys Leu Val Asp Glu Ile Gly Val Gly Tyr Val Tyr Asp Thr
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
        130                 135                 140

Val Leu Asp
145

<210> SEQ ID NO 71
<211> LENGTH: 147
<212> TYPE: PRT
<213> ORGANISM: Artificial Sequence
<220> FEATURE:
<223> OTHER INFORMATION: Synthesized

<400> SEQUENCE: 71

Lys Glu Phe Leu Leu Tyr Leu Ala Gly Phe Val Asp Gly Asp Gly Ser
1               5                   10                  15

Ile Phe Ala Ser Ile Tyr Pro His Gln Arg Ala Lys Phe Lys His Phe
            20                  25                  30

Leu Lys Leu Thr Phe Ala Val Tyr Gln Lys Thr Gln Arg Arg Trp Phe
        35                  40                  45

Leu Asp Lys Leu Val Asp Glu Ile Gly Val Gly Tyr Val Tyr Asp Ser
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95
```

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 72
<211> LENGTH: 147
<212> TYPE: PRT
<213> ORGANISM: Artificial Sequence
<220> FEATURE:
<223> OTHER INFORMATION: Synthesized

<400> SEQUENCE: 72

Lys Glu Phe Leu Leu Tyr Leu Ala Gly Phe Val Asp Gly Asp Gly Ser
1               5                   10                  15

Ile Phe Ala Thr Ile Val Pro Glu Gln Arg Ser Lys Phe Lys His Tyr
            20                  25                  30

Leu Lys Leu Thr Phe Ser Val Phe Gln Lys Thr Gln Arg Arg Trp Phe
        35                  40                  45

Leu Asp Arg Leu Val Asp Glu Ile Gly Val Gly Tyr Val Tyr Asp Ala
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 73
<211> LENGTH: 147
<212> TYPE: PRT
<213> ORGANISM: Artificial Sequence
<220> FEATURE:
<223> OTHER INFORMATION: Synthesized

<400> SEQUENCE: 73

Lys Glu Phe Leu Leu Tyr Leu Ala Gly Phe Val Asp Gly Asp Gly Ser
1               5                   10                  15

Ile Phe Ala Thr Ile Phe Pro Asp Gln Arg Met Lys Phe Lys His Gln
            20                  25                  30

Leu Arg Leu His Phe Cys Val His Gln Lys Thr Gln Arg Arg Trp Phe
        35                  40                  45

Leu Asp Lys Leu Val Asp Glu Ile Gly Val Gly Tyr Val Tyr Asp Ser
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala

```
                     85                  90                  95
Asn Leu Val Leu Lys Ile Ile Glu Gln Leu Pro Ser Ala Lys Glu Ser
                100                 105                 110
Pro Asp Lys Phe Leu Glu Val Cys Thr Trp Val Asp Gln Ile Ala Ala
            115                 120                 125
Leu Asn Asp Ser Lys Thr Arg Lys Thr Thr Ser Glu Thr Val Arg Ala
        130                 135                 140
Val Leu Asp
145

<210> SEQ ID NO 74
<211> LENGTH: 147
<212> TYPE: PRT
<213> ORGANISM: Artificial Sequence
<220> FEATURE:
<223> OTHER INFORMATION: Synthesized

<400> SEQUENCE: 74

Lys Glu Phe Leu Leu Tyr Leu Ala Gly Phe Val Asp Gly Asp Gly Ser
1               5                   10                  15
Ile Phe Ala Ser Ile Tyr Pro His Gln Arg Ala Lys Phe Lys His Phe
            20                  25                  30
Leu Lys Leu Thr Phe Ala Val Tyr Gln Lys Thr Gln Arg Arg Trp Phe
        35                  40                  45
Leu Asp Lys Leu Val Asp Glu Ile Gly Val Gly Tyr Val Tyr Asp Ser
    50                  55                  60
Gly Ser Val Ser Glu Tyr Arg Leu Ser Gln Ile Lys Pro Leu His Asn
65                  70                  75                  80
Phe Leu Thr Gln Leu Gln Pro Phe Leu Lys Leu Lys Gln Lys Gln Ala
                85                  90                  95
Asn Leu Val Leu Lys Ile Ile Glu Gln Leu Pro Ser Ala Lys Glu Ser
                100                 105                 110
Pro Asp Lys Phe Leu Glu Val Cys Thr Trp Val Asp Gln Ile Ala Ala
            115                 120                 125
Leu Asn Asp Ser Lys Thr Arg Lys Thr Thr Ser Glu Thr Val Arg Ala
        130                 135                 140
Val Leu Asp
145

<210> SEQ ID NO 75
<211> LENGTH: 147
<212> TYPE: PRT
<213> ORGANISM: Artificial Sequence
<220> FEATURE:
<223> OTHER INFORMATION: Synthesized

<400> SEQUENCE: 75

Lys Glu Phe Leu Leu Tyr Leu Ala Gly Phe Val Asp Gly Asp Gly Ser
1               5                   10                  15
Ile Phe Ala Thr Ile Phe Pro Asp Gln Arg Met Lys Phe Lys His Gln
            20                  25                  30
Leu Arg Leu His Phe Cys Val His Gln Lys Thr Gln Arg Arg Trp Phe
        35                  40                  45
Leu Asp Lys Leu Val Asp Glu Ile Gly Val Gly Tyr Val Tyr Asp Ser
    50                  55                  60
Gly Ser Val Ser Glu Tyr Arg Leu Ser Gln Ile Lys Pro Leu His Asn
65                  70                  75                  80
```

```
Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 76
<211> LENGTH: 147
<212> TYPE: PRT
<213> ORGANISM: Artificial Sequence
<220> FEATURE:
<223> OTHER INFORMATION: Synthesized

<400> SEQUENCE: 76

Lys Glu Phe Leu Leu Tyr Leu Ala Gly Phe Val Asp Gly Asp Gly Ser
1               5                   10                  15

Ile Phe Ala Thr Ile Phe Pro Asp Gln Arg Met Lys Phe Lys His Gln
            20                  25                  30

Leu Arg Leu His Phe Cys Val His Gln Lys Thr Gln Arg Arg Trp Phe
        35                  40                  45

Leu Asp Lys Leu Val Asp Glu Ile Gly Val Gly Tyr Val Tyr Asp Ser
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 77
<211> LENGTH: 147
<212> TYPE: PRT
<213> ORGANISM: Artificial Sequence
<220> FEATURE:
<223> OTHER INFORMATION: Synthesized

<400> SEQUENCE: 77

Lys Glu Phe Leu Leu Tyr Leu Ala Gly Phe Val Asp Gly Asp Gly Ser
1               5                   10                  15

Ile Phe Ala Thr Ile Phe Pro Asp Gln Arg Met Lys Phe Lys His Gln
            20                  25                  30

Leu Arg Leu Gly Phe Ala Val His Gln Lys Thr Gln Arg Arg Trp Phe
        35                  40                  45

Leu Asp Lys Leu Val Asp Glu Ile Gly Val Gly Tyr Val Tyr Asp Arg
    50                  55                  60

Gly Ser Val Ser Glu Tyr Arg Leu Ser Gln Ile Lys Pro Leu His Asn
65                  70                  75                  80
```

```
Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 78
<211> LENGTH: 147
<212> TYPE: PRT
<213> ORGANISM: Artificial Sequence
<220> FEATURE:
<223> OTHER INFORMATION: Synthesized

<400> SEQUENCE: 78

Lys Glu Phe Leu Leu Tyr Leu Ala Gly Phe Val Asp Gly Asp Gly Ser
1               5                   10                  15

Ile His Ala Cys Ile Gln Pro Gln Gln Asp Val Lys Phe Lys His Gln
            20                  25                  30

Leu His Leu Arg Phe Thr Val His Gln Lys Thr Gln Arg Arg Trp Phe
        35                  40                  45

Leu Asp Lys Leu Val Asp Glu Ile Gly Val Gly Tyr Val Tyr Asp Ala
    50                  55                  60

Gly Ser Val Ser Thr Tyr Cys Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 79
<211> LENGTH: 147
<212> TYPE: PRT
<213> ORGANISM: Artificial Sequence
<220> FEATURE:
<223> OTHER INFORMATION: Synthesized

<400> SEQUENCE: 79

Lys Glu Phe Leu Leu Tyr Leu Ala Gly Phe Val Asp Gly Asp Gly Ser
1               5                   10                  15

Ile His Ala Cys Ile Gln Pro Met Gln Ser Met Lys Phe Lys His Tyr
            20                  25                  30

Leu His Leu Arg Phe Thr Val His Gln Lys Thr Gln Arg Arg Trp Phe
        35                  40                  45

Leu Asp Lys Leu Val Asp Glu Thr Gly Val Gly Tyr Val Tyr Asp Ala
    50                  55                  60

Gly Ser Val Ser Thr Tyr Cys Leu Ser Gln Ile Lys Pro Leu His Asn
```

```
                65                  70                  75                  80
Phe Leu Thr Gln Leu Gln Pro Phe Leu Lys Leu Lys Gln Lys Gln Ala
                    85                  90                  95

Asn Leu Val Leu Lys Ile Ile Glu Gln Leu Pro Ser Ala Lys Glu Ser
                    100                 105                 110

Pro Asp Lys Phe Leu Glu Val Cys Thr Trp Val Asp Gln Ile Ala Ala
                    115                 120                 125

Leu Asn Asp Ser Lys Thr Arg Lys Thr Thr Ser Glu Thr Val Arg Ala
                    130                 135                 140

Val Leu Asp
145

<210> SEQ ID NO 80
<211> LENGTH: 147
<212> TYPE: PRT
<213> ORGANISM: Artificial Sequence
<220> FEATURE:
<223> OTHER INFORMATION: Synthesized

<400> SEQUENCE: 80

Lys Glu Phe Leu Leu Tyr Leu Ala Gly Phe Val Asp Gly Asp Gly Ser
1               5                   10                  15

Ile Val Ala Ser Ile Lys Pro Gln Gln Val Ala Lys Phe Lys His Arg
                20                  25                  30

Leu Met Leu Glu Phe Tyr Val Tyr Gln Lys Thr Gln Arg Arg Trp Phe
                35                  40                  45

Leu Asp Lys Leu Val Asp Glu Ile Gly Val Gly Tyr Val Tyr Asp Leu
            50                  55                  60

Gly Gly Ala Ser Arg Tyr Val Leu Ser Gln Ile Lys Pro Leu His Asn
65                  70                  75                  80

Phe Leu Thr Gln Leu Gln Pro Phe Leu Lys Leu Lys Gln Lys Gln Ala
                    85                  90                  95

Asn Leu Val Leu Lys Ile Ile Glu Gln Leu Pro Ser Ala Lys Glu Ser
                    100                 105                 110

Pro Asp Lys Phe Leu Glu Val Cys Thr Trp Val Asp Gln Ile Ala Ala
                    115                 120                 125

Leu Asn Asp Ser Lys Thr Arg Lys Thr Thr Ser Glu Thr Val Arg Ala
                    130                 135                 140

Val Leu Asp
145

<210> SEQ ID NO 81
<211> LENGTH: 147
<212> TYPE: PRT
<213> ORGANISM: Artificial Sequence
<220> FEATURE:
<223> OTHER INFORMATION: Synthesized

<400> SEQUENCE: 81

Lys Glu Phe Leu Leu Tyr Leu Ala Gly Phe Val Asp Gly Asp Gly Ser
1               5                   10                  15

Ile Tyr Ala Cys Ile Lys Pro Asp Gln Ala Ala Lys Phe Lys His Arg
                20                  25                  30

Leu Leu Leu Glu Phe Thr Val Cys Gln Lys Thr Gln Arg Arg Trp Phe
                35                  40                  45

Leu Asp Lys Leu Val Asp Glu Ile Gly Val Gly Tyr Val Val Asp Gln
            50                  55                  60
```

```
Gly Ser Val Ser Glu Tyr Arg Leu Ser Gln Ile Lys Pro Leu His Asn
 65                  70                  75                  80

Phe Leu Thr Gln Leu Gln Pro Phe Leu Lys Leu Lys Gln Lys Gln Ala
                 85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 82
<211> LENGTH: 147
<212> TYPE: PRT
<213> ORGANISM: Artificial Sequence
<220> FEATURE:
<223> OTHER INFORMATION: Synthesized

<400> SEQUENCE: 82

Lys Glu Phe Leu Leu Tyr Leu Ala Gly Phe Val Asp Gly Asp Gly Ser
 1               5                  10                  15

Ile Trp Ala Ser Ile Arg Pro Thr Gln Leu Ala Lys Phe Lys His Ala
            20                  25                  30

Leu Trp Leu Gly Phe Ala Val Tyr Gln Lys Thr Gln Arg Arg Trp Phe
        35                  40                  45

Leu Asp Lys Leu Val Asp Glu Ile Gly Val Gly Tyr Val Tyr Asp Ser
    50                  55                  60

Gly Ser Val Ser Lys Tyr Thr Leu Ser Glu Ile Lys Pro Leu His Asn
 65                  70                  75                  80

Phe Leu Thr Gln Leu Gln Pro Phe Leu Lys Leu Lys Gln Lys Gln Ala
                 85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 83
<211> LENGTH: 22
<212> TYPE: DNA
<213> ORGANISM: Homo sapiens

<400> SEQUENCE: 83
accggacctc gttgtttaga ct                                          22

<210> SEQ ID NO 84
<211> LENGTH: 22
<212> TYPE: DNA
<213> ORGANISM: Homo sapiens

<400> SEQUENCE: 84
tgtttacaca gtgtttcatt cc                                          22
```

```
<210> SEQ ID NO 85
<211> LENGTH: 22
<212> TYPE: DNA
<213> ORGANISM: Homo sapiens

<400> SEQUENCE: 85
gactacacat atagtgtctg tt                                              22

<210> SEQ ID NO 86
<211> LENGTH: 72
<212> TYPE: DNA
<213> ORGANISM: Homo sapiens

<400> SEQUENCE: 86
atggacttca agagcaacag tgctgtggcc tggagcaaca atctgactt tgcatgtgca      60 aacgccttca ac                                                         72

<210> SEQ ID NO 87
<211> LENGTH: 69
<212> TYPE: DNA
<213> ORGANISM: Artificial Sequence
<220> FEATURE:
<223> OTHER INFORMATION: Synthesized

<400> SEQUENCE: 87
atggacttca agagcaacag tgctgtggcc tggagcaaat ctgactttgc atgtgcaaac     60
gccttcaac                                                             69

<210> SEQ ID NO 88
<211> LENGTH: 55
<212> TYPE: DNA
<213> ORGANISM: Artificial Sequence
<220> FEATURE:
<223> OTHER INFORMATION: Synthesized

<400> SEQUENCE: 88
atggacttca agagcaacaa acaaatctga ctttgcatgt gcaaacgcct tcaac          55

<210> SEQ ID NO 89
<211> LENGTH: 67
<212> TYPE: DNA
<213> ORGANISM: Artificial Sequence
<220> FEATURE:
<223> OTHER INFORMATION: Synthesized

<400> SEQUENCE: 89
atggacttca agagcaacag tgctgtggcc tggagaatct gactttgcat gtgcaaacgc     60
cttcaac                                                               67

<210> SEQ ID NO 90
<211> LENGTH: 65
<212> TYPE: DNA
<213> ORGANISM: Artificial Sequence
<220> FEATURE:
<223> OTHER INFORMATION: Synthesized

<400> SEQUENCE: 90
atggacttca agagcaacag tgctgtggcc tggagtctga ctttgcatgt gcaaacgcct     60
tcaac                                                                 65

<210> SEQ ID NO 91
<211> LENGTH: 52
<212> TYPE: DNA
```

```
<213> ORGANISM: Artificial Sequence
<220> FEATURE:
<223> OTHER INFORMATION: Synthesized

<400> SEQUENCE: 91
atggacttca agagcaaaca atctgactt tgcatgtgca aacgccttca ac          52

<210> SEQ ID NO 92
<211> LENGTH: 70
<212> TYPE: DNA
<213> ORGANISM: Artificial Sequence
<220> FEATURE:
<223> OTHER INFORMATION: Synthesized

<400> SEQUENCE: 92
atggacttca agagcaacag tgctgtggcc tggagacaaa tctgactttg catgtgcaaa  60
cgccttcaac                                                        70

<210> SEQ ID NO 93
<211> LENGTH: 68
<212> TYPE: DNA
<213> ORGANISM: Artificial Sequence
<220> FEATURE:
<223> OTHER INFORMATION: Synthesized

<400> SEQUENCE: 93
atggacttca agagcaacag tgctgtggcc tggagcaatc tgactttgca tgtgcaaacg  60
ccttcaac                                                          68

<210> SEQ ID NO 94
<211> LENGTH: 77
<212> TYPE: DNA
<213> ORGANISM: Artificial Sequence
<220> FEATURE:
<223> OTHER INFORMATION: Synthesized

<400> SEQUENCE: 94
atggacttca agagcaacag tgctgtggcc tggagcaacg caacaaatct gactttgcat  60
gtgcaaacgc cttcaac                                                77

<210> SEQ ID NO 95
<211> LENGTH: 76
<212> TYPE: DNA
<213> ORGANISM: Artificial Sequence
<220> FEATURE:
<223> OTHER INFORMATION: Synthesized

<400> SEQUENCE: 95
atggacttca agagcaacag tgctgtggcc tggagcaaag aacaaatctg actttgcatg  60
tgcaaacgcc ttcaac                                                 76

<210> SEQ ID NO 96
<211> LENGTH: 70
<212> TYPE: DNA
<213> ORGANISM: Artificial Sequence
<220> FEATURE:
<223> OTHER INFORMATION: Synthesized

<400> SEQUENCE: 96
atggacttca agagcaacag tgctgtggcc tggcaacaaa tctgactttg catgtgcaaa  60
cgccttcaac                                                        70
```

<210> SEQ ID NO 97
<211> LENGTH: 62
<212> TYPE: DNA
<213> ORGANISM: Artificial Sequence
<220> FEATURE:
<223> OTHER INFORMATION: Synthesized

<400> SEQUENCE: 97
atggacttca agagcaacag tgctgtggca aatctgactt tgcatgtgca aacgccttca    60
ac                                                                  62

<210> SEQ ID NO 98
<211> LENGTH: 68
<212> TYPE: DNA
<213> ORGANISM: Artificial Sequence
<220> FEATURE:
<223> OTHER INFORMATION: Synthesized

<400> SEQUENCE: 98
atggacttca agagcaacag tgctgtggcc tggacaaatc tgactttgca tgtgcaaacg    60
ccttcaac                                                            68

<210> SEQ ID NO 99
<211> LENGTH: 69
<212> TYPE: DNA
<213> ORGANISM: Artificial Sequence
<220> FEATURE:
<223> OTHER INFORMATION: Synthesized

<400> SEQUENCE: 99
atggacttca agagcaacag tgctgtggcc tggagcaaat ctgactttgc atgtgcaaac    60
gccttcaac                                                           69

<210> SEQ ID NO 100
<211> LENGTH: 56
<212> TYPE: DNA
<213> ORGANISM: Artificial Sequence
<220> FEATURE:
<223> OTHER INFORMATION: Synthesized

<400> SEQUENCE: 100
atggacttca agagcaacag tgctgtggcc tggagcaatg tgcaaacgcc ttcaac        56

<210> SEQ ID NO 101
<211> LENGTH: 69
<212> TYPE: DNA
<213> ORGANISM: Artificial Sequence
<220> FEATURE:
<223> OTHER INFORMATION: Synthesized

<400> SEQUENCE: 101
atggacttca agagcaacag tgctgtggcc tggaacaaat ctgactttgc atgtgcaaac    60
gccttcaac                                                           69

<210> SEQ ID NO 102
<211> LENGTH: 71
<212> TYPE: DNA
<213> ORGANISM: Artificial Sequence
<220> FEATURE:
<223> OTHER INFORMATION: Synthesized

<400> SEQUENCE: 102
atggacttca agagcaacag tgctgtggcc tggagcacaa atctgacttt gcatgtgcaa    60
acgccttcaa c                                                          71

<210> SEQ ID NO 103
<211> LENGTH: 56
<212> TYPE: DNA
<213> ORGANISM: Artificial Sequence
<220> FEATURE:
<223> OTHER INFORMATION: Synthesized

<400> SEQUENCE: 103
atggacttca agagcaacag tgctgtggcc tggagcaatg tgcaaacgcc ttcaac         56

<210> SEQ ID NO 104
<211> LENGTH: 36
<212> TYPE: DNA
<213> ORGANISM: Artificial Sequence
<220> FEATURE:
<223> OTHER INFORMATION: Synthesized

<400> SEQUENCE: 104
atcaaatctg actttgcatg tgcaaacgcc ttcaac                               36

<210> SEQ ID NO 105
<211> LENGTH: 34
<212> TYPE: DNA
<213> ORGANISM: Homo sapiens

<400> SEQUENCE: 105
gtgctgtggc ctggagcaac aaatctgact ttgc                                 34

<210> SEQ ID NO 106
<211> LENGTH: 62
<212> TYPE: DNA
<213> ORGANISM: Artificial Sequence
<220> FEATURE:
<223> OTHER INFORMATION: Synthesized

<400> SEQUENCE: 106
gtgctgtggc ctggagcaag aattcatgcg gccgcaatct agagcaacaa atctgacttt     60
gc                                                                    62

<210> SEQ ID NO 107
<211> LENGTH: 6053
<212> TYPE: DNA
<213> ORGANISM: Artificial Sequence
<220> FEATURE:
<223> OTHER INFORMATION: Synthesized

<400> SEQUENCE: 107
cagcagctgg cgtaatagcg aagaggcccg caccgatcgc ccttcccaac agttgcgcag     60
cctgaatggc gaatggaatt ccagacgatt gagcgtcaaa atgtaggtat ttccatgagc    120
gtttttcctg ttgcaatggc tggcggtaat attgttctgg atattaccag caaggccgat    180
agtttgagtt cttctactca ggcaagtgat gttattacta atcaaagaag tattgcgaca    240
acggttaatt tgcgtgatgg acagactctt ttactcggtg gcctcactga ttataaaaac    300
acttctcagg attctggcgt accgttcctg tctaaaatcc ctttaatcgg cctcctgttt    360
agctcccgct ctgattctaa cgaggaaagc acgttatacg tgctcgtcaa agcaaccata    420
gtacgcgccc tgtagcggcg cattaagcgc ggcgggtgtg gtggttacgc gcagcgtgac    480
cgctacactt gccagcgccc tagcgcccgc tcctttcgct ttcttccctt cctttctcgc    540
cacgttcgcc ggctttcccc gtcaagctct aaatcggggg ctccctttag ggttccgatt    600

```
tagtgcttta cggcacctcg accccaaaaa acttgattag ggtgatggtt cacgtagtgg    660
gccatcgccc tgatagacgg ttttcgccc tttgacgttg gagtccacgt tctttaatag    720
tggactcttg ttccaaactg aacaacact caaccctatc tcggtctatt cttttgattt    780
ataagggatt ttgccgattt cggcctattg gttaaaaaat gagctgattt aacaaaaatt    840
taacgcgaat tttaacaaaa tattaacgtt tacaatttaa atatttgctt atacaatctt    900 cctgttttg gggcttttct gattatcaac cggggtacat atgattgaca tgctagtttt    960
acgattaccg ttcatcgccc tgcgcgctcg ctcgctcact gaggccgccc gggcaaagcc   1020
cgggcgtcgg gcgacctttg gtcgcccggc ctcagtgagc gagcgagcgc gcagagaggg   1080
agtggaattc acgcgtggat cttaatagta atcaattacg gggtcattag ttcatagccc   1140
atatatggag ttccgcgtta cataacttac ggtaaatggc ccgcctggct gaccgcccaa   1200
cgacccccgc ccattgacgt caataatgac gtatgttccc atagtaacgc caatagggac   1260
tttccattga cgtcaatggg tggagtattt acggtaaact gcccacttgg cagtacatca   1320
agtgtatcat atgccaagtc cgccccctat tgacgtcaat gacggtaaat ggcccgcctg   1380
gcattatgcc cagtacatga ccttacggga ctttcctact tggcagtaca tctacgtatt   1440
agtcatcgct attaccatgg tgatgcggtt ttggcagtac accaatgggc gtggatagcg   1500
gtttgactca cggggatttc caagtctcca ccccattgac gtcaatggga gtttgttttg   1560
gcaccaaaat caacgggact ttccaaaatg tcgtaataac cccgccccgt tgacgcaaat   1620
gggcggtagg cgtgtacggt gggaggtcta tataagcaga gctcgtttag tgaaccgtca   1680
gatcactaga agctttctgg gcacacccct catctgactt tttaattcct ccacttcaac   1740
acctggtgca ttcatgtgcc ggcacaatca gtgattggtg ggttaatgag tgactgcgtg   1800
agactgactt agtgagctgg gaaagatttt ttggcagaca gggagaaata aggagaggca   1860
acttggagaa ggggcttaga atgaggccta gaagagcagt aaggggcaaa cagtctgagc   1920
aaaggcaggc aggcaggaac tcagttggag agactgaggc tgggccacgt gccctctcct   1980
gccaccttct cttcatctgc ttttttcccg tgtcattctc tggactgcca gaacaaggct   2040 cactgttct tagtaaaaag agggttttgg tggcaatgga taaggccgag accaccaatc   2100
agaggagttt tagacatcat tgaccagagc tctgggcaga acctggccat tcctgaagca   2160
aggaaacagc ctgcgaaggc accaaagctg cccttacctg ggctggggaa gaaggtgtct   2220
tctggaataa tgctgttgtt gaaggcgttt gcacatgcaa agtcagattt gttgctctag   2280
attgcggccg catgaattct tgctccaggc cacagcactg ttgctcttga agtccataga   2340
cctcatgtct agcacagttt tgtctgtgat atacacatca gaatccttac tttgtgacac   2400
atttgtttga gaatcaaaat cggtgaatag gcagacagac ttgtcactgg atttagagtc   2460
tctcagctgg tacacggcag ggtcagggtt ctggatatct gtgggacaag aggatcaggg   2520
ttaggacatg atctcatttc cctctttgcc ccaacccagg ctggagtcca gatgccagtg   2580
atggacaagg gcgggctct gtggggctgg caagtcacgg tctcatgctt tatacgggaa   2640
atagcatctt agaaaccagc tgctcgtgat ggactgggac tcagggacag gcacaagcta   2700
tcaatcttgg ccaagaggcc atgatttcag tgaacgttca cggccaggcc tggcctgcca   2760
ctcaaggaaa cctgaaatgc agggctactt aataatactg cttattcttt tatttaatag   2820
gatcttcttc aaaccccag caatataact ctggcagagt aaaggcaggc atgggaaaaa   2880
ggcccagcaa agcaaactgt acatcttgga atctggagtg gtctccccaa cttaggctgg   2940
```

```
gcattagcag aatgggaggt ttatggtatg ttggcattaa gttgggaaat ctatcacatt    3000
accaggagat tgctctctca ttgatagagg ttttgaacta taaatcagaa cacctgcgtc    3060
taagccccag cgcaattgtt gttgttaact tgtttattgc agcttataat ggttacaaat    3120
aaagcaatag catcacaaat ttcacaaata aagcattttt ttcactgcat tctagttgtg    3180
gtttgtccaa actcatcaat gtatcttaag gcgggaattg atctaggaac ccctagtgat    3240
ggagttggcc actccctctc tgcgcgctcg ctcgctcact gaggccgccc gggcaaagcc    3300
cgggcgtcgg gcgacctttg gtcgcccggc ctcagtgagc gagcgagcgc gcagagaggg    3360
agtggccaac ccccccccc cccccccggc gattctcttg tttgctccag actctcaggc    3420
aatgacctga tagcctttgt agagacctct caaaaatagc taccctctcc ggcatgaatt    3480
tatcagctag aacggttgaa tatcatattg atggtgattt gactgtctcc ggcctttctc    3540
acccgtttga atctttacct acacattact caggcattgc atttaaaata tatgagggtt    3600 ctaaaattt ttatccttgc gttgaaataa aggcttctcc cgcaaaagta ttacagggtc    3660
ataatgtttt tggtacaacc gatttagctt tatgctctga ggcttattg cttaattttg    3720 ctaattcttt gccttgcctg tatgatttat tggatgttgg aattcctgat gcggtatttt    3780
ctccttacgc atctgtgcgg tatttcacac cgcatatggt gcactctcag tacaatctgc    3840
tctgatgccg catagttaag ccagccccga cacccgccaa cacccgctga cgcgccctga    3900
cgggcttgtc tgctcccggc atccgcttac agacaagctg tgaccgtctc cgggagctgc    3960
atgtgtcaga ggttttcacc gtcatcaccg aaacgcgcga gacgaaaggg cctcgtgata    4020
cgcctatttt tataggttaa tgtcatgata ataatggttt cttagacgtc aggtggcact    4080
tttcggggaa atgtgcgcgg aaccccctatt tgtttatttt tctaaataca ttcaaatatg    4140
tatccgctca tgagacaata accctgataa atgcttcaat aatattgaaa aaggaagagt    4200
atgagtattc aacatttccg tgtcgccctt attccctttt ttgcggcatt ttgccttcct    4260
gtttttgctc acccagaaac gctggtgaaa gtaaaagatg ctgaagatca gttgggtgca    4320
cgagtgggtt acatcgaact ggatctcaac agcggtaaga tccttgagag ttttcgcccc    4380
gaagaacgtt ttccaatgat gagcactttt aaagttctgc tatgtggcgc ggtattatcc    4440
cgtattgacg ccgggcaaga gcaactcggt cgccgcatac actattctca gaatgacttg    4500
gttgagtact caccagtcac agaaaagcat cttacggatg gcatgacagt aagagaatta    4560
tgcagtgctg ccataaccat gagtgataac actgcggcca acttacttct gacaacgatc    4620
ggaggaccga aggagctaac cgcttttttg cacaacatgg gggatcatgt aactcgcctt    4680
gatcgttggg aaccggagct gaatgaagcc ataccaaacg acgagcgtga ccacgatg    4740 cctgtagcaa tggcaacaac gttgcgcaaa ctattaactg gcgaactact tactctagct    4800
tcccggcaac aattaataga ctggatggag gcggataaag ttgcaggacc acttctgcgc    4860
tcggcccttc cggctggctg gtttattgct gataaatctg gagccggtga gcgtgggtct    4920
cgcggtatca ttgcagcact ggggccagat ggtaagccct cccgtatcgt agttatctac    4980
acgacgggga gtcaggcaac tatggatgaa cgaaatagac agatcgctga gataggtgcc    5040
tcactgatta gcattggta actgtcagac caagtttact catatatact ttagattgat    5100
ttaaaacttc atttttaatt taaaaggatc taggtgaaga tcctttttga taatctcatg    5160
accaaaatcc cttaacgtga gttttcgttc cactgagcgt cagaccccgt agaaaagatc    5220
aaaggatctt cttgagatcc ttttttttctg cgcgtaatct gctgcttgca acaaaaaaa    5280 ccaccgctac cagcggtggt ttgtttgccg gatcaagagc taccaactct ttttccgaag    5340
```

| | |
|---|---|
| gtaactggct tcagcagagc gcagatacca aatactgtcc ttctagtgta gccgtagtta | 5400 |
| ggccaccact tcaagaactc tgtagcaccg cctacatacc tcgctctgct aatcctgtta | 5460 |
| ccagtggctg ctgccagtgg cgataagtcg tgtcttaccg ggttggactc aagacgatag | 5520 |
| ttaccggata aggcgcagcg gtcgggctga acggggggtt cgtgcacaca gcccagcttg | 5580 |
| gagcgaacga cctacaccga actgagatac ctacagcgtg agctatgaga aagcgccacg | 5640 |
| cttcccgaag ggagaaaggc ggacaggtat ccggtaagcg gcagggtcgg aacaggagag | 5700 |
| cgcacgaggg agcttccagg gggaaacgcc tggtatcttt atagtcctgt cgggtttcgc | 5760 |
| cacctctgac ttgagcgtcg attttttgtga tgctcgtcag gggggcggag cctatggaaa | 5820 |
| aacgccagca acgcggcctt tttacggttc ctggcctttt gctggccttt tgctcacatg | 5880 |
| ttctttcctg cgttatcccc tgattctgtg gataaccgta ttaccgcctt tgagtgagct | 5940 |
| gataccgctc gccgcagccg aacgaccgag cgcagcgagt cagtgagcga ggaagcggaa | 6000 |
| gagcgcccaa tacgcaaacc gcctctcccc gcgcgttggc cgattcatta atg | 6053 |

<210> SEQ ID NO 108
<211> LENGTH: 5458
<212> TYPE: DNA
<213> ORGANISM: Artificial Sequence
<220> FEATURE:
<223> OTHER INFORMATION: Synthesized

<400> SEQUENCE: 108

| | |
|---|---|
| cagcagctgg cgtaatagcg aagaggcccg caccgatcgc ccttcccaac agttgcgcag | 60 |
| cctgaatggc gaatggaatt ccagacgatt gagcgtcaaa atgtaggtat ttccatgagc | 120 |
| gtttttcctg ttgcaatggc tggcggtaat attgttctgg atattaccag caaggccgat | 180 |
| agtttgagtt cttctactca ggcaagtgat gttattacta atcaaagaag tattgcgaca | 240 |
| acggttaatt tgcgtgatgg acagactctt ttactcggtg gcctcactga ttataaaaac | 300 |
| acttctcagg attctggcgt accgttcctg tctaaaatcc ctttaatcgg cctcctgttt | 360 |
| agctcccgct ctgattctaa cgaggaaagc acgttatacg tgctcgtcaa agcaaccata | 420 |
| gtacgcgccc tgtagcggcg cattaagcgc ggcgggtgtg gtggttacgc gcagcgtgac | 480 |
| cgctacactt gccagcgccc tagcgcccgc tcctttcgct ttcttccctt cctttctcgc | 540 |
| cacgttcgcc ggctttcccc gtcaagctct aaatcggggg ctcccttttag ggttccgatt | 600 |
| tagtgcttta cggcacctcg accccaaaaa acttgattag ggtgatggtt cacgtagtgg | 660 |
| gccatcgccc tgatagacgg ttttttcgccc tttgacgttg gagtccacgt tctttaatag | 720 |
| tggactcttg ttccaaactg gaacaacact caaccctatc tcggtctatt cttttgattt | 780 |
| ataagggatt ttgccgattt cggcctattg gttaaaaaat gagctgattt aacaaaaatt | 840 |
| taacgcgaat tttaacaaaa tattaacgtt tacaatttaa atatttgctt atacaatctt | 900 |
| cctgtttttg gggcttttct gattatcaac cgggtacat atgattgaca tgctagtttt | 960 |
| acgattaccg ttcatcgccc tgcgcgctcg ctcgctcact gaggccgccc gggcaaagcc | 1020 |
| cgggcgtcgg gcgacctttg gtcgcccggc ctcagtgagc gagcgagcgc gcagagaggg | 1080 |
| agtggaattc acgcgtgctt tctgggcaca cccctcatct gacttttaa ttcctccact | 1140 |
| tcaacacctg gtgcattcat gtgccggcac aatcagtgat tggtgggtta atgagtgact | 1200 |
| gcgtgagact gacttagtga gctgggaaag attttttggc agacagggag aaataaggag | 1260 |
| aggcaacttg gagaagggg cttagaatgag gcctagaaga gcagtaaggg gcaaacagtc | 1320 |

```
tgagcaaagg caggcaggca ggaactcagt tggagagact gaggctgggc cacgtgccct    1380
ctcctgccac cttctcttca tctgcttttt tcccgtgtca ttctctggac tgccagaaca    1440
aggctcactg tttcttagta aaaagagggt tttggtggca atggataagg ccgagaccac    1500
caatcagaga gtttagac atcattgacc agagctctgg gcagaacctg gccattcctg      1560
aagcaaggaa acagcctgcg aaggcaccaa agctgcccct acctgggctg gggaagaagg    1620
tgtcttctgg aataatgctg ttgttgaagg cgtttgcaca tgcaaagtca gatttgttgc    1680
tctagattgc ggccgcatga attcttgctc caggccacag cactgttgct cttgaagtcc    1740
atagacctca tgtctagcac agttttgtct gtgatataca catcagaatc cttactttgt    1800
gacacatttg tttgagaatc aaaatcggtg aataggcaga cagacttgtc actggattta    1860
gagtctctca gctggtacac ggcagggtca gggttctgga tatctgtggg acaagaggat    1920
cagggttagg acatgatctc atttccctct ttgccccaac ccaggctgga gtccagatgc    1980
cagtgatgga caagggcggg gctctgtggg gctggcaagt cacggtctca tgctttatac    2040
gggaaatagc atcttagaaa ccagctgctc gtgatggact gggactcagg acaggcaca    2100 agctatcaat cttggccaag aggccatgat tcagtgaac gttcacggcc aggcctggcc     2160
tgccactcaa ggaaacctga atgcaggc tacttaataa tactgcttat tcttttattt      2220
aataggatct tcttcaaaac cccagcaata taactctggc agagtaaagg caggcatggg    2280
aaaaaggccc agcaaagcaa actgtacatc ttggaatctg gagtggtctc cccaacttag    2340
gctgggcatt agcagaatgg gaggtttatg gtatgttggc attaagttgg gaaatctatc    2400
acattaccag gagattgctc tctcattgat agaggtttg aactataaat cagacacct      2460 gcgtctaagc cccagcgcaa ttgttgttgt taacttgttt attgcagctt ataatggtta    2520
caaataaagc aatagcatca caaatttcac aaataaagca ttttttttcac tgcattctag   2580 ttgtggtttg tccaaactca tcaatgtatc ttaaggcggg aattgatcta ggaacccta    2640 gtgatggagt tggccactcc ctctctgcgc gctcgctcgc tcactgaggc cgcccgggca    2700
aagcccgggc gtcgggcgac ctttggtcgc ccggcctcag tgagcgagcg agcgcgcaga    2760
gagggagtgg ccaacccccc ccccccccc cggcgattc tcttgtttgc tccagactct     2820
caggcaatga cctgatagcc tttgtagaga cctctcaaaa atagctaccc tctccggcat    2880
gaatttatca gctagaacgg ttgaatatca tattgatggt gatttgactg tctccggcct    2940
ttctcacccg tttgaatctt tacctacaca ttactcaggc attgcattta aaatatatga    3000
gggttctaaa aattttatc cttgcgttga aataaaggct tctcccgcaa agtattaca      3060 gggtcataat gttttggta caaccgattt agctttatgc tctgaggctt tattgcttaa     3120
ttttgctaat tctttgcctt gcctgtatga tttattggat gttggaattc ctgatgcggt    3180
attttctcct tacgcatctg tgcggtattt cacaccgcat atggtgcact ctcagtacaa    3240
tctgctctga tgccgcatag ttaagccagc cccgacaccc gccaacaccc gctgacgcgc    3300
cctgacgggc ttgtctgctc ccggcatccg cttacagaca agctgtgacc gtctccggga    3360
gctgcatgtg tcagaggttt tcaccgtcat caccgaaacg cgcgagacga agggcctcg    3420 tgatacgcct attttatag gttaatgtca tgataataat ggtttcttag acgtcaggtg     3480
gcacttttcg gggaaatgtg cgcggaaccc ctatttgttt attttctaa atacattcaa     3540 atatgtatcc gctcatgaga caataaccct gataaatgct tcaataatat tgaaaaagga    3600
agagtatgag tattcaacat ttccgtgtcg cccttattcc cttttttgcg gcattttgcc    3660
ttcctgtttt tgctcaccca gaaacgctgg tgaaagtaaa agatgctgaa gatcagttgg    3720
```

-continued

| | |
|---|---|
| gtgcacgagt gggttacatc gaactggatc tcaacagcgg taagatcctt gagagttttc | 3780 |
| gccccgaaga acgttttcca atgatgagca cttttaaagt tctgctatgt ggcgcggtat | 3840 |
| tatcccgtat tgacgccggg caagagcaac tcggtcgccg catacactat tctcagaatg | 3900 |
| acttggttga gtactcacca gtcacagaaa agcatcttac ggatggcatg acagtaagag | 3960 |
| aattatgcag tgctgccata accatgagtg ataacactgc ggccaactta cttctgacaa | 4020 |
| cgatcggagg accgaaggag ctaaccgctt ttttgcacaa catggggat catgtaactc | 4080 |
| gccttgatcg ttgggaaccg gagctgaatg aagccatacc aaacgacgag cgtgacacca | 4140 |
| cgatgcctgt agcaatggca acaacgttgc gcaaactatt aactggcgaa ctacttactc | 4200 |
| tagcttcccg gcaacaatta atagactgga tggaggcgga taaagttgca ggaccacttc | 4260 |
| tgcgctcggc ccttccggct ggctggttta ttgctgataa atctggagcc ggtgagcgtg | 4320 |
| ggtctcgcgg tatcattgca gcactggggc cagatggtaa gccctcccgt atcgtagtta | 4380 |
| tctacacgac ggggagtcag gcaactatgg atgaacgaaa tagacagatc gctgagatag | 4440 |
| gtgcctcact gattaagcat tggtaactgt cagaccaagt ttactcatat atactttaga | 4500 |
| ttgatttaaa acttcatttt taatttaaaa ggatctaggt gaagatcctt tttgataatc | 4560 |
| tcatgaccaa aatcccttaa cgtgagtttt cgttccactg agcgtcagac cccgtagaaa | 4620 |
| agatcaaagg atcttcttga gatccttttt ttctgcgcgt aatctgctgc ttgcaaacaa | 4680 |
| aaaaaccacc gctaccagcg gtggtttgtt tgccggatca agagctacca actctttttc | 4740 |
| cgaaggtaac tggcttcagc agagcgcaga taccaaatac tgtccttcta gtgtagccgt | 4800 |
| agttaggcca ccacttcaag aactctgtag caccgcctac atacctcgct ctgctaatcc | 4860 |
| tgttaccagt ggctgctgcc agtggcgata agtcgtgtct taccgggttg gactcaagac | 4920 |
| gatagttacc ggataaggcg cagcggtcgg gctgaacggg gggttcgtgc acacagccca | 4980 |
| gcttggagcg aacgacctac accgaactga gatacctaca gcgtgagcta tgagaaagcg | 5040 |
| ccacgcttcc cgaagggaga aaggcggaca ggtatccggt aagcggcagg gtcggaacag | 5100 |
| gagagcgcac gagggagctt ccagggggaa acgcctggta tctttatagt cctgtcgggt | 5160 |
| ttcgccacct ctgacttgag cgtcgatttt tgtgatgctc gtcaggggggg cggagcctat | 5220 |
| ggaaaaacgc cagcaacgcg gccttttac ggttcctggc cttttgctgg ccttttgctc | 5280 |
| acatgttctt cctgcgtta tcccctgatt ctgtggataa ccgtattacc gcctttgagt | 5340 |
| gagctgatac cgctcgccgc agccgaacga ccgagcgcag cgagtcagtg agcgaggaag | 5400 |
| cggaagagcg cccaatacgc aaaccgcctc tccccgcgcg ttggccgatt cattaatg | 5458 |

<210> SEQ ID NO 109
<211> LENGTH: 6082
<212> TYPE: DNA
<213> ORGANISM: Artificial Sequence
<220> FEATURE:
<223> OTHER INFORMATION: Synthesized

<400> SEQUENCE: 109

| | |
|---|---|
| cagcagctgg cgtaatagcg aagaggcccg caccgatcgc ccttcccaac agttgcgcag | 60 |
| cctgaatggc gaatggaatt ccagacgatt gagcgtcaaa atgtaggtat ttccatgagc | 120 |
| gttttttcctg ttgcaatggc tggcggtaat attgttctgg atattaccag caaggccgat | 180 |
| agtttgagtt cttctactca ggcaagtgat gttattacta atcaaagaag tattgcgaca | 240 |
| acggttaatt tgcgtgatgg acagactctt ttactcggtg gcctcactga ttataaaaac | 300 |

```
acttctcagg attctggcgt accgttcctg tctaaaatcc ctttaatcgg cctcctgttt      360
agctcccgct ctgattctaa cgaggaaagc acgttatacg tgctcgtcaa agcaaccata      420
gtacgcgccc tgtagcggcg cattaagcgc ggcgggtgtg gtggttacgc gcagcgtgac      480
cgctacactt gccagcgccc tagcgcccgc tcctttcgct ttcttccctt cctttctcgc      540
cacgttcgcc ggctttcccc gtcaagctct aaatcggggg ctcccttag ggttccgatt       600 tagtgcttta cggcacctcg accccaaaaa acttgattag ggtgatggtt cacgtagtgg      660
gccatcgccc tgatagacgg ttttcgccc tttgacgttg gagtccacgt tctttaatag       720
tggactcttg ttccaaactg gaacaacact caaccctatc tcggtctatt cttttgattt      780
ataagggatt ttgccgattt cggcctattg gttaaaaaat gagctgattt aacaaaaatt      840
taacgcgaat tttaacaaaa tattaacgtt tacaatttaa atatttgctt atacaatctt      900 cctgttttg gggcttttct gattatcaac cggggtacat atgattgaca tgctagtttt       960
acgattaccg ttcatcgccc tgcgcgctcg ctcgctcact gaggccgccc gggcaaagcc      1020
cgggcgtcgg gcgaccttg tcgcccggc ctcagtgagc gagcgagcgc gcagagaggg        1080
agtggaattc acgcgtactg gcatctggac tccagcctgg gttggggcaa agagggaaat     1140
gagatcatgt cctaaccctg atcctcttgt cccacagata tccagaaccc tgaccctgcc      1200
gtgtaccagc tgagagactc taaatccagt gacaagtctg tctgcctatt caccgatttt     1260
gattctcaaa caaatgtgtc acaaagtaag gattctgatg tgtatatcac agacaaaact     1320
gtgctagaca tgaggtctat ggacttcaag agcaacagtg ctgtggcctg gagcaactag     1380
tgggcagagc gcacatcgcc cacagtcccc gagaagttgg ggggagggt cggcaattga      1440 accggtgcct agagaaggtg gcgcggggta aactgggaaa gtgatgtcgt gtactggctc    1500 cgccttttc ccgagggtgg gggagaaccg tatataagtg cagtagtcgc cgtgaacgtt      1560 cttttttcgca acgggtttgc cgccagaaca cagctagcac catggcgctc ccagtgacag   1620
ccttactttt acctctggcg ttattattgc acgcggctcg tcctgacata cagatgactc     1680
agactacctc ttccctatct gcttctttag gcgaccgagt aacaatatct tgccgggca    1740 gccaggacat ctcaaaatac ttaaactggt atcagcagaa gccggacgga acagttaagt   1800
tgctcattta ccacacgtcg agattacact caggcgttcc tagccgattt cgggttccg     1860 gttccggtac ggactacagc ctgacaatca gtaaccttga gcaggaggac atcgccacct     1920
acttctgtca gcagggcaac acgctcccgt acacattcgg tggggaact aagctggaga     1980 ttaccggagg cggtggcagc ggtggcggcg gcagcggggg tggcggctcg gaggtcaagt    2040
tacaggagag cggaccgggc ttggtcgcac ctagccagag cctctcagtc acgtgcactg    2100
tgtctggagt cagtctccca gactacgggg tatcatggat acgacagccg cctagaaagg    2160
gcttagagtg gctgggggtt atctggggaa gtgaaaccac atactacaac tcagctctca    2220
agagccgcct caccatcatt aaggacaaca gtaagtcgca ggttttctta aagatgaact    2280
ctctccagac tgacgacacc gctatttact actgcgcgaa gcactactac tacggcggga    2340
gttacgcaat ggactactgg ggtcagggca cttctgtgac cgtatccagc actactaccc    2400
cagccccacg tccccccacg ccagctccaa cgatagcaag tcagcccta tctcttcgcc    2460 ctgaggcttg caggcccgcg gcgggcggcg ccgttcacac gcgaggacta gacttcgcct    2520
gcgacatcta catctgggca ccactagccg ggacttgcgg agtgttgttg ttgagcttgg    2580
taataacgct ctactgcaag cgtgggagaa agaagctctt gtacattttc aagcagccat    2640
tcatgcgtcc cgttcagacg actcaggagg aggacggctg ctcgtgccga ttcccggagg    2700
```

```
aggaggaggg cggttgcgaa ctcagagtga agttctctcg ctccgcggac gcacccgctt    2760
accagcaggg tcagaaccag ctatacaacg agttaaacct ggggcgccgg gaggagtacg    2820
acgtgttaga caagcgtaga ggtagggacc cggagatggg aggcaagcct cggagaaaga    2880
accccaggg gggcctgtac aacgaactcc agaaggacaa gatggctgag gcgtactcgg    2940
agattggtat gaagggcgag agacgtcgcg gaaagggaca cgacggctta taccaggggc    3000
tttccaccgc gaccaaggac acatacgacg cgctgcacat gcaagcctta ccacctcgat    3060
gataagatac attgatgagt ttggacaaac cacaactaga atgcagtgaa aaaaatgctt    3120
tatttgtgaa atttgtgatg ctattgcttt atttgtaacc attataagct gcaataaaca    3180
agttctagag caacaaatct gactttgcat gtgcaaacgc cttcaacaac agcattattc    3240
cagaagacac cttcttcccc agcccaggta agggcagctt tggtgccttc aattgcctct    3300
ctgcgcgctc gctcgctcac tgaggccgcc cgggcaaagc ccgggcgtcg ggcgaccttt    3360
ggtcgcccgg cctcagtgag cgagcgagcg cgcagagagg gagtggccaa ccccggcgat    3420
tctcttgttt gctccagact ctcaggcaat gacctgatag cctttgtacc tgcaggtctc    3480
aaaaatagct accctctccg gcatgaattt atcagctaga acggttgaat atcatattga    3540
tggtgatttg actgtctccg gcctttctca cccgtttgaa tctttaccta cacattactc    3600
aggcattgca tttaaaatat atgagggttc taaaaatttt tatccttgcg ttgaaataaa    3660
ggcttctccc gcaaaagtat tacagggtca taatgttttt ggtacaaccg atttagcttt    3720
atgctctgag gctttattgc ttaattttgc taattctttg ccttgcctgt atgatttatt    3780
ggatgttgga attcctgatg cggtattttc tccttacgca tctgtgcggt atttcacacc    3840
gcatatggtg cactctcagt acaatctgct ctgatgccgc atagttaagc cagccccgac    3900
acccgccaac acccgctgac gcgccctgac gggcttgtct gctcccggca tccgcttaca    3960
gacaagctgt gaccgtctcc gggagctgca tgtgtcagag gttttcaccg tcatcaccga    4020
aacgcgcgag acgaaagggc ctcgtgatac gcctattttt ataggttaat gtcatgataa    4080
taatggtttc ttagacgtca ggtggcactt ttcggggaaa tgtgcgcgga acccctattt    4140
gtttattttt ctaaatacat tcaaatatgt atccgctcat gagacaataa ccctgataaa    4200
tgcttcaata atattgaaaa aggaagagta tgagtattca acatttccgt gtcgccctta    4260
ttcccttttt tgcggcattt tgccttcctg tttttgctca cccagaaacg ctggtgaaag    4320
taaaagatgc tgaagatcag ttgggtgcac gagtgggtta catcgaactg gatctcaaca    4380
gcggtaagat ccttgagagt tttcgccccg aagaacgttt tccaatgatg agcacttta    4440
aagttctgct atgtggcgcg gtattatccc gtattgacgc cgggcaagag caactcggtc    4500
gccgcataca ctattctcag aatgacttgg ttgagtactc accagtcaca gaaaagcatc    4560
ttacggatgg catgacagta agagaattat gcagtgctgc cataaccatg agtgataaca    4620
ctgcggccaa cttacttctg acaacgatcg gaggaccgaa ggagctaacc gcttttttgc    4680
acaacatggg ggatcatgta actcgccttg atcgttggga accggagctg aatgaagcca    4740
taccaaacga cgagcgtgac accacgatgc ctgtagcaat ggcaacaacg ttgcgcaaac    4800
tattaactgg cgaactactt actctagctt cccggcaaca attaatagac tggatggagg    4860
cggataaagt tgcaggacca cttctgcgct cggcccttcc ggctggctgg tttattgctg    4920
ataaatctgg agccggtgag cgtgggtctc gcggtatcat tgcagcactg gggccagatg    4980
gtaagccctc ccgtatcgta gttatctaca cgacggggag tcaggcaact atggatgaac    5040
```

| | |
|---|---|
| gaaatagaca gatcgctgag ataggtgcct cactgattaa gcattggtaa ctgtcagacc | 5100 |
| aagtttactc atatatactt tagattgatt taaaacttca ttttaattt aaaaggatct | 5160 |
| aggtgaagat cctttttgat aatctcatga ccaaaatccc ttaacgtgag ttttcgttcc | 5220 |
| actgagcgtc agaccccgta gaaaagatca aaggatcttc ttgagatcct ttttttctgc | 5280 |
| gcgtaatctg ctgcttgcaa acaaaaaaac caccgctacc agcggtggtt tgtttgccgg | 5340 |
| atcaagagct accaactctt tttccgaagg taactggctt cagcagagcg cagataccaa | 5400 |
| atactgtcct tctagtgtag ccgtagttag gccaccactt caagaactct gtagcaccgc | 5460 |
| ctacatacct cgctctgcta atcctgttac cagtggctgc tgccagtggc gataagtcgt | 5520 |
| gtcttaccgg gttggactca agacgatagt taccggataa ggcgcagcgg tcgggctgaa | 5580 |
| cggggggttc gtgcacacag cccagcttgg agcgaacgac ctacaccgaa ctgagatacc | 5640 |
| tacagcgtga gctatgagaa agcgccacgc ttcccgaagg gagaaaggcg gacaggtatc | 5700 |
| cggtaagcgg cagggtcgga acaggagagc gcacgaggga gcttccaggg ggaaacgcct | 5760 |
| ggtatcttta tagtcctgtc gggtttcgcc acctctgact tgagcgtcga ttttgtgat | 5820 |
| gctcgtcagg gggcggagc ctatggaaaa acgccagcaa cgcggccttt ttacggttcc | 5880 |
| tggccttttg ctggccttt gctcacatgt tctttcctgc gttatcccct gattctgtgg | 5940 |
| ataaccgtat taccgccttt gagtgagctg ataccgctcg ccgcagccga acgaccgagc | 6000 |
| gcagcgagtc agtgagcgag gaagcggaag agcgcccaat acgcaaaccg cctctccccg | 6060 |
| cgcgttggcc gattcattaa tg | 6082 |

<210> SEQ ID NO 110
<211> LENGTH: 7887
<212> TYPE: DNA
<213> ORGANISM: Artificial Sequence
<220> FEATURE:
<223> OTHER INFORMATION: Synthesized

<400> SEQUENCE: 110

| | |
|---|---|
| cagcagctgg cgtaatagcg aagaggcccg caccgatcgc ccttcccaac agttgcgcag | 60 |
| cctgaatggc gaatggaatt ccagacgatt gagcgtcaaa atgtaggtat ttccatgagc | 120 |
| gttttttcctg ttgcaatggc tggcggtaat attgttctgg atattaccag caaggccgat | 180 |
| agtttgagtt cttctactca ggcaagtgat gttattacta atcaaagaag tattgcgaca | 240 |
| acggttaatt tgcgtgatgg acagactctt ttactcggtg gcctcactga ttataaaaac | 300 |
| acttctcagg attctggcgt accgttcctg tctaaaatcc ctttaatcgg cctcctgttt | 360 |
| agctcccgct ctgattctaa cgaggaaagc acgttatacg tgctcgtcaa agcaaccata | 420 |
| gtacgcgccc tgtagcggcg cattaagcgc ggcgggtgtg gtggttacgc gcagcgtgac | 480 |
| cgctacactt gccagcgccc tagcgcccgc tcctttcgct ttcttccctt cctttctcgc | 540 |
| cacgttcgcc ggctttcccc gtcaagctct aaatcggggg ctcccttag ggttccgatt | 600 |
| tagtgcttta cggcacctcg accccaaaaa acttgattag ggtgatggtt cacgtagtgg | 660 |
| gccatcgccc tgatagacgg ttttcgccc tttgacgttg gagtccacgt tctttaatag | 720 |
| tggactcttg ttccaaactg gaacaacact caacccatc tcgtctatt cttttgattt | 780 |
| ataagggatt ttgccgattt cggcctattg gttaaaaaat gagctgattt aacaaaaatt | 840 |
| taacgcgaat tttaacaaaa tattaacgtt tacaatttaa atatttgctt atacaatctt | 900 |
| cctgtttttg ggcttttct gattatcaac cggggtacat atgattgaca tgctagtttt | 960 |
| acggcgcgcc gggttggcca ctccctctct gcgcgctcgc tcgctcactg aggccgggcg | 1020 |

```
accaaaggtc gcccgacgcc cgggctttgc ccgggcggcc tcagtgagcg agcgagcgcg    1080
cagagaggga gtggccaact ccatcactag gggttcctac gcgtagatct catattctgg    1140
cagggtcagt ggctccaact aacatttgtt tggtacttta cagtttatta aatagatgtt    1200
tatatggaga agctctcatt tctttctcag aagagcctgg ctaggaaggt ggatgaggca    1260
ccatattcat tttgcaggtg aaattcctga gatgtaagga gctgctgtga cttgctcaag    1320
gccttatatc aagtaaacgg tagcgctggg gcttagacgc aggtgttctg atttatagtt    1380
caaaacctct atcaatgaga gagcaatctc ctggtaatgt gatagatttc caacttaat     1440 gccaacatac cataaacctc ccattctgct aatgcccagc ctaagttggg gagaccactc    1500
cagattccaa gatgtacagt ttgctttgct gggccttttt cccatgcctg cctttactct    1560
gccagagtta tattgctggg gttttgaaga agatcctatt aaataaaaga ataagcagta    1620
ttattaagta gccctgcatt tcaggtttcc ttgagtggca ggccaggcct ggccgtgaac    1680
gttcactgaa atcatggcct cttggccaag attgatagct tgtgcctgtc cctgagtccc    1740
agtccatcac gagcagctgg tttctaagat gctatttccc gtataaagca tgagaccgtg    1800
acttgccagc cccacagagc cccgcccttg tccatcactg gcatctggac tccagcctgg    1860
gttggggcaa agagggaaat gagatcatgt cctaaccctg atcctcttgt cccacagata    1920
tccagaaccc tgaccctgcc gtgtaccagc tgagagactc taaatccagt gacaagtctg    1980
tctgcctatt caccgatttt gattctcaaa caaatgtgtc acaaagtaag gattctgatg    2040
tgtatatcac agacaaaact gtgctagaca tgaggtctat ggacttcaag agcaacagtg    2100
ctgtggcctg gagcaactag tggatctgcg atcgctccgg tgcccgtcag tgggcagagc    2160
gcacatcgcc cacagtcccc gagaagttgg ggggaggggt cggcaattga acgggtgcct    2220
agagaaggtg gcgcggggta aactgggaaa gtgatgtcgt gtactggctc cgccttttc     2280 ccgagggtgg gggagaaccg tatataagtg cagtagtcgc cgtgaacgtt cttttcgca    2340 acgggtttgc cgccagaaca cagctgaagc ttcgagggc tcgcatctct ccttcacgcg     2400
cccgccgccc tacctgaggc cgccatccac gccggttgag tcgcgttctg ccgcctcccg    2460
cctgtggtgc ctcctgaact gcgtccgccg tctaggtaag tttaaagctc aggtcgagac    2520
cgggcctttg tccggcgctc ccttggagcc tacctagact cagccggctc tccacgcttt    2580 gcctgacccct gcttgctcaa ctctacgtct ttgtttcgtt ttctgttctg cgccgttaca    2640
gatccaagct gtgaccggcg cctactctag agctagcgca gtcagtgctt ctgacacaac    2700
agtctcgaac ttaactagca ccatggcgct cccagtgaca gccttacttt tacctctggc    2760
gttattattg cacgcggctc gtcctgacat acagatgact cagactacct cttccctatc    2820
tgcttcttta ggcgaccgag taacaatatc ttgccgggcc agccaggaca tctcaaaata    2880
cttaaactgg tatcagcaga agccggacgg aacagttaag ttgctcattt accacacgtc    2940
gagattacac tcaggcgttc ctagccgatt ttcgggttcc ggttccggta cggactacag    3000
cctgacaatc agtaaccttg agcaggagga catcgccacc tacttctgtc agcagggcaa    3060
cacgctcccg tacacattcg gtgggggaac taagctggag attaccggag gcggtggcag    3120
cggtggcggc ggcagcgggg gtggcggctc ggaggtcaag ttacaggaga gcggaccggg    3180
cttggtcgca cctagccaga gcctctcagt cacgtgcact gtgtctggag tcagtctccc    3240
agactacggg gtatcatgga tacgacagcc gcctagaaag ggcttagagt ggctgggggt    3300
tatctgggga agtgaaacca catactacaa ctcagctctc aagagccgcc tcaccatcat    3360
```

```
taaggacaac agtaagtcgc aggttttctt aaagatgaac tctctccaga ctgacgacac    3420
cgctatttac tactgcgcga agcactacta ctacggcggg agttacgcaa tggactactg    3480
gggtcagggc acttctgtga ccgtatccag cactactacc ccagcccac gtcccccac     3540
gccagctcca acgatagcaa gtcagccctt atctcttcgc cctgaggctt gcaggcccgc    3600
ggcgggcggc gccgttcaca cgcgaggact agacttcgcc tgcgacatct acatctgggc    3660
accactagcc gggacttgcg gagtgttgtt gttgagcttg gtaataacgc tctactgcaa    3720
gcgtgggaga aagaagctct tgtacatttt caagcagcca ttcatgcgtc ccgttcagac    3780
gactcaggag gaggacggct gctcgtgccg attcccggag gaggaggagg gcggttgcga    3840
actcagagtg aagttctctc gctccgcgga cgcacccgct taccagcagg gtcagaacca    3900
gctatacaac gagttaaacc tggggcgccg ggaggagtac gacgtgttag acaagcgtag    3960
aggtagggac ccggagatgg gaggcaagcc tcggagaaag aaccccccagg agggcctgta    4020
caacgaactc cagaaggaca agatggctga ggcgtactcg gagattggta tgaagggcga    4080
gagacgtcgc ggaaagggac acgacggctt ataccagggg ctttccaccg cgaccaagga    4140
cacatacgac gcgctgcaca tgcaagcctt accacctcga tgaggtacca gcggccgctt    4200
cgagcagaca tgataagata cattgatgag tttggacaaa ccacaactag aatgcagtga    4260
aaaaaatgct ttatttgtga aatttgtgat gctattgctt tatttgtaac cattataagc    4320
tgcaataaac aagttaacaa caacaattcg aatttaaatc ggatccgcaa caaatctgac    4380
tttgcatgtg caaacgcctt caacaacagc attattccag aagacacctt cttccccagc    4440
ccaggtaagg gcagctttgg tgccttcgca ggctgtttcc ttgcttcagg aatggccagg    4500
ttctgcccag agctctggtc aatgatgtct aaaactcctc tgattggtgg tctcggcctt    4560
atccattgcc accaaaaccc tcttttttact aagaaacagt gagccttgtt ctggcagtcc    4620
agagaatgac acgggaaaaa agcagatgaa gagaaggtgg caggagaggg cacgtggccc    4680
agcctcagtc tctccaactg agttcctgcc tgcctgcctt tgctcagact gttttgcccct    4740
tactgctctt ctaggcctca ttctaagccc cttctccaag ttgcctctcc ttatttctcc    4800
ctgtctgcca aaaaatcttt cccagctcac taagtcagtc tcacgcagtc actcattaac    4860
ccaccaatca ctgattgtgc cggcacatga atgcaccagg tgttgaagtg gaggaattaa    4920
aaagtcagat gaggggtgtg cccagaggaa gcaccattct agttggggga gcccatctgt    4980
cagctgggaa aagtccaaat aacttcagat tggaatgtgt tttaactcag ggttgagaaa    5040
acagccacct tcaggacaaa agtcaggaa gggctctctg aagaaatgct acttgaagat    5100
accagcccta ccaagggcag ggagaggacc aattgatgga gttggccact ccctctctgc    5160
gcgctcgctc gctcactgag gccgcccggg caaagcccgg gcgtcgggcg acctttggtc    5220
gcccggcctc agtgagcgag cgagcgcgca gagagggagt ggccaacggc gcgcctgcag    5280
gtctcaaaaa tagctacccct ctccggcatg aatttatcag ctagaacggt tgaatatcat    5340
attgatggtg atttgactgt ctccggcctt tctcacccgt ttgaatcttt acctacacat    5400
tactcaggca ttgcatttaa aatatatgag ggttctaaaa attttttatcc ttgcgttgaa    5460
ataaaggctt ctcccgcaaa agtattacag ggtcataatg ttttttggtac aaccgattta    5520
gctttatgct ctgaggcttt attgcttaat tttgctaatt ctttgccttg cctgtatgat    5580
ttattggatg ttggaattcc tgatgcggta ttttctcctt acgcatctgt gcggtatttc    5640
acaccgcata tggtgcactc tcagtacaat ctgctctgat gccgcatagt taagccagcc    5700
ccgacacccg ccaacacccg ctgacgcgcc ctgacgggct tgtctgctcc cggcatccgc    5760
```

```
ttacagacaa gctgtgaccg tctccgggag ctgcatgtgt cagaggtttt caccgtcatc   5820
accgaaacgc gcgagacgaa agggcctcgt gatacgccta tttttatagg ttaatgtcat   5880
gataataatg gtttcttaga cgtcaggtgg cacttttcgg ggaaatgtgc gcggaaccc    5940 tatttgttta ttttctaaa tacattcaaa tatgtatccg ctcatgagac aataaccctg    6000
ataaatgctt caataatatt gaaaaggaa gagtatgagt attcaacatt tccgtgtcgc    6060
ccttattccc ttttttgcgg catttt gcct tcctgttttt gctcacccag aaacgctggt   6120
gaaagtaaaa gatgctgaag atcagttggg tgcacgagtg ggttacatcg aactggatct   6180
caacagcggt aagatccttg agagttttcg ccccgaagaa cgttttccaa tgatgagcac   6240
ttttaaagtt ctgctatgtg gcgcggtatt atcccgtatt gacgccgggc aagagcaact   6300
cggtcgccgc atacactatt ctcagaatga cttggttgag tactcaccag tcacagaaaa   6360
gcatcttacg gatggcatga cagtaagaga attatgcagt gctgccataa ccatgagtga   6420
taacactgcg gccaacttac ttctgacaac gatcggagga ccgaaggagc taaccgcttt   6480
tttgcacaac atgggggatc atgtaactcg ccttgatcgt tgggaaccgg agctgaatga   6540
agccatacca aacgacgagc gtgacaccac gatgcctgta gcaatggcaa caacgttgcg   6600
caaactatta actggcgaac tacttactct agcttcccgg caacaattaa tagactggat   6660
ggaggcggat aaagttgcag gaccacttct gcgctcggcc cttccggctg gctggtttat   6720
tgctgataaa tctggagccg gtgagcgtgg gtctcgcggt atcattgcag cactggggcc   6780
agatggtaag ccctcccgta tcgtagttat ctacacgacg gggagtcagg caactatgga   6840
tgaacgaaat agacagatcg ctgagatagg tgcctcactg attaagcatt ggtaactgtc   6900
agaccaagtt tactcatata ctttagat tgatttaaaa cttcattttt aatttaaaag   6960
gatctaggtg aagatccttt ttgataatct catgaccaaa atcccttaac gtgagttttc   7020
gttccactga gcgtcagacc ccgtagaaaa gatcaaagga tcttcttgag atccttttt    7080 tctgcgcgta atctgctgct tgcaaacaaa aaaaccaccg ctaccagcgg tggtttgttt   7140
gccggatcaa gagctaccaa ctcttttttcc gaaggtaact ggcttcagca gagcgcagat   7200
accaaatact gtccttctag tgtagccgta gttaggccac cacttcaaga actctgtagc   7260
accgcctaca tacctcgctc tgctaatcct gttaccagtg gctgctgcca gtggcgataa   7320
gtcgtgtctt accgggttgg actcaagacg atagttaccg gataaggcgc agcggtcggg   7380
ctgaacgggg ggttcgtgca cacagcccag cttggagcga acgacctaca ccgaactgag   7440
atacctacag cgtgagctat gagaaagcgc cacgcttccc gaaggagaa aggcggacag   7500 gtatccggta agcggcaggg tcggaacagg agagcgcacg agggagcttc caggggggaa   7560
cgcctggtat ctttatagtc ctgtcgggtt tcgccacctc tgacttgagc gtcgattttt   7620
gtgatgctcg tcaggggggc ggagcctatg gaaaaacgcc agcaacgcgg cctttttacg   7680
gttcctggcc ttttgctggc cttttgctca catgttcttt cctgcgttat cccctgattc   7740
tgtggataac cgtattaccg cctttgagtg agctgatacc gctcgccgca gccgaacgac   7800
cgagcgcagc gagtcagtga gcgaggaagc ggaagagcgc ccaatacgca aaccgcctct   7860
ccccgcgcgt tggccgattc attaatg                                      7887

<210> SEQ ID NO 111
<211> LENGTH: 486
<212> TYPE: PRT
<213> ORGANISM: Artificial Sequence
<220> FEATURE:
```

<223> OTHER INFORMATION: Synthesized

<400> SEQUENCE: 111

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Ser Gly Gly Gly Gly Ser Glu
130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Gln Gln Gly Gln Asn Gln Leu Tyr Asn Glu Leu Asn Leu
385                 390                 395                 400
```

-continued

```
Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 112
<211> LENGTH: 242
<212> TYPE: PRT
<213> ORGANISM: Artificial Sequence
<220> FEATURE:
<223> OTHER INFORMATION: Synthesized

<400> SEQUENCE: 112

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Ser Glu Val Lys Leu Gln Glu
            115                 120                 125

Ser Gly Pro Gly Leu Val Ala Pro Ser Gln Ser Leu Ser Val Thr Cys
    130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
225                 230                 235                 240

Ser Ser

<210> SEQ ID NO 113
<211> LENGTH: 112
<212> TYPE: PRT
```

<213> ORGANISM: Artificial Sequence
<220> FEATURE:
<223> OTHER INFORMATION: Synthesized

<400> SEQUENCE: 113

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 114
<211> LENGTH: 42
<212> TYPE: PRT
<213> ORGANISM: Artificial Sequence
<220> FEATURE:
<223> OTHER INFORMATION: Synthesized

<400> SEQUENCE: 114

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 115
<211> LENGTH: 21
<212> TYPE: PRT
<213> ORGANISM: Artificial Sequence
<220> FEATURE:
<223> OTHER INFORMATION: Synthesized

<400> SEQUENCE: 115

Met Ala Leu Pro Val Thr Ala Leu Leu Leu Pro Leu Ala Leu Leu Leu
1               5                   10                  15

His Ala Ala Arg Pro
            20

<210> SEQ ID NO 116
<211> LENGTH: 45
<212> TYPE: PRT
<213> ORGANISM: Artificial Sequence
<220> FEATURE:
<223> OTHER INFORMATION: Synthesized

<400> SEQUENCE: 116

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp

<210> SEQ ID NO 117
<211> LENGTH: 24
<212> TYPE: PRT
<213> ORGANISM: Artificial Sequence
<220> FEATURE:
<223> OTHER INFORMATION: Synthesized

<400> SEQUENCE: 117

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 118
<211> LENGTH: 493
<212> TYPE: DNA
<213> ORGANISM: Artificial Sequence
<220> FEATURE:
<223> OTHER INFORMATION: Synthesized

<400> SEQUENCE: 118
gggcagagcg cacatcgccc acagtccccg agaagttggg gggaggggtc ggcaattgaa      60
cgggtgccta gagaaggtgg cgcggggtaa actgggaaag tgatgtcgtg tactggctcc     120 gccttttttcc cgagggtggg ggagaaccgt atataagtgc agtagtcgcc gtgaacgttc    180
tttttcgcaa cgggtttgcc gccagaacac agctgaagct tcgaggggct cgcatctctc    240
cttcacgcgc ccgccgccct acctgaggcc gccatccacg ccggttgagt cgcgttctgc    300
cgcctcccgc ctgtggtgcc tcctgaactg cgtccgccgt ctaggtaagt ttaaagctca    360
ggtcgagacc gggcctttgt ccggcgctcc cttggagcct acctagactc agccggctct    420
ccacgctttg cctgaccctg cttgctcaac tctacgtctt tgtttcgttt tctgttctgc    480
gccgttacag atc                                                       493

<210> SEQ ID NO 119
<211> LENGTH: 2184
<212> TYPE: DNA
<213> ORGANISM: Artificial Sequence
<220> FEATURE:
<223> OTHER INFORMATION: Synthesized

<400> SEQUENCE: 119
gggcagagcg cacatcgccc acagtccccg agaagttggg gggaggggtc ggcaattgaa      60
cgggtgccta gagaaggtgg cgcggggtaa actgggaaag tgatgtcgtg tactggctcc     120 gccttttttcc cgagggtggg ggagaaccgt atataagtgc agtagtcgcc gtgaacgttc    180
tttttcgcaa cgggtttgcc gccagaacac agctgaagct tcgaggggct cgcatctctc    240
cttcacgcgc ccgccgccct acctgaggcc gccatccacg ccggttgagt cgcgttctgc    300
cgcctcccgc ctgtggtgcc tcctgaactg cgtccgccgt ctaggtaagt ttaaagctca    360
ggtcgagacc gggcctttgt ccggcgctcc cttggagcct acctagactc agccggctct    420
ccacgctttg cctgaccctg cttgctcaac tctacgtctt tgtttcgttt tctgttctgc    480
gccgttacag atccaagctg tgaccggcgc ctactctaga gctagcgcag tcagtgcttc    540
tgacacaaca gtctcgaact taactagcac catggcgctc ccagtgacag ccttactttt    600
acctctggcg ttattattgc acgcggctcg tcctgacata cagatgactc agactacctc    660
ttccctatct gcttctttag cgaccgagt aacaatatct tgccgggcca gccaggacat      720

```
ctcaaaatac ttaaactggt atcagcagaa gccggacgga acagttaagt tgctcattta    780
ccacacgtcg agattacact caggcgttcc tagccgattt tcgggttccg gttccggtac    840
ggactacagc ctgacaatca gtaaccttga gcaggaggac atcgccacct acttctgtca    900
gcagggcaac acgctcccgt acacattcgg tgggggaact aagctggaga ttaccggagg    960
cggtggcagc ggtggcggcg gcagcggggg tggcggctcg gaggtcaagt tacaggagag   1020
cggaccgggc ttggtcgcac ctagccgaga cctctcagtc acgtgcactg tgtctggagt   1080
cagtctccca gactacgggg tatcatggat acgacagccg cctagaaagg cttagagtg    1140
gctgggggtt atctgggaa gtgaaaccac atactacaac tcagctctca agagccgcct    1200
caccatcatt aaggacaaca gtaagtcgca ggttttctta agatgaact ctctccagac     1260
tgacgacacc gctatttact actgcgcgaa gcactactac tacggcggga gttacgcaat   1320
ggactactgg ggtcagggca cttctgtgac cgtatccagc actactaccc cagccccacg   1380
tcccccacg ccagctccaa cgatagcaag tcagcccta tctcttcgcc ctgaggcttg     1440
caggcccgcg gcgggcggcg ccgttcacac gcgaggacta gacttcgcct gcgacatcta   1500
catctgggca ccactagccg ggacttgcgg agtgttgttg ttgagcttgg taataacgct   1560
ctactgcaag cgtgggagaa agaagctctt gtacattttc aagcagccat tcatgcgtcc   1620
cgttcagacg actcaggagg aggacggctg ctcgtgccga ttcccggagg aggaggaggg   1680
cggttgcgaa ctcagagtga agttctctcg ctccgcggac gcacccgctt accagcaggg   1740
tcagaaccag ctatacaacg agttaaacct ggggcgccgg gaggagtacg acgtgttaga   1800
caagcgtaga ggtagggacc cggagatggg aggcaagcct cggagaaaga accccagga    1860
gggcctgtac aacgaactcc agaaggacaa gatggctgag gcgtactcgg agattggtat   1920
gaagggcgag agacgtcgcg gaaagggaca cgacggctta taccaggggc tttccaccgc   1980
gaccaaggac acatcgacg cgctgcacat gcaagcctta ccacctcgat gaggtaccag    2040
cggccgcttc gagcagacat gataagatac attgatgagt ttggacaaac cacaactaga   2100
atgcagtgaa aaaatgctt tatttgtgaa atttgtgatg ctattgcttt atttgtaacc    2160
attataagct gcaataaaca agtt                                          2184
```

<210> SEQ ID NO 120
<211> LENGTH: 6811
<212> TYPE: DNA
<213> ORGANISM: Artificial Sequence
<220> FEATURE:
<223> OTHER INFORMATION: Synthesized

<400> SEQUENCE: 120

```
atatccagaa ccctgaccct gccgtgtacc agctgagaga ctctaaatcc agtgacaagt     60
ctgtctgcct attcaccgat tttgattctc aaacaaatgt gtcacaaagt aaggattctg    120
atgtgtatat cacagacaaa actgtgctag acatgaggtc tatggacttc aagagcaaca    180
gtgctgtggc ctggagcaag ggcagagcgc acatcgccca cagtccccga aagttggggg   240
ggaggggtcg gcaattgaac gggtgcctag agaaggtggc gcggggtaaa ctgggaaagt    300
gatgtcgtgt actggctccg ccttttccc gagggtgggg gagaaccgta tataagtgca    360
gtagtcgccg tgaacgttct ttttcgcaac gggtttgccg ccagaacaca gctgaagctt    420
cgaggggctc gcatctctcc ttcacgcgcc cgccgcccta cctgaggccg ccatccacgc    480
cggttgagtc gcgttctgcc gcctcccgcc tgtggtgcct cctgaactgc gtccgccgtc   540
```

```
taggtaagtt taaagctcag gtcgagaccg ggcctttgtc cggcgctccc ttggagccta    600
cctagactca gccggctctc cacgctttgc ctgaccctgc ttgctcaact ctacgtcttt    660
gtttcgtttt ctgttctgcg ccgttacaga tccaagctgt gaccggcgcc tactctagag    720
ctagcgcagt cagtgcttct gacacaacag tctcgaactt aactagcacc atggcgctcc    780
cagtgacagc cttactttta cctctggcgt tattattgca cgcggctcgt cctgacatac    840
agatgactca gactacctct tccctatctg cttctttagg cgaccgagta acaatatctt    900
gccgggccag ccaggacatc tcaaaatact taaactggta tcagcagaag ccggacggaa    960
cagttaagtt gctcatttac cacacgtcga gattacactc aggcgttcct agccgatttt   1020
cgggttccgg ttccggtacg gactacagcc tgacaatcag taaccttgag caggaggaca   1080
tcgccaccta cttctgtcag cagggcaaca cgctcccgta cattcggt gggggaacta     1140
agctggagat taccggaggc ggtggcagcg gtggcggcgg cagcggggt ggcggctcgg     1200
aggtcaagtt acaggagagc ggaccgggct tggtcgcacc tagccagagc ctctcagtca   1260
cgtgcactgt gtctggagtc agtctcccag actacgggt atcatggata cgacagccgc    1320
ctagaaaggg cttagagtgg ctggggtta tctggaaag tgaaaccaca tactacaact      1380
cagctctcaa gagccgcctc accatcatta aggacaacag taagtcgcag gttttcttaa   1440
agatgaactc tctccagact gacgacaccg ctatttacta ctgcgcgaag cactactact   1500
acggcggag ttacgcaatg gactactggg gtcagggcac ttctgtgacc gtatccagca    1560
ctactacccc agccccacgt ccccccacgc cagctccaac gatagcaagt cagcccttat   1620
ctcttcgccc tgaggcttgc aggcccgcgg cgggcggcgc cgttcacacg cgaggactag   1680
acttcgcctg cgacatctac atctgggcac cactagccgg gacttgcgga gtgttgttgt   1740
tgagcttggt aataacgctc tactgcaagc gtgggagaaa gaagctcttg tacatttca     1800
agcagccatt catgcgtccc gttcagacga ctcaggagga ggacggctgc tcgtgccgat   1860
tcccggagga ggaggagggc ggttgcgaac tcagagtgaa gttctctcgc tccgcggacg   1920
cacccgctta ccagcagggt cagaaccagc tatacaacga gttaaacctg ggcgccggg    1980
aggagtacga cgtgttagac aagcgtagag gtagggaccc ggagatggga ggcaagcctc   2040
ggagaaagaa ccccccaggag ggcctgtaca acgaactcca gaaggacaag atggctgagg  2100
cgtactcgga gattggtatg aagggcgaga cgtcgcgg aaaggacac gacgcttat       2160
accaggggct ttccaccgcg accaaggaca catacgacgc gctgcacatg caagccttac   2220
cacctcgatg aggtaccagc ggccgcttcg agcagacatg ataagataca ttgatgagtt   2280
tggacaaacc acaactagaa tgcagtgaaa aaatgcttt atttgtgaaa tttgtgatgc     2340
tattgcttta tttgtaacca ttataagctg caataaacaa gttcaaatct gactttgcat   2400
gtgcaaacgc cttcaacaac agcattattc cagaagacac cttcttcccc agcccaggta   2460
agggcagctt tggtgccttc gcaggctgtt tccttgcttc aggaatggcc aggttctgcc   2520
cagagctctg gtcaatgatg tctaaaactc ctctgattgg tggtctcggc cttatccatt   2580
gccaccaaaa ccctcttttt actaagaaac agtgagcctt gttctggcag tccagagaat   2640
gacacgggaa aaaagcagat gaagagaagg tggcaggaga gggcacgtgg cccagcctca   2700
gtctctccaa ctgagttcct gcctgcctgc ctttgctcag actgtttgcc ccttactgct   2760
cttctaggcc tcattctaag ccccttctc aagttgcctc tccttatttc tccctgtctg    2820
ccaaaaaatc tttcccagct cactaagtca gtctcacgca gtcactcatt aacccaccaa   2880
tcactgattg tgccggcaca tgaatgcacc aggtgttgaa gtggaggaat taaaaagtca   2940
```

```
gatgagggg t gtgcccagag gaagcaccat tctagttggg ggagcccatc tgtcagctgg    3000
gaaaagtcca ataacttca gattggaatg tgttttaact caggggttgag aaaacagcta    3060
ccttcaggac aaaagtcagg gaagggctct ctgaagaaat gctacttgaa gataccagcc    3120
ctaccaaggg cagggagagg acctataga ggcctgggac aggagctcaa tgagaaagga    3180
gaagagcagc aggcatgagt tgaatgaagg aggcagggcc gggtcacagg gccttctagg    3240
ccatgagagg gtagacagta ttctaaggac gccagaaagc tgttgatcgg cttcaagcag    3300
gggagggaca cctaatttgc ttttcttttt tttttttttt tttttttttt ttttttgagat    3360
ggagttttgc tcttgttgcc caggctggag tgcaatggtg catcttggct cactgcaacc    3420
tccgcctccc aggttcaagt gattctcctg cctcagcctc ccgagtagct gagattacag    3480
gcacccgcca ccatgcctgg ctaatttttt gtattttttag tagagacagg gtttcactat    3540
gttggccagg ctggtctcga actcctgacc tcaggtgatc cacccgcttc agcctcccaa    3600
agtgctggga ttacaggcgt gagccaccac acccggcctg cttttcttaa agatcaatct    3660
gagtgctgta cggagagtgg gttgtaagcc aagagtagaa gcagaaaggg agcagttgca    3720
gcagagagat gatggaggcc tgggcagggt ggtggcaggg aggtaaccaa caccattcag    3780
gtttcaaagg tagaaccatg cagggatgag aaagcaaaga ggggatcaag gaaggcagct    3840
ggattttggc ctgagcagct gagtcaatga tagtgccgtt tactaagaag aaaccaagga    3900
aaaaatttgg ggtgcaggga tcaaaacttt ttggaacata tgaaagtacg tgtttatact    3960
ctttatggcc cttgtcacta tgtatgcctc gctgcctcca ttggactcta gaatgaagcc    4020
aggcaagagc agggtctatg tgtgatggca catgtggcca gggtcatgca acatgtactt    4080
tgtacaaaca gtgtatattg agtaaataga aatggtgtcc aggagccgag gtatcggtcc    4140
tgccagggcc aggggctctc cctagcaggt gctcatatgc tgtaagttcc ctccagatct    4200
ctccacaagg aggcatggaa aggctgtagt tgttcacctg cccaagaact aggaggtctg    4260
gggtgggaga gtcagcctgc tctggatgct gaaagaatgt ctgttttttcc ttttagaaag    4320
ttcctgtgat gtcaagctgg tcgagaaaag cttttgaaaca ggtaagacag ggtctagcc    4380
tgggtttgca caggattgcg gaagtgatga acccgcaata accctgcctg gatgagggag    4440
tgggaagaaa ttagtagatg tgggaatgaa tgatgaggaa tggaaacagc ggttcaagac    4500
ctgcccagag ctgggtgggg tctctcctga atccctctca ccatctctga cttttccattc    4560
taagcacttt gaggatgagt ttctagcttc aatagaccaa ggactctctc ctaggcctct    4620
gtattccttt caacagctcc actgtcaaga gagccagaga gagcttctgg gtggcccagc    4680
tgtgaaattt ctgagtccct tagggatagc cctaaacgaa ccagatcatc ctgaggacag    4740
ccaagaggtt ttgccttctt tcaagacaag caacagtact cacataggct gtgggcaatg    4800
gtcctgtctc tcaagaatcc cctgccactc ctcacaccca cctgggccc atattcattt    4860
ccatttgagt tgttcttatt gagtcatcct tcctgtggta gcggaactca ctaagggggcc    4920
catctggacc cgaggtattg tgatgataaa ttctgagcac ctaccccatc cccagaaggg    4980
ctcagaaata aaataagagc caagtctagt cggtgtttcc tgtcttgaaa cacaatactg    5040
ttggccctgg aagaatgcac agaatctgtt tgtaagggga tatgcacaga agctgcaagg    5100
gacaggaggt gcaggagctg caggcctccc ccacccagcc tgctctgcct tgggaaaaac    5160
cgtgggtgtg tcctgcaggc catgcaggcc tgggacatgc aagcccataa ccgctgtggc    5220
ctcttggttt tacagatacg aacctaaact ttcaaaacct gtcagtgatt gggttccgaa    5280
```

```
tcctcctcct gaaagtggcc gggtttaatc tgctcatgac gctgcggctg tggtccagct    5340
gaggtgaggg gccttgaagc tgggagtggg gtttagggac gcgggtctct gggtgcatcc    5400
taagctctga gagcaaacct ccctgcaggg tcttgctttt aagtccaaag cctgagccca    5460
ccaaactctc ctacttcttc ctgttacaaa ttcctcttgt gcaataataa tggcctgaaa    5520
cgctgtaaaa tatcctcatt tcagccgcct cagttgcact ctcccctat gaggtaggaa     5580 gaacagttgt ttagaaacga agaaactgag gccccacagc taatgagtgg aggaagagag    5640
acacttgtgt acaccacatg ccttgtgttg tacttctctc accgtgtaac ctcctcatgt    5700
cctctctccc cagtacggct ctcttagctc agtagaaaga agacattaca ctcatattac    5760
accccaatcc tggctagagt ctccgcaccc tcctccccca gggtcccag tcgtcttgct     5820 gacaactgca tcctgttcca tcaccatcaa aaaaaaactc caggctgggt gcggggctc     5880 acacctgtaa tcccagcact tgggaggca gaggcaggag gagcacagga gctggagacc     5940
agcctgggca acacagggag accccgcctc tacaaaagt gaaaaaatta accaggtgtg      6000
gtgctgcaca cctgtagtcc cagctactta agaggctgag atgggaggat cgcttgagcc    6060
ctggaatgtt gaggctacaa tgagctgtga ttgcgtcact gcactccagc ctggaagaca    6120
aagcaagatc ctgtctcaaa taataaaaaa aataagaact ccagggtaca tttgctccta    6180
gaactctacc acatagcccc aaacagagcc atcaccatca catccctaac agtcctgggt    6240
cttcctcagt gtccagcctg acttctgttc ttcctcattc cagatctgca agattgtaag    6300
acagcctgtg ctccctcgct ccttcctctg cattgcccct cttctcccc tccaaacaga     6360 gggaactctc ctaccccaa ggaggtgaaa gctgctacca cctctgtgcc ccccggcaa      6420 tgccaccaac tggatcctac ccgaatttat gattaagatt gctgaagagc tgccaaacac    6480
tgctgccacc ccctctgttc ccttattgct gcttgtcact gcctgacatt cacggcagag    6540
gcaaggctgc tgcagcctcc cctggctgtg cacattccct cctgctcccc agagactgcc    6600
tccgccatcc cacagatgat ggatcttcag tgggttctct tgggctctag gtcctgcaga    6660
atgttgtgag gggtttattt ttttttaata gtgttcataa agaaatacat agtattcttc    6720
ttctcaagac gtggggggaa attatctcat tatcgaggcc ctgctatgct gtgtatctgg    6780
gcgtgttgta tgtcctgctg ccgatgcctt c                                   6811

<210> SEQ ID NO 121
<211> LENGTH: 6811
<212> TYPE: DNA
<213> ORGANISM: Artificial Sequence
<220> FEATURE:
<223> OTHER INFORMATION: Synthesized

<400> SEQUENCE: 121
atatccagaa ccctgaccct gccgtgtacc agctgagaga ctctaaatcc agtgacaagt      60
ctgtctgcct attcaccgat tttgattctc aaacaaatgt gtcacgggca gagcgcacat     120
cgcccacagt ccccgagaag ttgggggag gggtcggcaa ttgaacgggt gcctagagaa      180
ggtggcgcgg ggtaaactgg gaaagtgatg tcgtgtactg gctccgcctt tttcccgagg    240
gtgggggaga accgtatata agtgcagtag tcgccgtgaa cgttcttttt cgcaacgggt     300
ttgccgccag aacacagctg aagcttcgag gggctcgcat ctctccttca cgcgcccgcc     360
gccctacctg aggccgccat ccacgccggt tgagtcgcgt tctgccgcct cccgcctgtg    420
gtgcctcctg aactgcgtcc gccgtctagg taagtttaaa gctcaggtcg agaccgggcc     480
tttgtccggc gctcccttgg agcctaccta gactcagccg gctctccacg ctttgcctga    540
```

```
ccctgcttgc tcaactctac gtctttgttt cgttttctgt tctgcgccgt tacagatcca    600
agctgtgacc ggcgcctact ctagagctag cgcagtcagt gcttctgaca caacagtctc    660
gaacttaact agcaccatgg cgctcccagt gacagcctta cttttacctc tggcgttatt    720
attgcacgcg gctcgtcctg acatacagat gactcagact acctcttccc tatctgcttc    780
tttaggcgac cgagtaacaa tatcttgccg ggccagccag gacatctcaa aatacttaaa    840
ctggtatcag cagaagccgg acggaacagt taagttgctc atttaccaca cgtcgagatt    900
acactcaggc gttcctagcc gattttcggg ttccggttcc ggtacggact acagcctgac    960
aatcagtaac cttgagcagg aggacatcgc cacctacttc tgtcagcagg gcaacacgct   1020
cccgtacaca ttcggtgggg gaactaagct ggagattacc ggaggcggtg gcagcggtgg   1080
cggcggcagc gggggtggcg gctcggaggt caagttacag gagagcggac cgggcttggt   1140
cgcacctagc cagagcctct cagtcacgtg cactgtgtct ggagtcagtc tcccagacta   1200
cggggtatca tggatacgac agccgcctag aaagggctta gagtggctgg gggttatctg   1260
gggaagtgaa accacatact acaactcagc tctcaagagc cgcctcacca tcattaagga   1320
caacagtaag tcgcaggttt tcttaaagat gaactctctc cagactgacg acaccgctat   1380
ttactactgc gcgaagcact actactacgg cgggagttac gcaatggact actggggtca   1440
gggcacttct gtgaccgtat ccagcactac taccccagcc ccacgtcccc ccacgccagc   1500
tccaacgata gcaagtcagc ccttatctct tcgccctgag gcttgcaggc ccgcggcggg   1560
cggcgccgtt cacacgcgag gactagactt cgcctgcgac atctacatct gggcaccact   1620
agccgggact tgcggagtgt tgttgttgag cttggtaata acgctctact gcaagcgtgg   1680
gagaaagaag ctcttgtaca ttttcaagca gccattcatg cgtcccgttc agacgactca   1740
ggaggaggac ggctgctcgt gccgattccc ggaggaggag gagggcggtt gcgaactcag   1800
agtgaagttc tctcgctccg cggacgcacc cgcttaccag cagggtcaga accagctata   1860
caacgagtta aacctggggc gccgggagga gtacgacgtg ttagacaagc gtagaggtag   1920
ggacccggag atgggaggca agcctcggag aaagaacccc caggagggcc tgtacaacga   1980
actccagaag gacaagatgg ctgaggcgta ctcggagatt ggtatgaagg gcgagagacg   2040
tcgcggaaag ggacacgacg gcttatacca ggggctttcc accgcgacca aggacacata   2100
cgacgcgctg cacatgcaag ccttaccacc tcgatgaggt accagcggcc gcttcgagca   2160
gacatgataa gatacattga tgagtttgga caaaccacaa ctagaatgca gtgaaaaaaa   2220
tgctttattt gtgaaatttg tgatgctatt gctttatttg taaccattat aagctgcaat   2280
aaacaagtta agtaaggat tctgatgtgt atatcacaga caaaactgtg ctagacatga   2340
ggtctatgga cttcaagagc aacagtgctg tggcctggag caacaaatct gactttgcat   2400
gtgcaaacgc cttcaacaac agcattattc cagaagacac cttcttcccc agcccaggta   2460
agggcagctt tggtgccttc gcaggctgtt tccttgcttc aggaatggcc aggttctgcc   2520
cagagctctg gtcaatgatg tctaaaactc ctctgattgg tggtctcggc cttatccatt   2580
gccaccaaaa ccctcttttt actaagaaac agtgagcctt gttctggcag tccagagaat   2640
gacacgggaa aaaagcagat gaagagaagg tggcaggaga gggcacgtgg cccagcctca   2700
gtctctccaa ctgagttcct gcctgcctgc ctttgctcag actgtttgcc ccttactgct   2760
cttctaggcc tcattctaag ccccttctcc aagttgcctc tccttatttc tccctgtctg   2820
ccaaaaaatc tttcccagct cactaagtca gtctcacgca gtcactcatt aacccaccaa   2880
```

```
tcactgattg tgccggcaca tgaatgcacc aggtgttgaa gtggaggaat taaaaagtca    2940
gatgaggggt gtgcccagag gaagcaccat tctagttggg ggagcccatc tgtcagctgg    3000
gaaaagtcca ataacttca gattggaatg tgttttaact cagggttgag aaaacagcta    3060
ccttcaggac aaaagtcagg gaagggctct ctgaagaaat gctacttgaa gataccagcc    3120
ctaccaaggg cagggagagg accctataga ggcctgggac aggagctcaa tgagaaagga    3180
gaagagcagc aggcatgagt tgaatgaagg aggcagggcc gggtcacagg gccttctagg    3240
ccatgagagg gtagacagta ttctaaggac gccagaaagc tgttgatcgg cttcaagcag    3300
gggagggaca cctaatttgc ttttctttt tttttttttt tttttttttt ttttgagat      3360
ggagttttgc tcttgttgcc caggctggag tgcaatggtg catcttggct cactgcaacc    3420
tccgcctccc aggttcaagt gattctcctg cctcagcctc ccgagtagct gagattacag    3480
gcacccgcca ccatgcctgg ctaattttt gtattttag tagagacagg gtttcactat       3540
gttggccagg ctggtctcga actcctgacc tcaggtgatc cacccgcttc agcctcccaa    3600
agtgctggga ttacaggcgt gagccaccac acccggcctg ctttttcttaa agatcaatct    3660
gagtgctgta cggagagtgg gttgtaagcc aagagtagaa gcagaagggg agcagttgca    3720
gcagagagat gatggaggcc tgggcagggt ggtggcaggg aggtaaccaa caccattcag    3780
gtttcaaagg tagaaccatg cagggatgag aaagcaaaga ggggatcaag gaaggcagct    3840
ggattttggc ctgagcagct gagtcaatga tagtgccgtt tactaagaag aaaccaagga    3900
aaaaatttgg ggtgcaggga tcaaaacttt ttggaacata tgaaagtacg tgtttatact    3960
ctttatggcc cttgtcacta tgtatgcctc gctgcctcca ttggactcta gaatgaagcc    4020
aggcaagagc agggtctatg tgtgatggca catgtggcca gggtcatgca acatgtactt    4080
tgtacaaaca gtgtatattg agtaaataga aatggtgtcc aggagccgag gtatcggtcc    4140
tgccagggcc aggggctctc cctagcaggt gctcatatgc tgtaagttcc ctccagatct    4200
ctccacaagg aggcatggaa aggctgtagt tgttcacctg cccaagaact aggaggtctg    4260
gggtgggaga gtcagcctgc tctggatgct gaaagaatgt ctgttttcc ttttagaaag     4320
ttcctgtgat gtcaagctgg tcgagaaaag ctttgaaaca ggtaagacag ggtctagcc     4380
tgggtttgca caggattgcg gaagtgatga acccgcaata accctgcctg gatgagggag    4440
tgggaagaaa ttagtagatg tgggaatgaa tgatgaggaa tggaaacagc ggttcaagac    4500
ctgcccagag ctgggtgggg tctctcctga atccctctca ccatctctga cttccattc     4560
taagcacttt gaggatgagt ttctagcttc aatagaccaa ggactctctc ctaggcctct    4620
gtattccttt caacagctcc actgtcaaga gagccagaga gagcttctgg gtggcccagc    4680
tgtgaaattt ctgagtccct tagggatagc cctaaacgaa ccagatcatc ctgaggacag    4740
ccaagaggtt ttgccttctt tcaagacaag caacagtact cacataggct gtgggcaatg    4800
gtcctgtctc tcaagaatcc cctgccactc ctcacaccca ccctgggccc atattcattt    4860
ccatttgagt tgttcttatt gagtcatcct tcctgtggta gcggaactca ctaaggggcc    4920
catctggacc cgaggtattg tgatgataaa ttctgagcac ctaccccatc cccagaaggg    4980
ctcagaaata aaataagagc caagtctagt cggtgtttcc tgtcttgaaa cacaatactg    5040
ttggccctgg aagaatgcac agaatctgtt tgtaagggga tatgcacaga agctgcaagg    5100
gacaggaggt gcaggagctg caggcctccc ccacccagcc tgctctgcct tggggaaaac    5160
cgtgggtgtg tcctgcaggc catgcaggcc tgggacatga agcccataa  ccgctgtggc    5220
ctcttggttt tacagatacg aacctaaact ttcaaaacct gtcagtgatt gggttccgaa    5280
```

| | | |
|---|---|---|
| tcctcctcct gaaagtggcc gggtttaatc tgctcatgac gctgcggctg tggtccagct | 5340 |
| gaggtgaggg gccttgaagc tgggagtggg gtttagggac gcgggtctct gggtgcatcc | 5400 |
| taagctctga gagcaaacct ccctgcaggg tcttgctttt aagtccaaag cctgagccca | 5460 |
| ccaaactctc ctacttcttc ctgttacaaa ttcctcttgt gcaataataa tggcctgaaa | 5520 |
| cgctgtaaaa tatcctcatt tcagccgcct cagttgcact tctccctat gaggtaggaa | 5580 |
| gaacagttgt ttagaaacga agaaactgag gccccacagc taatgagtgg aggaagagag | 5640 |
| acacttgtgt acaccacatg ccttgtgttg tacttctctc accgtgtaac tcctcatgt | 5700 |
| cctctctccc cagtacggct ctcttagctc agtagaaaga agacattaca ctcatattac | 5760 |
| accccaatcc tggctagagt ctccgcaccc tcctccccca gggtcccag tcgtcttgct | 5820 |
| gacaactgca tcctgttcca tcaccatcaa aaaaaaactc caggctgggt gcggggctc | 5880 |
| acacctgtaa tcccagcact tgggaggca gaggcaggag gagcacagga gctggagacc | 5940 |
| agcctgggca acacagggag accccgcctc tacaaaaagt gaaaaaatta accaggtgtg | 6000 |
| gtgctgcaca cctgtagtcc cagctactta agaggctgag atgggaggat cgcttgagcc | 6060 |
| ctggaatgtt gaggctacaa tgagctgtga ttgcgtcact gcactccagc ctggaagaca | 6120 |
| aagcaagatc ctgtctcaaa taataaaaaa aataagaact ccagggtaca tttgctccta | 6180 |
| gaactctacc acatagcccc aaacagagcc atcaccatca catccctaac agtcctgggt | 6240 |
| cttcctcagt gtccagcctg acttctgttc ttcctcattc cagatctgca agattgtaag | 6300 |
| acagcctgtg ctccctcgct ccttcctctg cattgcccct cttctccctc tccaaacaga | 6360 |
| gggaactctc ctaccccaa ggaggtgaaa gctgctacca cctctgtgcc cccccggcaa | 6420 |
| tgccaccaac tggatcctac ccgaatttat gattaagatt gctgaagagc tgccaaacac | 6480 |
| tgctgccacc ccctctgttc ccttattgct gcttgtcact gctgacatt cacggcagag | 6540 |
| gcaaggctgc tgcagcctcc cctggctgtg cacattccct cctgctcccc agagactgcc | 6600 |
| tccgccatcc cacagatgat ggatcttcag tgggttctct tgggctctag gtcctgcaga | 6660 |
| atgttgtgag gggtttattt tttttttaata gtgttcataa agaaatacat agtattcttc | 6720 |
| ttctcaagac gtgggggaa attatctcat tatcgaggcc ctgctatgct gtgtatctgg | 6780 |
| gcgtgttgta tgtcctgctg ccgatgcctt c | 6811 |

<210> SEQ ID NO 122
<211> LENGTH: 6811
<212> TYPE: DNA
<213> ORGANISM: Artificial Sequence
<220> FEATURE:
<223> OTHER INFORMATION: Synthesized

<400> SEQUENCE: 122

| | | |
|---|---|---|
| atatccagaa ccctgaccct gccgtgtacc agctgagaga ctctaaatcc agtgacaagt | 60 |
| ctgtctgcct attcaccgat tttgattctc aaacaaatgt gtcacaaagt aaggattctg | 120 |
| atgtgtatat gggcagagcg cacatcgccc acagtccccg agaagttggg gggaggggtc | 180 |
| ggcaattgaa cgggtgccta gagaaggtgg cgcggggtaa actgggaaag tgatgtcgtg | 240 |
| tactggctcc gccttttttcc cgagggtggg ggagaaccgt atataagtgc agtagtcgcc | 300 |
| gtgaacgttc ttttttcgcaa cgggtttgcc gccagaacac agctgaagct tcgaggggct | 360 |
| cgcatctctc cttcacgcgc ccgccgcct acctgaggcc gccatccacg ccggttgagt | 420 |
| cgcgttctgc cgcctcccgc ctgtggtgcc tcctgaactg cgtccgccgt ctaggtaagt | 480 |

```
ttaaagctca ggtcgagacc gggcctttgt ccggcgctcc cttggagcct acctagactc     540
agccggctct ccacgctttg cctgaccctg cttgctcaac tctacgtctt tgtttcgttt     600
tctgttctgc gccgttacag atccaagctg tgaccggcgc ctactctaga gctagcgcag     660
tcagtgcttc tgacacaaca gtctcgaact taactagcac catggcgctc ccagtgacag     720
ccttactttt acctctggcg ttattattgc acgcggctcg tcctgacata cagatgactc     780
agactacctc ttccctatct gcttctttag gcgaccgagt aacaatatct gccgggcca     840 gccaggacat ctcaaaatac ttaaactggt atcagcagaa gccggacgga acagttaagt     900
tgctcattta ccacacgtcg agattacact caggcgttcc tagccgattt tcgggttccg     960
gttccggtac ggactacagc ctgacaatca gtaaccttga gcaggaggac atcgccacct    1020
acttctgtca gcagggcaac acgctcccgt acacattcgg tggggaact aagctggaga     1080 ttaccggagg cggtggcagc ggtggcggcg gcagcggggg tggcggctcg gaggtcaagt    1140
tacaggagag cggaccgggc ttggtcgcac ctagccagag cctctcagtc acgtgcactg    1200
tgtctggagt cagtctccca gactacgggg tatcatggat acgacagccg cctagaaagg    1260
gcttagagtg gctgggggtt atctgggaa gtgaaaccac atactacaac tcagctctca    1320
agagccgcct caccatcatt aaggacaaca gtaagtcgca ggttttctta aagatgaact    1380
ctctccagac tgacgacacc gctatttact actgcgcgaa gcactactac tacggcggga    1440
gttacgcaat ggactactgg ggtcagggca cttctgtgac cgtatccagc actactaccc    1500
cagccccacg tccccccacg ccagctccaa cgatagcaag tcagcccta tctcttcgcc     1560 ctgaggcttg caggcccgcg gcgggcggcg ccgttcacac gcgaggacta gacttcgcct    1620
gcgacatcta catctgggca ccactagccg ggacttgcgg agtgttgttg ttgagcttgg    1680
taataacgct ctactgcaag cgtgggagaa agaagctctt gtacatttc aagcagccat    1740 tcatgcgtcc cgttcagacg actcaggagg aggacggctg ctcgtgccga ttcccggagg    1800
aggaggaggg cggttgcgaa ctcagagtga agttctctcg ctccgcggac gcacccgctt    1860
accagcaggg tcagaaccag ctatacaacg agttaaacct ggggcgccgg gaggagtacg    1920
acgtgttaga caagcgtaga ggtagggacc cggagatggg aggcaagcct cggagaaaga    1980
acccccagga gggcctgtac aacgaactcc agaaggacaa gatggctgag gcgtactcgg    2040
agattggtat gaagggcgag agacgtcgcg gaaagggaca cgacggctta taccagggc    2100 tttccaccgc gaccaaggac acatacgacg cgctgcacat gcaagcctta ccacctcgat    2160
gaggtaccag cggccgcttc gagcagacat gataagatac attgatgagt ttggacaaac    2220
cacaactaga atgcagtgaa aaaatgctt tatttgtgaa atttgtgatg ctattgcttt    2280
atttgtaacc attataagct gcaataaaca agttcacaga caaactgtg ctagacatga     2340 ggtctatgga cttcaagagc aacagtgctg tggcctggag caacaaatct gactttgcat    2400
gtgcaaacgc cttcaacaac agcattattc cagaagacac cttcttcccc agcccaggta    2460
agggcagctt tggtgccttc gcaggctgtt tccttgcttc aggaatggcc aggttctgcc    2520
cagagctctg gtcaatgatg tctaaaactc ctctgattgg tggtctcggc cttatccatt    2580
gccaccaaaa ccctcttttt actaagaaac agtgagcctt gttctggcag tccagagaat    2640
gacacgggaa aaaagcagat gaagagaagg tggcaggaga gggcacgtgg cccagcctca    2700
gtctctccaa ctgagttcct gcctgcctgc ctttgctcag actgtttgcc ccttactgct    2760
cttctaggcc tcattctaag ccccttctcc aagttgcctc tccttatttc tccctgtctg    2820
ccaaaaaatc tttcccagct cactaagtca gtctcacgca gtcactcatt aacccaccaa    2880
```

```
tcactgattg tgccggcaca tgaatgcacc aggtgttgaa gtggaggaat taaaaagtca    2940
gatgaggggt gtgcccagag gaagcaccat tctagttggg ggagcccatc tgtcagctgg    3000
gaaaagtcca aataacttca gattggaatg tgttttaact cagggttgag aaaacagcta    3060
ccttcaggac aaaagtcagg gaagggctct ctgaagaaat gctacttgaa gataccagcc    3120
ctaccaaggg cagggagagg accctataga ggcctgggac aggagctcaa tgagaaagga    3180
gaagagcagc aggcatgagt tgaatgaagg aggcagggcc gggtcacagg gccttctagg    3240
ccatgagagg gtagacagta ttctaaggac gccagaaagc tgttgatcgg cttcaagcag    3300
gggagggaca cctaatttgc tttctttttt ttttttttt tttttttttt tttttgagat      3360
ggagttttgc tcttgttgcc caggctggag tgcaatggtg catcttggct cactgcaacc    3420
tccgcctccc aggttcaagt gattctcctg cctcagcctc ccgagtagct gagattacag    3480
gcacccgcca ccatgcctgg ctaatttttt gtattttag tagagacagg gtttcactat      3540
gttggccagg ctggtctcga actcctgacc tcaggtgatc cacccgcttc agcctcccaa    3600
agtgctggga ttacaggcgt gagccaccac acccggcctg ctttcttaa agatcaatct     3660
gagtgctgta cggagagtgg gttgtaagcc aagagtagaa gcagaaaggg agcagttgca    3720
gcagagagat gatggaggcc tgggcagggt ggtggcaggg aggtaaccaa caccattcag    3780
gtttcaaagg tagaaccatg cagggatgag aaagcaaaga ggggatcaag gaaggcagct    3840
ggattttggc ctgagcagct gagtcaatga tagtgccgtt tactaagaag aaaccaagga    3900
aaaaatttgg ggtgcaggga tcaaaacttt ttggaacata tgaaagtacg tgtttatact    3960
ctttatggcc cttgtcacta tgtatgcctc gctgcctcca ttggactcta gaatgaagcc    4020
aggcaagagc agggtctatg tgtgatggca catgtggcca gggtcatgca acatgtactt    4080
tgtacaaaca gtgtatattg agtaaataga aatggtgtcc aggagccgag gtatcggtcc    4140
tgccagggcc aggggctctc cctagcaggt gctcatatgc tgtaagttcc ctccagatct    4200
ctccacaagg aggcatggaa aggctgtagt tgttcacctg cccaagaact aggaggtctg    4260
gggtggggga tcagcctgc tctggatgct gaaagaatgt ctgttttcc ttttagaaag       4320
ttcctgtgat gtcaagctgg tcgagaaaag cttgaaaca ggtaagacag gggtctagcc     4380
tgggtttgca caggattgcg gaagtgatga acccgcaata accctgcctg gatgagggag    4440
tgggaagaaa ttagtagatg tgggaatgaa tgatgaggaa tggaaacagc ggttcaagac    4500
ctgcccagag ctgggtgggg tctctcctga atccctctca ccatctctga ctttccattc    4560
taagcacttt gaggatgagt ttctagcttc aatagaccaa ggactctctc ctaggcctct    4620
gtattccttt caacagctcc actgtcaaga gagccagaga gagcttctgg gtggcccagc    4680
tgtgaaattt ctgagtccct tagggatagc cctaaacgaa ccagatcatc ctgaggacag    4740
ccaagaggtt ttgccttctt tcaagacaag caacagtact cacataggct gtgggcaatg    4800
gtcctgtctc tcaagaatcc cctgccactc ctcacaccca ccctgggccc atattcattt    4860
ccatttgagt tgttcttatt gagtcatcct tcctgtggta gcggaactca ctaaggggcc    4920
catctggacc cgaggtattg tgatgataaa ttctgagcac ctaccccatc cccagaaggg    4980
ctcagaaata aaataagagc caagtctagt cggtgtttcc tgtcttgaaa cacaatactg    5040
ttggccctgg aagaatgcac agaatctgtt tgtaagggga tatgcacaga agctgcaagg    5100
gacaggaggt gcaggagctg caggcctccc ccacccagcc tgctctgcct tgggaaaaac    5160
cgtgggtgtg tcctgcaggc catgcaggcc tgggacatgc aagcccataa ccgctgtggc    5220
```

| | |
|---|---|
| ctcttggttt tacagatacg aacctaaact ttcaaaacct gtcagtgatt gggttccgaa | 5280 |
| tcctcctcct gaaagtggcc gggtttaatc tgctcatgac gctgcggctg tggtccagct | 5340 |
| gaggtgaggg gccttgaagc tgggagtggg gtttagggac gcgggtctct gggtgcatcc | 5400 |
| taagctctga gagcaaacct ccctgcaggg tcttgctttt aagtccaaag cctgagccca | 5460 |
| ccaaactctc ctacttcttc ctgttacaaa ttcctcttgt gcaataataa tggcctgaaa | 5520 |
| cgctgtaaaa tatcctcatt tcagccgcct cagttgcact tctcccctat gaggtaggaa | 5580 |
| gaacagttgt ttagaaacga agaaactgag gccccacagc taatgagtgg aggaagagag | 5640 |
| acacttgtgt acaccacatg ccttgtgttg tacttctctc accgtgtaac ctcctcatgt | 5700 |
| cctctctccc cagtacggct tcttagctc agtagaaaga agacattaca ctcatattac | 5760 |
| accccaatcc tggctagagt ctccgcaccc tcctccccca gggtcccag tcgtcttgct | 5820 |
| gacaactgca tcctgttcca tcaccatcaa aaaaaaactc caggctgggt gcggggctc | 5880 |
| acacctgtaa tcccagcact tgggaggca gaggcaggag gagcacagga gctggagacc | 5940 |
| agcctgggca acacagggag accccgcctc tacaaaaagt gaaaaaatta accaggtgtg | 6000 |
| gtgctgcaca cctgtagtcc cagctactta agaggctgag atgggaggat cgcttgagcc | 6060 |
| ctggaatgtt gaggctacaa tgagctgtga ttgcgtcact gcactccagc ctggaagaca | 6120 |
| aagcaagatc ctgtctcaaa taataaaaaa aataagaact ccagggtaca tttgctccta | 6180 |
| gaactctacc acatagcccc aaacagagcc atcaccatca catccctaac agtcctgggt | 6240 |
| cttcctcagt gtccagcctg acttctgttc ttcctcattc cagatctgca agattgtaag | 6300 |
| acagcctgtg ctccctcgct ccttcctctg cattgcccct cttctccctc tccaaacaga | 6360 |
| gggaactctc ctaccccaa ggaggtgaaa gctgctacca cctctgtgcc ccccggcaa | 6420 |
| tgccaccaac tggatcctac ccgaatttat gattaagatt gctgaagagc tgccaaacac | 6480 |
| tgctgccacc cctctgttc ccttattgct gcttgtcact gcctgacatt cacggcagag | 6540 |
| gcaaggctgc tgcagcctcc cctggctgtg cacattccct cctgctcccc agagactgcc | 6600 |
| tccgccatcc cacagatgat ggatcttcag tgggttctct tgggctctag gtcctgcaga | 6660 |
| atgttgtgag gggtttattt ttttttaata gtgttcataa agaaatacat agtattcttc | 6720 |
| ttctcaagac gtgggggga attatctcat tatcgaggcc ctgctatgct gtgtatctgg | 6780 |
| gcgtgttgta tgtcctgctg ccgatgcctt c | 6811 |

<210> SEQ ID NO 123
<211> LENGTH: 6040
<212> TYPE: DNA
<213> ORGANISM: Artificial Sequence
<220> FEATURE:
<223> OTHER INFORMATION: Synthesized

<400> SEQUENCE: 123

| | |
|---|---|
| cagcagctgg cgtaatagcg aagaggcccg caccgatcgc ccttcccaac agttgcgcag | 60 |
| cctgaatggc gaatggaatt ccagacgatt gagcgtcaaa atgtaggtat ttccatgagc | 120 |
| gttttcctg ttgcaatggc tggcggtaat attgttctgg atattaccag caaggccgat | 180 |
| agtttgagtt cttctactca ggcaagtgat gttattacta atcaaagaag tattgcgaca | 240 |
| acggttaatt tgcgtgatgg acagactctt ttactcggtg gcctcactga ttataaaaac | 300 |
| acttctcagg attctggcgt accgttcctg tctaaaatcc ctttaatcgg cctcctgttt | 360 |
| agctcccgct ctgattctaa cgaggaaagc acgttatacg tgctcgtcaa agcaaccata | 420 |
| gtacgcgccc tgtagcggcg cattaagcgc ggcgggtgtg gtggttacgc gcagcgtgac | 480 |

```
cgctacactt gccagcgccc tagcgcccgc tcctttcgct ttcttcccctt cctttctcgc    540
cacgttcgcc ggctttcccc gtcaagctct aaatcggggg ctcccttag ggttccgatt    600
tagtgcttta cggcacctcg accccaaaaa acttgattag ggtgatggtt cacgtagtgg    660
gccatcgccc tgatagacgg ttttttcgcc tttgacgttg gagtccacgt tctttaatag    720
tggactcttg ttccaaactg gaacaacact caaccctatc tcggtctatt cttttgattt    780
ataagggatt ttgccgattt cggcctattg gttaaaaaat gagctgattt aacaaaaatt    840
taacgcgaat tttaacaaaa tattaacgct tacaatttaa atatttgctt atacaatctt    900
cctgtttttg gggcttttct gattatcaac cggggtacat atgattgaca tgctagtttt    960
acgattaccg ttcatcgccc tgcgcgctcg ctcgctcact gaggccgccc gggcaaagcc   1020
cgggcgtcgg gcgacctttg gtcgcccggc ctcagtgagc gagcgagcgc gcagagaggg   1080
agtggaattc acgcgtgata tccagaaccc tgaccctgcc gtgtaccagc tgagagactc   1140
taaatccagt gacaagtctg tctgcctatt caccgatttt gattctcaaa caaatgtgtc   1200
acaaagtaag gattctgatg tgcatatcac agacaaaact gtgctagaca tgaggtctat   1260
ggacttcaag agcaacagtg ctgtggcctg gagcaactag tgggcggagt tagggcggag   1320
ccaatcagcg tgcgccgttc cgaaagttgc cttttatggc tgggcggaga atgggcggtg   1380
aacgccgatg attatataag gacgcgccgg gtgtggcaca gctagttccg tcgcagccgg   1440
gatttgggtc gcggttcttg tttgttccgg aaagccacca tggcgctccc agtgacagcc   1500
ttacttttac ctctggcgtt attattgcac gcggctcgtc ctgacataca gatgactcag   1560
actacctctt ccctatctgc ttctttaggc gaccgagtaa caatatcttg ccgggccagc   1620
caggacatct caaaatactt aaactggtat cagcagaagc cggacggaac agttaagttg   1680
ctcatttacc acacgtcgag attacactca ggcgttccta gccgatttc gggttccggt   1740
tccggtacgg actacagcct gacaatcagt aaccttgagc aggaggacat cgccacctac   1800
ttctgtcagc agggcaacac gctcccgtac acattcggtg ggggaactaa gctggagatt   1860
accggaggcg gtggcagcgg tggcggcggc agcggggggtg gcggctcgga ggtcaagtta   1920
caggagagcg gaccgggctt ggtcgcacct agccagagcc tctcagtcac gtgcactgtg   1980
tctggagtca gtctcccaga ctacggggta tcatggatac gacagccgcc tagaaagggc   2040
ttagagtggc tgggggttat ctggggaagt gaaaccacat actacaactc agctctcaag   2100
agccgcctca ccatcattaa ggacaacagt aagtcgcagg ttttcttaaa gatgaactct   2160
ctccagactg acgacaccgc tatttactac tgcgcgaagc actactacta cggcgggagt   2220
tacgcaatgg actactgggg tcagggcact tctgtgaccg tatccagcac tactacccca   2280
gccccacgtc cccccacgcc agctccaacg atagcaagtc agcccttatc tcttcgccct   2340
gaggcttgca ggcccgcggc gggcggcgcc gttcacacgc gaggactaga cttcgcctgc   2400
gacatctaca tctgggcacc actagccggg acttgcggag tgttgttgtt gagcttggta   2460
ataacgctct actgcaagcg tgggagaaag aagctcttgt acattttcaa gcagccattc   2520
atgcgtcccg ttcagacgac tcaggaggag gacggctgct cgtgccgatt cccggaggag   2580
gaggagggcg gttgcgaact cagagtgaag ttctctcgct ccgcggacgc acccgcttac   2640
cagcagggtc agaaccagct atacaacgag ttaaacctgg ggcgccggga ggagtacgac   2700
gtgttagaca gcgtagagg tagggacccg gagatgggag gcaagcctcg gagaaagaac   2760
cccccaggagg gcctgtacaa cgaactccag aaggacaaga tggctgaggc gtactcggag   2820
```

-continued

| | |
|---|---|
| attggtatga agggcgagag acgtcgcgga aagggacacg acggcttata ccaggggctt | 2880 |
| tccaccgcga ccaaggacac atacgacgcg ctgcacatgc aagccttacc acctcgatga | 2940 |
| taagatacat tgatgagttt ggacaaacca caactagaat gcagtgaaaa aaatgcttta | 3000 |
| tttgtgaaat ttgtgatgct attgctttat ttgtaaccat tataagctgc aataaacaag | 3060 |
| ttctagagca acaaatctga ctttgcatgt gcaaacgcct tcaacaacag cattattcca | 3120 |
| gaagacacct tcttccccag cccaggtaag ggcagctttg gtgccttcgc aggctgtttc | 3180 |
| cttgcttcag gaatggccag gttctgccca gagctctggt caatgatgtc taaaactcct | 3240 |
| ctgattgcaa ttgcctctct gcgcgctcgc tcgctcactg aggccgcccg ggcaaagccc | 3300 |
| gggcgtcggg cgacctttgg tcgcccggcc tcagtgagcg agcgagcgcg cagagaggga | 3360 |
| gtggccaacc ccggcgattc tcttgtttgc tccagactct caggcaatga cctgatagcc | 3420 |
| tttgtacctg caggtctcaa aaatagctac cctctccggc atgaatttat cagctagaac | 3480 |
| ggttgaatat catattgatg gtgatttgac tgtctccggc ctttctcacc cgtttgaatc | 3540 |
| tttacctaca cattactcag gcattgcatt taaaatatat gagggttcta aaatttttta | 3600 |
| tccttgcgtt gaaataaagg cttctcccgc aaaagtatta cagggtcata atgttttttgg | 3660 |
| tacaaccgat ttagctttat gctctgaggc tttattgctt aattttgcta attctttgcc | 3720 |
| ttgcctgtat gatttattgg atgttggaat tcctgatgcg gtattttctc cttacgcatc | 3780 |
| tgtgcggtat ttcacaccgc atatggtgca ctctcagtac aatctgctct gatgccgcat | 3840 |
| agttaagcca gccccgacac ccgccaacac ccgctgacgc gccctgacgg gcttgtctgc | 3900 |
| tcccggcatc cgcttacaga caagctgtga ccgtctccgg gagctgcatg tgtcagaggt | 3960 |
| tttcaccgtc atcaccgaaa cgcgcgagac gaaagggcct cgtgatacgc ctatttttat | 4020 |
| aggttaatgt catgataata atggtttctt agacgtcagg tggcacttttt cggggaaatg | 4080 |
| tgcgcggaac ccctatttgt ttatttttct aaatacattc aaatatgtat ccgctcatga | 4140 |
| gacaataacc ctgataaatg cttcaataat attgaaaaag gaagagtatg agtattcaac | 4200 |
| atttccgtgt cgcccttatt cccttttttg cggcattttg ccttcctgtt tttgctcacc | 4260 |
| cagaaacgct ggtgaaagta aaagatgctg aagatcagtt gggtgcacga gtgggttaca | 4320 |
| tcgaactgga tctcaacagc ggtaagatcc ttgagagttt cgccccgaa gaacgttttc | 4380 |
| caatgatgag cacttttaaa gttctgctat gtggcgcggt attatcccgt attgacgccg | 4440 |
| ggcaagagca actcggtcgc cgcatacact attctcagaa tgacttggtt gagtactcac | 4500 |
| cagtcacaga aaagcatctt acggatggca tgacagtaag agaattatgc agtgctgcca | 4560 |
| taaccatgag tgataacact gcggccaact tacttctgac aacgatcgga ggaccgaagg | 4620 |
| agctaaccgc ttttttgcac aacatggggg atcatgtaac tcgccttgat cgttgggaac | 4680 |
| cggagctgaa tgaagccata ccaaacgacg agcgtgacac cacgatgcct gtagcaatgg | 4740 |
| caacaacgtt gcgcaaacta ttaactggcg aactacttac tctagcttcc cggcaacaat | 4800 |
| taatagactg gatggaggcg gataaagttg caggaccact tctgcgctcg gcccttccgg | 4860 |
| ctggctggtt tattgctgat aaatctggag ccggtgagcg tgggtctcgc ggtatcattg | 4920 |
| cagcactggg gccagatggt aagccctccc gtatcgtagt tatctacacg acggggagtc | 4980 |
| aggcaactat ggatgaacga atagacaga tcgctgagat aggtgcctca ctgattaagc | 5040 |
| attggtaact gtcagaccaa gtttactcat atatacttta gattgattta aaacttcatt | 5100 |
| tttaatttaa aaggatctag gtgaagatcc ttttttgataa tctcatgacc aaaatccctt | 5160 |
| aacgtgagtt ttcgttccac tgagcgtcag accccgtaga aaagatcaaa ggatcttctt | 5220 |

```
gagatccttt ttttctgcgc gtaatctgct gcttgcaaac aaaaaaacca ccgctaccag      5280
cggtggtttg tttgccggat caagagctac caactctttt tccgaaggta actggcttca      5340
gcagagcgca gataccaaat actgtccttc tagtgtagcc gtagttaggc caccacttca      5400
agaactctgt agcaccgcct acatacctcg ctctgctaat cctgttacca gtggctgctg      5460
ccagtggcga taagtcgtgt cttaccgggt tggactcaag acgatagtta ccggataagg      5520
cgcagcggtc gggctgaacg gggggttcgt gcacacagcc cagcttggag cgaacgacct      5580
acaccgaact gagatgccta cagcgtgagc tatgagaaag cgccacgctt cccgaaggga      5640
gaaaggcgga caggtatccg gtaagcggca gggtcggaac aggagagcgc acgagggagc      5700 ttccagggg aaacgcctgg tatctttata gtcctgtcgg gtttcgccac ctctgacttg       5760
agcgtcgatt tttgtgatgc tcgtcagggg gcggagcct atggaaaaac gccagcaacg       5820 cggcctttt acgttcctg gccttttgct ggcctttgc tcacatgttc tttcctgcgt         5880
tatcccctga ttctgtggat aaccgtatta ccgcctttga gtgagctgat accgctcgcc      5940
gcagccgaac gaccgagcgc agcgagtcag tgagcgagga gcggaagag cgcccaatac       6000 gcaaaccgcc tctccccgcg cgttggccga ttcattaatg                            6040

<210> SEQ ID NO 124
<211> LENGTH: 8342
<212> TYPE: DNA
<213> ORGANISM: Artificial Sequence
<220> FEATURE:
<223> OTHER INFORMATION: Synthesized

<400> SEQUENCE: 124
cagcagctgg cgtaatagcg aagaggcccg caccgatcgc ccttcccaac agttgcgcag        60
cctgaatggc gaatggaatt ccagacgatt gagcgtcaaa atgtaggtat ttccatgagc       120
gtttttcctg ttgcaatggc tggcggtaat attgttctgg atattaccag caaggccgat       180
agtttgagtt cttctactca ggcaagtgat gttattacta atcaaagaag tattgcgaca       240
acggttaatt tgcgtgatgg acagactctt ttactcggtg gcctcactga ttataaaaac      300
acttctcagg attctggcgt accgttcctg tctaaaatcc ctttaatcgg cctcctgttt      360
agctcccgct ctgattctaa cgaggaaagc acgttatacg tgctcgtcaa agcaaccata     420
gtacgcgccc tgtagcggcg cattaagcgc ggcgggtgtg tggttacgc gcagcgtgac        480 cgctacactt gccagcgccc tagcgcccgc tcctttcgct ttcttccctt cctttctcgc      540
cacgttcgcc ggctttcccc gtcaagctct aaatcggggg ctcccttag ggttccgatt       600 tagtgcttta cggcacctcg accccaaaaa acttgattag ggtgatggtt cacgtagtgg      660
gccatcgccc tgatagacgg ttttcgccc tttgacgttg gagtccacgt tctttaatag      720
tggactcttg ttccaaactg gaacaacact caaccctatc tcggtctatt cttttgattt     780
ataagggatt ttgccgattt cggcctattg gttaaaaaat gagctgattt aacaaaaatt     840
taacgcgaat tttaacaaaa tattaacgtt tacaatttaa atatttgctt atacaatctt     900 cctgttttg gggcttttct gattatcaac cggggtacat atgattgaca tgctagtttt     960
acggcgcgcc gggttggcca ctccctctct gcgcgctcgc tcgctcactg aggccgggcg   1020
accaaaggtc gcccgacgcc cgggctttgc ccgggcggcc tcagtgagcg agcgagcgcg   1080
cagagaggga gtggccaact ccatcactag gggttcctac gcgtagatct catattctgg   1140
cagggtcagt ggctccaact aacatttgtt tggtacttta cagtttatta aatagatgtt   1200
```

| | |
|---|---|
| tatatggaga agctctcatt tctttctcag aagagcctgg ctaggaaggt ggatgaggca | 1260 |
| ccatattcat tttgcaggtg aaattcctga gatgtaagga gctgctgtga cttgctcaag | 1320 |
| gccttatatc gagtaaacgg tagcgctggg gcttagacgc aggtgttctg atttatagtt | 1380 |
| caaaacctct atcaatgaga gagcaatctc ctggtaatgt gatagatttc ccaacttaat | 1440 |
| gccaacatac cataaacctc ccattctgct aatgcccagc ctaagttggg gagaccactc | 1500 |
| cagattccaa gatgtacagt ttgctttgct gggccttttt cccatgcctg cctttactct | 1560 |
| gccagagtta tattgctggg gttttgaaga agatcctatt aaataaaaga ataagcagta | 1620 |
| ttattaagta gccctgcatt tcaggtttcc ttgagtggca ggccaggcct ggccgtgaac | 1680 |
| gttcactgaa atcatggcct cttggccaag attgatagct tgtgcctgtc cctgagtccc | 1740 |
| agtccatcac gagcagctgg tttctaagat gctatttccc gtataaagca tgagaccgtg | 1800 |
| acttgccagc cccacagagc cccgcccttg tccatcactg gcatctggac tccagcctgg | 1860 |
| gttgggcaa agagggaaat gagatcatgt cctaaccctg atcctcttgt cccacagata | 1920 |
| tccagaaccc tgaccctgcc gtgtaccagc tgagagactc taaatccagt gacaagtctg | 1980 |
| tctgcctatt caccgatttt gattctcaaa caaatgtgtc acaaagtaag gattctgatg | 2040 |
| tgtatatcac agacaaaact gtgctagaca tgaggtctat ggacttcaag agcaacagtg | 2100 |
| ctgtggcctg gagcaactag tcaatattgg ccattagcca tattattcat tggttatata | 2160 |
| gcataaatca atattggcta ttggccattg catacgttgt atctatatca taatatgtac | 2220 |
| atttatattg gctcatgtcc aatatgaccg ccatgttggc attgattatt gaccagttat | 2280 |
| taatagtaat caattacggg gtcattagtt catagcccat atatggagtt ccgcgttaca | 2340 |
| taacttacgg taaatggccc gcctggctga ccgcccaacg acccccgccc attgacgtca | 2400 |
| ataatgacgt atgttcccat agtaacgcca atagggactt tccattgacg tcaatgggtg | 2460 |
| gagtatttac ggtaaactgc ccacttggca gtacatcaag tgtatcataa tccaagtccg | 2520 |
| cccccctattg acgtcaatga cggtaaatgg cccgcctggc attatgccca gtacatgacc | 2580 |
| ttacgggact ttcctacttg gcagtacatc tacgtattag tcatcgctat taccatgatg | 2640 |
| atgcggtttt ggcagtacac caatgggcgt ggatagcggt ttgactcacg ggatttccaa | 2700 |
| agtctccacc ccattgacgt caatgggagt ttgttttggc accaaaatca acgggacttt | 2760 |
| ccaaaatgtc gtaataaccc cgccccgttg acgcaaatgg gcggtaggcg tgtacggtgg | 2820 |
| gaggtctata taagcagagc tcgtttagtg aaccgtcaga tcactagaag ctttattgcg | 2880 |
| gtagtttatc acagttaaat tgctaacgca gtcagtgctt ctgacacaac agtctcgaac | 2940 |
| ttaagctgca gaagttggtc gtgaggcact gggcaggtaa gtatcaaggt tacaagacag | 3000 |
| gtttaaggag accaatagaa actgggcttg tcgagacaga gaagactctt gcgtttctga | 3060 |
| taggcaccta ttggtcttac tgacatccac tttgcctttc tctccacagg tgtccactcc | 3120 |
| cagttcaatt acagctctta aggctagagt acttaatacg actcactata ggccaccatg | 3180 |
| gcgctcccag tgacagcctt acttttacct ctggcgttat tattgcacgc ggctcgtcct | 3240 |
| gacatacaga tgactcagac tacctcttcc ctatctgctt ctttaggcga ccgagtaaca | 3300 |
| atatcttgcc gggccagcca ggacatctca aaatacttaa actggtatca gcagaagccg | 3360 |
| gacggaacag ttaagttgct catttaccac acgtcgagat tacactcagg cgttcctagc | 3420 |
| cgattttcgg gttccggttc cggtacggac tacagcctga caatcagtaa ccttgagcag | 3480 |
| gaggacatcg ccacctactt ctgtcagcag ggcaacacgc tcccgtacac attcggtggg | 3540 |
| ggaactaagc tggagattac cggaggcggt ggcagcggtg gcggcggcag cggggtggc | 3600 |

```
ggctcggagg tcaagttaca ggagagcgga ccgggcttgg tcgcacctag ccagagcctc    3660
tcagtcacgt gcactgtgtc tggagtcagt ctcccagact acggggtatc atggatacga    3720
cagccgccta gaaagggctt agagtggctg ggggttatct ggggaagtga aaccacatac    3780
tacaactcag ctctcaagag ccgcctcacc atcattaagg acaacagtaa gtcgcaggtt    3840
ttcttaaaga tgaactctct ccagactgac gacaccgcta tttactactg cgcgaagcac    3900
tactactacg gcgggagtta cgcaatggac tactggggtc agggcacttc tgtgaccgta    3960
tccagcacta ctaccccagc cccacgtccc cccacgccag ctccaacgat agcaagtcag    4020
cccttatctc ttcgccctga ggcttgcagg cccgcggcgg gcggcgccgt tcacacgcga    4080
ggactagact tcgcctgcga catctacatc tgggcaccac tagccgggac ttgcggagtg    4140
ttgttgttga gcttggtaat aacgctctac tgcaagcgtg ggagaaagaa gctcttgtac    4200
attttcaagc agccattcat gcgtcccgtt cagacgactc aggaggagga cggctgctcg    4260
tgccgattcc cggaggagga ggagggcggt tgcgaactca gagtgaagtt ctctcgctcc    4320
gcggacgcac ccgcttacca gcagggtcag aaccagctat acaacgagtt aaacctgggg    4380
cgccgggagg agtacgacgt gttagacaag cgtagaggta gggacccgga gatgggaggc    4440
aagcctcgga gaaagaaccc ccaggagggc ctgtacaacg aactccagaa ggacaagatg    4500
gctgaggcgt actcggagat tggtatgaag gcgagagac gtcgcggaaa gggacacgac    4560
ggcttatacc agggcttc caccgcgacc aaggacacat acgacgcgct gcacatgcaa    4620
gccttaccac ctcgatgagg taccagcggc cgcttcgagc agacatgata agatacattg    4680
atgagtttgg acaaaccaca actagaatgc agtgaaaaaa atgctttatt tgtgaaattt    4740
gtgatgctat tgcttttattt gtaaccatta taagctgcaa taaacaagtt aacaacaaca    4800
attcgaattt aaatcggatc cgcaacaaat ctgactttgc atgtgcaaac gccttcaaca    4860
acagcattat tccagaagac accttcttcc ccagcccagg taaggcagc tttggtgcct    4920 tcgcaggctg tttccttgct tcaggaatgg ccaggttctg cccagagctc tggtcaatga    4980
tgtctaaaac tcctctgatt ggtggtctcg gccttatcca ttgccaccaa aaccctcttt    5040
ttactaagaa acagtgagcc ttgttctggc agtccagaga atgacacggg aaaaaagcag    5100
atgaagagaa ggtggcagga gagggcacgt ggcccagcct cagtctctcc aactgagttc    5160
ctgcctgcct gcctttgctc agactgtttg ccccttactg ctcttctagg cctcattcta    5220
agccccttct ccaagttgcc tctccttatt tctccctgtc tgccaaaaaa tctttcccag    5280
ctcactaagt cagtctcacg cagtcactca ttaacccacc aatcactgat tgtgccggca    5340
catgaatgca ccaggtgttg aagtggagga attaaaaagt cagatgaggg gtgtgcccag    5400
aggaagcacc attctagttg ggggagcca tctgtcagct gggaaaagtc aaataactt    5460 cagattggaa tgtgtttaa ctcagggttg agaaaacagc caccttcagg acaaaagtca    5520
gggaagggct ctctgaagaa atgctacttg aagataccag ccctaccaag gcagggaga    5580 ggaccaattg atggagttgg ccactccctc tctgcgcgct cgctcgctca ctgaggccgc    5640
ccgggcaaag cccgggcgtc gggcgacctt tggtcgcccg gcctcagtga gcgagcgagc    5700
gcgcagagag ggagtggcca acggcgcgcc tgcaggtctc aaaatagct accctctccg    5760 gcatgaattt atcagctaga acggttgaat atcatattga tggtgatttg actgtctccg    5820
gcctttctca cccgtttgaa tctttaccta cacattactc aggcattgca tttaaaatat    5880
atgagggttc taaaaatttt tatccttgcg ttgaaataaa ggcttctccc gcaaaagtat    5940
```

```
tacagggtca taatgttttt ggtacaaccg atttagcttt atgctctgag gctttattgc   6000
ttaattttgc taattctttg ccttgcctgt atgatttatt ggatgttgga attcctgatg   6060
cggtattttc tccttacgca tctgtgcggt atttcacacc gcatatggtg cactctcagt   6120
acaatctgct ctgatgccgc atagttaagc cagccccgac acccgccaac acccgctgac   6180
gcgccctgac gggcttgtct gctcccggca tccgcttaca gacaagctgt gaccgtctcc   6240
gggagctgca tgtgtcagag gttttcaccg tcatcaccga aacgcgcgag acgaaagggc   6300
ctcgtgatac gcctattttt ataggttaat gtcatgataa taatggtttc ttagacgtca   6360
ggtggcactt ttcggggaaa tgtgcgcgga acccctattt gtttattttt ctaaatacat   6420
tcaaatatgt atccgctcat gagacaataa ccctgataaa tgcttcaata atattgaaaa   6480
aggaagagta tgagtattca acatttccgt gtcgccctta ttcccttttt tgcggcattt   6540
tgccttcctg ttttgctca cccagaaacg ctggtgaaag taaaagatgc tgaagatcag   6600
ttgggtgcac gagtgggtta catcgaactg gatctcaaca gcggtaagat ccttgagagt   6660
tttcgccccg aagaacgttt tccaatgatg agcacttta aagttctgct atgtggcgcg   6720
gtattatccc gtattgacgc cgggcaagag caactcggtc gccgcataca ctattctcag   6780
aatgacttgg ttgagtactc accagtcaca gaaaagcatc ttacgatgg catgacagta   6840 agagaattat gcagtgctgc cataaccatg agtgataaca ctgcggccaa cttacttctg   6900
acaacgatcg gaggaccgaa ggagctaacc gcttttttgc acaacatggg ggatcatgta   6960
actcgccttg atcgttggga accggagctg aatgaagcca taccaaacga cgagcgtgac   7020
accacgatgc ctgtagcaat ggcaacaacg ttgcgcaaac tattaactgg cgaactactt   7080
actctagctt cccggcaaca attaatagac tggatggagg cggataaagt tgcaggacca   7140
cttctgcgct cggcccttcc ggctggctgg tttattgctg ataaatctgg agccggtgag   7200
cgtgggtctc gcggtatcat tgcagcactg gggccagatg gtaagccctc ccgtatcgta   7260
gttatctaca cgacggggag tcaggcaact atggatgaac gaaatagaca gatcgctgag   7320
ataggtgcct cactgattaa gcattggtaa ctgtcagacc aagtttactc atatatactt   7380
tagattgatt taaaacttca ttttaattt aaaaggatct aggtgaagat cctttttgat   7440
aatctcatga ccaaaatccc ttaacgtgag ttttcgttcc actgagcgtc agaccccgta   7500
gaaaagatca aaggatcttc ttgagatcct tttttctgc gcgtaatctg ctgcttgcaa   7560
acaaaaaaac caccgctacc agcggtggtt tgtttgccgg atcaagagct accaactctt   7620
tttccgaagg taactggctt cagcagagcg cagataccaa atactgtcct tctagtgtag   7680
ccgtagttag gccaccactt caagaactct gtagcaccgc ctacatacct cgctctgcta   7740
atcctgttac cagtggctgc tgccagtggc gataagtcgt gtcttaccgg gttggactca   7800
agacgatagt taccggataa ggcgcagcgg tcgggctgaa cggggggttc gtgcacacag   7860
cccagcttgg agcgaacgac ctacaccgaa ctgagatacc tacagcgtga gctatgagaa   7920
agcgccacgc ttcccgaagg gagaaaggcg gacaggtatc cggtaagcgg cagggtcgga   7980
acaggagagc gcacgaggga gcttccaggg ggaaacgcct ggtatcttta tagtcctgtc   8040
gggtttcgcc acctctgact tgagcgtcga ttttgtgat gctcgtcagg ggggcggagc   8100
ctatggaaaa acgccagcaa cgcggccttt ttacggttcc tggccttttg ctggcctttt   8160
gctcacatgt tctttcctgc gttatcccct gattctgtgg ataaccgtat taccgccttt   8220
gagtgagctg ataccgctcg ccgcagccga acgaccgagc gcagcgagtc agtgagcgag   8280
gaagcggaag agcgcccaat acgcaaaccg cctctccccg cgcgttggcc gattcattaa   8340
```

<210> SEQ ID NO 125
<211> LENGTH: 7464
<212> TYPE: DNA
<213> ORGANISM: Artificial Sequence
<220> FEATURE:
<223> OTHER INFORMATION: Synthesized

<400> SEQUENCE: 125

| | | |
|---|---|---|
| cagcagctgg cgtaatagcg aagaggcccg caccgatcgc ccttcccaac agttgcgcag | 60 |
| cctgaatggc gaatggaatt ccagacgatt gagcgtcaaa atgtaggtat ttccatgagc | 120 |
| gttttccctg ttgcaatggc tggcggtaat attgttctgg atattaccag caaggccgat | 180 |
| agtttgagtt cttctactca ggcaagtgat gttattacta atcaaagaag tattgcgaca | 240 |
| acggttaatt tgcgtgatgg acagactctt ttactcggtg gcctcactga ttataaaaac | 300 |
| acttctcagg attctggcgt accgttcctg tctaaaatcc ctttaatcgg cctcctgttt | 360 |
| agctcccgct ctgattctaa cgaggaaagc acgttatacg tgctcgtcaa agcaaccata | 420 |
| gtacgcgccc tgtagcggcg cattaagcgc ggcgggtgtg gtggttacgc gcagcgtgac | 480 |
| cgctacactt gccagcgccc tagcgcccgc tcctttcgct ttcttccctt cctttctcgc | 540 |
| cacgttcgcc ggctttcccc gtcaagctct aaatcggggg ctcccttag ggttccgatt | 600 |
| tagtgcttta cggcacctcg accccaaaaa acttgattag ggtgatggtt cacgtagtgg | 660 |
| gccatcgccc tgatagacgg ttttcgccc tttgacgttg gagtccacgt tctttaatag | 720 |
| tggactcttg ttccaaactg gaacaacact caaccctatc tcggtctatt cttttgattt | 780 |
| ataagggatt tgccgatttc ggcctattg gttaaaaaat gagctgattt aacaaaaatt | 840 |
| taacgcgaat tttaacaaaa tattaacgtt tacaatttaa atatttgctt atacaatctt | 900 |
| cctgtttttg ggcttttct gattatcaac cggggtacat atgattgaca tgctagtttt | 960 |
| acggcgcgcc gggttggcca ctccctctct gcgcgctcgc tcgctcactg aggccgggcg | 1020 |
| accaaaggtc gcccgacgcc cgggctttgc ccggcggcc tcagtgagcg agcgagcgcg | 1080 |
| cagagaggga gtggccaact ccatcactag gggttcctac gcgtagatct catattctgg | 1140 |
| cagggtcagt ggctccaact aacatttgtt tggtacttta cagtttatta aatagatgtt | 1200 |
| tatatggaga agctctcatt tctttctcag aagagcctgg ctaggaaggt ggatgaggca | 1260 |
| ccatattcat tttgcaggtg aaattcctga gatgtaagga gctgctgtga cttgctcaag | 1320 |
| gccttatatc gagtaaacgg tagcgctggg gcttagacgc aggtgttctg atttatagtt | 1380 |
| caaaacctct atcaatgaga gagcaatctc ctggtaatgt gatagatttc ccaacttaat | 1440 |
| gccaacatac cataaacctc ccattctgct aatgcccagc ctaagttggg gagaccactc | 1500 |
| cagattccaa gatgtacagt ttgctttgct gggccttttt cccatgcctg cctttactct | 1560 |
| gccagagtta tattgctggg gttttgaaga agatcctatt aaataaaaga taagcagta | 1620 |
| ttattaagta gccctgcatt tcaggtttcc ttgagtggca ggccaggcct ggccgtgaac | 1680 |
| gttcactgaa atcatggcct cttggccaag attgatagct tgtgcctgtc cctgagtccc | 1740 |
| agtccatcac gagcagctgg tttctaagat gctatttccc gtataaagca tgagaccgtg | 1800 |
| acttgccagc cccacagagc cccgcccttg tccatcactg gcatctggac tccagcctgg | 1860 |
| gttgggcaa agaggaaat gagatcatgt cctaaccctg atcctcttgt cccacagata | 1920 |
| tccagaaccc tgaccctgcc gtgtaccagc tgagagactc taaatccagt gacaagtctg | 1980 |

```
tctgcctatt caccgatttt gattctcaaa caaatgtgtc acaaagtaag gattctgatg    2040
tgtatatcac agacaaaact gtgctagaca tgaggtctat ggacttcaag agcaacagtg    2100
ctgtggcctg gagcaactag tgggcggagt tagggcggag ccaatcagcg tgcgccgttc    2160
cgaaagttgc cttttatggc tgggcggaga atgggcggtg aacgccgatg attatataag    2220
gacgcgccgg gtgtggcaca gctagttccg tcgcagccgg gatttgggtc gcggttcttg    2280
tttgttccgg aaagccacca tggcgctccc agtgacagcc ttacttttac ctctggcgtt    2340
attattgcac gcggctcgtc ctgacataca gatgactcag actacctctt ccctatctgc    2400
ttctttaggc gaccgagtaa caatatcttg ccgggccagc caggacatct caaaatactt    2460
aaactggtat cagcagaagc cggacggaac agttaagttg ctcatttacc acacgtcgag    2520
attacactca ggcgttccta gccgattttc gggttccggt tccggtacgg actacagcct    2580
gacaatcagt aaccttgagc aggaggacat cgccacctac ttctgtcagc agggcaacac    2640
gctcccgtac acattcggtg gggaactaa gctggagatt accggaggcg gtggcagcgg    2700
tggcggcggc agcggggtg gcggctcgga ggtcaagtta caggagagcg gacccgggctt    2760 ggtcgcacct agccagagcc tctcagtcac gtgcactgtg tctggagtca gtctcccaga    2820
ctacggggta tcatggatac gacagccgcc tagaaagggc ttagagtggc tgggggttat    2880
ctggggaagt gaaaccacat actacaactc agctctcaag agccgcctca ccatcattaa    2940
ggacaacagt aagtcgcagg ttttcttaaa gatgaactct ctccagactg acgacaccgc    3000
tatttactac tgcgcgaagc actactacta cggcgggagt tacgcaatgg actactgggg    3060
tcagggcact tctgtgaccg tatccagcac tactacccca gccccacgtc ccccacgcc    3120 agctccaacg atagcaagtc agcccttatc tcttcgccct gaggcttgca ggcccgcggc    3180
gggcggcgcc gttcacacgc gaggactaga cttcgcctgc gacatctaca tctgggcacc    3240
actagccggg acttgcggag tgttgttgtt gagcttggta ataacgctct actgcaagcg    3300
tgggagaaag aagctcttgt acattttcaa gcagccattc atgcgtcccg ttcagacgac    3360
tcaggaggag gacggctgct cgtgccgatt cccggaggag gaggagggcg gttgcgaact    3420
cagagtgaag ttctctcgct ccgcggacgc acccgcttac cagcagggtc agaaccagct    3480
atacaacgag ttaaacctgg ggcgccggga ggagtacgac gtgttagaca agcgtagagg    3540
tagggacccg gagatgggag gcaagcctcg gagaaagaac ccccaggagg gcctgtacaa    3600
cgaactccag aaggacaaga tggctgaggc gtactcggag attggtatga agggcgagag    3660
acgtcgcgga aagggacacg acggcttata ccagggcctt ccaccgcgca ccaaggacac    3720
atacgacgcg ctgcacatgc aagccttacc acctcgatga ggtaccagcg gccgcttcga    3780
gcagacatga taagatacat tgatgagttt ggacaaacca caactagaat gcagtgaaaa    3840
aaatgcttta tttgtgaaat tgtgatgct attgctttat ttgtaaccat tataagctgc    3900
aataaacaag ttaacaacaa caattcgaat ttaaatcgga tccgcaacaa atctgacttt    3960
gcatgtgcaa acgccttcaa caacagcatt attccagaag acaccttctt ccccagccca    4020
ggtaagggca gctttggtgc cttcgcaggc tgtttccttg cttcaggaat ggccaggttc    4080
tgcccagagc tctggtcaat gatgtctaaa actcctctga ttggtggtct cggccttatc    4140
cattgccacc aaaaccctct ttttactaag aaacagtgag ccttgttctg gcagtccaga    4200
gaatgacacg ggaaaaaagc agatgaagag aaggtggcag gagagggcac gtggcccagc    4260
ctcagtctct ccaactgagt tcctgcctgc ctgcctttgc tcagactgtt tgcccttac    4320 tgctcttcta ggcctcattc taagcccctt ctccaagttg cctctcctta tttctccctg    4380
```

```
tctgccaaaa aatctttccc agctcactaa gtcagtctca cgcagtcact cattaaccca    4440
ccaatcactg attgtgccgg cacatgaatg caccaggtgt tgaagtggag gaattaaaaa    4500
gtcagatgag gggtgtgccc agaggaagca ccattctagt tgggggagcc catctgtcag    4560
ctgggaaaag tccaaataac ttcagattgg aatgtgtttt aactcagggt tgagaaaaca    4620
gccaccttca ggacaaaagt cagggaaggg ctctctgaag aaatgctact tgaagatacc    4680
agccctacca agggcaggga gaggaccaat tgatggagtt ggccactccc tctctgcgcg    4740
ctcgctcgct cactgaggcc gcccgggcaa agcccgggcg tcgggcgacc tttggtcgcc    4800
cggcctcagt gagcgagcga gcgcgcagag agggagtggc caacggcgcg cctgcaggtc    4860
tcaaaaatag ctaccctctc cggcatgaat ttatcagcta gaacggttga atatcatatt    4920
gatggtgatt tgactgtctc cggcctttct cacccgtttg aatctttacc tacacattac    4980
tcaggcattg catttaaaat atatgagggt tctaaaaatt tttatccttg cgttgaaata    5040
aaggcttctc ccgcaaaagt attacagggt cataatgttt ttggtacaac cgatttagct    5100
ttatgctctg aggctttatt gcttaatttt gctaattctt tgccttgcct gtatgattta    5160
ttggatgttg gaattcctga tgcggtattt tctccttacg catctgtgcg gtatttcaca    5220
ccgcatatgg tgcactctca gtacaatctg ctctgatgcc gcatagttaa gccagccccg    5280
acacccgcca cacccgctg acgcgccctg acgggcttgt ctgctcccgg catccgctta    5340
cagacaagct gtgaccgtct ccgggagctg catgtgtcag aggttttcac cgtcatcacc    5400
gaaacgcgcg agacgaaagg gcctcgtgat acgcctattt ttataggtta atgtcatgat    5460
aataatggtt tcttagacgt caggtggcac ttttcgggga atgtgcgcg gaacccctat    5520 ttgtttattt ttctaaatac attcaaatat gtatccgctc atgagacaat aaccctgata    5580
aatgcttcaa taatattgaa aaaggaagag tatgagtatt caacatttcc gtgtcgccct    5640
tattcccttt tttgcggcat tttgccttcc tgttttgct cacccagaaa cgctggtgaa    5700
agtaaaagat gctgaagatc agttgggtgc acagtgggt tacatcgaac tggatctcaa    5760
cagcggtaag atccttgaga gttttcgccc cgaagaacgt tttccaatga tgagcacttt    5820
taaagttctg ctatgtggcg cggtattatc ccgtattgac gccgggcaag agcaactcgg    5880
tcgccgcata cactattctc agaatgactt ggttgagtac tcaccagtca cagaaaagca    5940
tcttacggat ggcatgacag taagagaatt atgcagtgct gccataacca tgagtgataa    6000
cactgcggcc aacttacttc tgacaacgat cggaggaccg aaggagctaa ccgcttttt    6060 gcacaacatg gggatcatg taactcgcct tgatcgttgg gaaccggagc tgaatgaagc    6120
cataccaaac gacgagcgtg acaccacgat gcctgtagca atggcaacaa cgttgcgcaa    6180
actattaact ggcgaactac ttactctagc ttcccggcaa caattaatag actggatgga    6240
ggcggataaa gttgcaggac cacttctgcg ctcggccctt ccggctggct ggtttattgc    6300
tgataaatct ggagccggtg agcgtgggtc tcgcggtatc attgcagcac tggggccaga    6360
tggtaagccc tcccgtatcg tagttatcta cacgacgggg agtcaggcaa ctatggatga    6420
acgaaataga cagatcgctg agataggtgc ctcactgatt aagcattggt aactgtcaga    6480
ccaagtttac tcatatatac tttagattga tttaaaactt catttttaat ttaaaaggat    6540
ctaggtgaag atcctttttg ataatctcat gaccaaaatc ccttaacgtg agttttcgtt    6600
ccactgagcg tcagaccccg tagaaaagat caaaggatct tcttgagatc ctttttttct    6660
gcgcgtaatc tgctgcttgc aaacaaaaaa accaccgcta ccagcggtgg tttgtttgcc    6720
```

```
ggatcaagag ctaccaactc tttttccgaa ggtaactggc ttcagcagag cgcagatacc    6780
aaatactgtc cttctagtgt agccgtagtt aggccaccac ttcaagaact ctgtagcacc    6840
gcctacatac ctcgctctgc taatcctgtt accagtggct gctgccagtg gcgataagtc    6900
gtgtcttacc ggggttggact caagacgata gttaccggat aaggcgcagc ggtcgggctg    6960 aacgggggt tcgtgcacac agcccagctt ggagcgaacg acctacaccg aactgagata     7020
cctacagcgt gagctatgag aaagcgccac gcttcccgaa gggagaaagg cggacaggta    7080
tccggtaagc ggcagggtcg gaacaggaga gcgcacgagg gagcttccag ggggaaacgc    7140
ctggtatctt tatagtcctg tcgggtttcg ccacctctga cttgagcgtc gatttttgtg    7200
atgctcgtca gggggcgga gcctatgaa aaacgccagc aacgcggcct ttttacggtt      7260 cctggcct tgctggcctt ttgctcacat gttctttcct gcgttatccc ctgattctgt      7320
ggataaccgt attaccgcct ttgagtgagc tgataccgct cgccgcagcc gaacgaccga    7380
gcgcagcgag tcagtgagcg aggaagcgga agagcgccca atacgcaaac cgcctctccc    7440
cgcgcgttgg ccgattcatt aatg                                           7464
```

NUCLEIC ACIDS ENCODING ENGINEERED MEGANUCLEASES WITH RECOGNITION SEQUENCES FOUND IN THE HUMAN T CELL RECEPTOR ALPHA CONSTANT REGION GENE

CROSS REFERENCE TO RELATED APPLICATIONS

This application is a divisional of U.S. application Ser. No. 15/766,290, now U.S. Pat. No. 10,799,535, filed Apr. 5, 2018, which is a national stage filing under 35 U.S.C. § 371 of international application number PCT/US2016/055472, filed Oct. 5, 2016, and claims priority to U.S. Provisional Application No. 62/297,445, entitled "Engineered Meganucleases With Recognition Sequences Found In The Human T Cell Receptor Alpha Constant Region Gene," filed Feb. 19, 2016, and U.S. Provisional Application No. 62/237,382, entitled "Engineered Meganucleases With Recognition Sequences Found In The Human T Cell Receptor Alpha Constant Region Gene," filed Oct. 5, 2015, the disclosures of each of which are hereby incorporated by reference in their entireties.

FIELD OF THE INVENTION

The invention relates to the fields of oncology, cancer immunotherapy, molecular biology and recombinant nucleic acid technology. In particular, the invention relates to recombinant meganucleases engineered to recognize and cleave a recognition sequence found in the human T cell receptor alpha constant region gene. The invention further relates to the use of such recombinant meganucleases in methods for producing genetically-modified eukaryotic cells.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Sep. 9, 2020, is named P109070013US03-SEQ-EPG, and is 257 kilobytes in size.

BACKGROUND OF THE INVENTION

T cell adoptive immunotherapy is a promising approach for cancer treatment. This strategy utilizes isolated human T cells that have been genetically-modified to enhance their specificity for a specific tumor associated antigen. Genetic modification may involve the expression of a chimeric antigen receptor (CAR) or an exogenous T cell receptor to graft antigen specificity onto the T cell. By contrast to exogenous T cell receptors, chimeric antigen receptors derive their specificity from the variable domains of a monoclonal antibody. Thus, T cells expressing chimeric antigen receptors (CAR T cells) induce tumor immunoreactivity in a major histocompatibility complex non-restricted manner. To date, T cell adoptive immunotherapy has been utilized as a clinical therapy for a number of cancers, including B cell malignancies (e.g., acute lymphoblastic leukemia (ALL), B cell non-Hodgkin lymphoma (NHL), and chronic lymphocytic leukemia), multiple myeloma, neuroblastoma, glioblastoma, advanced gliomas, ovarian cancer, mesothelioma, melanoma, and pancreatic cancer.

Despite its potential usefulness as a cancer treatment, adoptive immunotherapy with CAR T cells has been limited, in part, by expression of the endogenous T cell receptor on the cell surface. CAR T cells expressing an endogenous T cell receptor may recognize major and minor histocompatibility antigens following administration to an allogeneic patient, which can lead to the development of graft-versus-host-disease (GVHD). As a result, clinical trials have largely focused on the use of autologous CAR T cells, wherein a patient's T cells are isolated, genetically-modified to incorporate a chimeric antigen receptor, and then re-infused into the same patient. An autologous approach provides immune tolerance to the administered CAR T cells; however, this approach is constrained by both the time and expense necessary to produce patient-specific CAR T cells after a patient's cancer has been diagnosed.

Thus, it would be advantageous to develop "off the shelf" CAR T cells, prepared using T cells from a third party donor, that have reduced expression of the endogenous T cell receptor and do not initiate GVHD upon administration. Such products could be generated and validated in advance of diagnosis, and could be made available to patients as soon as necessary. Therefore, a need exists for the development of allogeneic CAR T cells that lack an endogenous T cell receptor in order to prevent the occurrence of GVHD.

Genetic modification of genomic DNA can be performed using site-specific, rare-cutting, homing endonucleases (also called "meganucleases") that are engineered to recognize specific DNA sequences in a locus of interest. Homing endonucleases are a group of naturally-occurring nucleases that recognize 15-40 base pair cleavage sites commonly found in the genomes of plants and fungi. They are frequently associated with parasitic DNA elements, such as group 1 self-splicing introns and inteins. They naturally promote homologous recombination or gene insertion at specific locations in the host genome by producing a double-stranded break in the chromosome, which recruits the cellular DNA-repair machinery (Stoddard (2006), *Q. Rev. Biophys.* 38:49-95). Homing endonucleases are commonly grouped into four families: the LAGLIDADG (SEQ ID NO:7) family, the GIY-YIG family, the His-Cys box family and the HNH family. These families are characterized by structural motifs, which affect catalytic activity and recognition sequence. For instance, members of the LAGLIDADG (SEQ ID NO:7) family are characterized by having either one or two copies of the conserved LAGLIDADG (SEQ ID NO:7) motif (Chevalier et al. (2001), *Nucleic Acids Res.* 29(18): 3757-3774). The LAGLIDADG (SEQ ID NO:7) homing endonucleases with a single copy of the LAGLIDADG (SEQ ID NO:7) motif form homodimers, whereas members with two copies of the LAGLIDADG (SEQ ID NO:7) motif are found as monomers.

Methods for producing engineered, site-specific recombinant meganucleases are known in the art. I-CreI (SEQ ID NO:6) is a member of the LAGLIDADG (SEQ ID NO:7) family of homing endonucleases that recognizes and cuts a 22 base pair recognition sequence in the chloroplast chromosome of the algae *Chlamydomonas reinhardtii*. Genetic selection techniques have been used to modify the wild-type I-CreI cleavage site preference (Sussman et al. (2004), *J. Mol. Biol.* 342: 31-41; Chames et al. (2005), *Nucleic Acids Res.* 33: e178; Seligman et al. (2002), *Nucleic Acids Res.* 30: 3870-9, Arnould et al. (2006), *J. Mol. Biol.* 355: 443-58). More recently, a method of rationally-designing mono-LAGLIDADG (SEQ ID NO:7) homing endonucleases was described that is capable of comprehensively redesigning I-CreI and other homing endonucleases to target widely-divergent DNA sites, including sites in mammalian, yeast, plant, bacterial, and viral genomes (WO 2007/047859).

As first described in WO 2009/059195, I-CreI and its engineered derivatives are normally dimeric but can be fused into a single polypeptide using a short peptide linker that joins the C-terminus of a first subunit to the N-terminus of a second subunit (Li et al. (2009), *Nucleic Acids Res.* 37:1650-62; Grizot et al. (2009), *Nucleic Acids Res.* 37:5405-19.) Thus, a functional "single-chain" meganuclease can be expressed from a single transcript. Such engineered meganucleases exhibit an extremely low frequency of off-target cutting. By delivering a gene encoding a single-chain meganuclease to a cell, it is possible to specifically and preferentially target, cleave, and disrupt the TCR alpha constant region gene.

The use of engineered meganucleases for cleaving DNA targets in the human T cell receptor alpha constant region was previously disclosed in International Publication No. WO 2014/191527. The '527 publication discloses variants of the I-OnuI meganuclease that are engineered to target a recognition sequence (SEQ ID NO:3 of the '527 publication) within exon 1 of the TCR alpha constant region gene. Although the '527 publication discusses that a chimeric antigen receptor can be expressed in TCR knockout cells, the authors do not disclose the insertion of the chimeric antigen receptor coding sequence into the meganuclease cleavage site in the TCR alpha constant region gene.

The use of other nucleases and mechanisms for disrupting expression of the endogenous TCR have also been disclosed. For example, the use of zinc finger nucleases for disrupting TCR genes in human T cells was described by U.S. Pat. No. 8,995,828 and by U.S. Patent Application Publication No. US2014/034902. U.S. Patent Application Publication No. US2014/0301990 describes the use of zinc finger nucleases and transcription-activator like effector nucleases (TALENs), and a CRISPR/Cas system with an engineered single guide RNA for targeting TCR genes in an isolated T cell. U.S. Patent Application Publication No. US2012/0321667 discloses the use of small-hairpin RNAs that target nucleic acids encoding specific TCRs and/or CD3 chains in T cells.

However, the present invention improves upon the teachings of the prior art. The present inventors are the first to teach genetically-modified cells that comprise an exogenous polynucleotide sequence (e.g., a chimeric antigen receptor or exogenous TCR coding sequence) inserted into the human TCR alpha constant region gene, which simultaneously disrupts expression of the endogenous T cell receptor at the cell surface. Further, the prior art does not teach the meganucleases or the recognition sequences described herein, or their use for producing such genetically-modified cells.

SUMMARY OF THE INVENTION

The present invention provides recombinant meganucleases that are engineered to recognize and cleave recognition sequences found within residues 93-208 of the human T cell receptor (TCR) alpha constant region gene (SEQ ID NO:1). Such meganuclease are useful for disrupting the TCR alpha constant region gene and, consequently, disrupting the expression and/or function of the cell surface TCR. Therefore, the meganucleases of the invention have utility in immunotherapy, including cancer immunotherapy. Meganuclease cleavage can disrupt gene function either by the mutagenic action of non-homologous end joining or by promoting the introduction of an exogenous polynucleotide into the gene via homologous recombination. In some embodiments, the introduced exogenous polynucleotide comprises a nucleic acid sequence encoding a chimeric antigen receptor, such that the meganuclease is useful for generating an allogeneic CAR T cell that lacks an endogenous TCR.

The present invention further provides methods comprising the delivery of a recombinant meganuclease protein, or genes encoding a recombinant meganuclease, to a eukaryotic cell in order to produce a genetically-modified eukaryotic cell.

Thus, in one aspect, the invention provides a recombinant meganuclease that recognizes and cleaves a recognition sequence within residues 93-208 of the human T cell receptor alpha constant region gene (SEQ ID NO:1). Such a recombinant meganuclease comprises a first subunit and a second subunit, wherein the first subunit binds to a first recognition half-site of the recognition sequence and comprises a first hypervariable (HVR1) region, and wherein the second subunit binds to a second recognition half-site of the recognition sequence and comprises a second hypervariable (HVR2) region.

In one embodiment, the recognition sequence comprises SEQ ID NO:3 (i.e., the TRC 1-2 recognition sequence).

In one such embodiment, the first meganuclease subunit comprises an amino acid sequence having at least 80%, at least 85%, at least 90%, or at least 95% sequence identity to residues 198-344 of any one of SEQ ID NOs:8-18 or residues 7-153 of any one of SEQ ID NOs:19-27, and the second meganuclease subunit comprises an amino acid sequence having at least 80%, at least 85%, at least 90%, or at least 95% sequence identity to residues 7-153 of any one of SEQ ID NOs:8-18 or residues 198-344 of any one of SEQ ID NOs:19-27.

In another such embodiment, the HVR1 region comprises Y at a position corresponding to: (a) position 215 of any one of SEQ ID NOs:8-18; or (b) position 24 of any one of SEQ ID NOs:19-27. In another such embodiment, the HVR1 region comprises G at a position corresponding to: (a) position 233 of any one of SEQ ID NOs:8-18; or (b) position 42 of any one of SEQ ID NOs:19-27. In another such embodiment, the HVR1 region comprises one or more of Y and G at positions corresponding to (a) positions 215 and 233, respectively, of any one of SEQ ID NOs:8-18; or (b) positions 24 and 42, respectively, of any one of SEQ ID NOs:19-27.

In another such embodiment, the HVR2 region comprises T at a position corresponding to: (a) position 26 of any one of SEQ ID NOs:8-18; or (b) position 217 of any one of SEQ ID NOs:19-27. In another such embodiment, the HVR2 region comprises F or Y at a position corresponding to: (a) position 28 of any one of SEQ ID NOs:8-18; or (b) position 219 of any one of SEQ ID NOs:19-27. In another such embodiment, the HVR2 region comprises F at a position corresponding to: (a) position 38 of any one of SEQ ID NOs:8-18; or (b) position 229 of any one of SEQ ID NOs:19-27. In another such embodiment, the HVR2 region comprises S at a position corresponding to: (a) position 44 of any one of SEQ ID NOs:8-18; or (b) position 235 of any one of SEQ ID NOs:19-27. In another such embodiment, the HVR2 region comprises F or Y at a position corresponding to: (a) position 46 of any one of SEQ ID NOs:8-18; or (b) position 237 of any one of SEQ ID NOs:19-27. In another such embodiment, the HVR2 region comprises one or more of T, F or Y, F, S, and F or Y, and R at positions corresponding to: (a) positions 26, 28, 38, 44, and 46, respectively, of any one of SEQ ID NOs:8-18; or (b) positions 217, 219, 229, 235, and 237, respectively, of any one of SEQ ID NOs:19-27.

In another such embodiment, the HVR1 region comprises residues 215-270 of any one of SEQ ID NOs:8-18 or residues 24-79 of any one of SEQ ID NOs:19-27. In another such embodiment, the HVR2 region comprises residues 24-79 of any one of SEQ ID NOs:8-18 or residues 215-270 of any one of SEQ ID NOs:19-27.

In another such embodiment, the first meganuclease subunit comprises residues 198-344 of any one of SEQ ID NOs:8-18 or residues 7-153 of any one of SEQ ID NOs: 19-27. In another such embodiment, the second meganuclease subunit comprises residues 7-153 of any one of SEQ ID NOs:8-18 or residues 198-344 of any one of SEQ ID NOs:19-27.

In another such embodiment, the recombinant meganuclease is a single-chain meganuclease comprising a linker, wherein the linker covalently joins the first subunit and the second subunit.

In another such embodiment, the recombinant meganuclease comprises the amino acid sequence of any one of SEQ ID NOs:8-27.

In a further embodiment, the recognition sequence comprises SEQ ID NO:4 (i.e., the TRC 3-4 recognition sequence).

In one such embodiment, the first meganuclease subunit comprises an amino acid sequence having at least 80%, at least 85%, at least 90%, or at least 95% sequence identity to residues 7-153 of SEQ ID NO:28 or 29, and the second meganuclease subunit comprises an amino acid sequence having at least 80%, at least 85%, at least 90%, or at least 95% sequence identity to residues 198-344 of SEQ ID NO:28 or 29.

In another such embodiment, the HVR1 region comprises Y at a position corresponding to position 24 of SEQ ID NO:28 or 29. In another such embodiment, the HVR1 region comprises T at a position corresponding to position 26 of SEQ ID NO:28 or 29. In another such embodiment, the HVR1 region comprises Y at a position corresponding to position 46 of SEQ ID NO:28 or 29. In another such embodiment, the HVR1 region comprises one or more of Y, T, and Y at positions corresponding to positions 24, 26, and 46, respectively, of SEQ ID NO:28 or 29.

In another such embodiment, the HVR2 region comprises H at a position corresponding to position 215 of SEQ ID NO:28 or 29. In another such embodiment, the HVR2 region comprises T at a position corresponding to position 266 of SEQ ID NO:28 or 29. In another such embodiment, the HVR2 region comprises C at a position corresponding to position 268 of SEQ ID NO:28 or 29. In another such embodiment, the HVR2 region comprises one or more of H, T, and C at positions corresponding to positions 215, 266, and 268 of SEQ ID NOs:28 or 29.

In another such embodiment, the HVR1 region comprises residues 24-79 of SEQ ID NO:28 or 29. In another such embodiment, the HVR2 region comprises residues 215-270 of SEQ ID NO:28 or 29.

In another such embodiment, the first meganuclease subunit comprises residues 7-153 of SEQ ID NO:28 or 29. In another such embodiment, the second meganuclease subunit comprises residues 198-344 of SEQ ID NO:28 or 29.

In another such embodiment, the recombinant meganuclease is a single-chain meganuclease comprising a linker, wherein the linker covalently joins the first subunit and the second subunit.

In another such embodiment, the recombinant meganuclease comprises the amino acid sequence of SEQ ID NO:28 or 29.

In a further embodiment, the recognition sequence comprises SEQ ID NO:5 (i.e., the TRC 7-8 recognition sequence).

In one such embodiment, the first meganuclease subunit comprises an amino acid sequence having at least 80%, at least 85%, at least 90%, or at least 95% sequence identity to residues 7-153 of SEQ ID NO:30 or residues 198-344 of SEQ ID NO:31 or 32, and the second meganuclease subunit comprises an amino acid sequence having at least 80%, at least 85%, at least 90%, or at least 95% sequence identity to residues 198-344 of SEQ ID NO:30 or residues 7-153 of SEQ ID NO:31 or 32.

In another such embodiment, the HVR1 region comprises Y at a position corresponding to: (a) position 24 of SEQ ID NO:30; or (b) position 215 of SEQ ID NO:31 or 32.

In another such embodiment, the HVR2 region comprises Y or W at a position corresponding to: (a) position 215 of SEQ ID NO:30; or (b) position 24 of SEQ ID NO:31 or 32. In another such embodiment, the HVR2 region comprises M, L, or W at a position corresponding to: (a) position 231 of SEQ ID NO:30; or (b) position 40 of SEQ ID NO:31 or 32. In another such embodiment, the HVR2 region comprises Y at a position corresponding to: (a) position 237 of SEQ ID NO:30; or (b) position 46 of SEQ ID NO:31 or 32. In another such embodiment, the HVR2 region comprises one or more of Y or W, M, L, or W, and Y at positions corresponding to: (a) positions 215, 231, and 237, respectively, of SEQ ID NO:30; or (b) positions 24, 40, and 46, respectively, of SEQ ID NO:31 or 32.

In another such embodiment, the HVR1 region comprises residues 24-79 of SEQ ID NO:30 or residues 215-270 of SEQ ID NO:31 or 32. In another such embodiment, the HVR2 region comprises residues 215-270 of SEQ ID NO:30 or residues 24-79 of SEQ ID NO:31 or 32.

In another such embodiment, the first meganuclease subunit comprises residues 7-153 of SEQ ID NO:30 or residues 198-344 of SEQ ID NO:31 or 32. In another such embodiment, the second meganuclease subunit comprises residues 198-344 of SEQ ID NO:30 or residues 7-153 of SEQ ID NO:31 or 32.

In another such embodiment, the recombinant meganuclease is a single-chain meganuclease comprising a linker, wherein the linker covalently joins the first subunit and the second subunit.

In another such embodiment, the recombinant meganuclease comprises the amino acid sequence of any one of SEQ ID NOs:30-32.

In another aspect, the invention provides an isolated polynucleotide comprising a nucleic acid sequence encoding a recombinant meganuclease described herein.

In the various aspects of the invention, the isolated polynucleotide can be an mRNA. In one embodiment, the mRNA can encode a single recombinant meganuclease described herein. In other embodiments, the mRNA can be a polycistronic mRNA (e.g., bicistronic, tricistronic, etc.) comprising a coding sequence for at least one meganuclease described herein and a coding sequence for at least one additional protein (e.g., a second nuclease). In particular embodiments, a polycistronic mRNA can encode two or more meganucleases described herein that target different recognition sequences within the same gene (e.g., the T cell receptor alpha constant region gene). In other embodiments, a polycistronic mRNA can encode a meganuclease described herein and a second nuclease that recognizes and cleaves a different recognition sequence within the same gene (e.g., the T cell receptor alpha constant region gene) or, alternatively, recognizes and cleaves a different recognition sequence within another gene of interest in the genome. In such embodiments, genetically-modified cells produced using such polycistronic mRNA can have multiple genes knocked out simultaneously. Further, genetically-modified cells produced using such polycistronic mRNA can have an exogenous sequence of interest inserted into the genome at one or more of the cleavage sites produced by the encoded nucleases. In additional embodiments, a polycistronic mRNA can encode at least one meganuclease described herein and one additional protein that is beneficial to the cell, improves efficiency of insertion of an exogenous sequence of interest into a cleavage site, and/or is beneficial in the treatment of a disease.

In another aspect, the invention provides a recombinant DNA construct comprising an isolated polynucleotide, wherein the isolated polynucleotide comprises a nucleic acid sequence encoding a recombinant meganuclease described herein. In one embodiment, the recombinant DNA construct encodes a viral vector. In one embodiment, the recombinant DNA construct encodes a recombinant AAV vector.

In another aspect, the invention provides a viral vector comprising an isolated polynucleotide, wherein the isolated polynucleotide comprises a nucleic acid sequence encoding a recombinant meganuclease described herein. In another aspect, the invention provides a recombinant AAV vector comprising an isolated polynucleotide, wherein the isolated polynucleotide comprises a nucleic acid sequence encoding a recombinant meganuclease described herein.

In another aspect, the invention provides a method for producing a genetically-modified eukaryotic cell comprising an exogenous sequence of interest inserted into a chromosome of the eukaryotic cell, the method comprising transfecting a eukaryotic cell with one or more nucleic acids including: (a) a first nucleic acid sequence encoding a recombinant meganuclease described herein; and (b) a second nucleic acid sequence including the sequence of interest; wherein the recombinant meganuclease produces a cleavage site in the chromosome at a recognition sequence comprising SEQ ID NO:3, SEQ ID NO:4, or SEQ ID NO:5, and wherein the sequence of interest is inserted into the chromosome at the cleavage site.

In one embodiment of the method, the second nucleic acid further comprises sequences homologous to sequences flanking the cleavage site, and the sequence of interest is inserted at the cleavage site by homologous recombination.

In another embodiment of the method, the second nucleic acid lacks substantial homology to the cleavage site, and the sequence of interest is inserted into the chromosome by non-homologous end-joining.

In another embodiment of the method, the eukaryotic cell is a human T cell or a cell derived therefrom.

In another embodiment of the method, the sequence of interest encodes a chimeric antigen receptor. In another embodiment of the method, the sequence of interest encodes an exogenous T cell receptor.

In another embodiment of the method, at least the first nucleic acid sequence is introduced into the cell by an mRNA. In some such embodiments, the mRNA can be a polycistronic mRNA encoding at least one recombinant meganuclease described herein and at least one additional protein (e.g., a second nuclease).

In another embodiment of the method, at least the second nucleic acid sequence is introduced into the eukaryotic cell by a viral vector. In another embodiment of the method, the first nucleic acid sequence and the second nucleic acid sequence are introduced into the eukaryotic cell by the same viral vector or, alternatively, by separate viral vectors.

In another embodiment of the method, at least the second nucleic acid sequence is introduced into the eukaryotic cell by a recombinant AAV vector. In another embodiment of the method, the first nucleic acid sequence and the second nucleic acid sequence are introduced into the eukaryotic cell by the same recombinant AAV vector or, alternatively, by separate recombinant AAV vectors.

In another embodiment of the method, at least the second nucleic acid sequence is introduced into the eukaryotic cell using a single-stranded DNA template.

In a particular embodiment of the method, the first nucleic acid sequence encoding a recombinant meganuclease described herein is introduced into the cell by an mRNA, and the second nucleic acid sequence including the exogenous sequence of interest is introduced into the cell using a viral vector, preferably a recombinant AAV vector, wherein the cell is a human T cell, and wherein the sequence of interest encodes a chimeric antigen receptor. In such an embodiment, the method produces a genetically-modified T cell that comprises a chimeric antigen receptor and that has reduced cell-surface expression of the endogenous T cell receptor when compared to a control cell.

In another aspect, the invention provides a method for producing a genetically-modified eukaryotic cell comprising an exogenous sequence of interest inserted into a chromosome of the eukaryotic cell, the method comprising: (a) introducing a recombinant meganuclease described herein into a eukaryotic cell; and (b) transfecting the eukaryotic cell with a nucleic acid including the sequence of interest; wherein the recombinant meganuclease produces a cleavage site in the chromosome at a recognition sequence comprising SEQ ID NO:3, SEQ ID NO:4, or SEQ ID NO:5, and wherein the sequence of interest is inserted into the chromosome at the cleavage site.

In one embodiment of the method, the nucleic acid further comprises sequences homologous to sequences flanking the cleavage site, and the sequence of interest is inserted at the cleavage site by homologous recombination.

In another embodiment of the method, the nucleic acid lacks substantial homology to the cleavage site, and the sequence of interest is inserted into the chromosome by non-homologous end-joining.

In another embodiment of the method, the eukaryotic cell is a human T cell or a cell derived therefrom.

In another embodiment of the method, the sequence of interest encodes a chimeric antigen receptor. In another embodiment of the method, the sequence of interest encodes an exogenous T cell receptor.

In another embodiment of the method, the nucleic acid sequence is introduced into the eukaryotic cell by a viral vector.

In another embodiment of the method, the nucleic acid sequence is introduced into the eukaryotic cell by a recombinant AAV vector.

In another embodiment of the method, the nucleic acid sequence is introduced into the eukaryotic cell using a single-stranded DNA template.

In another aspect, the invention provides a method for producing a genetically-modified eukaryotic cell by disrupting a target sequence in a chromosome of the eukaryotic cell, the method comprising: transfecting a eukaryotic cell with a nucleic acid encoding a recombinant meganuclease described herein; wherein the recombinant meganuclease produces a cleavage site in the chromosome at a recognition sequence comprising SEQ ID NO:3, SEQ ID NO:4, or SEQ ID NO:5, and wherein the target sequence is disrupted by non-homologous end-joining at the cleavage site.

In one embodiment of the method, the eukaryotic cell is a human T cell or a cell derived therefrom.

In another embodiment of the method, the nucleic acid encoding the recombinant meganuclease is an mRNA. In some such embodiments, the mRNA can be a polycistronic mRNA encoding at least one recombinant meganuclease described herein and at least one additional protein (e.g., a second nuclease).

In another embodiment, the method further comprises transfecting the eukaryotic cell with a second nucleic acid including an exogenous sequence of interest. In one such embodiment of the method, the second nucleic acid further comprises sequences homologous to sequences flanking the cleavage site, and the sequence of interest is inserted at the cleavage site by homologous recombination.

In another embodiment of the method, the sequence of interest encodes a chimeric antigen receptor. In another embodiment of the method, the sequence of interest encodes an exogenous T cell receptor.

In another embodiment of the method, at least the second nucleic acid is introduced into the eukaryotic cell by a viral vector.

In another embodiment of the method, at least the second nucleic acid is introduced into the eukaryotic cell by a recombinant AAV vector.

In another embodiment of the method, at least the second nucleic acid sequence is introduced into the eukaryotic cell using a single-stranded DNA template.

In another aspect, the invention provides a method for producing a genetically-modified eukaryotic cell by disrupting a target sequence in a chromosome of the eukaryotic cell, the method comprising: introducing a recombinant meganuclease described herein into a eukaryotic cell; wherein the meganuclease produces a cleavage site in the chromosome at a recognition sequence comprising SEQ ID NO:3, SEQ ID NO:4, or SEQ ID NO:5, and the target sequence is disrupted by non-homologous end-joining at the cleavage site.

In one embodiment of the method, the eukaryotic cell is a human T cell or a cell derived therefrom.

In another embodiment, the method further comprises transfecting the eukaryotic cell with a nucleic acid including an exogenous sequence of interest.

In one such embodiment of the method, the nucleic acid further comprises sequences homologous to sequences flanking the cleavage site, and the sequence of interest is inserted at the cleavage site by homologous recombination.

In another such embodiment of the method, the sequence of interest encodes a chimeric antigen receptor. In another such embodiment of the method, the sequence of interest encodes an exogenous T cell receptor.

In another such embodiment of the method, the nucleic acid is introduced into the eukaryotic cell by a viral vector.

In another such embodiment of the method, the nucleic acid is introduced into the eukaryotic cell by a recombinant AAV vector.

In another embodiment of the method, the nucleic acid sequence is introduced into the eukaryotic cell using a single-stranded DNA template.

In another aspect, the invention provides a method of producing a genetically-modified non-human organism comprising: producing a genetically-modified non-human eukaryotic cell according to the methods described herein; and (b) growing the genetically-modified non-human eukaryotic cell to produce the genetically-modified non-human organism.

In one embodiment of the method, the non-human eukaryotic cell is selected from the group consisting of a gamete, a zygote, a blastocyst cell, an embryonic stem cell, and a protoplast cell.

In another aspect, the invention provides a genetically-modified eukaryotic cell described herein for use as a medicament. The invention further provides the use of a genetically-modified eukaryotic cell described herein in the manufacture of a medicament for treating a disease in a subject in need thereof. In one such aspect, the medicament is useful in the treatment of cancer.

In some embodiments, the CAR comprises an extracellular antigen-binding domain. In some embodiments, the extracellular ligand-binding domain or moiety can be in the form of a single-chain variable fragment (scFv) derived from a monoclonal antibody, which provides specificity for a particular epitope or antigen (e.g., an epitope or antigen preferentially present on the surface of a cell, such as a cancer cell or other disease-causing cell or particle). The scFv can be attached via a linker sequence. The extracellular ligand-binding domain can be specific for any antigen or epitope of interest. In some embodiments, the scFv can be humanized. The extracellular domain of a chimeric antigen receptor can also comprise an autoantigen (see, Payne et al. (2016), Science 353 (6295): 179-184), which can be recognized by autoantigen-specific B cell receptors on B lymphocytes, thus directing T cells to specifically target and kill autoreactive B lymphocytes in antibody-mediated autoimmune diseases. Such CARs can be referred to as chimeric autoantibody receptors (CAARs), and their use is encompassed by the invention.

In another aspect, the invention provides a method of immunotherapy for treating cancer in a subject in need thereof comprising administering to the subject a pharmaceutical composition comprising a genetically-modified cell produced by the methods disclosed herein and a pharmaceutically acceptable carrier.

In some embodiments, the cancer is selected from the group consisting of a cancer of carcinoma, lymphoma, sarcoma, blastomas, and leukemia.

In some embodiments, the cancer is selected from the group consisting of a cancer of B-cell origin, breast cancer, gastric cancer, neuroblastoma, osteosarcoma, lung cancer, melanoma, prostate cancer, colon cancer, renal cell carcinoma, ovarian cancer, rhabdomyo sarcoma, leukemia, and Hodgkin's lymphoma. In some embodiments, the cancer of B-cell origin is selected from the group consisting of B-lineage acute lymphoblastic leukemia, B-cell chronic lymphocytic leukemia, and B-cell non-Hodgkin's lymphoma.

The foregoing and other aspects and embodiments of the present invention can be more fully understood by reference to the following detailed description and claims. Certain features of the invention, which are, for clarity, described in the context of separate embodiments, may also be provided in combination in a single embodiment. All combinations of the embodiments are specifically embraced by the present invention and are disclosed herein just as if each and every combination was individually and explicitly disclosed. Conversely, various features of the invention, which are, for brevity, described in the context of a single embodiment, may also be provided separately or in any suitable sub-combination. All sub-combinations of features listed in the embodiments are also specifically embraced by the present invention and are disclosed herein just as if each and every such sub-combination was individually and explicitly disclosed herein. Embodiments of each aspect of the present invention disclosed herein apply to each other aspect of the invention mutatis mutandis.

BRIEF DESCRIPTION OF THE FIGURES

FIG. 1. TRC recognition sequences in the human TRC alpha constant region gene. A) Each recognition sequence targeted by a recombinant meganuclease of the invention comprises two recognition half-sites. Each recognition half-site comprises 9 base pairs, separated by a 4 base pair central sequence. The TRC 1-2 recognition sequence (SEQ ID NO:3) spans nucleotides 187-208 of the human T cell alpha constant region (SEQ ID NO:1), and comprises two recognition half-sites referred to as TRC1 and TRC2. The TRC 3-4 recognition sequence (SEQ ID NO:4) spans nucleotides 93-114 of the human T cell alpha constant region (SEQ ID NO:1), and comprises two recognition half-sites referred to as TRC3 and TRC4. The TRC 7-8 recognition sequence (SEQ ID NO:5) spans nucleotides 118-139 of the human T cell alpha constant region (SEQ ID NO:1), and comprises two recognition half-sites referred to as TRC7 and TRC8. B) The recombinant meganucleases of the invention comprise two subunits, wherein the first subunit comprising the HVR1 region binds to a first recognition half-site (e.g., TRC1, TRC3, or TRC7) and the second subunit comprising the HVR2 region binds to a second recognition half-site (e.g., TRC2, TRC4, or TRC8). In embodiments where the recombinant meganuclease is a single-chain meganuclease, the first subunit comprising the HVR1 region can be positioned as either the N-terminal or C-terminal subunit. Likewise, the second subunit comprising the HVR2 region can be positioned as either the N-terminal or C-terminal subunit.

FIGS. 2A-B. Amino acid alignment of TRC1-binding subunits. A-B) Some recombinant meganucleases encompassed by the invention comprise one subunit that binds the 9 base pair TRC1 recognition half-site of SEQ ID NO:3. Amino acid sequence alignments are provided for the TRC1-binding subunits (SEQ ID NOs:33-52) of the recombinant meganucleases set forth in SEQ ID NOs:8-27. As shown, the TRC1-binding subunit of SEQ ID NOs:8-18 comprises residues 198-344, whereas the TRC1-binding subunit of SEQ ID NOs:19-27 comprises residues 7-153. Each TRC1-binding subunit comprises a 56 amino acid hypervariable region as indicated. Variable residues within the hypervariable region are shaded, with the most frequent amino acids at each position further highlighted; the most prevalent residues are bolded, whereas the second most prevalent are bolded and italicized. Residues outside of the hypervariable region are identical in each subunit, with the exception of a Q or E residue at position 80 or position 271 (see, U.S. Pat. No. 8,021,867). All TRC1-binding subunits provided in FIG. 2 share at least 90% sequence identity to the TRC1-binding subunit (residues 198-344) of the TRC 1-2x.87 EE meganuclease (SEQ ID NO:33). Residue numbers shown are those of SEQ ID NOs:8-27.

FIGS. 3A-B. Amino acid alignment of TRC2-binding subunits. A-B) Some recombinant meganucleases encompassed by the invention comprise one subunit that binds the 9 base pair TRC2 recognition half-site of SEQ ID NO:3. Amino acid sequence alignments are provided for the TRC2-binding subunits (SEQ ID NOs:58-77) of the recombinant meganucleases set forth in SEQ ID NOs:8-27. As shown, the TRC2-binding subunit of SEQ ID NOs:8-18 comprises residues 7-153, whereas the TRC2-binding subunit of SEQ ID NOs:19-27 comprises residues 198-344. Each TRC2-binding subunit comprises a 56 amino acid hypervariable region as indicated. Variable residues within the hypervariable region are shaded, with the most frequent amino acids at each position further highlighted; the most prevalent residues are bolded, whereas the second most prevalent are bolded and italicized. Residues outside of the hypervariable region are identical in each subunit, with the exceptions of a Q or E residue at position 80 or position 271 (see, U.S. Pat. No. 8,021,867), and an R residue at position 139 of meganucleases TRC 1-2x.87 EE, TRC 1-2x.87 QE, TRC 1-2x.87 EQ, TRC 1-2x.87, and TRC 1-2x.163 (shaded grey and underlined). All TRC2-binding subunits provided in FIG. 3 share at least 90% sequence identity to the TRC2-binding subunit (residues 7-153) of the TRC 1-2x.87 EE meganuclease (SEQ ID NO:58). Residue numbers shown are those of SEQ ID NOs:8-27.

FIG. 4. Amino acid alignment of TRC3-binding subunits. Some recombinant meganucleases encompassed by the invention comprise one subunit that binds the 9 base pair TRC3 recognition half-site of SEQ ID NO:4. Amino acid sequence alignments are provided for the TRC3-binding subunits (SEQ ID NOs:53 and 54) of the recombinant meganucleases set forth in SEQ ID NOs:28 and 29. As shown, the TRC3-binding subunit of SEQ ID NOs:28 and 29 comprises residues 7-153. Each TRC3-binding subunit comprises a 56 amino acid hypervariable region as indicated. Variable residues within the hypervariable region are shaded. Residues outside of the hypervariable region are identical in each subunit, with the exceptions of a Q or E residue at position 80 (see, U.S. Pat. No. 8,021,867). The TRC3-binding subunits of the TRC 3-4x.3 and TRC 3-4x.19 meganucleases share 97% sequence identity. Residue numbers shown are those of SEQ ID NOs:28 and 29.

FIG. 5. Amino acid alignment of TRC4-binding subunits. Some recombinant meganucleases encompassed by the invention comprise one subunit that binds the 9 base pair TRC4 recognition half-site of SEQ ID NO:4. Amino acid sequence alignments are provided for the TRC4-binding subunits (SEQ ID NOs:78 and 79) of the recombinant meganucleases set forth in SEQ ID NOs:28 and 29. As shown, the TRC4-binding subunit of SEQ ID NOs:28 and 29 comprises residues 198-344. Each TRC4-binding subunit comprises a 56 amino acid hypervariable region as indicated. Variable residues within the hypervariable region are shaded. Residues outside of the hypervariable region are identical in each subunit, with the exceptions of a Q or E residue at position 80 (see, U.S. Pat. No. 8,021,867). The TRC4-binding subunits of the TRC 3-4x.3 and TRC 3-4x.19 meganucleases share 97% sequence identity. Residue numbers shown are those of SEQ ID NOs:28 and 29.

FIGS. 6A-B. Amino acid alignment of TRC7-binding subunits. A-B) Some recombinant meganucleases encompassed by the invention comprise one subunit that binds the 9 base pair TRC7 recognition half-site of SEQ ID NO:5. Amino acid sequence alignments are provided for the TRC7-binding subunits (SEQ ID NOs:55-57) of the recombinant meganucleases set forth in SEQ ID NOs:30-32. As shown, the TRC7-binding subunit of SEQ ID NO:30 comprises residues 7-153, whereas the TRC7-binding subunit of SEQ ID NOs:31 and 32 comprises residues 198-344. Each TRC7-binding subunit comprises a 56 amino acid hypervariable region as indicated. Variable residues within the hypervariable region are shaded, with the most frequent amino acids at each position further highlighted; the most prevalent residues are bolded, whereas the second most prevalent are bolded and italicized. Residues outside of the hypervariable region are identical in each subunit, with the exception of a Q or E residue at position 80 or position 271

(see, U.S. Pat. No. 8,021,867). All TRC7-binding subunits provided in FIG. 6 share at least 90% sequence identity to the TRC7-binding subunit (residues 7-153) of the TRC 7-8x.7 meganuclease (SEQ ID NO:55). Residue numbers shown are those of SEQ ID NOs:30-32.

FIGS. 7A-B. Amino acid alignment of TRC8-binding subunits. A-B) Some recombinant meganucleases encompassed by the invention comprise one subunit that binds the 9 base pair TRC8 recognition half-site of SEQ ID NO:5. Amino acid sequence alignments are provided for the TRC8-binding subunits (SEQ ID NOs:80-82) of the recombinant meganucleases set forth in SEQ ID NOs:30-32. As shown, the TRC8-binding subunit of SEQ ID NO:30 comprises residues 198-344, whereas the TRC8-binding subunit of SEQ ID NOs:31 and 32 comprises residues 7-153. Each TRC8-binding subunit comprises a 56 amino acid hypervariable region as indicated. Variable residues within the hypervariable region are shaded, with the most frequent amino acids at each position further highlighted; the most prevalent residues are bolded, whereas the second most prevalent are bolded and italicized. Residues outside of the hypervariable region are identical in each subunit, with the exception of a Q or E residue at position 80 or position 271 (see, U.S. Pat. No. 8,021,867). All TRC8-binding subunits provided in FIG. 7 share at least 90% sequence identity to the TRC8-binding subunit (residues 198-344) of the TRC 7-8x.7 meganuclease (SEQ ID NO:80). Residue numbers shown are those of SEQ ID NOs:30-32.

Figure 8:
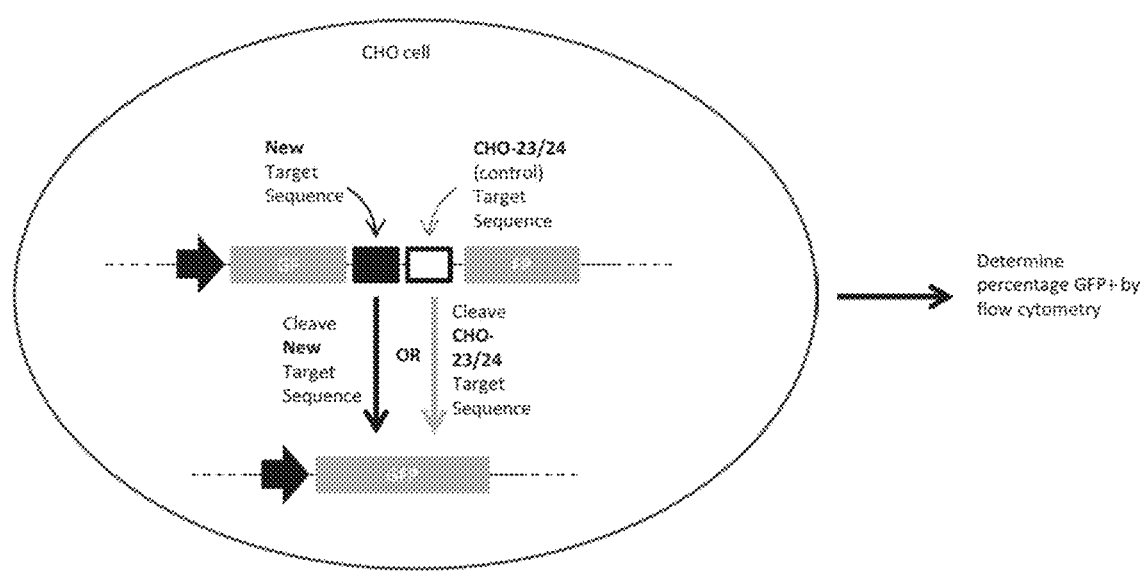

FIG. 8. Schematic of reporter assay in CHO cells for evaluating recombinant meganucleases targeting recognition sequences found in the T cell receptor alpha constant region (SEQ ID NO:1). For the recombinant meganucleases described herein, a CHO cell line was produced in which a reporter cassette was integrated stably into the genome of the cell. The reporter cassette comprised, in 5' to 3' order: an SV40 Early Promoter; the 5' 2/3 of the GFP gene; the recognition sequence for an engineered meganuclease of the invention (e.g., the TRC 1-2 recognition sequence, the TRC 3-4 recognition sequence, or the TRC 7-8 recognition sequence); the recognition sequence for the CHO-23/24 meganuclease (WO/2012/167192); and the 3' 2/3 of the GFP gene. Cells stably transfected with this cassette did not express GFP in the absence of a DNA break-inducing agent. Meganucleases were introduced by transduction of plasmid DNA or mRNA encoding each meganuclease. When a DNA break was induced at either of the meganuclease recognition sequences, the duplicated regions of the GFP gene recombined with one another to produce a functional GFP gene. The percentage of GFP-expressing cells could then be determined by flow cytometry as an indirect measure of the frequency of genome cleavage by the meganucleases.

Figure 9:
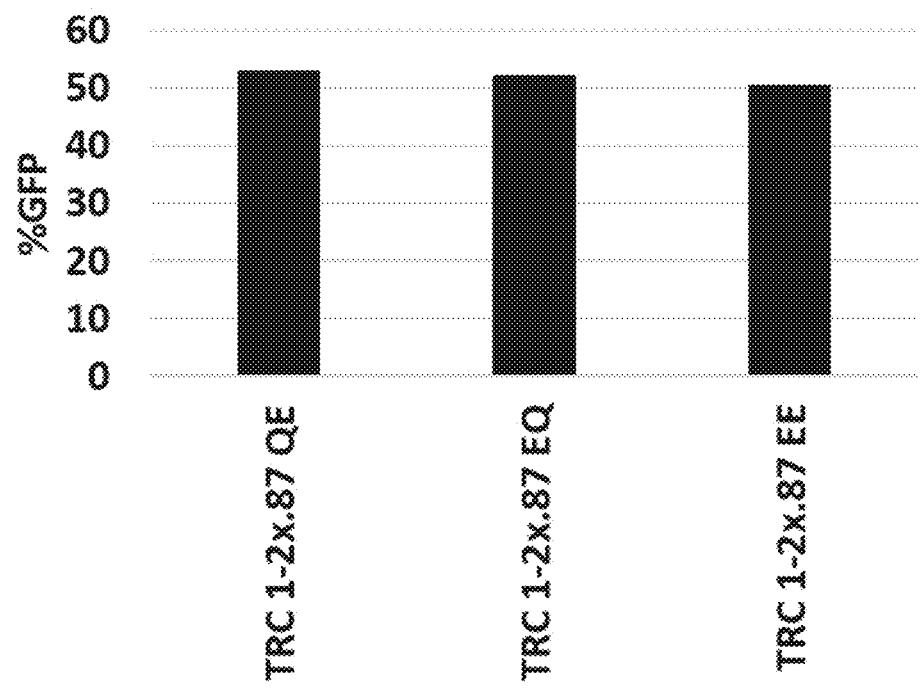

FIG. 9. Efficiency of recombinant meganucleases for recognizing and cleaving recognition sequences in the human T cell receptor alpha constant region (SEQ ID NO:1) in a CHO cell reporter assay. Each of the recombinant meganucleases set forth in SEQ ID NOs:8-32 were engineered to target the TRC 1-2 recognition sequence (SEQ ID NO:3), the TRC 3-4 recognition sequence (SEQ ID NO:4), or the TRC 7-8 recognition sequence (SEQ ID NO:5), and were screened for efficacy in the CHO cell reporter assay. The results shown provide the percentage of GFP-expressing cells observed in each assay, which indicates the efficacy of each meganuclease for cleaving a TRC target recognition sequence or the CHO-23/24 recognition sequence. A negative control (RHO 1-2 bs) was further included in each assay. A)-C) Meganucleases targeting the TRC 1-2 recognition sequence. D) Meganucleases targeting the TRC 3-4 recognition sequence. E)-F) Meganucleases targeting the TRC 7-8 recognition sequence. G) Variants of the TRC 1-2x.87 meganuclease, wherein the Q at position 271 is substituted with E (TRC 1-2x.87 QE), the Q at position 80 is substituted with E (TRC 1-2x.87 EQ), or the Q at position 80 and the Q at position 271 are both substituted with E (TRC 1-2x.87 EE).

Figure 10:
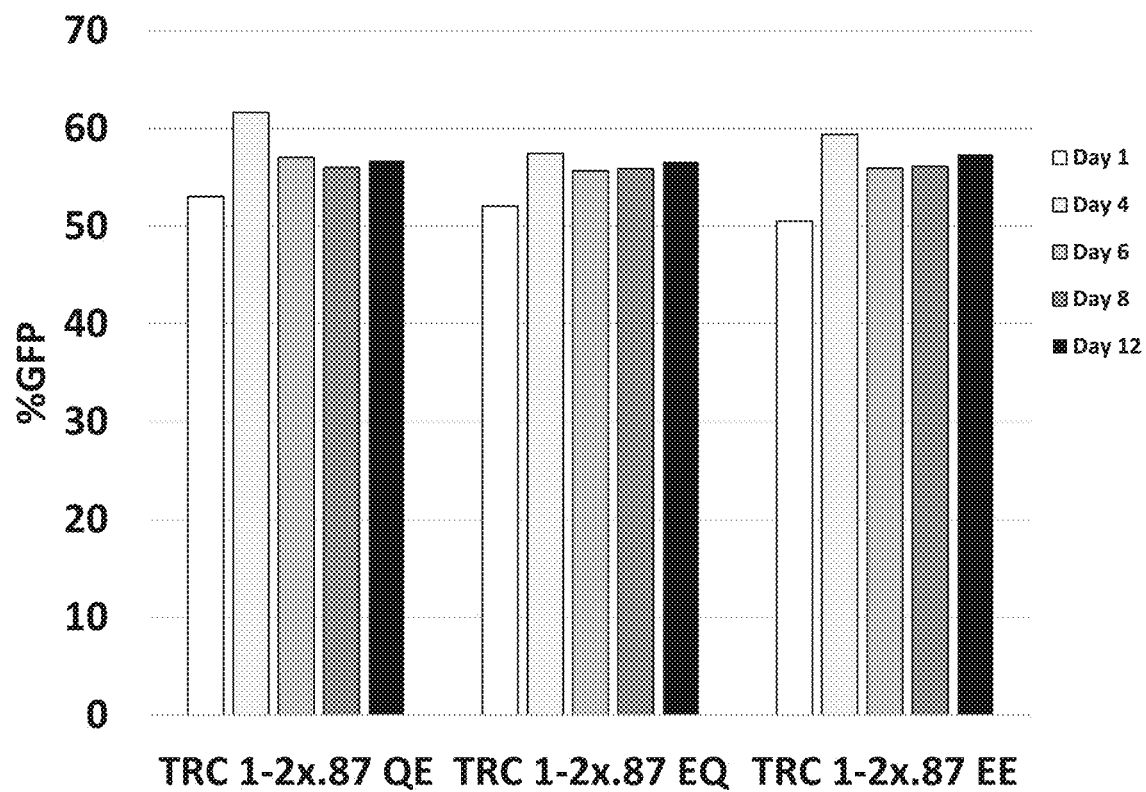

FIG. 10. Time course of recombinant meganuclease efficacy in CHO cell reporter assay. The TRC 1-2x.87 QE, TRC 1-2x.87 EQ, and TRC 1-2x.87 EE meganucleases were evaluated in the CHO reporter assay, with the percentage of GFP-expressing cells determined 1, 4, 6, 8, and 12 days after introduction of meganuclease-encoding mRNA into the CHO reporter cells.

Figure 11:
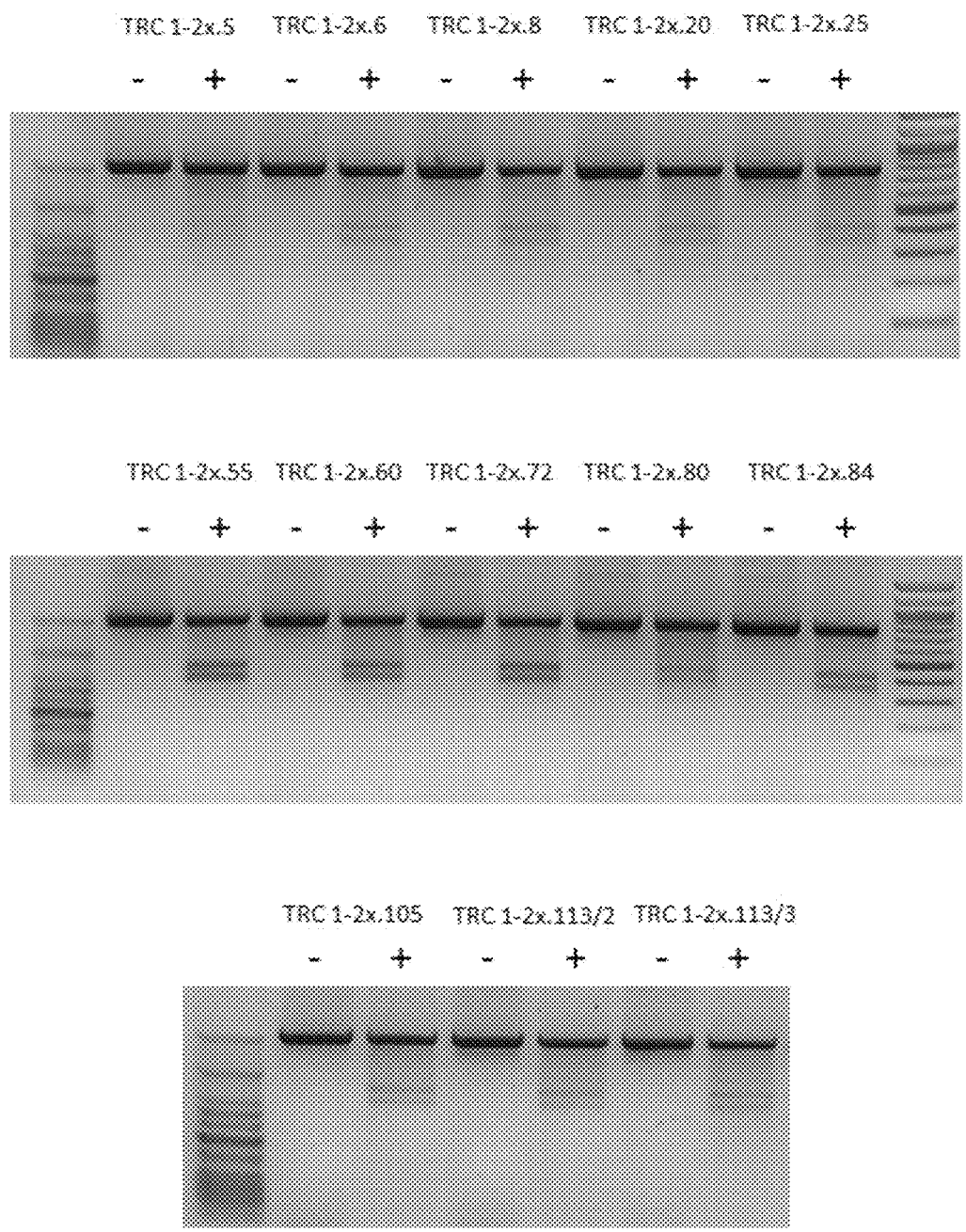

FIG. 11. Analysis of Jurkat cell genomic DNA following transfection with TRC 1-2 meganucleases. At 72 hours post-transfection with mRNA encoding TRC 1-2 meganucleases, genomic DNA was harvested and a T7 endonuclease assay was performed to estimate genetic modification at the endogenous TRC 1-2 recognition sequence.

Figure 12:
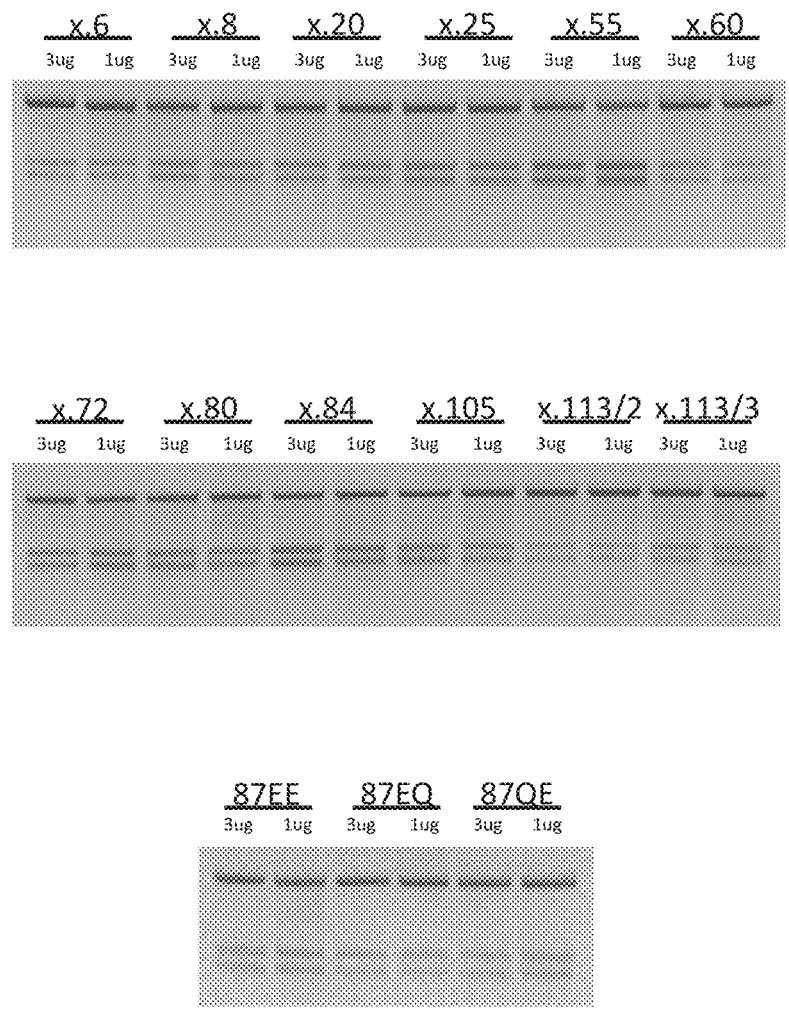

FIG. 12. Dose-response of TRC 1-2 meganuclease expression in Jurkat cells on genetic modification at the endogenous TRC 1-2 recognition sequence. Jurkat cells were transfected with either 3 µg or 1 µg of a given TRC 1-2 meganuclease mRNA. At 96 hours, genomic DNA was analyzed using a T7 endonuclease assay.

Figure 13:
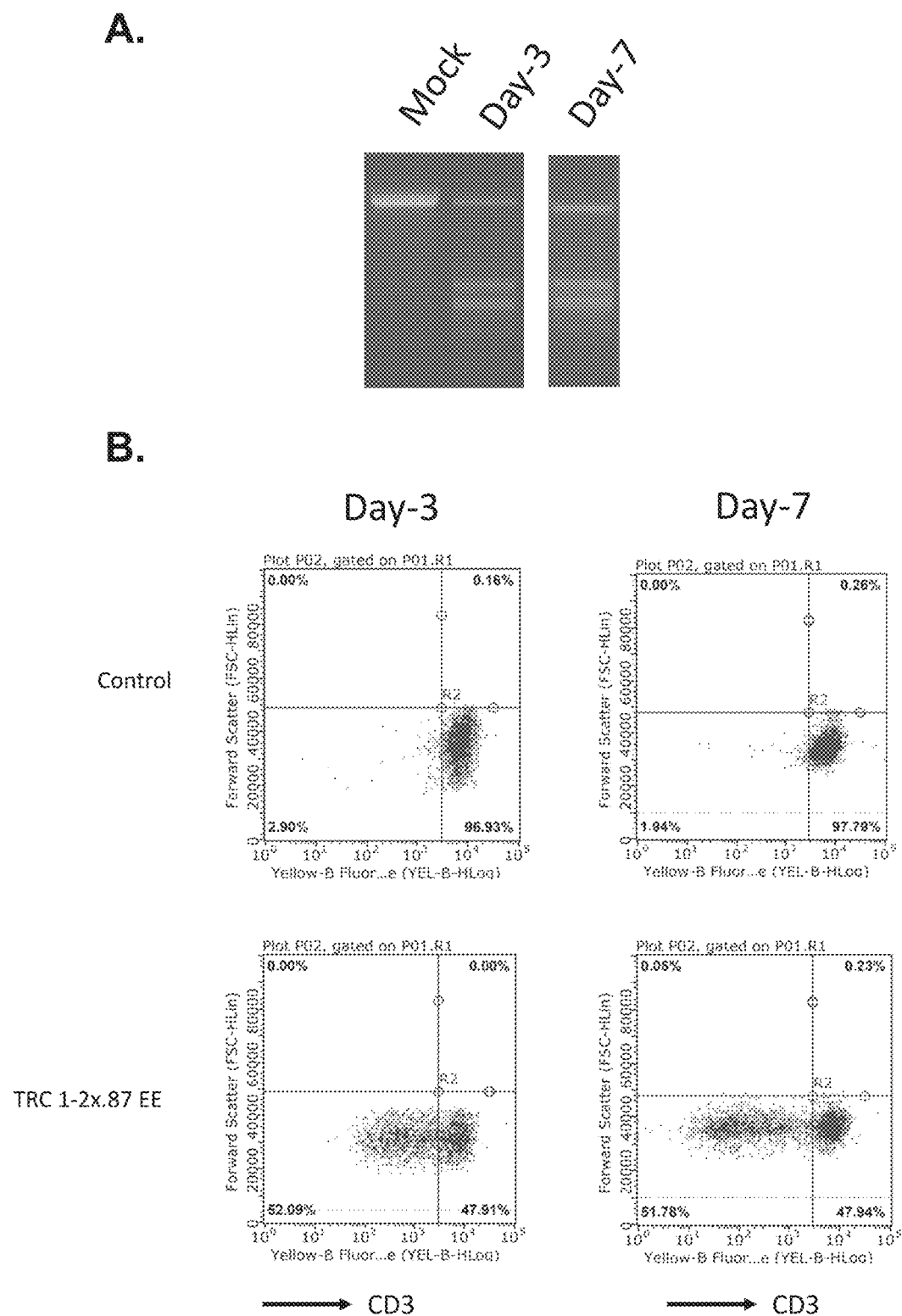

FIG. 13. Cleavage of TRC 1-2 recognition sequence in human T cells. A) CD3+ T cells were stimulated with anti-CD3 and anti-CD28 antibodies for 3 days, then electroporated with mRNA encoding the TRC 1-2x.87 EE meganuclease. Genomic DNA was harvested at 3 days and 7 days post-transfection, and analyzed using a T7 endonuclease assay. B) To determine whether mutations at the endogenous TRC 1-2 recognition sequence were sufficient to eliminate surface expression of the T cell receptor, cells were analyzed by flow cytometry using an anti-CD3 antibody. Control cells (transfected with water) and TRC 1-2x.87 EE-transfected cells were analyzed at day 3 and day 7 post-transfection, and the percentage of CD3-positive and CD3-negative T cells was determined.

FIG. 14. Nucleic acid sequences of representative deletions that were observed at the TRC 1-2 recognition sequence in human T cells following expression of TRC 1-2 meganucleases.

Figure 15:
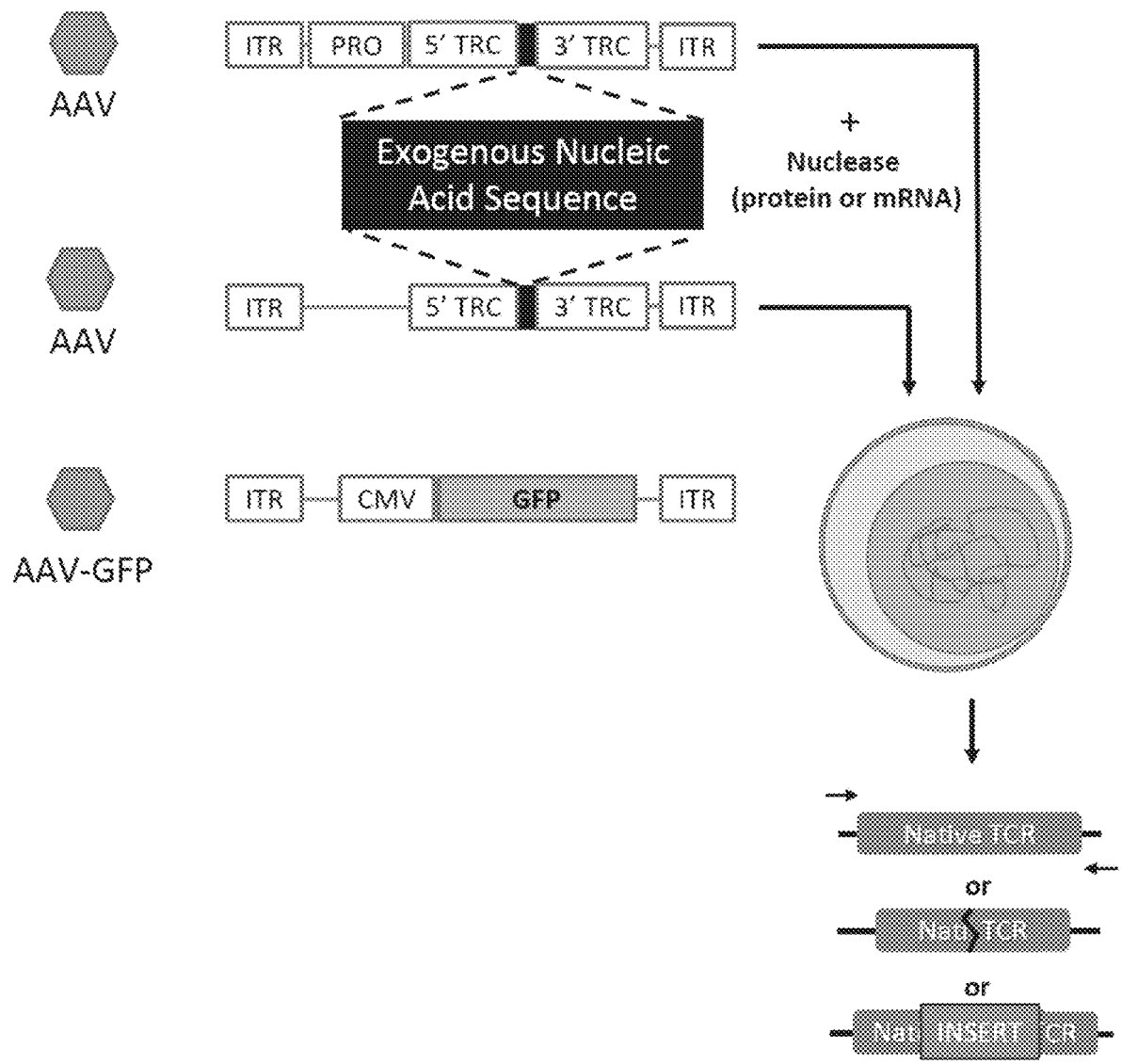

FIG. 15. Diagram illustrating sequence elements of recombinant AAV vectors and their use in combination with an engineered nuclease to insert an exogenous nucleic acid sequence into the endogenous TCR alpha constant region gene.

Figure 16:
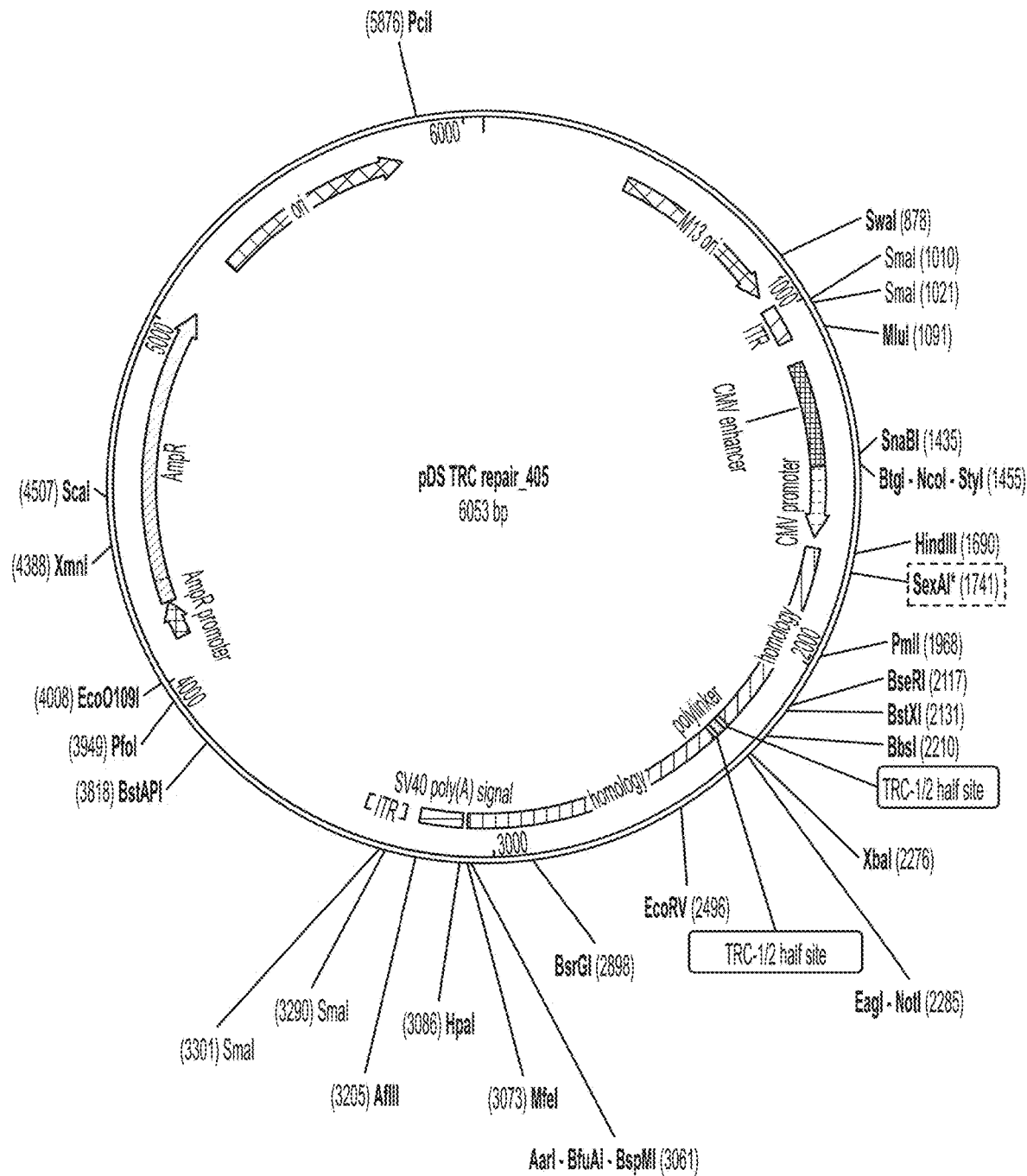

FIG. 16. Map of plasmid used to produce the AAV405 vector.

Figure 17:
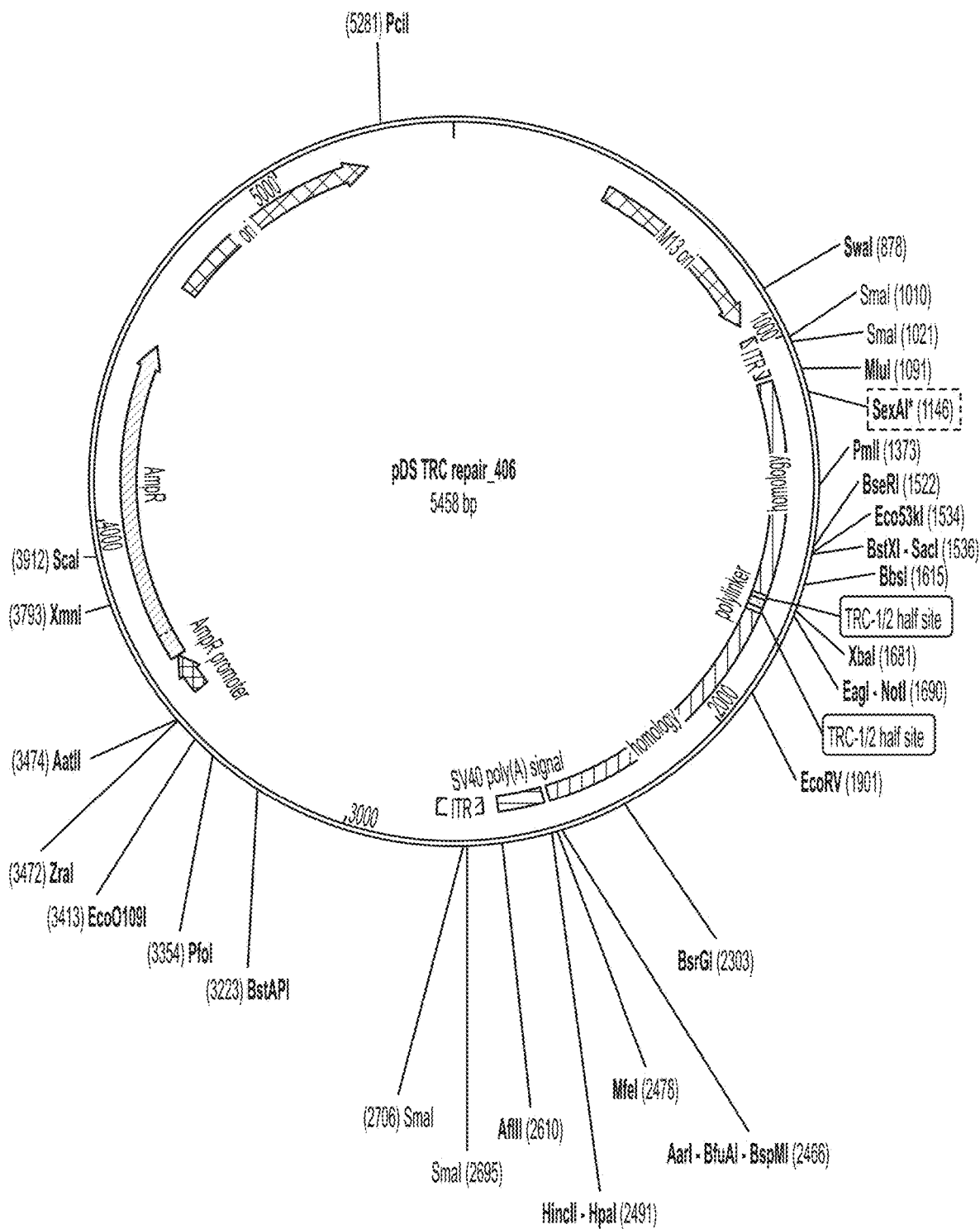

FIG. 17. Map of plasmid used to produce the AAV406 vector.

FIG. 18. Determining the timing of meganuclease mRNA transfection and recombinant AAV transduction to enhance AAV transduction efficiency. Human CD3+ T cells were electroporated with mRNA encoding the TRC 1-2x.87 EE meganuclease and at 2, 4, or 8 hours post-transfection, cells were transduced with a recombinant AAV vector encoding GFP (GFP-AAV). T cells were analyzed by flow cytometry for GFP expression at 72 hours post-transduction to determine transduction efficiency.

Figure 19:
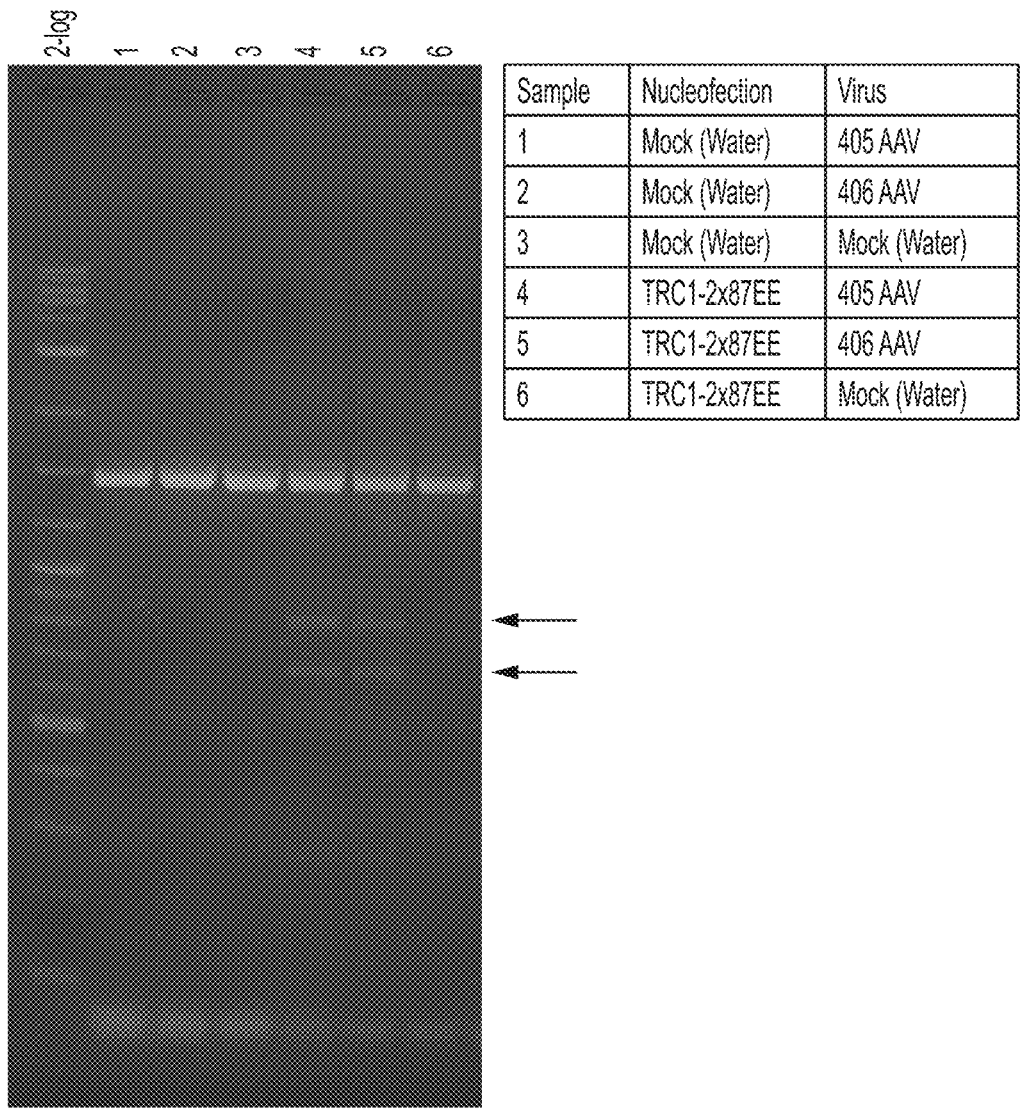

FIG. 19. Analyzing human T cells for insertion of an exogenous nucleic acid sequence using recombinant AAV vectors. CD3+ T cells transfected with TRC 1-2x.87 EE mRNA and subsequently transduced (2 hours post-transfection) with AAV405 or AAV406. Transduction-only controls were mock transfected (with water) and transduced with either AAV405 or AAV406. Meganuclease-only controls were transfected with TRC 1-2x.87 EE and then mock transduced (with water) at 2 hours post-transfection. Genomic DNA was harvested from T cells and the TRC 1-2 locus was amplified by PCR using primers that recognized sequences beyond the region of homology in the AAV vectors. PCR primers outside of the homology regions only allowed for amplification of the T cell genome, not from the AAV vectors. PCR products were purified and digested with EagI. PCR products were then analyzed for cleavage.

FIG. 20. Characterization of EagI insertion into the TRC 1-2 recognition sequence of human T cells using AAV405. A) Undigested PCR product generated from previous experiments was cloned into a pCR-blunt vector. Colony PCR was performed using M13 forward and reverse primers and a portion of PCR products from cells transfected with TRC 1-2x.87 EE and AAV405 was analyzed by gel electrophoresis. Analysis shows a mix of full-length PCR products (approximately 1600 bp), smaller inserts, and empty plasmids (approximately 300 bp). B) In parallel, another portion of PCR products were digested with EagI to determine the percent of clones that contain the EagI recognition site inserted into the TRC 1-2 recognition sequence. PCR products cleaved with EagI generated expected fragments of approximately 700 and 800 bp.

FIG. 21. Characterization of EagI insertion into the TRC 1-2 recognition sequence of human T cells using AAV406. A) Undigested PCR product generated from previous experiments was cloned into a pCR-blunt vector. Colony PCR was performed using M13 forward and reverse primers and a portion of PCR products from cells transfected with TRC 1-2x.87 EE and AAV406 was analyzed by gel electrophoresis. Analysis shows a mix of full-length PCR products (approximately 1600 bp), smaller inserts, and empty plasmids (approximately 300 bp). B) In parallel, another portion of PCR products were digested with EagI to determine the percent of clones that contain the EagI recognition site inserted into the TRC 1-2 recognition sequence. PCR products cleaved with EagI generated expected fragments of approximately 700 and 800 bp.

FIG. 22. A) Nucleic acid sequences of representative deletions and insertions (i.e., indels) that were observed at the TRC 1-2 recognition sequence in human T cells following expression of TRC 1-2 meganucleases. B) Nucleic acid sequence of the TRC 1-2 recognition sequence confirming insertion of the exogenous nucleic acid sequence comprising the EagI restriction site.

Figure 23:
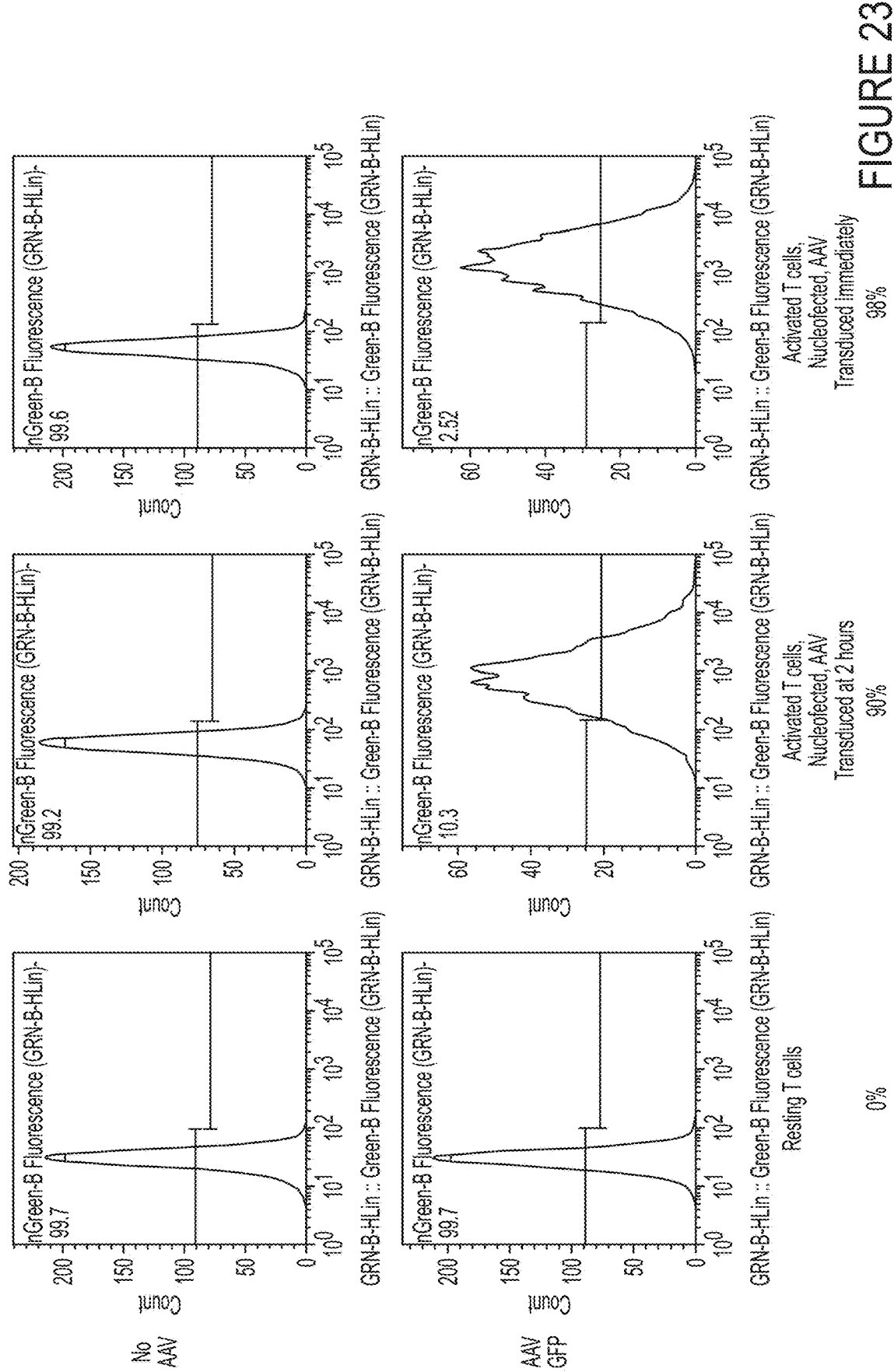

FIG. 23. Enhancement of recombinant AAV transduction efficiency. Transduction efficiency was further analyzed by optimizing the timing of meganuclease mRNA transfection and subsequent AAV transduction. Human CD3+ T cells were electroporated with mRNA encoding the TRC 1-2x.87 EE meganuclease and subsequently transduced with GFP-AAV immediately after transfection or 2 hours post-transfection. Additionally, non-stimulated resting T cells were transduced with GFP-AAV. Mock transduced cells were also analyzed. At 72 hours post-transduction, cells were analyzed by flow cytometry for GFP expression to determine AAV transduction efficiency.

Figure 24:
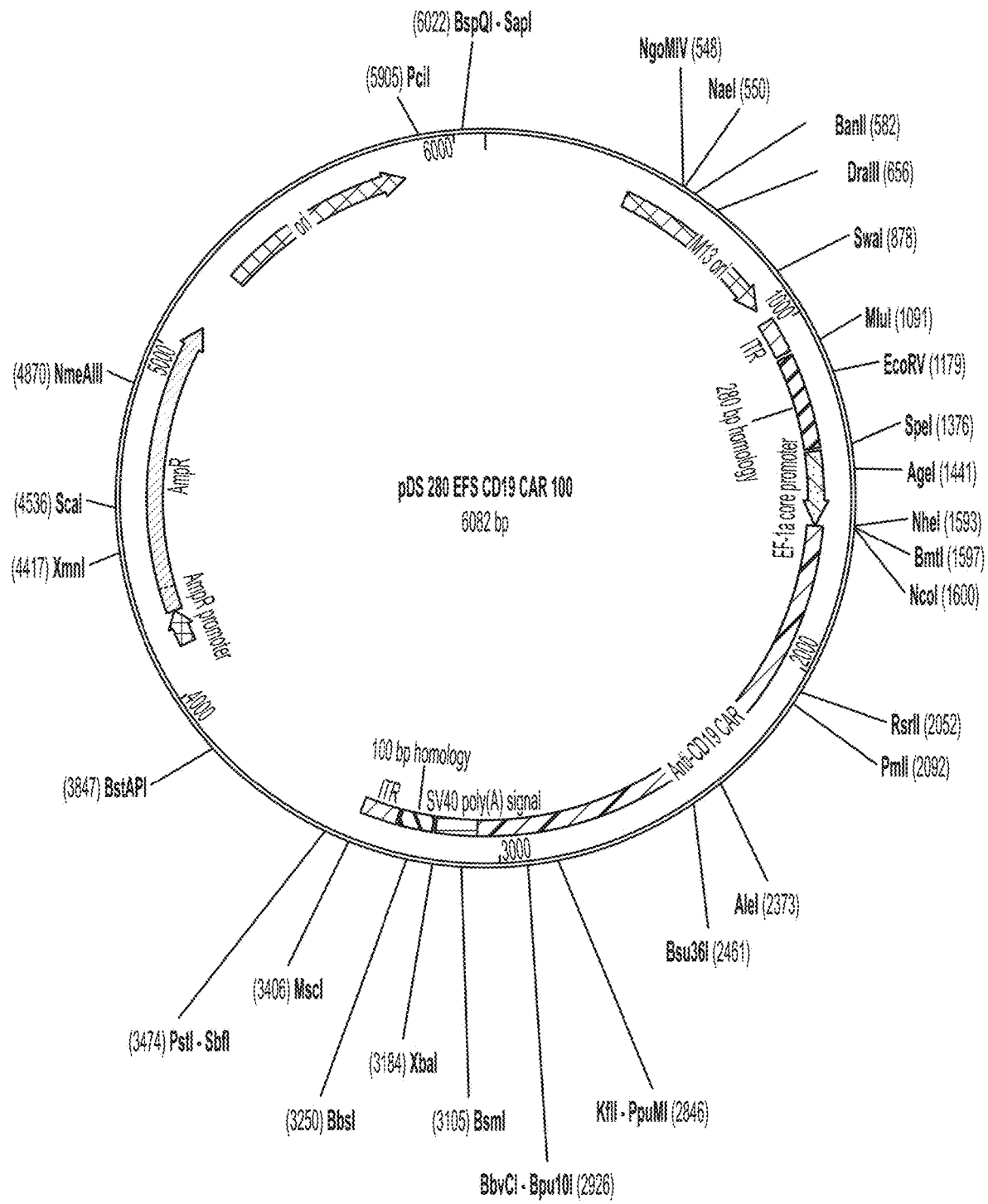

FIG. 24. Map of plasmid used to produce the AAV-CAR100 (AAV408) vector.

Figure 25:
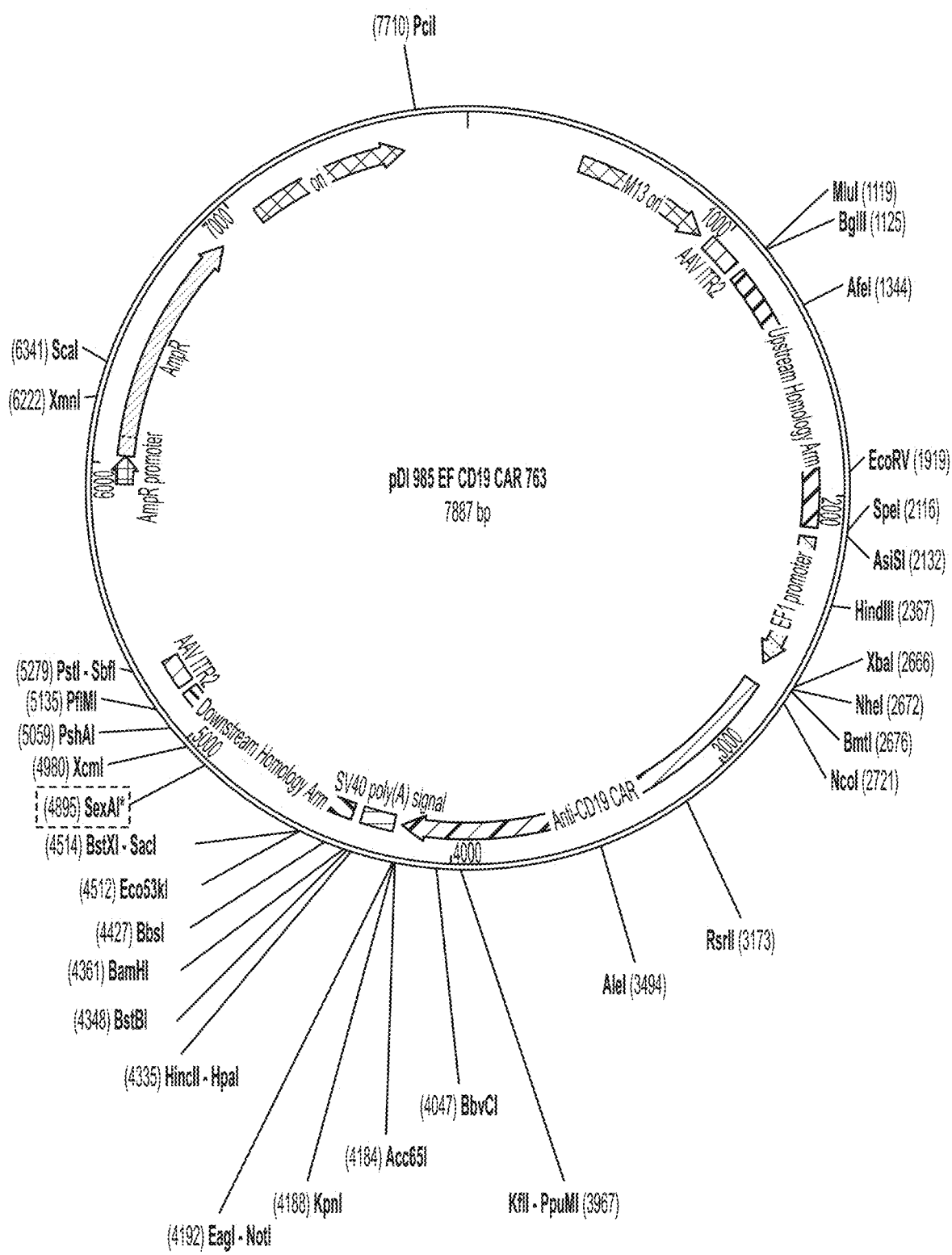

FIG. 25. Map of plasmid used to produce the AAV-CAR763 (AAV412) vector.

Figure 26:
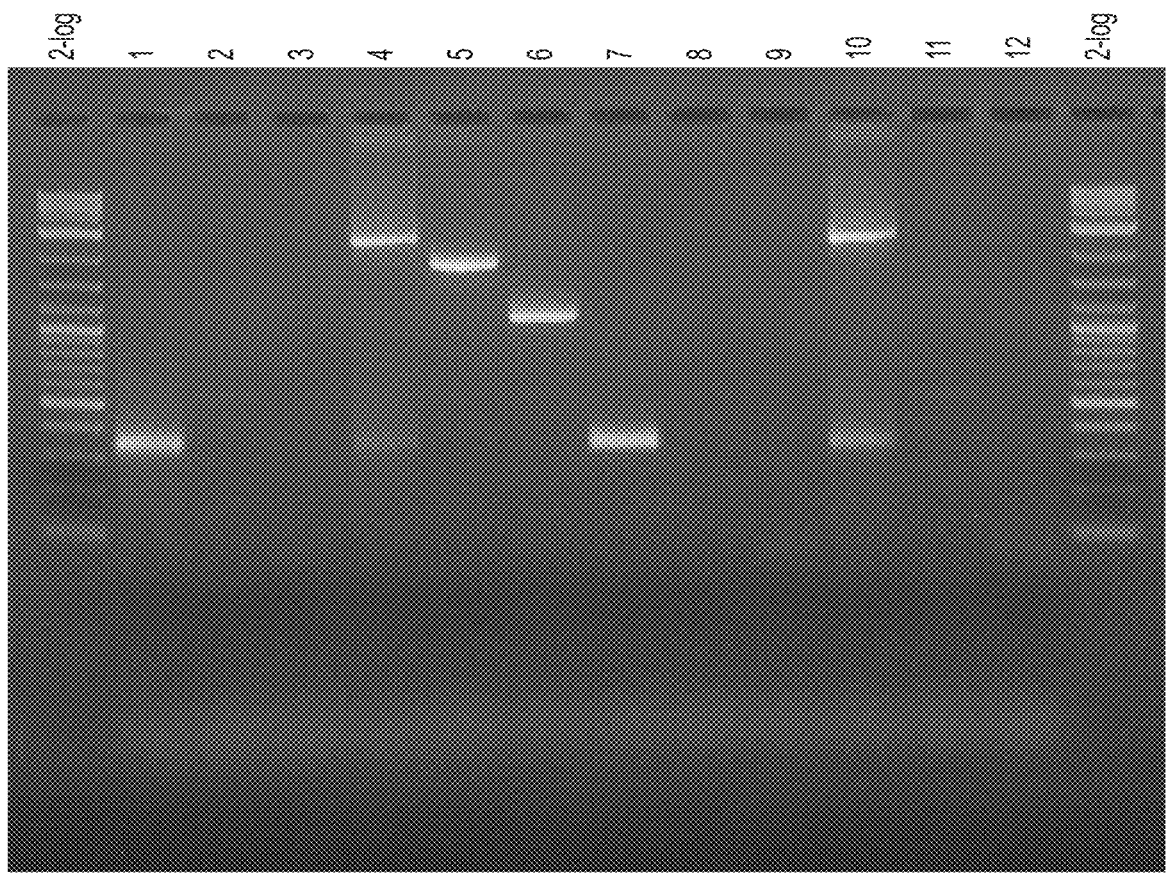

FIG. 26. Insertion of chimeric antigen receptor coding sequence at TRC 1-2 recognition site in human T cells. A PCR-based assay was developed to determine whether the AAV412 HDR template was utilized to repair double-strand breaks at the TRC 1-2 recognition sequence.

FIG. 27. Insertion of chimeric antigen receptor coding sequence at TRC 1-2 recognition site in human T cells. A PCR-based assay was developed to determine whether the AAV408 HDR template was utilized to repair double-strand breaks at the TRC 1-2 recognition sequence. A) PCR products generated using a primer pair that only amplifies a product on the 5' end of the TRC 1-2 recognition sequence locus if the CAR gene has been inserted into that locus. B) PCR products generated using a primer pair that only amplifies a product on the 3' end of the TRC 1-2 recognition sequence locus if the CAR gene has been inserted into that locus.

FIG. 28. Digital PCR. A) Schematic of a digital PCR assay developed to quantitatively determine insertion efficiency of the chimeric antigen receptor coding sequence into the TRC 1-2 recognition site in human T cells. B) Results of digital PCR on genomic DNA from human T cells electroporated with a TRC 1-2x.87EE meganuclease mRNA and/or increasing amounts of AAV408.

Figure 29:
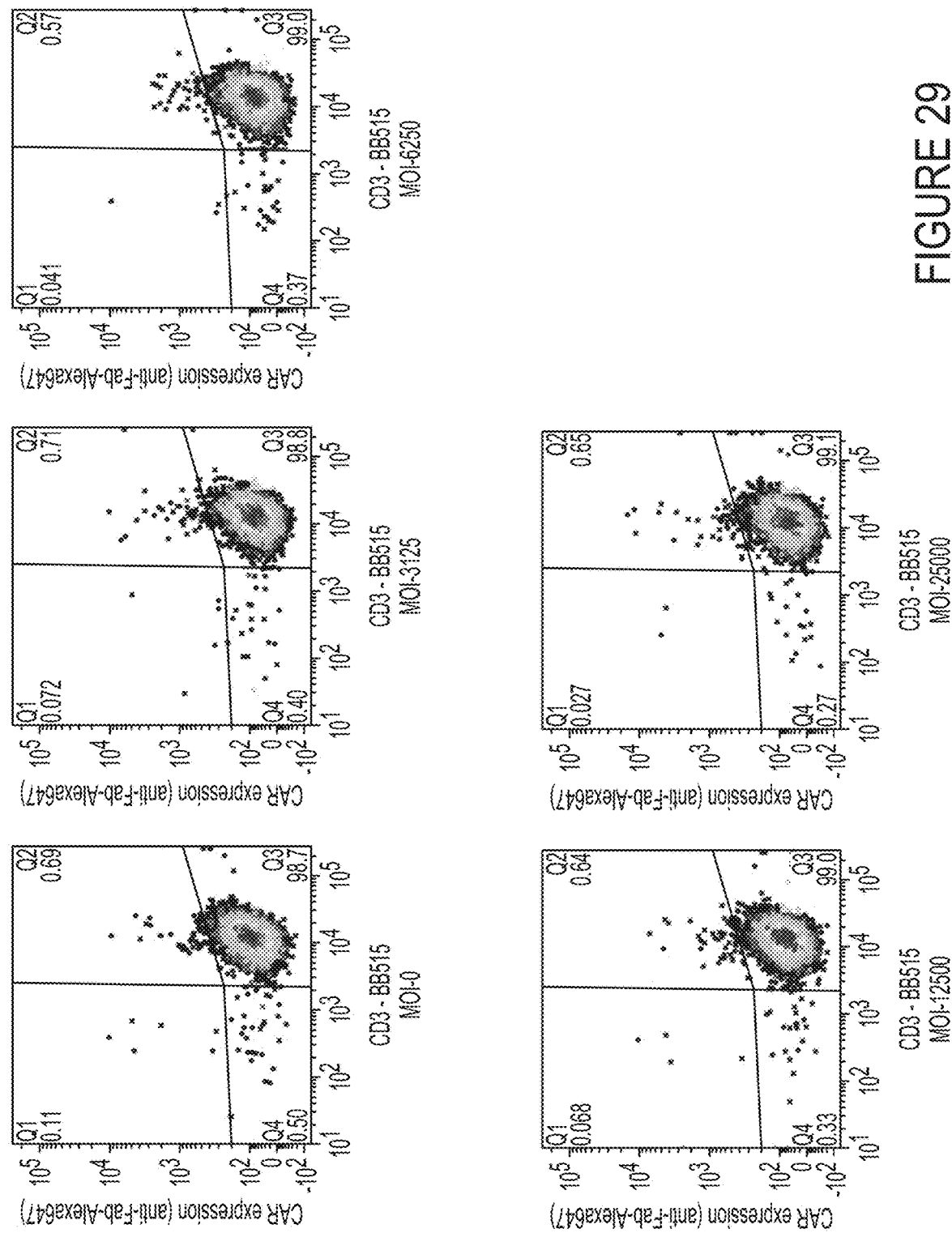
Figure 29:
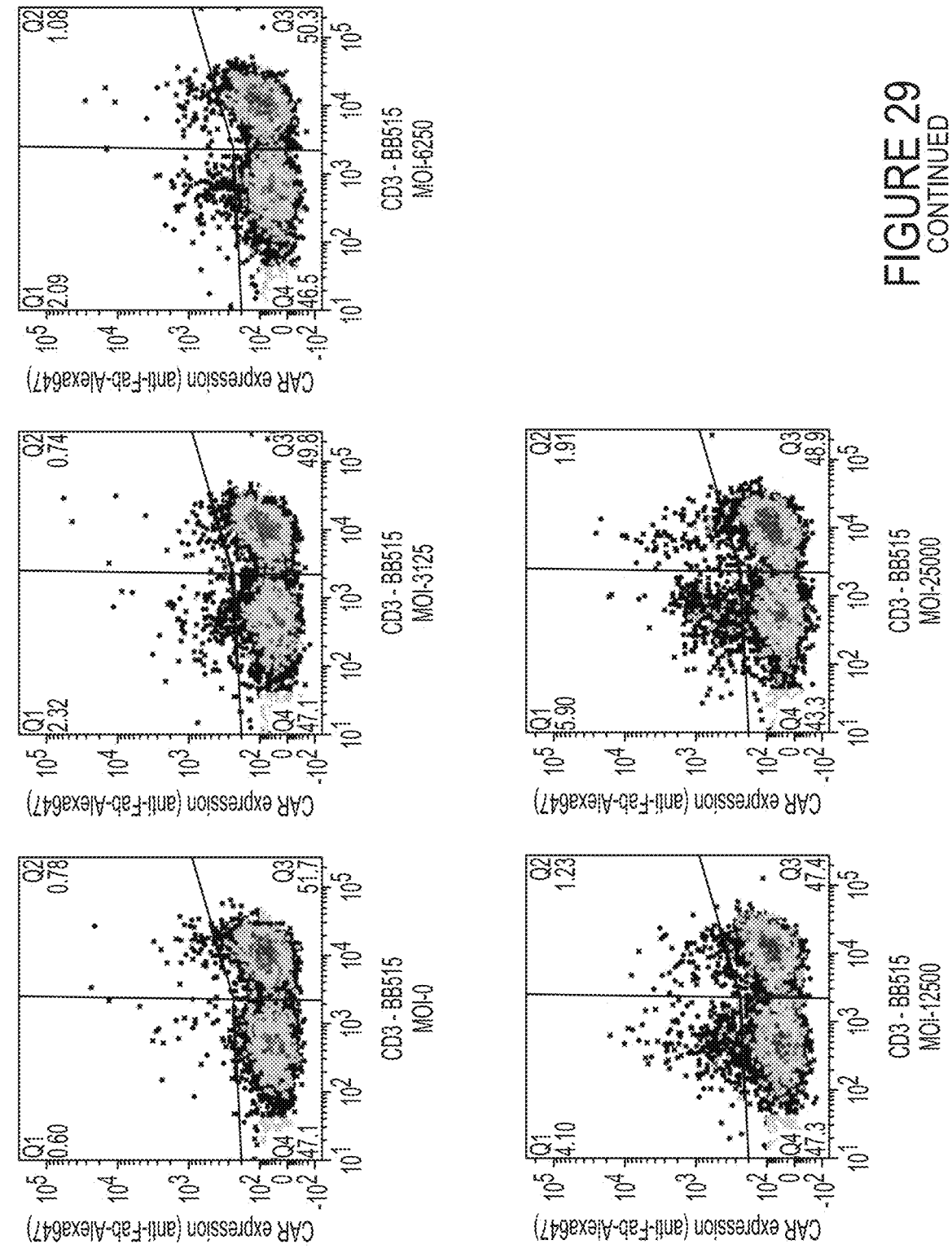

FIG. 29. Cell-surface expression of CD19 chimeric antigen receptor on human T cells. The expression level of the anti-CD19 chimeric antigen receptor was determined in cells that had the CAR gene inserted into the TRC 1-2 recognition sequence using AAV408 as the HDR template. Cell-surface expression was analyzed by flow cytometry. A) Cells that were mock electroporated and mock transduced (MOI—0), and cells that were mock electroporated and transduced with increasing amounts of AAV408. B) Cells that were electroporated with TRC 1-2x.87EE and mock transduced (MOI—0), and cells that were electroporated with TRC 1-2x.87EE and transduced with increasing amounts of AAV408.

Figure 30:
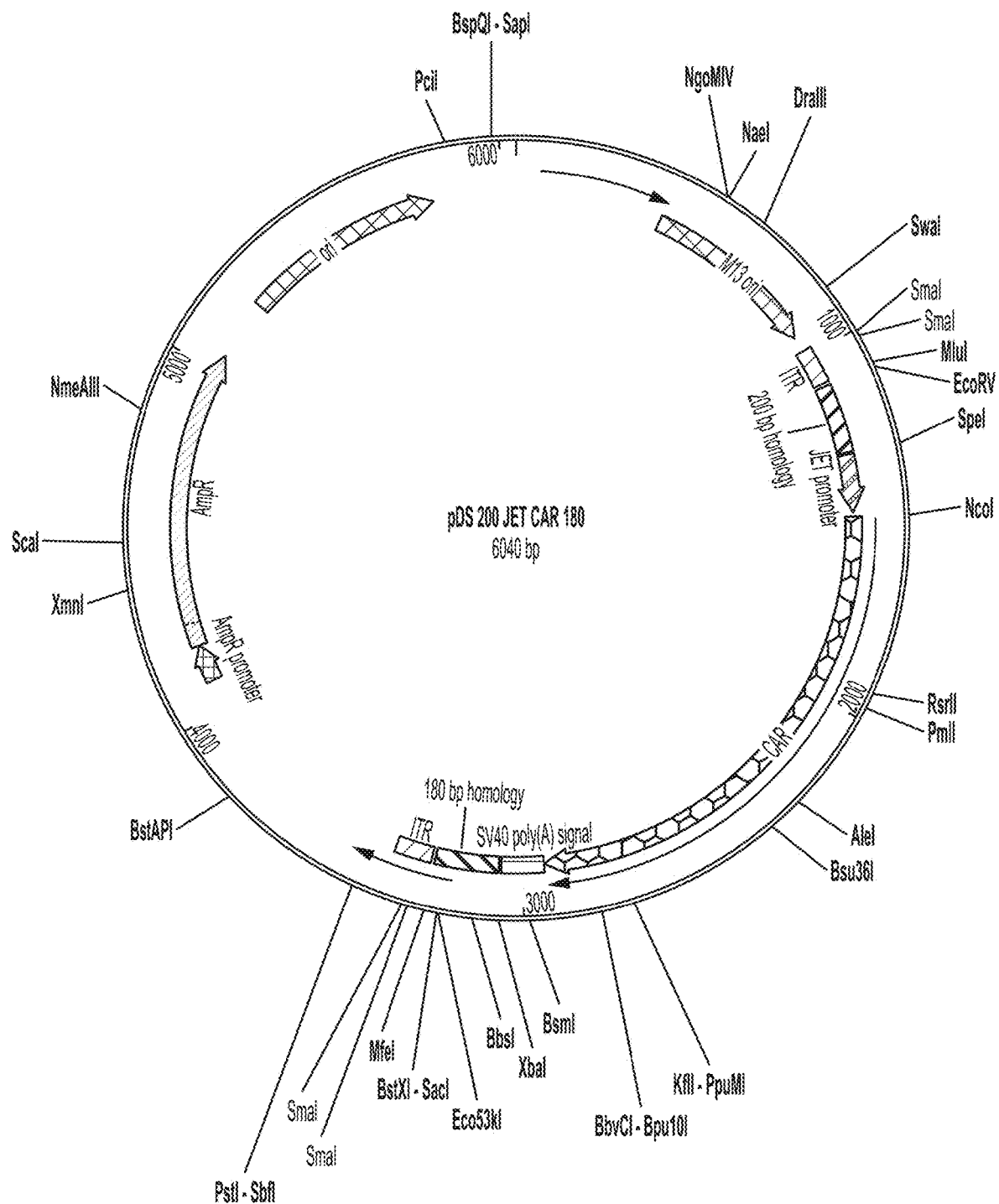

FIG. 30. Map of plasmid used to produce the AAV421 vector.

Figure 31:
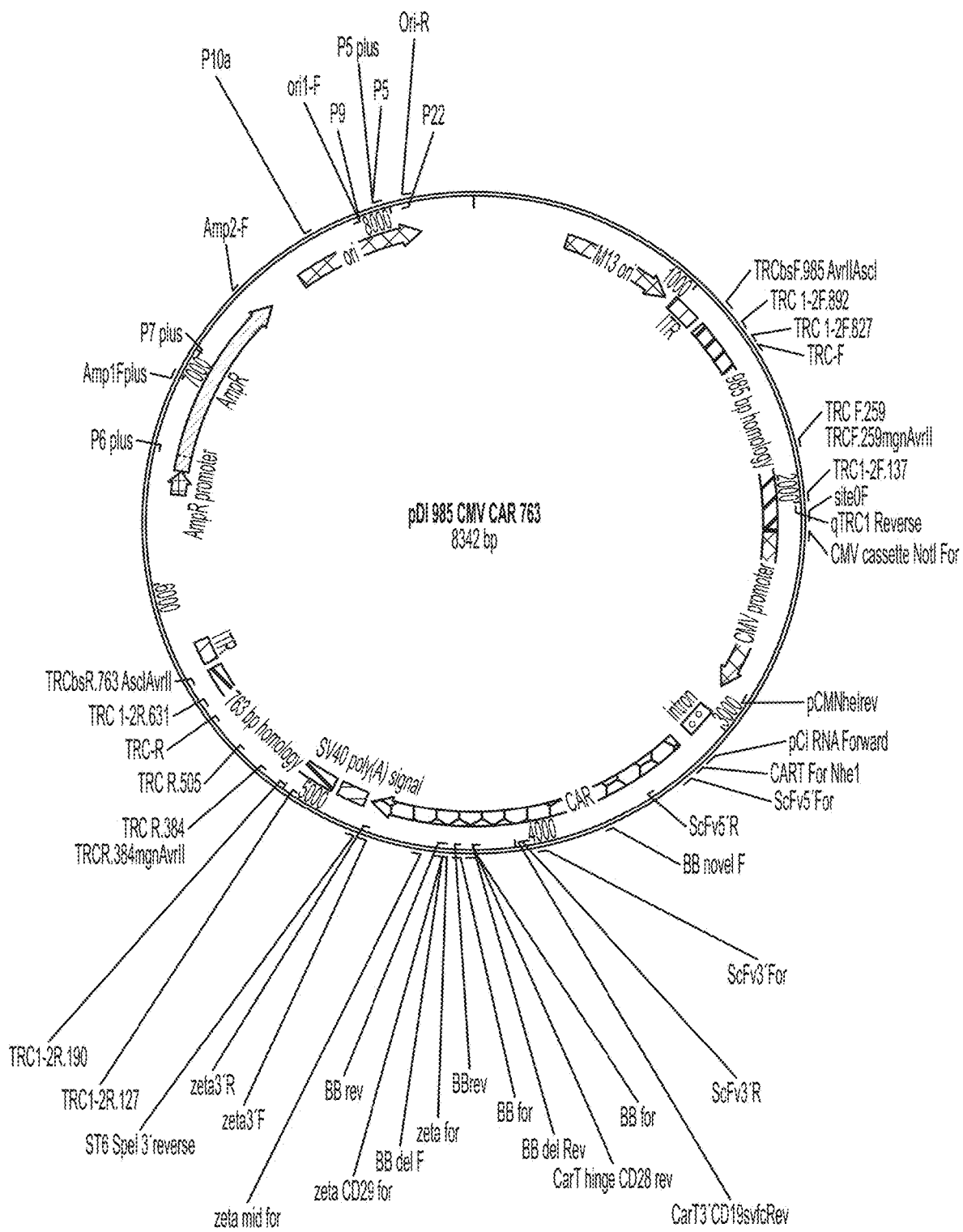

FIG. 31. Map of plasmid used to produce the AAV422 vector.

FIG. 32. Insertion of chimeric antigen receptor coding sequence. PCR methods were used to determine if the chimeric antigen receptor coding sequence introduced by AAV421 or AAV422 inserted at the TRC 1-2 recognition site cleaved by the TRC 1-2x.87EE meganuclease. A) Analysis of insertion following transduction with AAV421. B) Analysis of insertion following transduction with AAV422.

Figure 33:
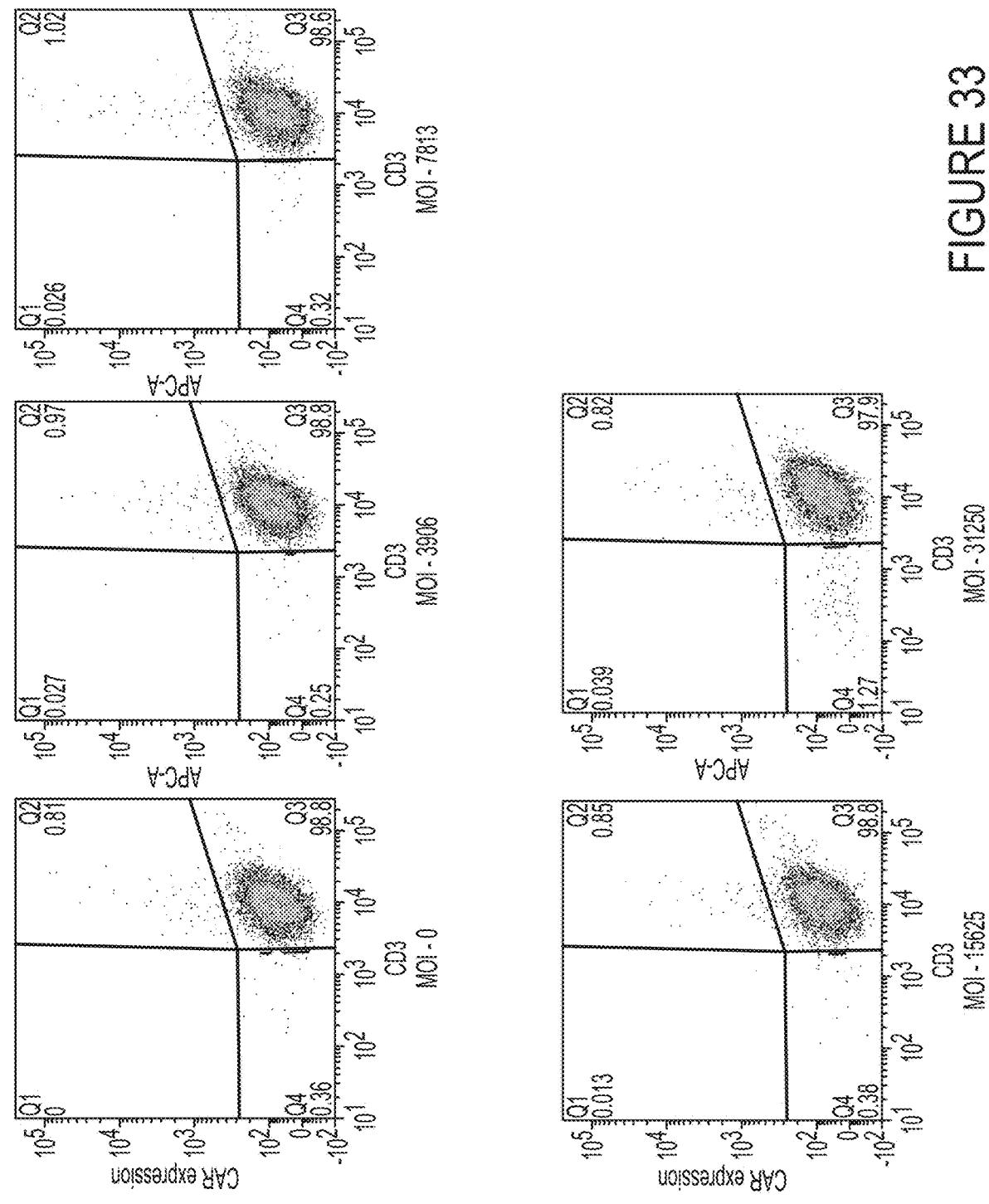
Figure 33:
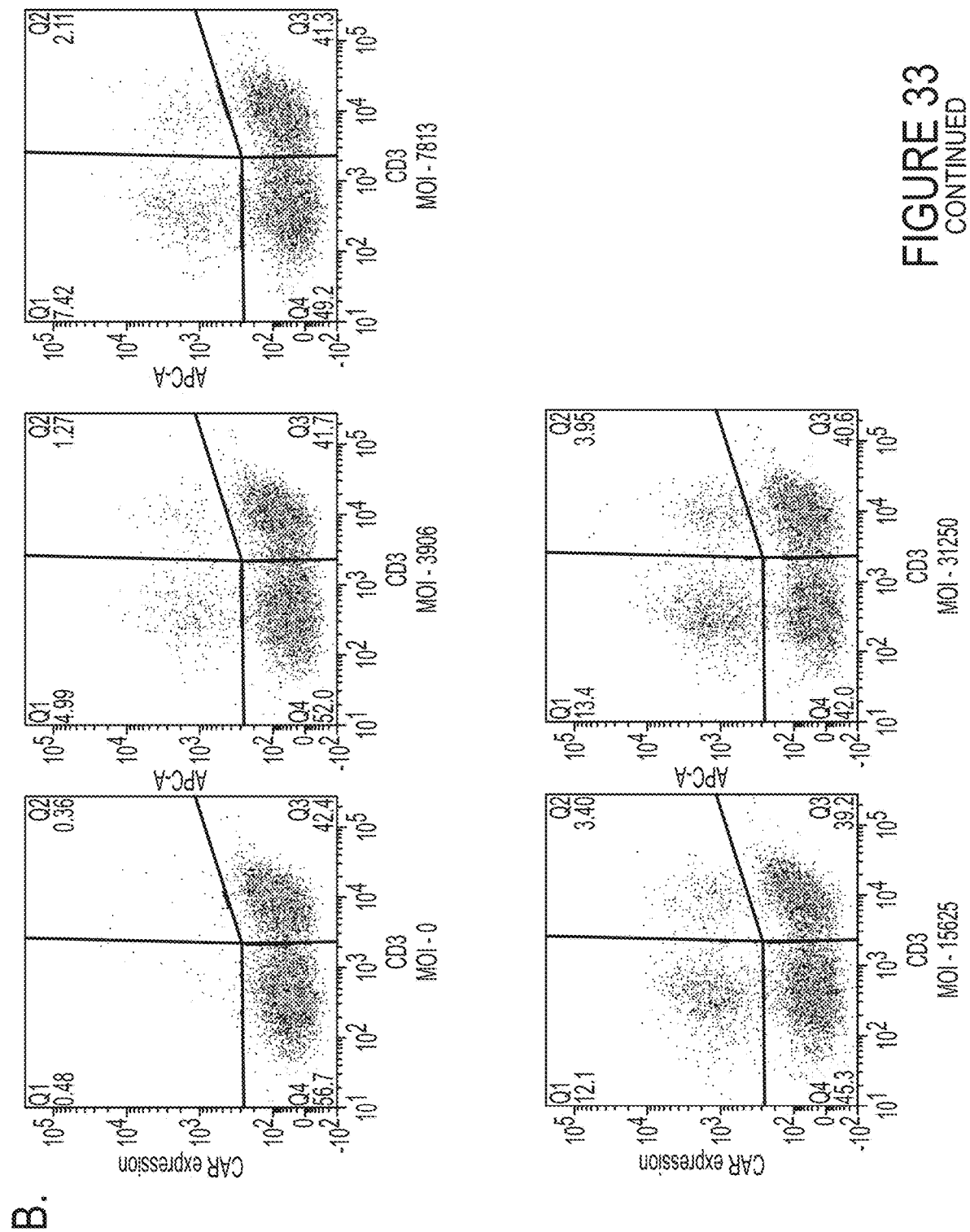

FIG. 33. Cell-surface expression of CD19 chimeric antigen receptor on human T cells. The expression level of the anti-CD19 chimeric antigen receptor was determined in cells that had the CAR gene inserted into the TRC 1-2 recognition sequence using AAV421 as the HDR template. Cell-surface expression was analyzed by flow cytometry. A) Cells that were mock electroporated and mock transduced (MOI—0), and cells that were mock electroporated and transduced with increasing amounts of AAV421. B) Cells that were electroporated with TRC 1-2x.87EE and mock transduced (MOI—0), and cells that were electroporated with TRC 1-2x.87EE and transduced with increasing amounts of AAV421.

Figure 34:
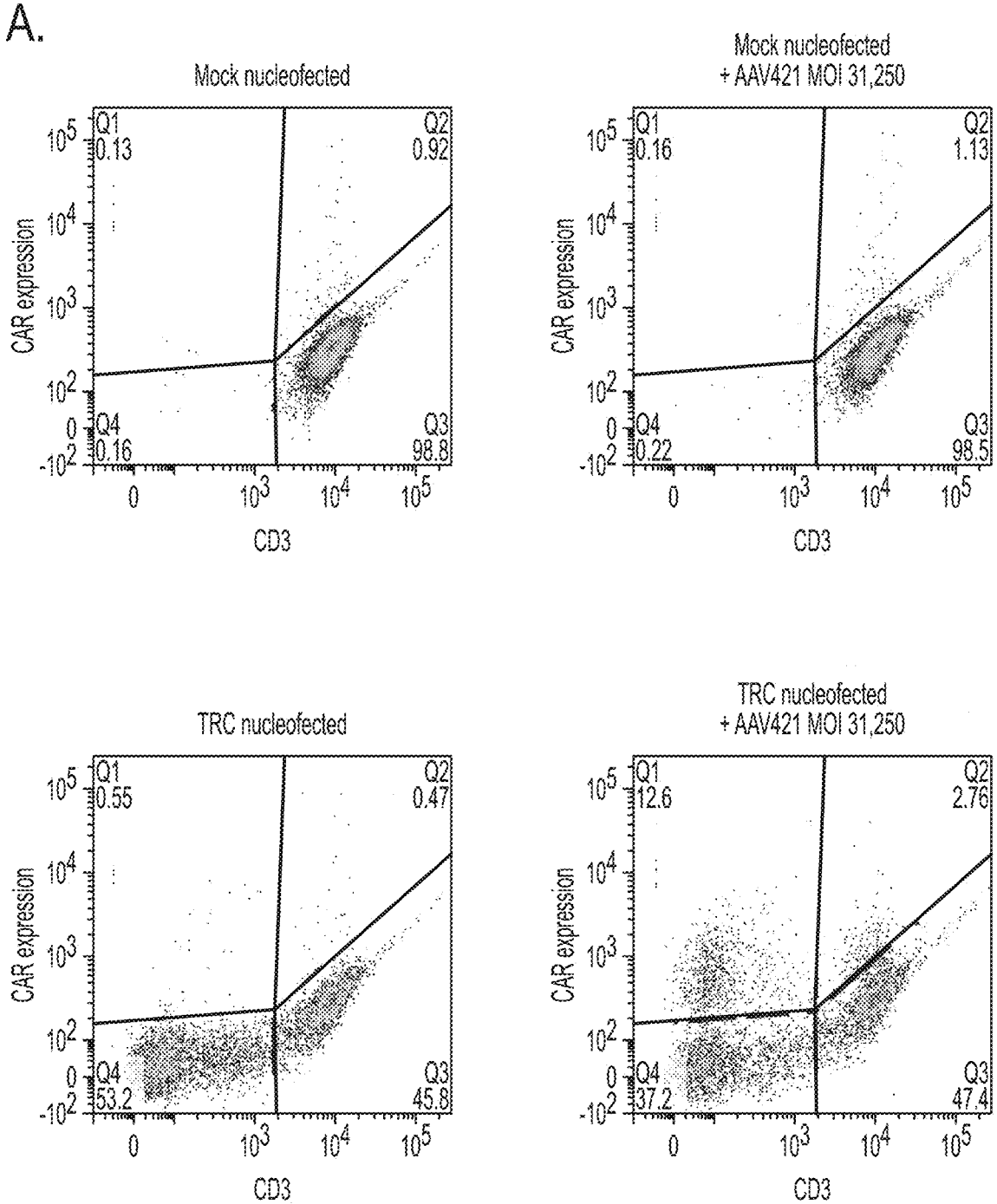
Figure 34:
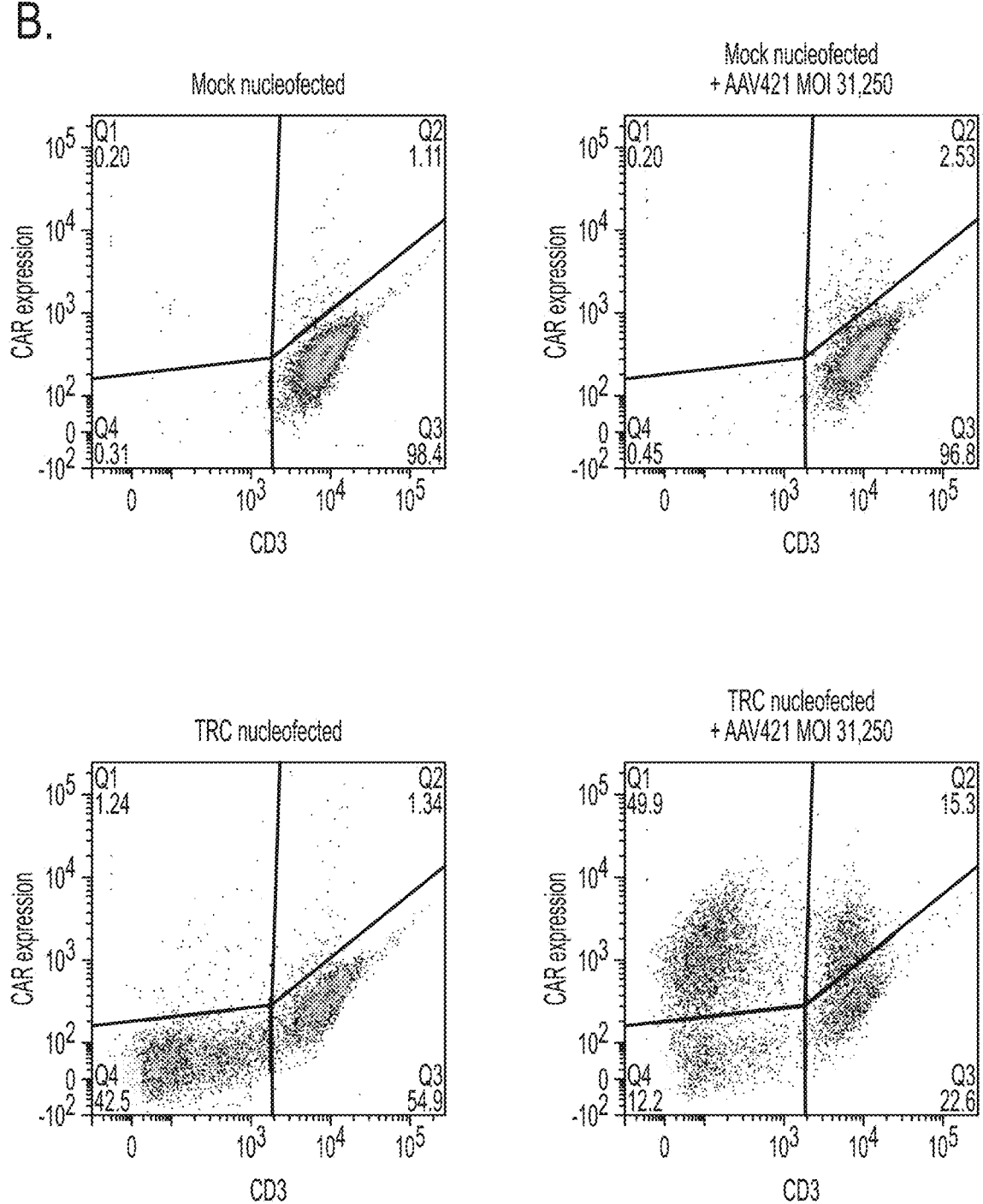
Figure 34:
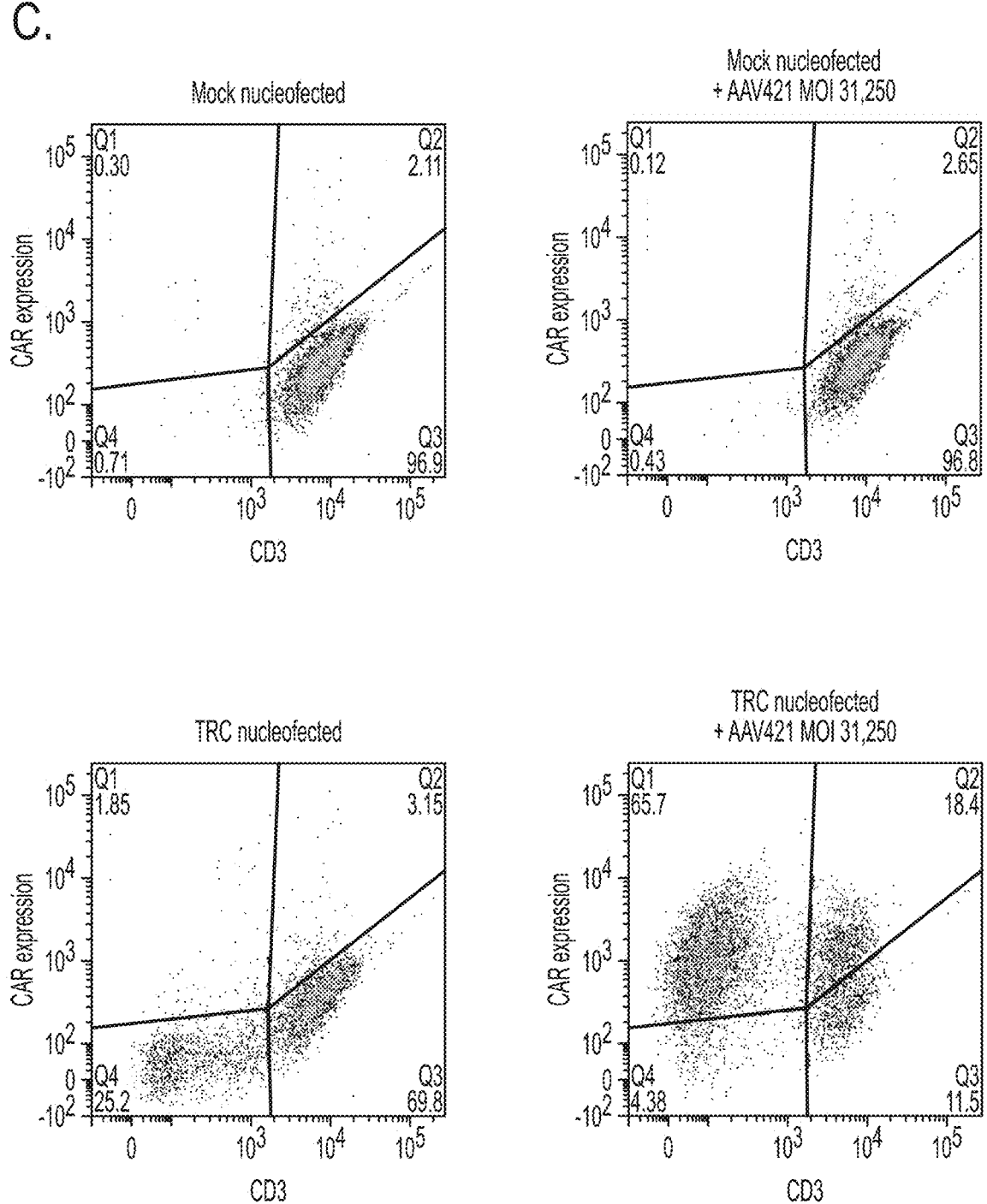

FIG. 34. Expansion of human T cells expressing a cell-surface chimeric antigen receptor. Methods were determined for preferentially expanding and enriching a $CD3^-/CAR^+$ T cell population following electroporation with mRNA for the TRC 1-2x.87EE meganuclease and transduction with AAV421. A) Supplementation with IL-7 (10 ng/mL) and IL-15 (10 ng/mL). B) Supplementation with IL-7 (10 ng/mL) and IL-15 (10 ng/mL), and incubation with mitomycin C-inactivated IM-9 cells. C) Supplementation with IL-7 (10 ng/mL) and IL-15 (10 ng/mL), and two incubations with mitomycin C-inactivated IM-9 cells.

Figure 35:
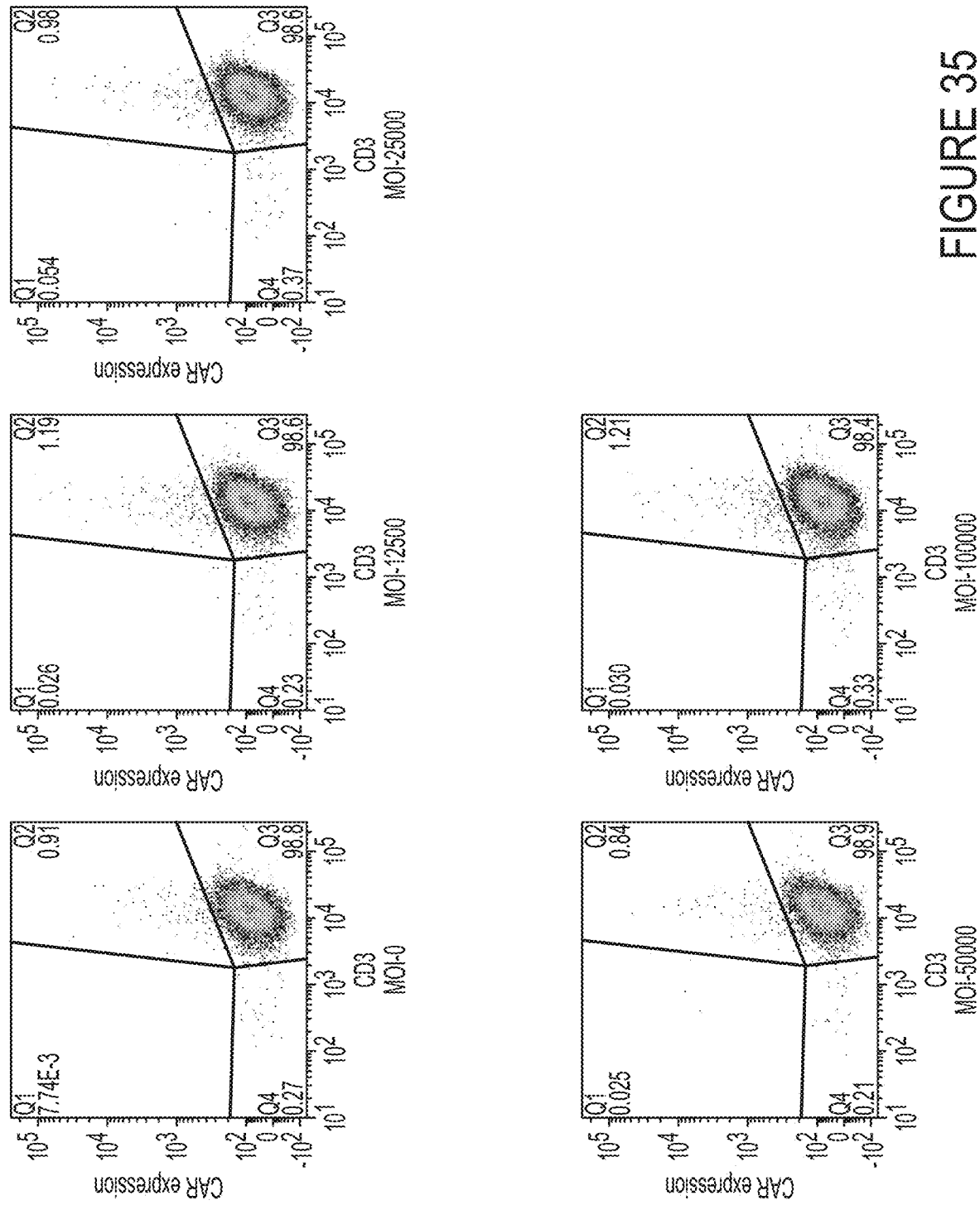

FIG. 35. Cell-surface expression of CD19 chimeric antigen receptor on human T cells. The expression level of the anti-CD19 chimeric antigen receptor was determined in cells that had the CAR gene inserted into the TRC 1-2 recognition sequence using AAV422 as the HDR template. Cell-surface expression was analyzed by flow cytometry. A) Cells that were mock electroporated and mock transduced (MOI—0), and cells that were mock electroporated and transduced with increasing amounts of AAV422. B) Cells that were electroporated with TRC 1-2x.87EE and mock transduced (MOI—0), and cells that were electroporated with TRC 1-2x.87EE and transduced with increasing amounts of AAV422.

FIG. 36. Expansion of human T cells expressing a cell-surface chimeric antigen receptor. Methods were determined for preferentially expanding and enriching a CD3$^-$/CAR$^+$ T cell population following electroporation with mRNA for the TRC 1-2x.87EE meganuclease and transduction with AAV422. A) Supplementation with IL-7 (10 ng/mL) and IL-15 (10 ng/mL). B) Supplementation with IL-7 (10 ng/mL) and IL-15 (10 ng/mL), and incubation with mitomycin C-inactivated IM-9 cells. C) Supplementation with IL-7 (10 ng/mL) and IL-15 (10 ng/mL), and two incubations with mitomycin C-inactivated IM-9 cells.

Figure 37:
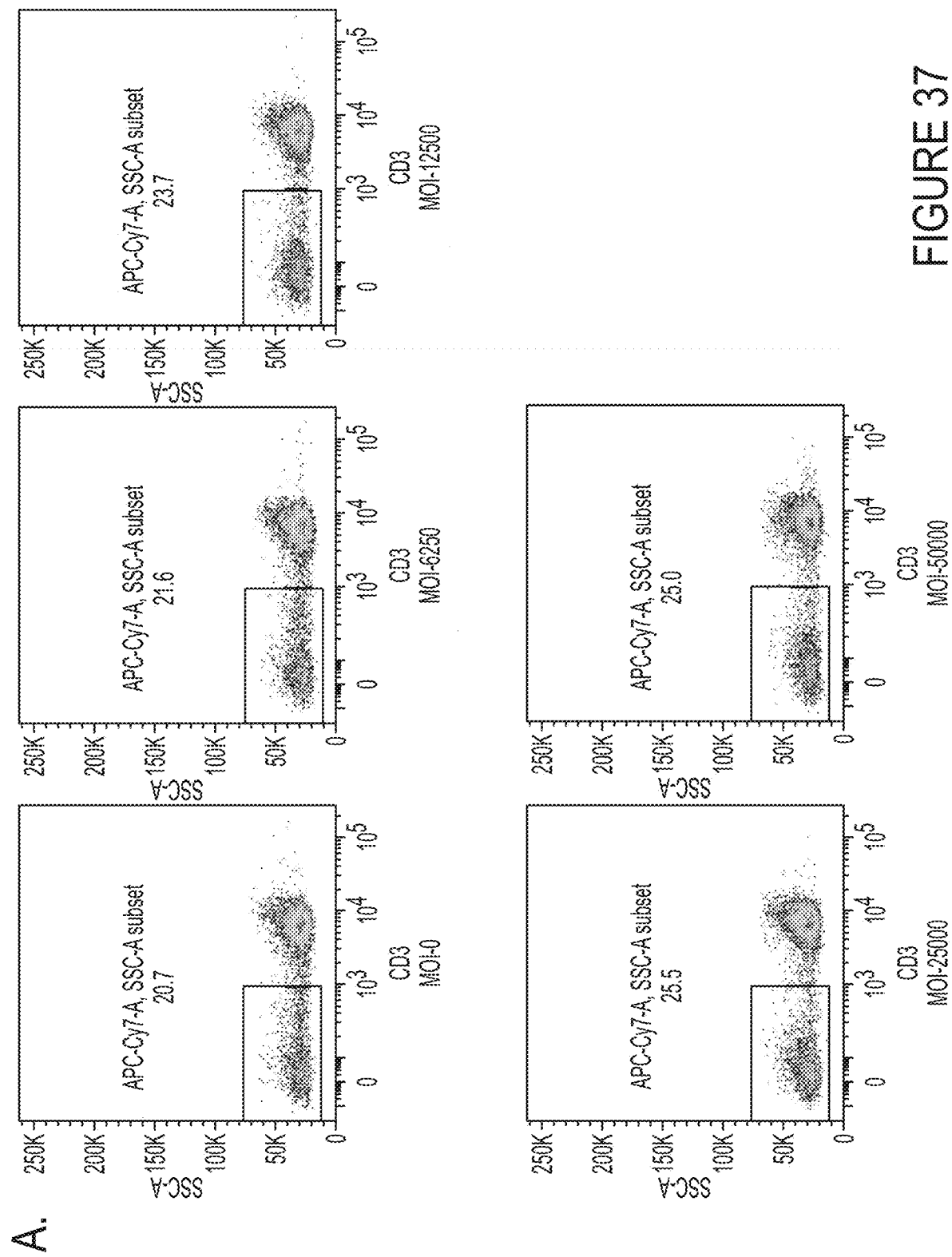
Figure 37:
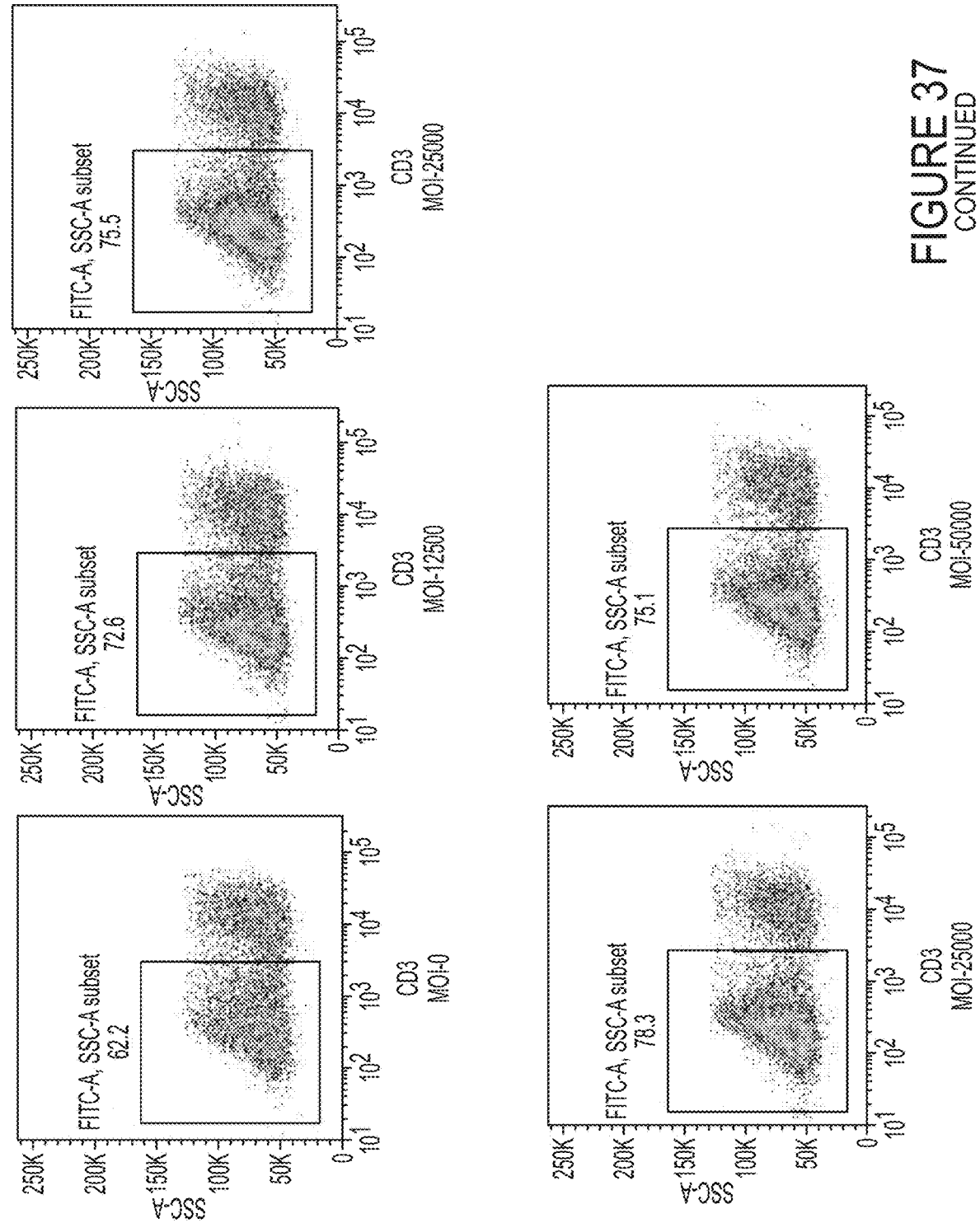

FIG. 37. Meganuclease knockout efficiency using single-strand AAV. Experiments were conducted to examine the knockout efficiency of two meganucleases in human T cells when simultaneously transduced with a single-stranded AAV vector. A) Cells electroporated with mRNA for TRC 1-2x.87EE and transduced with increasing amounts of the single-stranded AAV412. B) Cells electroporated with mRNA for a meganuclease targeting the beta-2 microglobulin gene and transduced with increasing amounts of the single-stranded AAV412. C) Cells electroporated with mRNA for TRC 1-2x.87EE and transduced with increasing amounts of the single-stranded AAV422.

FIG. 38. Functional activity of anti-CD19 CAR T cells. A) IFN-gamma ELISPOT assay, in which either CD19$^+$ Raji cells or CD19$^-$ U937 cells were the target population. B) Cell killing assay in which luciferase-labeled CD19$^+$ Raji cells were the target.

Figure 39:
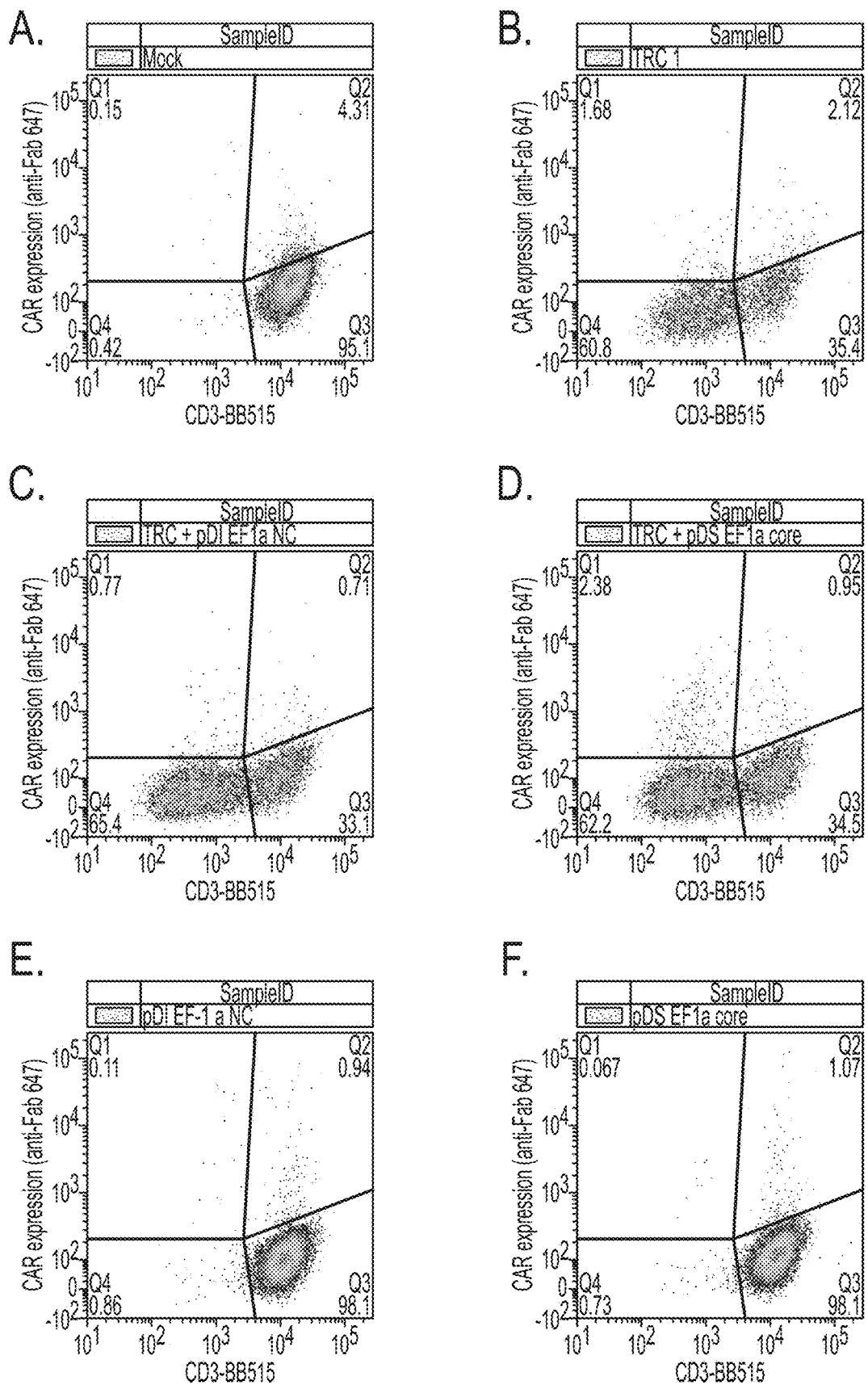

FIG. 39. Expression of chimeric antigen receptors following transduction with linearized DNA donor templates. These experiments generated plasmids that contain an anti-CD19 CAR gene flanked by homology arms that are homologous to the TRC 1-2 recognition sequence locus. Different promoters were used in some plasmids, and homology arms were either "short" (200 bp on the 5' homology arm and 180 bp on the 3' homology arm) or "long" (985 bp on the 5' homology arm and 763 bp on the 3' homology arm). CAR donor plasmids were linearized at a restriction site in the vector backbone and gel purified. A) Background CD3$^-$/CAR$^+$ staining. B) Cells electroporated with TRC 1-2x.87EE mRNA alone. C) Cells co-electroporated with TRC 1-2x.87EE mRNA and a long homology arm vector with an EF1α core promoter with an HTLV enhancer. D) Cells co-electroporated with TRC 1-2x.87EE mRNA and a short homology arm vector with EF1α core promoter (with no enhancer). E) Cells electroporated with a long homology arm vector with an EF1α core promoter with an HTLV enhancer in the absence of TRC 1-2x.87EE mRNA. F) Cells electroporated with a short homology arm vector with EF1α core promoter (with no enhancer) in the absence of TRC 1-2x.87EE mRNA. G) Cells electroporated with a long homology arm construct that contains an MND promoter driving expression of the CAR and an intron in the 5' end of the CAR gene, as well as TRC 1-2x.87EE mRNA. H) Cells electroporated with a long homology arm construct that contains an MND promoter driving expression of the CAR and no intron, as well as TRC 1-2x.87EE mRNA. I) Cells electroporated with a short homology arm plasmid with the MND promoter and no intron, as well as TRC 1-2x.87EE mRNA. J) Cells electroporated with a long homology arm construct that contains an MND promoter driving expression of the CAR and an intron in the 5' end of the CAR gene, but no TRC 1-2x.87EE mRNA. K) Cells electroporated with a long homology arm construct that contains an MND promoter driving expression of the CAR and no intron, but no TRC 1-2x.87EE mRNA. L) Cells electroporated with a short homology arm plasmid with the MND promoter and no intron, but no TRC 1-2x.87EE mRNA. M) Cells electroporated with a short homology arm construct that contained a JeT promoter, as well as TRC 1-2x.87EE mRNA. N) Cells electroporated with a long homology arm construct that contained a CMV promoter, as well as TRC 1-2x.87EE mRNA. 0) Cells electroporated with a short homology arm construct that contained a JeT promoter, but no TRC 1-2x.87EE mRNA. P) Cells electroporated with a long homology arm construct that contained a CMV promoter, but no TRC 1-2x.87EE mRNA.

Figure 40:
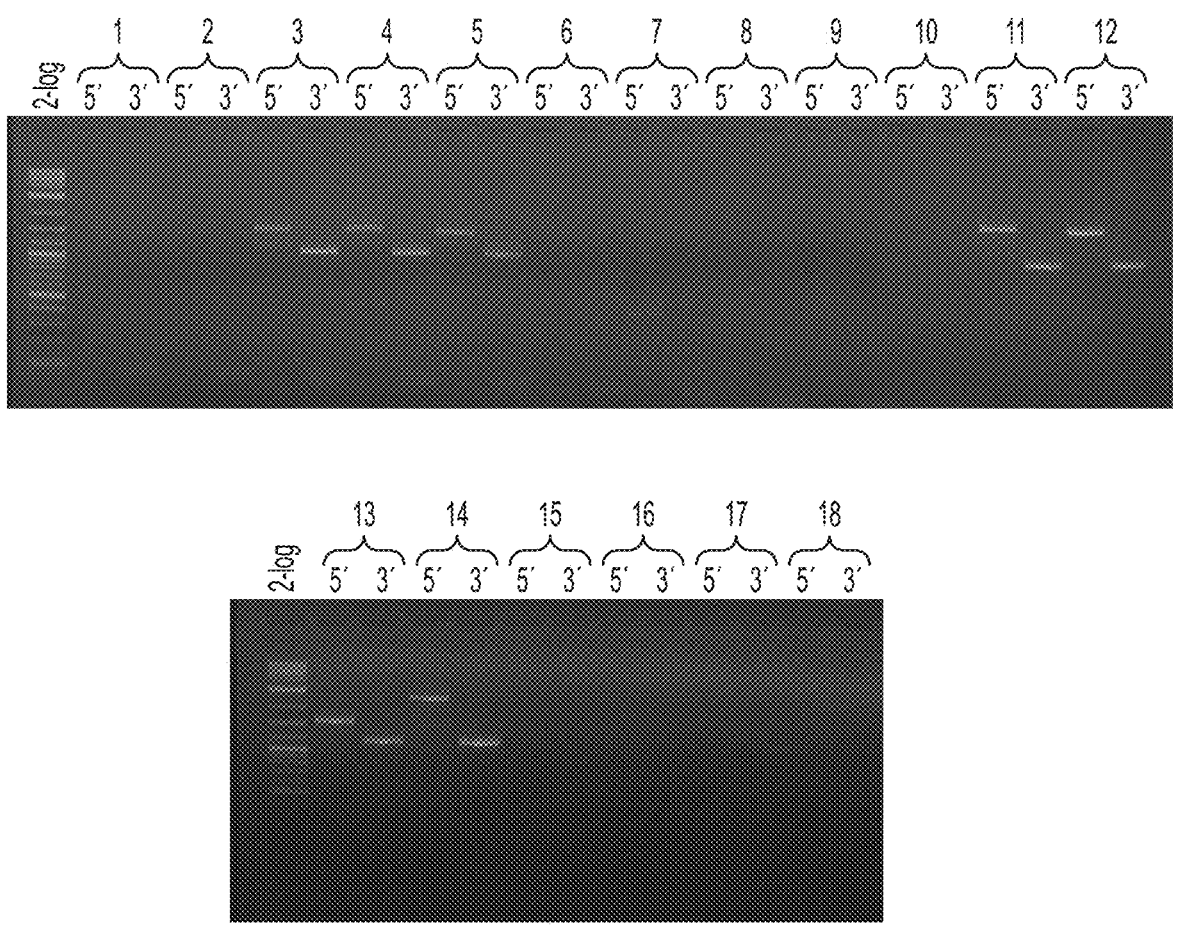

FIG. 40. PCR analysis to determine whether the chimeric antigen receptor coding region delivered by linearized DNA constructs was inserted into the TRC 1-2 recognition sequence in human T cells.

Figure 41:
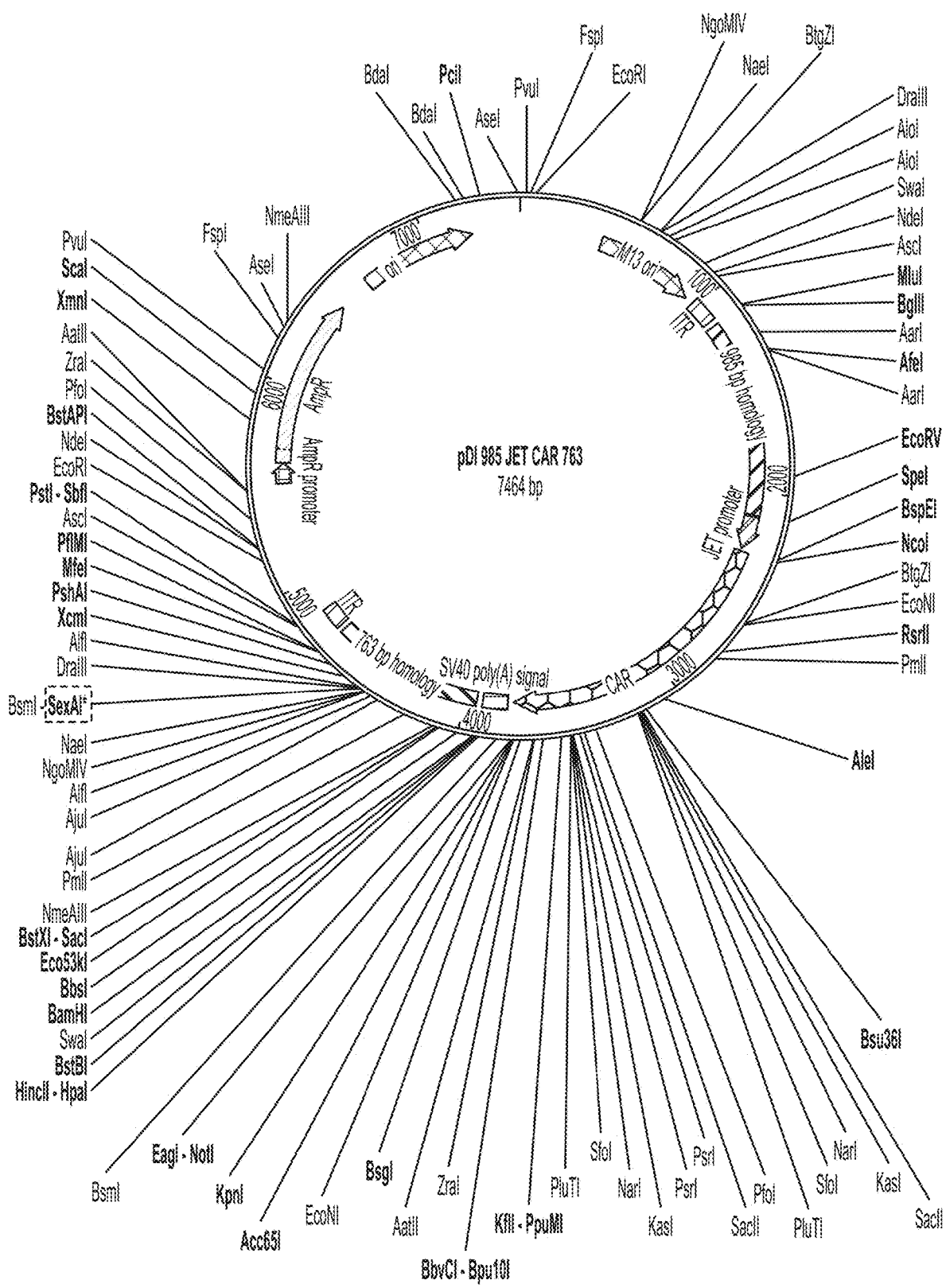

FIG. 41. Map of plasmid used to produce the AAV423 vector.

Figure 42:
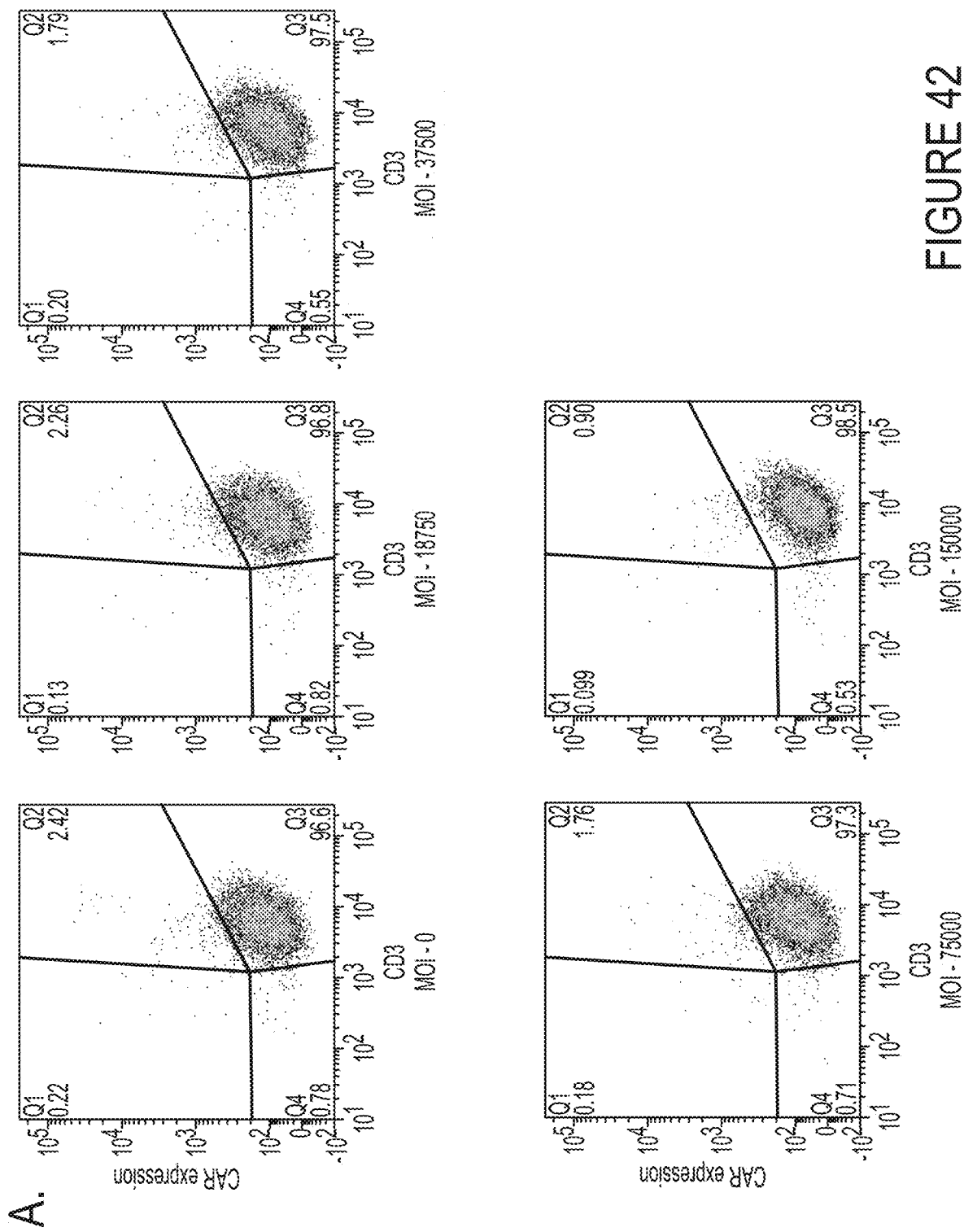
Figure 42:
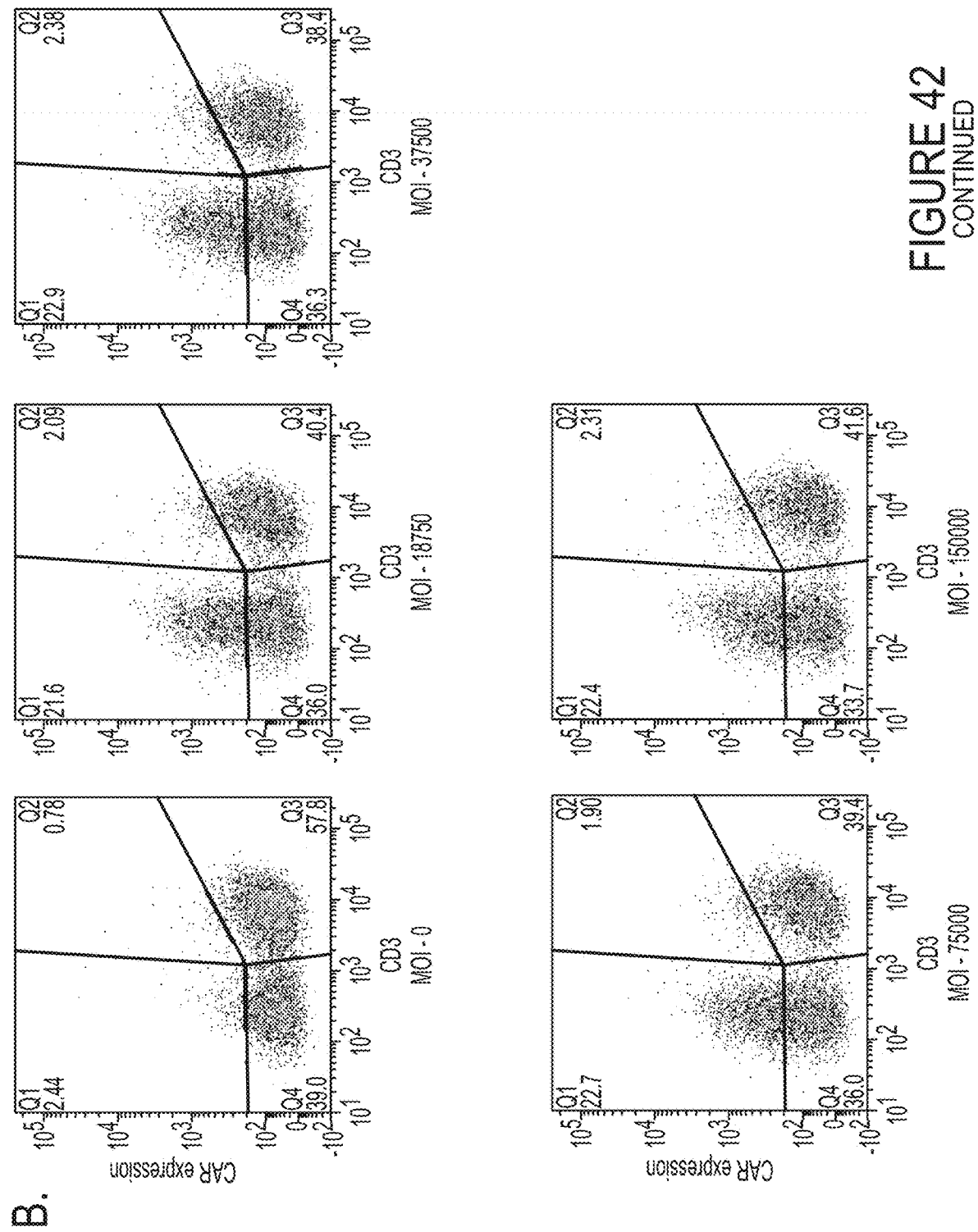

FIG. 42. Cell-surface expression of CD19 chimeric antigen receptor on human T cells. The expression level of the anti-CD19 chimeric antigen receptor was determined in cells that had the CAR gene inserted into the TRC 1-2 recognition sequence using AAV423 as the HDR template. Cell-surface expression was analyzed by flow cytometry. A) Cells that were mock electroporated and mock transduced (MOI—0), and cells that were mock electroporated and transduced with increasing amounts of AAV423. B) Cells that were electroporated with TRC 1-2x.87EE and mock transduced (MOI—0), and cells that were electroporated with TRC 1-2x.87EE and transduced with increasing amounts of AAV423.

Figure 43:
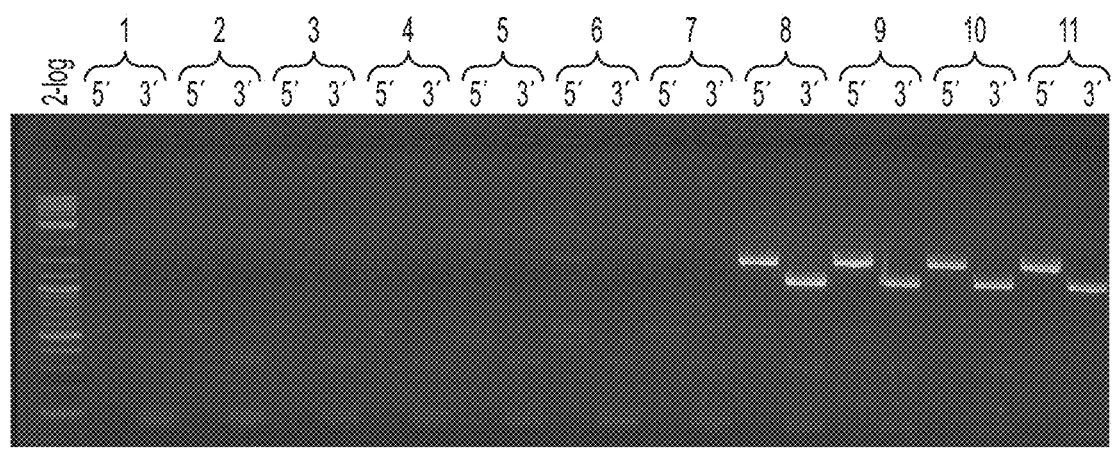

FIG. 43. Insertion of chimeric antigen receptor coding sequence. PCR methods were used to determine if the chimeric antigen receptor coding sequence introduced by AAV423 inserted at the TRC 1-2 recognition site cleaved by the TRC 1-2x.87EE meganuclease.

Figure 44:
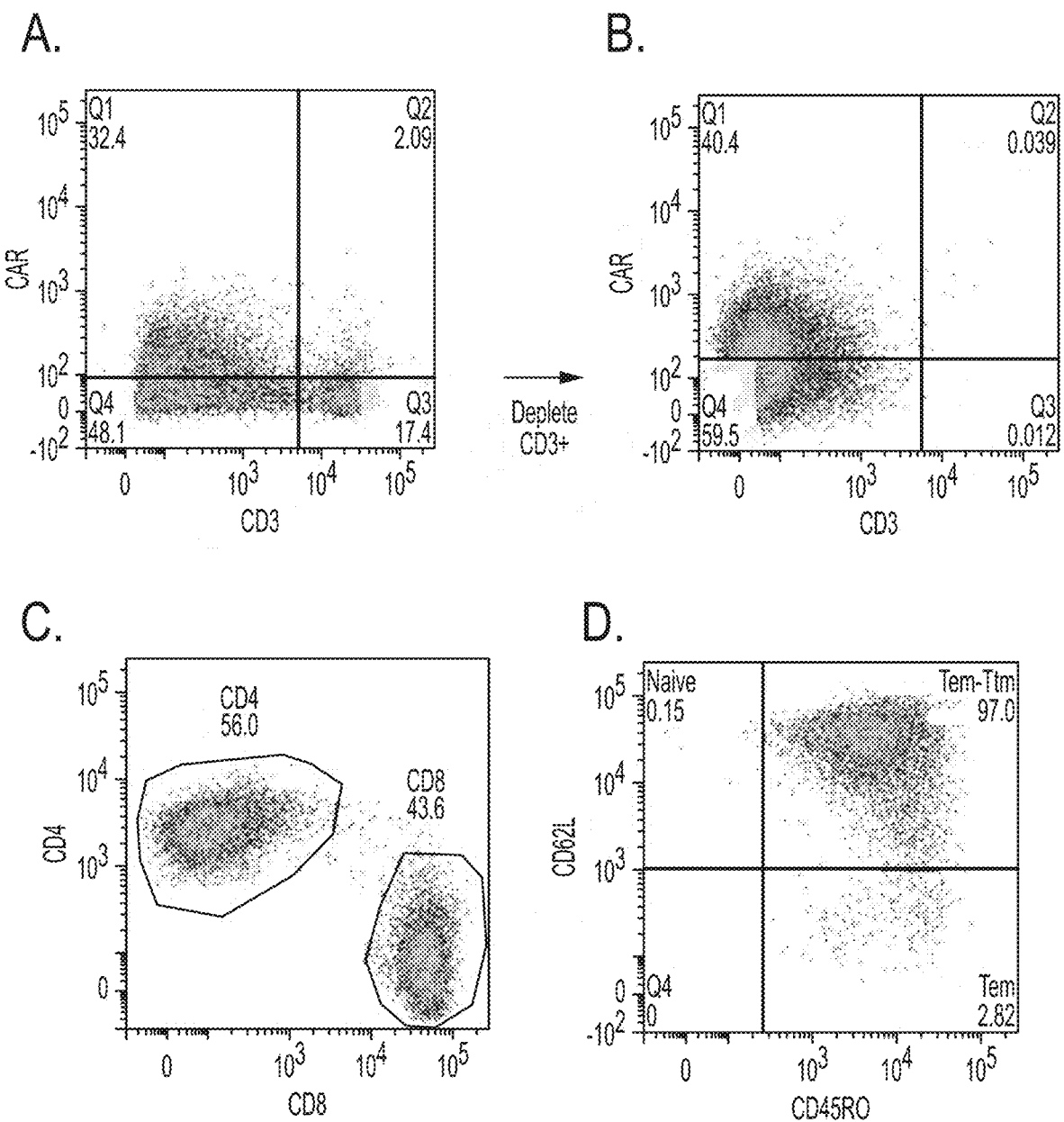

FIG. 44. Phenotype analysis of anti-CD19 CAR T cells. A) Activated T cells were electroporated with TRC 1-2x.87 EE mRNA, then transduced with an AAV6 vector comprising an anti-CD19 CAR expression cassette driven by a JeT promoter and flanked by homology arms. Following 5 days of culture with IL-2 (10 ng/mL), cells were analyzed for cell-surface CD3 and anti-CD19 CAR expression by flow cytometry. B) CD3$^-$ cells were enriched by depleting CD3$^+$ cells using anti-CD3 magnetic beads. Depleted cells were then cultured for 3 days in IL-15 (10 ng/mL) and IL-21 (10 ng/mL) and re-analyzed for cell-surface expression of CD3 and anti-CD19 CAR. C) The purified population of CD3$^-$ CD19-CAR T cells was analyzed by flow cytometry to determine the percentage of cells that were CD4$^+$ and CD8$^+$. D) The purified population of CD3$^-$ CD19-CAR T cells was further analyzed by flow cytometry to determine whether they were central memory T cells, transitional memory T cells, or effector memory T cells by staining for CD62L and CD45RO.

Figure 45:
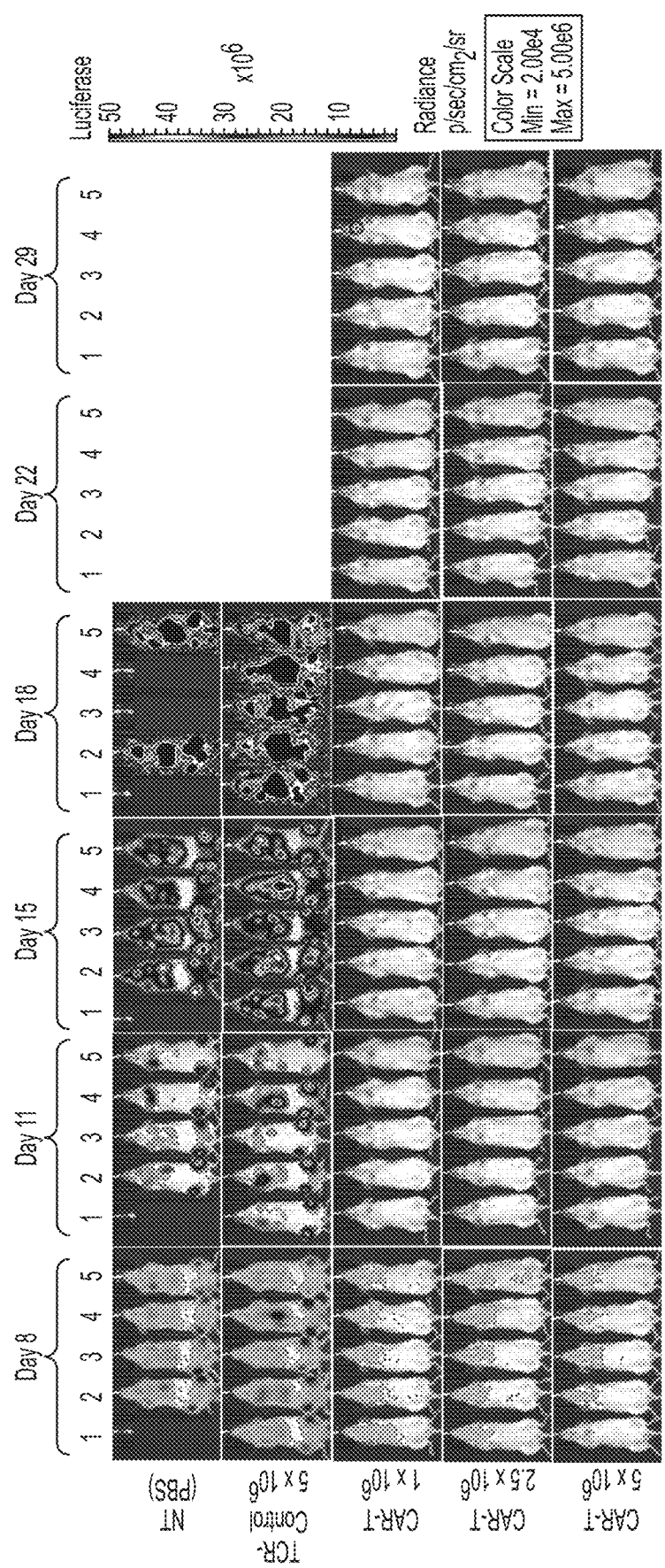

FIG. 45. Raji disseminated lymphoma model. Raji cells stably expressing firefly luciferase (ffLuc)[44] were injected i.v. into 5-6 week old female NSG mice on Day 1, at a dose of $2.0 \times 10^5$ cells per mouse. On Day 4 mice were injected i.v. with PBS or PBS containing gene edited control TCR KO T cells prepared from the same healthy donor PBMC or PBS containing the indicated doses of CAR T cells prepared from the same donor. On the indicated days, live mice were injected i.p. with Luciferin substrate (150 mg/kg in saline), anesthetized, and Luciferase activity measured after 7 minutes using IVIS SpectrumCT® (Perkin Elmer, Waltham, Mass.). Data was analyzed and exported using Living Image software 4.5.1 (Perkin Elmer, Waltham, Mass.). Luminescence signal intensity is represented by radiance in p/sec/cm$^2$/sr.

BRIEF DESCRIPTION OF THE SEQUENCES

SEQ ID NO: 1 sets forth the nucleotide sequence of the human T cell receptor alpha constant region gene (NCBI Gene ID NO. 28755).

SEQ ID NO: 2 sets forth the amino acid sequence encoded by the human T cell receptor alpha constant region.

SEQ ID NO: 3 sets forth the amino acid sequence of the TRC 1-2 recognition sequence.

SEQ ID NO: 4 sets forth the nucleotide sequence of the TRC 3-4 recognition sequence.

SEQ ID NO: 5 sets forth the nucleotide sequence of the TRC 7-8 recognition sequence.

SEQ ID NO: 6 sets forth the amino acid sequence of I-CreI.

SEQ ID NO: 7 sets forth the amino acid sequence of the LAGLIDADG motif.

SEQ ID NO: 8 sets forth the amino acid sequence of the TRC 1-2x.87 EE meganuclease.

SEQ ID NO: 9 sets forth the amino acid sequence of the TRC 1-2x.87 QE meganuclease.

SEQ ID NO: 10 sets forth the amino acid sequence of the TRC 1-2x.87 EQ meganuclease.

SEQ ID NO: 11 sets forth the amino acid sequence of the TRC 1-2x.87 meganuclease.

SEQ ID NO: 12 sets forth the amino acid sequence of the TRC 1-2x.6 meganuclease.

SEQ ID NO: 13 sets forth the amino acid sequence of the TRC 1-2x.20 meganuclease.

SEQ ID NO: 14 sets forth the amino acid sequence of the TRC 1-2x.55 meganuclease.

SEQ ID NO: 15 sets forth the amino acid sequence of the TRC 1-2x.60 meganuclease.

SEQ ID NO: 16 sets forth the amino acid sequence of the TRC 1-2x.105 meganuclease.

SEQ ID NO: 17 sets forth the amino acid sequence of the TRC 1-2x.163 meganuclease.

SEQ ID NO: 18 sets forth the amino acid sequence of the TRC 1-2x.113_3 meganuclease.

SEQ ID NO: 19 sets forth the amino acid sequence of the TRC 1-2x.5 meganuclease.

SEQ ID NO: 20 sets forth the amino acid sequence of the TRC 1-2x.8 meganuclease.

SEQ ID NO: 21 sets forth the amino acid sequence of the TRC 1-2x.25 meganuclease.

SEQ ID NO: 22 sets forth the amino acid sequence of the TRC 1-2x.72 meganuclease.

SEQ ID NO: 23 sets forth the amino acid sequence of the TRC 1-2x.80 meganuclease.

SEQ ID NO: 24 sets forth the amino acid sequence of the TRC 1-2x.84 meganuclease.

SEQ ID NO: 25 sets forth the amino acid sequence of the TRC 1-2x.120 meganuclease.

SEQ ID NO: 26 sets forth the amino acid sequence of the TRC 1-2x.113_1 meganuclease.

SEQ ID NO: 27 sets forth the amino acid sequence of the TRC 1-2x.113_2 meganuclease.

SEQ ID NO: 28 sets forth the amino acid sequence of the TRC 3-4x.3 meganuclease.

SEQ ID NO: 29 sets forth the amino acid sequence of the TRC 3-4x.19 meganuclease.

SEQ ID NO: 30 sets forth the amino acid sequence of the TRC 7-8x.7 meganuclease.

SEQ ID NO: 31 sets forth the amino acid sequence of the TRC 7-8x.9 meganuclease.

SEQ ID NO: 32 sets forth the amino acid sequence of the TRC 7-8x.14 meganuclease.

SEQ ID NO: 33 sets forth residues 198-344 of the TRC 1-2x.87 EE meganuclease.

SEQ ID NO: 34 sets forth residues 198-344 of the TRC 1-2x.87 QE meganuclease.

SEQ ID NO: 35 sets forth residues 198-344 of the TRC 1-2x.87 EQ meganuclease.

SEQ ID NO: 36 sets forth residues 198-344 of the TRC 1-2x.87 meganuclease.

SEQ ID NO: 37 sets forth residues 198-344 of the TRC 1-2x.6 meganuclease.

SEQ ID NO: 38 sets forth residues 198-344 of the TRC 1-2x.20 meganuclease.

SEQ ID NO: 39 sets forth residues 198-344 of the TRC 1-2x.55 meganuclease.

SEQ ID NO: 40 sets forth residues 198-344 of the TRC 1-2x.60 meganuclease.

SEQ ID NO: 41 sets forth residues 198-344 of the TRC 1-2x.105 meganuclease.

SEQ ID NO: 42 sets forth residues 198-344 of the TRC 1-2x.163 meganuclease.

SEQ ID NO: 43 sets forth residues 198-344 of the TRC 1-2x.113_3 meganuclease.

SEQ ID NO: 44 sets forth residues 7-153 of the TRC 1-2x.5 meganuclease.

SEQ ID NO: 45 sets forth residues 7-153 of the TRC 1-2x.8 meganuclease.

SEQ ID NO: 46 sets forth residues 7-153 of the TRC 1-2x.25 meganuclease.

SEQ ID NO: 47 sets forth residues 7-153 of the TRC 1-2x.72 meganuclease.

SEQ ID NO: 48 sets forth residues 7-153 of the TRC 1-2x.80 meganuclease.

SEQ ID NO: 49 sets forth residues 7-153 of the TRC 1-2x.84 meganuclease.

SEQ ID NO: 50 sets forth residues 7-153 of the TRC 1-2x.120 meganuclease.

SEQ ID NO: 51 sets forth residues 7-153 of the TRC 1-2x.113_1 meganuclease.

SEQ ID NO: 52 sets forth residues 7-153 of the TRC 1-2x.113_2 meganuclease.

SEQ ID NO: 53 sets forth residues 7-153 of the TRC 3-4x.3 meganuclease.

SEQ ID NO: 54 sets forth residues 7-153 of the TRC 3-4x.19 meganuclease.

SEQ ID NO: 55 sets forth residues 7-153 of the TRC 7-8x.7 meganuclease.

SEQ ID NO: 56 sets forth residues 198-344 of the TRC 7-8x.9 meganuclease.

SEQ ID NO: 57 sets forth residues 198-344 of the TRC 7-8x.14 meganuclease.

SEQ ID NO: 58 sets forth residues 7-153 of the TRC 1-2x.87 EE meganuclease.

SEQ ID NO: 59 sets forth residues 7-153 of the TRC 1-2x.87 QE meganuclease.

SEQ ID NO: 60 sets forth residues 7-153 of the TRC 1-2x.87 EQ meganuclease.

SEQ ID NO: 61 sets forth residues 7-153 of the TRC 1-2x.87 meganuclease.

SEQ ID NO: 62 sets forth residues 7-153 of the TRC 1-2x.6 meganuclease.

SEQ ID NO: 63 sets forth residues 7-153 of the TRC 1-2x.20 meganuclease.

SEQ ID NO: 64 sets forth residues 7-153 of the TRC 1-2x.55 meganuclease.

SEQ ID NO: 65 sets forth residues 7-153 of the TRC 1-2x.60 meganuclease.

SEQ ID NO: 66 sets forth residues 7-153 of the TRC 1-2x.105 meganuclease.

SEQ ID NO: 67 sets forth residues 7-153 of the TRC 1-2x.163 meganuclease.

SEQ ID NO: 68 sets forth residues 7-153 of the TRC 1-2x.113_3 meganuclease.

SEQ ID NO: 69 sets forth residues 198-344 of the TRC 1-2x.5 meganuclease.

SEQ ID NO: 70 sets forth residues 198-344 of the TRC 1-2x.8 meganuclease.

SEQ ID NO: 71 sets forth residues 198-344 of the TRC 1-2x.25 meganuclease.

SEQ ID NO: 72 sets forth residues 198-344 of the TRC 1-2x.72 meganuclease.

SEQ ID NO: 73 sets forth residues 198-344 of the TRC 1-2x.80 meganuclease.

SEQ ID NO: 74 sets forth residues 198-344 of the TRC 1-2x.84 meganuclease.

SEQ ID NO: 75 sets forth residues 198-344 of the TRC 1-2x.120 meganuclease.

SEQ ID NO: 76 sets forth residues 198-344 of the TRC 1-2x.113_1 meganuclease.

SEQ ID NO: 77 sets forth residues 198-344 of the TRC 1-2x.113_2 meganuclease.

SEQ ID NO: 78 sets forth residues 198-344 of the TRC 3-4x.3 meganuclease.

SEQ ID NO: 79 sets forth residues 198-344 of the TRC 3-4x.19 meganuclease.

SEQ ID NO: 80 sets forth residues 198-344 of the TRC 7-8x.7 meganuclease.

SEQ ID NO: 81 sets forth residues 7-153 of the TRC 7-8x.9 meganuclease.

SEQ ID NO: 82 sets forth residues 7-153 of the TRC 7-8x.14 meganuclease.

SEQ ID NO: 83 sets forth the nucleotide sequence of the antisense strand of the TRC 1-2 recognition sequence.

SEQ ID NO: 84 sets forth the nucleotide sequence of the antisense strand of the TRC 3-4 recognition sequence.

SEQ ID NO: 85 sets forth the nucleotide sequence of the antisense strand of the TRC 7-8 recognition sequence.

SEQ ID NO: 86 sets forth nucleotides 162-233 of SEQ ID NO:1.

SEQ ID NO: 87 sets forth nucleotides 162-233 of SEQ ID NO:1 comprising a deletion resulting from cleavage and NHEJ.

SEQ ID NO: 88 sets forth nucleotides 162-233 of SEQ ID NO:1 comprising a deletion resulting from cleavage and NHEJ.

SEQ ID NO: 89 sets forth nucleotides 162-233 of SEQ ID NO:1 comprising a deletion resulting from cleavage and NHEJ.

SEQ ID NO: 90 sets forth nucleotides 162-233 of SEQ ID NO:1 comprising a deletion resulting from cleavage and NHEJ.

SEQ ID NO: 91 sets forth nucleotides 162-233 of SEQ ID NO:1 comprising a deletion resulting from cleavage and NHEJ.

SEQ ID NO: 92 sets forth nucleotides 162-233 of SEQ ID NO:1 comprising a deletion resulting from cleavage and NHEJ.

SEQ ID NO: 93 sets forth nucleotides 162-233 of SEQ ID NO:1 comprising a deletion resulting from cleavage and NHEJ.

SEQ ID NO: 94 sets forth nucleotides 162-233 of SEQ ID NO:1 comprising an insertion resulting from cleavage and NHEJ.

SEQ ID NO: 95 sets forth nucleotides 162-233 of SEQ ID NO:1 comprising an insertion resulting from cleavage and NHEJ.

SEQ ID NO: 96 sets forth nucleotides 162-233 of SEQ ID NO:1 comprising a deletion resulting from cleavage and NHEJ.

SEQ ID NO: 97 sets forth nucleotides 162-233 of SEQ ID NO:1 comprising a deletion resulting from cleavage and NHEJ.

SEQ ID NO: 98 sets forth nucleotides 162-233 of SEQ ID NO:1 comprising a deletion resulting from cleavage and NHEJ.

SEQ ID NO: 99 sets forth nucleotides 162-233 of SEQ ID NO:1 comprising a deletion resulting from cleavage and NHEJ.

SEQ ID NO: 100 sets forth nucleotides 162-233 of SEQ ID NO:1 comprising a deletion resulting from cleavage and NHEJ.

SEQ ID NO: 101 sets forth nucleotides 162-233 of SEQ ID NO:1 comprising a deletion resulting from cleavage and NHEJ.

SEQ ID NO: 102 sets forth nucleotides 162-233 of SEQ ID NO:1 comprising a deletion resulting from cleavage and NHEJ.

SEQ ID NO: 103 sets forth nucleotides 162-233 of SEQ ID NO:1 comprising a deletion resulting from cleavage and NHEJ.

SEQ ID NO: 104 sets forth nucleotides 162-233 of SEQ ID NO:1 comprising a deletion resulting from cleavage and NHEJ.

SEQ ID NO: 105 sets forth nucleotides 181-214 of SEQ ID NO:1.

SEQ ID NO: 106 sets forth nucleotides 181-214 of SEQ ID NO:1 comprising an exogenous nucleic acid sequence inserted via homologous recombination.

SEQ ID NO: 107 sets forth the nucleotide sequence of a plasmid used to generate the AAV405 vector.

SEQ ID NO: 108 sets forth the nucleotide sequence of a plasmid used to generate the AAV406 vector.

SEQ ID NO: 109 sets forth the nucleotide sequence of a plasmid used to generate the AAV-CAR100 (AAV408) vector.

SEQ ID NO: 110 sets forth the nucleotide sequence of a plasmid used to generate the AAV-CAR763 (AAV412) vector.

SEQ ID NO: 111 sets forth the amino acid sequence of an anti-CD19 chimeric antigen receptor.

SEQ ID NO: 112 sets forth the amino acid sequence of an anti-CD19 extracellular ligand-binding domain.

SEQ ID NO: 113 sets forth the amino acid sequence of a chimeric antigen receptor intracellular cytoplasmic signaling domain.

SEQ ID NO: 114 sets forth the amino acid sequence of a chimeric antigen receptor intracellular co-stimulatory domain.

SEQ ID NO: 115 sets forth the amino acid sequence of a chimeric antigen receptor signal peptide domain.

SEQ ID NO: 116 sets forth the amino acid sequence of a chimeric antigen receptor hinge region.

SEQ ID NO: 117 sets forth the amino acid sequence of a chimeric antigen receptor transmembrane domain.

SEQ ID NO: 118 sets forth the nucleotide sequence of an EF-1 alpha core promoter.

SEQ ID NO: 119 sets forth the nucleotide sequence of an exogenous polynucleotide insert.

SEQ ID NO: 120 sets forth the nucleotide sequence of the human TCR alpha constant region gene comprising an exogenous nucleic acid sequence inserted within the TRC 1-2 recognition sequence.

SEQ ID NO: 121 sets forth the nucleotide sequence of the human TCR alpha constant region gene comprising an exogenous nucleic acid sequence inserted within the TRC 3-4 recognition sequence.

SEQ ID NO: 122 sets forth the nucleotide sequence of the human TCR alpha constant region gene comprising an exogenous nucleic acid sequence inserted within the TRC 7-8 recognition sequence.

SEQ ID NO: 123 sets forth the nucleic acid sequence of a plasmid used to generate the AAV421 vector.

SEQ ID NO: 124 sets forth the nucleic acid sequence of a plasmid used to generate the AAV422 vector.

SEQ ID NO: 125 sets forth the nucleic acid sequence of a plasmid used to generate the AAV423 vector.

DETAILED DESCRIPTION OF THE INVENTION

1.1 References and Definitions

The patent and scientific literature referred to herein establishes knowledge that is available to those of skill in the art. The issued US patents, allowed applications, published foreign applications, and references, including GenBank database sequences, which are cited herein are hereby incorporated by reference to the same extent as if each was specifically and individually indicated to be incorporated by reference.

The present invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference herein in their entirety.

As used herein, "a," "an," or "the" can mean one or more than one. For example, "a" cell can mean a single cell or a multiplicity of cells.

As used herein, unless specifically indicated otherwise, the word "or" is used in the inclusive sense of "and/or" and not the exclusive sense of "either/or."

As used herein, the term "meganuclease" refers to an endonuclease that binds double-stranded DNA at a recognition sequence that is greater than 12 base pairs. Preferably, the recognition sequence for a meganuclease of the invention is 22 base pairs. A meganuclease can be an endonuclease that is derived from I-CreI, and can refer to an engineered variant of I-CreI that has been modified relative to natural I-CreI with respect to, for example, DNA-binding specificity, DNA cleavage activity, DNA-binding affinity, or dimerization properties. Methods for producing such modified variants of I-CreI are known in the art (e.g. WO 2007/047859). A meganuclease as used herein binds to double-stranded DNA as a heterodimer or as a "single-chain meganuclease" in which a pair of DNA-binding domains are joined into a single polypeptide using a peptide linker. The term "homing endonuclease" is synonymous with the term "meganuclease." Meganucleases of the invention are substantially non-toxic when expressed in cells, particularly in human T cells, such that cells can be transfected and maintained at 37° C. without observing deleterious effects on cell viability or significant reductions in meganuclease cleavage activity when measured using the methods described herein.

As used herein, the term "single-chain meganuclease" refers to a polypeptide comprising a pair of meganuclease subunits joined by a linker. A single-chain meganuclease has the organization: N-terminal subunit—Linker—C-terminal subunit. The two meganuclease subunits will generally be non-identical in amino acid sequence and will recognize non-identical DNA sequences. Thus, single-chain meganucleases typically cleave pseudo-palindromic or non-palindromic recognition sequences. A single-chain meganuclease may be referred to as a "single-chain heterodimer" or "single-chain heterodimeric meganuclease" although it is not, in fact, dimeric. For clarity, unless otherwise specified, the term "meganuclease" can refer to a dimeric or single-chain meganuclease.

As used herein, the term "linker" refers to an exogenous peptide sequence used to join two meganuclease subunits into a single polypeptide. A linker may have a sequence that is found in natural proteins, or may be an artificial sequence that is not found in any natural protein. A linker may be flexible and lacking in secondary structure or may have a propensity to form a specific three-dimensional structure under physiological conditions. A linker can include, without limitation, those encompassed by U.S. Pat. No. 8,445,251. In some embodiments, a linker may have an amino acid sequence comprising residues 154-195 of any one of SEQ ID NOs:8-32.

As used herein, with respect to a protein, the term "recombinant" means having an altered amino acid sequence as a result of the application of genetic engineering techniques to nucleic acids that encode the protein, and cells or organisms that express the protein. With respect to a nucleic acid, the term "recombinant" means having an altered nucleic acid sequence as a result of the application of genetic engineering techniques. Genetic engineering techniques include, but are not limited to, PCR and DNA cloning technologies; transfection, transformation and other gene transfer technologies; homologous recombination; site-directed mutagenesis; and gene fusion. In accordance with this definition, a protein having an amino acid sequence identical to a naturally-occurring protein, but produced by cloning and expression in a heterologous host, is not considered recombinant.

As used herein, the term "wild-type" refers to the most common naturally occurring allele (i.e., polynucleotide sequence) in the allele population of the same type of gene, wherein a polypeptide encoded by the wild-type allele has its original functions. The term "wild-type" also refers a polypeptide encoded by a wild-type allele. Wild-type alleles (i.e., polynucleotides) and polypeptides are distinguishable from mutant or variant alleles and polypeptides, which comprise one or more mutations and/or substitutions relative to the wild-type sequence(s). Whereas a wild-type allele or polypeptide can confer a normal phenotype in an organism, a mutant or variant allele or polypeptide can, in some instances, confer an altered phenotype. Wild-type homing endonucleases are distinguishable from recombinant or non-naturally-occurring meganucleases.

As used herein with respect to recombinant proteins, the term "modification" means any insertion, deletion or substitution of an amino acid residue in the recombinant sequence relative to a reference sequence (e.g., a wild-type or a native sequence).

As used herein, the term "recognition sequence" refers to a DNA sequence that is bound and cleaved by a meganuclease. In the case of a recombinant meganuclease of the invention, a recognition sequence comprises a pair of inverted, 9 base pair "half-sites" or "recognition half-sites" that are separated by four base pairs. In the case of a single-chain meganuclease, the N-terminal subunit of the protein contacts a first half-site and the C-terminal subunit of the protein contacts a second half-site. Cleavage by a meganuclease produces four base pair 3' "overhangs". "Overhangs", or "sticky ends" are short, single-stranded DNA segments that can be produced by meganuclease cleavage of a double-stranded DNA sequence. In the case of meganucleases of the present invention, the overhang comprises bases 10-13 of the 22 base pair recognition sequence.

As used herein, the term "target site" or "target sequence" refers to a region of the chromosomal DNA of a cell comprising a recognition sequence for a meganuclease.

As used herein, the term "DNA-binding affinity" or "binding affinity" means the tendency of a meganuclease to non-covalently associate with a reference DNA molecule (e.g., a recognition sequence or an arbitrary sequence). Binding affinity is measured by a dissociation constant, $K_d$. As used herein, a meganuclease has "altered" binding affinity if the $K_d$ of the recombinant meganuclease for a reference recognition sequence is increased or decreased by a statistically significant percent change relative to a reference meganuclease.

As used herein, the term "homologous recombination" or "HR" refers to the natural, cellular process in which a double-stranded DNA-break is repaired using a homologous DNA sequence as the repair template (see, e.g., Cahill et al. (2006), *Front. Biosci.* 11:1958-1976). The homologous DNA sequence may be an endogenous chromosomal sequence or an exogenous nucleic acid that was delivered to the cell.

As used herein, the term "non-homologous end-joining" or "NHEJ" refers to the natural, cellular process in which a double-stranded DNA-break is repaired by the direct joining of two non-homologous DNA segments (see, e.g., Cahill et al. (2006), *Front. Biosci.* 11:1958-1976). DNA repair by non-homologous end-joining is error-prone and frequently results in the untemplated addition or deletion of DNA sequences at the site of repair. In some instances, cleavage at a target recognition sequence results in NHEJ at a target recognition site. Nuclease-induced cleavage of a target site in the coding sequence of a gene followed by DNA repair by NHEJ can introduce mutations into the coding sequence, such as frameshift mutations, that disrupt gene function. Thus, engineered nucleases such as meganucleases can be used to effectively knock-out a gene in a population of cells.

As used herein, a "chimeric antigen receptor" or "CAR" refers to an engineered receptor that confers or grafts specificity for an antigen onto an immune effector cell (e.g., a human T cell). A chimeric antigen receptor typically comprises an extracellular ligand-binding domain or moiety and an intracellular domain that comprises one or more stimulatory domains that transduce the signals necessary for T cell activation. In some embodiments, the extracellular ligand-binding domain or moiety can be in the form of single-chain variable fragments (scFvs) derived from a monoclonal antibody, which provide specificity for a particular epitope or antigen (e.g., an epitope or antigen preferentially present on the surface of a cancer cell or other disease-causing cell or particle). The extracellular ligand-binding domain can be specific for any antigen or epitope of interest. In a particular embodiment, the ligand-binding domain is specific for CD19. In other embodiments, the scFv can be humanized.

The extracellular domain of a chimeric antigen receptor can also comprise an autoantigen (see, Payne et al. (2016), *Science* 353(6295):179-184), which can be recognized by autoantigen-specific B cell receptors on B lymphocytes, thus directing T cells to specifically target and kill autoreactive B lymphocytes in antibody-mediated autoimmune diseases. Such CARs can be referred to as chimeric autoantibody receptors (CAARs), and their use is encompassed by the invention.

The scFvs can be attached via a linker sequence. The intracellular stimulatory domain can include one or more cytoplasmic signaling domains that transmit an activation signal to the immune effector cell following antigen binding. Such cytoplasmic signaling domains can include, without limitation, CD3-zeta. The intracellular stimulatory domain can also include one or more intracellular co-stimulatory domains that transmit a proliferative and/or cell-survival signal after ligand binding. Such intracellular co-stimulatory domains can include, without limitation, a CD28 domain, a 4-1BB domain, an OX40 domain, or a combination thereof. A chimeric antigen receptor can further include additional structural elements, including a transmembrane domain that is attached to the extracellular ligand-binding domain via a hinge or spacer sequence.

As used herein, an "exogenous T cell receptor" or "exogenous TCR" refers to a TCR whose sequence is introduced into the genome of an immune effector cell (e.g., a human T cell) that may or may not endogenously express the TCR. Expression of an exogenous TCR on an immune effector cell can confer specificity for a specific epitope or antigen (e.g., an epitope or antigen preferentially present on the surface of a cancer cell or other disease-causing cell or particle). Such exogenous T cell receptors can comprise alpha and beta chains or, alternatively, may comprise gamma and delta chains. Exogenous TCRs useful in the invention may have specificity to any antigen or epitope of interest.

As used herein, the term "reduced expression" refers to any reduction in the expression of the endogenous T cell receptor at the cell surface of a genetically-modified cell when compared to a control cell. The term reduced can also refer to a reduction in the percentage of cells in a population of cells that express an endogenous polypeptide (i.e., an endogenous T cell receptor) at the cell surface when compared to a population of control cells. Such a reduction may be up to 5%, 10%, 20%, 30%, 40%, 50%, 60%, 70%, 80%, 90%, 95%, or up to 100%. Accordingly, the term "reduced" encompasses both a partial knockdown and a complete knockdown of the endogenous T cell receptor.

As used herein with respect to both amino acid sequences and nucleic acid sequences, the terms "percent identity," "sequence identity," "percentage similarity," "sequence similarity" and the like refer to a measure of the degree of similarity of two sequences based upon an alignment of the sequences that maximizes similarity between aligned amino acid residues or nucleotides, and that is a function of the number of identical or similar residues or nucleotides, the number of total residues or nucleotides, and the presence and length of gaps in the sequence alignment. A variety of algorithms and computer programs are available for determining sequence similarity using standard parameters. As used herein, sequence similarity is measured using the BLASTp program for amino acid sequences and the BLASTn program for nucleic acid sequences, both of which are available through the National Center for Biotechnology Information website, and are described in, for example, Altschul et al. (1990), *J. Mol. Biol.* 215:403-410; Gish and States (1993), *Nature Genet.* 3:266-272; Madden et al. (1996), *Meth. Enzymol.* 266:131-141; Altschul et al. (1997), *Nucleic Acids Res.* 25:33 89-3402; Zhang et al. (2000), *J. Comput. Biol.* 7(1-2):203-14. As used herein, percent similarity of two amino acid sequences is the score based upon the following parameters for the BLASTp algorithm: word size=3; gap opening penalty=−11; gap extension penalty=−1; and scoring matrix=BLOSUM62. As used herein, percent similarity of two nucleic acid sequences is the score based upon the following parameters for the BLASTn algorithm: word size=11; gap opening penalty=−5; gap extension penalty=−2; match reward=1; and mismatch penalty=−3.

As used herein with respect to modifications of two proteins or amino acid sequences, the term "corresponding to" is used to indicate that a specified modification in the first protein is a substitution of the same amino acid residue as in the modification in the second protein, and that the amino acid position of the modification in the first proteins corresponds to or aligns with the amino acid position of the modification in the second protein when the two proteins are subjected to standard sequence alignments (e.g., using the BLASTp program). Thus, the modification of residue "X" to amino acid "A" in the first protein will correspond to the modification of residue "Y" to amino acid "A" in the second protein if residues X and Y correspond to each other in a sequence alignment, and despite the fact that X and Y may be different numbers.

As used herein, the term "recognition half-site," "recognition sequence half-site," or simply "half-site" means a nucleic acid sequence in a double-stranded DNA molecule that is recognized by a monomer of a homodimeric or heterodimeric meganuclease, or by one subunit of a single-chain meganuclease.

As used herein, the term "hypervariable region" refers to a localized sequence within a meganuclease monomer or subunit that comprises amino acids with relatively high variability. A hypervariable region can comprise about 50-60 contiguous residues, about 53-57 contiguous residues, or preferably about 56 residues. In some embodiments, the residues of a hypervariable region may correspond to positions 24-79 or positions 215-270 of any one of SEQ ID NOs:8-32. A hypervariable region can comprise one or more residues that contact DNA bases in a recognition sequence and can be modified to alter base preference of the monomer or subunit. A hypervariable region can also comprise one or more residues that bind to the DNA backbone when the meganuclease associates with a double-stranded DNA recognition sequence. Such residues can be modified to alter the binding affinity of the meganuclease for the DNA backbone and the target recognition sequence. In different embodiments of the invention, a hypervariable region may comprise between 1-20 residues that exhibit variability and can be modified to influence base preference and/or DNA-binding affinity. In particular embodiments, a hypervariable region comprises between about 15-18 residues that exhibit variability and can be modified to influence base preference and/or DNA-binding affinity. In some embodiments, variable residues within a hypervariable region correspond to one or more of positions 24, 26, 28, 29, 30, 32, 33, 38, 40, 42, 44, 46, 66, 68, 70, 72, 73, 75, and 77 of any one of SEQ ID NOs:8-32. In other embodiments, variable residues within a hypervariable region correspond to one or more of positions 215, 217, 219, 221, 223, 224, 229, 231, 233, 235, 237, 248, 257, 259, 261, 263, 264, 266, and 268 of any one of SEQ ID NOs:8-32.

As used herein, the terms "T cell receptor alpha constant region gene" and "TCR alpha constant region gene" are used interchangeably and refer to the human gene identified by NCBI Gen ID NO. 28755 (SEQ ID NO:1).

The terms "recombinant DNA construct," "recombinant construct," "expression cassette," "expression construct," "chimeric construct," "construct," and "recombinant DNA fragment" are used interchangeably herein and are single or double-stranded polynucleotides. A recombinant construct comprises an artificial combination of single or double-stranded polynucleotides, including, without limitation, regulatory and coding sequences that are not found together in nature. For example, a recombinant DNA construct may comprise regulatory sequences and coding sequences that are derived from different sources, or regulatory sequences and coding sequences derived from the same source and arranged in a manner different than that found in nature. Such a construct may be used by itself or may be used in conjunction with a vector.

As used herein, a "vector" or "recombinant DNA vector" may be a construct that includes a replication system and sequences that are capable of transcription and translation of a polypeptide-encoding sequence in a given host cell. If a vector is used then the choice of vector is dependent upon the method that will be used to transform host cells as is well known to those skilled in the art. Vectors can include, without limitation, plasmid vectors and recombinant AAV vectors, or any other vector known in that art suitable for delivering a gene encoding a meganuclease of the invention to a target cell. The skilled artisan is well aware of the genetic elements that must be present on the vector in order to successfully transform, select and propagate host cells comprising any of the isolated nucleotides or nucleic acid sequences of the invention.

As used herein, a "vector" can also refer to a viral vector. Viral vectors can include, without limitation, retroviral vectors, lentiviral vectors, adenoviral vectors, and adeno-associated viral vectors (AAV).

As used herein, a "polycistronic" mRNA refers to a single messenger RNA that comprises two or more coding sequences (i.e., cistrons) and encodes more than one protein. A polycistronic mRNA can comprise any element known in the art to allow for the translation of two or more genes from the same mRNA molecule including, but not limited to, an IRES element, a T2A element, a P2A element, an E2A element, and an F2A element.

As used herein, a "human T cell" or "T cell" refers to a T cell isolated from a human donor. Human T cells, and cells derived therefrom, include isolated T cells that have not been passaged in culture, T cells that have been passaged and maintained under cell culture conditions without immortalization, and T cells that have been immortalized and can be maintained under cell culture conditions indefinitely.

As used herein, a "control" or "control cell" refers to a cell that provides a reference point for measuring changes in genotype or phenotype of a genetically-modified cell. A control cell may comprise, for example: (a) a wild-type cell, i.e., of the same genotype as the starting material for the genetic alteration that resulted in the genetically-modified cell; (b) a cell of the same genotype as the genetically-modified cell but that has been transformed with a null construct (i.e., with a construct that has no known effect on the trait of interest); or, (c) a cell genetically identical to the genetically-modified cell but that is not exposed to conditions or stimuli or further genetic modifications that would induce expression of altered genotype or phenotype.

As used herein, the recitation of a numerical range for a variable is intended to convey that the invention may be practiced with the variable equal to any of the values within that range. Thus, for a variable that is inherently discrete, the variable can be equal to any integer value within the numerical range, including the end-points of the range. Similarly, for a variable that is inherently continuous, the variable can be equal to any real value within the numerical range, including the end-points of the range. As an example, and without limitation, a variable that is described as having values between 0 and 2 can take the values 0, 1 or 2 if the variable is inherently discrete, and can take the values 0.0, 0.1, 0.01, 0.001, or any other real values ≥0 and ≤2 if the variable is inherently continuous.

2.1 Principle of the Invention

The present invention is based, in part, on the discovery that recombinant meganucleases can be engineered to recognize and cleave recognition sequences found within the human TCR alpha constant region gene (SEQ ID NO:1), particularly within residues 93-208. Cleavage at such recognition sequences can allow for NHEJ at the cleavage site and disrupted expression of the human T cell receptor alpha chain subunit, leading to reduced expression and/or function of the T cell receptor at the cell surface.

Additionally, cleavage at such recognition sequences can further allow for homologous recombination of exogenous nucleic acid sequences directly into the TCR alpha constant region gene. Such exogenous nucleic acid sequences can comprise a sequence of interest, such as a sequence encoding a chimeric antigen receptor, an exogenous TCR receptor, or any other polypeptide of interest. Thus, the present invention allows for both the knockout of the endogenous T cell receptor and the expression of an exogenous nucleic acid sequence (e.g., a chimeric antigen receptor or exogenous TCR) by targeting a single recognition site with a single engineered nuclease. Such cells can exhibit reduced or no induction of graft-versus-host-disease (GVHD) when administered to an allogeneic subject.

2.2 Meganucleases for Recognizing and Cleaving Recognition Sequences within the T Cell Receptor Alpha Constant Region Gene It is known in the art that it is possible to use a site-specific nuclease to make a DNA break in the genome of a living cell, and that such a DNA break can result in permanent modification of the genome via mutagenic NHEJ repair or via homologous recombination with a transgenic DNA sequence. NHEJ can produce mutagenesis at the cleavage site, resulting in inactivation of the allele. NHEJ-associated mutagenesis may inactivate an allele via generation of early stop codons, frameshift mutations producing aberrant non-functional proteins, or could trigger mechanisms such as nonsense-mediated mRNA decay. The use of meganucleases to induce mutagenesis via NHEJ can be used to target a specific mutation or a sequence present in a wild-type allele. The use of meganucleases to induce a double-strand break in a target locus is known to stimulate homologous recombination, particularly of transgenic DNA sequences flanked by sequences that are homologous to the genomic target. In this manner, exogenous nucleic acid sequences can be inserted into a target locus. Such exogenous nucleic acids can encode, for example, a chimeric antigen receptor, an exogenous TCR, or any sequence or polypeptide of interest.

In preferred embodiments, the nucleases used to practice the invention are single-chain meganucleases. A single-chain meganuclease comprises an N-terminal subunit and a C-terminal subunit joined by a linker peptide. Each of the two domains recognizes half of the recognition sequence (i.e., a recognition half-site) and the site of DNA cleavage is at the middle of the recognition sequence near the interface of the two subunits. DNA strand breaks are offset by four base pairs such that DNA cleavage by a meganuclease generates a pair of four base pair, 3' single-strand overhangs.

In some examples, recombinant meganucleases of the invention have been engineered to recognize and cleave the TRC 1-2 recognition sequence (SEQ ID NO:3). Such recombinant meganucleases are collectively referred to herein as "TRC 1-2 meganucleases." Exemplary TRC 1-2 meganucleases are provided in SEQ ID NOs:8-27.

In additional examples, recombinant meganucleases of the invention have been engineered to recognize and cleave the TRC 3-4 recognition sequence (SEQ ID NO:4). Such recombinant meganucleases are collectively referred to herein as "TRC 3-4 meganucleases." Exemplary TRC 3-4 meganucleases are provided in SEQ ID NOs:28 and 29.

In further examples, recombinant meganucleases of the invention have been engineered to recognize and cleave the TRC 7-8 recognition sequence (SEQ ID NO:5). Such recombinant meganucleases are collectively referred to herein as "TRC 7-8 meganucleases." Exemplary TRC 7-8 meganucleases are provided in SEQ ID NOs:30-32.

Recombinant meganucleases of the invention comprise a first subunit, comprising a first hypervariable (HVR1) region, and a second subunit, comprising a second hypervariable (HVR2) region. Further, the first subunit binds to a first recognition half-site in the recognition sequence (e.g., the TRC1, TRC3, or TRC7 half-site), and the second subunit binds to a second recognition half-site in the recognition sequence (e.g., the TRC2, TRC4, or TRC8 half-site). In embodiments where the recombinant meganuclease is a single-chain meganuclease, the first and second subunits can be oriented such that the first subunit, which comprises the HVR1 region and binds the first half-site, is positioned as the N-terminal subunit, and the second subunit, which comprises the HVR2 region and binds the second half-site, is positioned as the C-terminal subunit. In alternative embodiments, the first and second subunits can be oriented such that the first subunit, which comprises the HVR1 region and binds the first half-site, is positioned as the C-terminal subunit, and the second subunit, which comprises the HVR2 region and binds the second half-site, is positioned as the N-terminal subunit. Exemplary TRC 1-2 meganucleases of the invention are provided in Table 1. Exemplary TRC 3-4 meganucleases of the invention are provided in Table 2. Exemplary TRC 7-8 meganucleases of the invention are provided in Table 3.

TABLE 1

Exemplary recombinant meganucleases engineered to recognize and cleave the TRC 1-2 recognition sequence (SEQ ID NO:3)

| Meganuclease | AA SEQ ID | TRC1 Subunit Residues | TRC1 Subunit SEQ ID | *TRC1 Subunit % | TRC2 Subunit Residues | TRC2 Subunit SEQ ID | *TRC2 Subunit % |
|---|---|---|---|---|---|---|---|
| TRC 1-2x.87 EE | 8 | 198-344 | 33 | 100 | 7-153 | 58 | 100 |
| TRC 1-2x.87 QE | 9 | 198-344 | 34 | 100 | 7-153 | 59 | 99.3 |
| TRC 1-2x.87 EQ | 10 | 198-344 | 35 | 99.3 | 7-153 | 60 | 100 |
| TRC 1-2x.87 | 11 | 198-344 | 36 | 99.3 | 7-153 | 61 | 99.3 |
| TRC 1-2x.6 | 12 | 198-344 | 37 | 99.3 | 7-153 | 62 | 94.6 |
| TRC 1-2x.20 | 13 | 198-344 | 38 | 99.3 | 7-153 | 63 | 91.2 |
| TRC 1-2x.55 | 14 | 198-344 | 39 | 95.9 | 7-153 | 64 | 91.8 |
| TRC 1-2x.60 | 15 | 198-344 | 40 | 91.8 | 7-153 | 65 | 91.2 |
| TRC 1-2x.105 | 16 | 198-344 | 41 | 95.2 | 7-153 | 66 | 95.2 |
| TRC 1-2x.163 | 17 | 198-344 | 42 | 99.3 | 7-153 | 67 | 99.3 |
| TRC 1-2x.113_3 | 18 | 198-344 | 43 | 99.3 | 7-153 | 68 | 91.2 |
| TRC 1-2x.5 | 19 | 7-153 | 44 | 99.3 | 198-344 | 69 | 93.2 |
| TRC 1-2x.8 | 20 | 7-153 | 45 | 92.5 | 198-344 | 70 | 92.5 |
| TRC 1-2x.25 | 21 | 7-153 | 46 | 99.3 | 198-344 | 71 | 98.6 |
| TRC 1-2x.72 | 22 | 7-153 | 47 | 99.3 | 198-344 | 72 | 92.5 |
| TRC 1-2x.80 | 23 | 7-153 | 48 | 99.3 | 198-344 | 73 | 92.5 |
| TRC 1-2x.84 | 24 | 7-153 | 49 | 95.2 | 198-344 | 74 | 98.6 |
| TRC 1-2x.120 | 25 | 7-153 | 50 | 99.3 | 198-344 | 75 | 92.5 |
| TRC 1-2x.113_1 | 26 | 7-153 | 51 | 100 | 198-344 | 76 | 92.5 |
| TRC 1-2x.113_2 | 27 | 7-153 | 52 | 99.3 | 198-344 | 77 | 92.5 |

*"TRC1 Subunit %" and "TRC2 Subunit %" represent the amino acid sequence identity between the TRC1-binding and TRC2-binding subunit regions of each meganuclease and the TRC1-binding and TRC2-binding subunit regions, respectively, of the TRC 1-2x.87 EE meganuclease.

TABLE 2

Exemplary recombinant meganucleases engineered to recognize and cleave the TRC 3-4 recognition sequence (SEQ ID NO:4)

| Meganuclease | AA SEQ ID | TRC3 Subunit Residues | TRC3 Subunit SEQ ID | *TRC3 Subunit % | TRC4 Subunit Residues | TRC4 Subunit SEQ ID | *TRC4 Subunit % |
|---|---|---|---|---|---|---|---|
| TRC3-4x.3 | 28 | 7-153 | 53 | 100 | 198-344 | 78 | 100 |
| TRC 3-4x.19 | 29 | 7-153 | 54 | 96.6 | 198-344 | 79 | 96.6 |

*"TRC3 Subunit %" and "TRC4 Subunit %" represent the amino acid sequence identity between the TRC3-binding and TRC4-binding subunit regions of each meganuclease and the TRC3-binding and TRC4-binding subunit regions, respectively, of the TRC 3-4x.3 meganuclease.

TABLE 3

Exemplary recombinant meganucleases engineered to recognize and cleave the TRC 7-8 recognition sequence (SEQ ID NO:5)

| Meganuclease | AA SEQ ID | TRC7 Subunit Residues | TRC7 Subunit SEQ ID | *TRC7 Subunit % | TRC8 Subunit Residues | TRC8 Subunit SEQ ID | *TRC8 Subunit % |
|---|---|---|---|---|---|---|---|
| TRC 7-8x.7 | 30 | 7-153 | 55 | 100 | 198-344 | 80 | 100 |
| TRC 7-8x.9 | 31 | 198-344 | 56 | 97.3 | 7-153 | 81 | 91.2 |
| TRC7-8x.14 | 32 | 198-344 | 57 | 97.9 | 7-153 | 82 | 90.5 |

*"TRC7 Subunit %" and "TRC8 Subunit %" represent the amino acid sequence identity between the TRC7-binding and TRC8-binding subunit regions of each meganuclease and the TRC7-binding and TRC8-binding subunit regions, respectively, of the TRC 7-8x.7 meganuclease.

2.3 Methods for Producing Genetically-Modified Cells

The invention provides methods for producing genetically-modified cells using recombinant meganucleases that recognize and cleave recognition sequences found within the human TCR alpha constant region gene (SEQ ID NO:1). Cleavage at such recognition sequences can allow for NHEJ at the cleavage site and disrupted expression of the human T cell receptor alpha chain subunit, leading to reduced expression and/or function of the T cell receptor at the cell surface. Additionally, cleavage at such recognition sequences can further allow for homologous recombination of exogenous nucleic acid sequences directly into the TCR alpha constant region gene.

Recombinant meganucleases of the invention can be delivered into a cell in the form of protein or, preferably, as a nucleic acid encoding the recombinant meganuclease. Such nucleic acid can be DNA (e.g., circular or linearized plasmid DNA or PCR products) or RNA.

For embodiments in which the recombinant meganuclease coding sequence is delivered in DNA form, it should be operably linked to a promoter to facilitate transcription of the meganuclease gene. Mammalian promoters suitable for the invention include constitutive promoters such as the cytomegalovirus early (CMV) promoter (Thomsen et al. (1984), *Proc Natl Acad Sci USA.* 81(3):659-63) or the SV40 early promoter (Benoist and Chambon (1981), *Nature.* 290 (5804):304-10) as well as inducible promoters such as the tetracycline-inducible promoter (Dingermann et al. (1992), *Mol Cell Biol.* 12(9):4038-45).

In some embodiments, mRNA encoding the engineered nuclease is delivered to the cell because this reduces the likelihood that the gene encoding the engineered nuclease will integrate into the genome of the cell. Such mRNA encoding an engineered nuclease can be produced using methods known in the art such as in vitro transcription. In some embodiments, the mRNA is capped using 7-methylguanosine. In some embodiments, the mRNA may be polyadenylated.

In particular embodiments, an mRNA encoding an engineered nuclease of the invention can be a polycistronic mRNA encoding two or more nucleases that are simultaneously expressed in the cell. A polycistronic mRNA can encode two or more nucleases of the invention that target different recognition sequences in the same target gene. Alternatively, a polycistronic mRNA can encode at least one nuclease described herein and at least one additional nuclease targeting a separate recognition sequence positioned in the same gene, or targeting a second recognition sequence positioned in a second gene such that cleavage sites are produced in both genes. A polycistronic mRNA can comprise any element known in the art to allow for the translation of two or more genes (i.e., cistrons) from the same mRNA molecule including, but not limited to, an IRES element, a T2A element, a P2A element, an E2A element, and an F2A element.

Purified recombinant meganuclease proteins can be delivered into cells to cleave genomic DNA, which allows for homologous recombination or non-homologous end-joining at the cleavage site with a sequence of interest, by a variety of different mechanisms known in the art.

In some embodiments, recombinant meganuclease proteins, or DNA/mRNA encoding recombinant meganucleases, are coupled to a cell penetrating peptide or targeting ligand to facilitate cellular uptake. Examples of cell penetrating peptides known in the art include poly-arginine (Jearawiriyapaisarn, et al. (2008) *Mol Ther.* 16:1624-9), TAT peptide from the HIV virus (Hudecz et al. (2005), *Med. Res. Rev.* 25: 679-736), MPG (Simeoni, et al. (2003) *Nucleic Acids Res.* 31:2717-2724), Pep-1 (Deshayes et al. (2004) *Biochemistry* 43: 7698-7706, and HSV-1 VP-22 (Deshayes et al. (2005) *Cell Mol Life Sci.* 62:1839-49. In an alternative embodiment, recombinant meganucleases, or DNA/mRNA encoding recombinant meganucleases, are coupled covalently or non-covalently to an antibody that recognizes a specific cell-surface receptor expressed on target cells such that the meganuclease protein/DNA/mRNA binds to and is internalized by the target cells. Alternatively, recombinant meganuclease protein/DNA/mRNA can be coupled covalently or non-covalently to the natural ligand (or a portion of the natural ligand) for such a cell-surface receptor. (McCall, et al. (2014) *Tissue Barriers.* 2(4):e944449; Dinda, et al. (2013) *Curr Pharm Biotechnol.* 14:1264-74; Kang, et al. (2014) *Curr Pharm Biotechnol.* 15(3):220-30; Qian et al. (2014) *Expert Opin Drug Metab Toxicol.* 10(11):1491-508).

In some embodiments, recombinant meganuclease proteins, or DNA/mRNA encoding recombinant meganucleases, are coupled covalently or, preferably, non-covalently to a nanoparticle or encapsulated within such a nanoparticle using methods known in the art (Sharma, et al. (2014) Biomed Res Int. 2014). A nanoparticle is a nanoscale delivery system whose length scale is <1 μm, preferably <100 nm. Such nanoparticles may be designed using a core composed of metal, lipid, polymer, or biological macromolecule, and multiple copies of the recombinant meganuclease proteins, mRNA, or DNA can be attached to or encapsulated with the nanoparticle core. This increases the copy number of the protein/mRNA/DNA that is delivered to each cell and, so, increases the intracellular expression of each recombinant meganuclease to maximize the likelihood that the target recognition sequences will be cut. The surface of such nanoparticles may be further modified with polymers or lipids (e.g., chitosan, cationic polymers, or cationic lipids) to form a core-shell nanoparticle whose surface confers additional functionalities to enhance cellular delivery and uptake of the payload (Jian et al. (2012) Biomaterials. 33(30): 7621-30). Nanoparticles may additionally be advantageously coupled to targeting molecules to direct the nanoparticle to the appropriate cell type and/or increase the likelihood of cellular uptake. Examples of such targeting molecules include antibodies specific for cell-surface receptors and the natural ligands (or portions of the natural ligands) for cell surface receptors.

In some embodiments, the meganuclease proteins or DNA/mRNA encoding the meganucleases are encapsulated within liposomes or complexed using cationic lipids (see, e.g., Lipofectamine™, Life Technologies Corp., Carlsbad, Calif.; Zuris et al. (2015) *Nat Biotechnol.* 33: 73-80; Mishra et al. (2011) *J Drug Deliv.* 2011:863734). The liposome and lipoplex formulations can protect the payload from degradation, and facilitate cellular uptake and delivery efficiency through fusion with and/or disruption of the cellular membranes of the cells.

In some embodiments, recombinant meganuclease proteins, or DNA/mRNA encoding recombinant meganucleases, are encapsulated within polymeric scaffolds (e.g., PLGA) or complexed using cationic polymers (e.g., PEI, PLL) (Tamboli et al. (2011) *Ther Deliv.* 2(4): 523-536).

In some embodiments, recombinant meganuclease proteins, or DNA/mRNA encoding recombinant meganucleases, are combined with amphiphilic molecules that self-assemble into micelles (Tong et al. (2007) *J Gene Med.* 9(11): 956-66). Polymeric micelles may include a micellar shell formed with a hydrophilic polymer (e.g., polyethyleneglycol) that can prevent aggregation, mask charge interactions, and reduce nonspecific interactions outside of the cell.

In some embodiments, recombinant meganuclease proteins, or DNA/mRNA encoding recombinant meganucleases, are formulated into an emulsion or a nanoemulsion (i.e., having an average particle diameter of <1 nm) for delivery to the cell. The term "emulsion" refers to, without limitation, any oil-in-water, water-in-oil, water-in-oil-in-water, or oil-in-water-in-oil dispersions or droplets, including lipid structures that can form as a result of hydrophobic forces that drive apolar residues (e.g., long hydrocarbon chains) away from water and polar head groups toward water, when a water immiscible phase is mixed with an aqueous phase. These other lipid structures include, but are not limited to, unilamellar, paucilamellar, and multilamellar lipid vesicles, micelles, and lamellar phases. Emulsions are composed of an aqueous phase and a lipophilic phase (typically containing an oil and an organic solvent). Emulsions also frequently contain one or more surfactants. Nanoemulsion formulations are well known, e.g., as described in US Patent Application Nos. 2002/0045667 and 2004/0043041, and U.S. Pat. Nos. 6,015,832, 6,506,803, 6,635,676, and 6,559,189, each of which is incorporated herein by reference in its entirety.

In some embodiments, recombinant meganuclease proteins, or DNA/mRNA encoding recombinant meganucleases, are covalently attached to, or non-covalently associated with, multifunctional polymer conjugates, DNA dendrimers, and polymeric dendrimers (Mastorakos et al. (2015) *Nanoscale.* 7(9): 3845-56; Cheng et al. (2008) *J Pharm Sci.* 97(1): 123-43). The dendrimer generation can control the payload capacity and size, and can provide a high payload capacity. Moreover, display of multiple surface groups can be leveraged to improve stability and reduce nonspecific interactions.

In some embodiments, genes encoding a recombinant meganuclease are introduced into a cell using a viral vector. Such vectors are known in the art and include lentiviral vectors, adenoviral vectors, and adeno-associated virus (AAV) vectors (reviewed in Vannucci, et al. (2013 *New Microbiol.* 36:1-22). Recombinant AAV vectors useful in the invention can have any serotype that allows for transduction of the virus into the cell and insertion of the meganuclease gene into the cell genome. In particular embodiments, recombinant AAV vectors have a serotype of AAV2 or AAV6. Recombinant AAV vectors can also be self-complementary such that they do not require second-strand DNA synthesis in the host cell (McCarty, et al. (2001) *Gene Ther.* 8:1248-54).

If the recombinant meganuclease genes are delivered in DNA form (e.g. plasmid) and/or via a viral vector (e.g. AAV) they must be operably linked to a promoter. In some embodiments, this can be a viral promoter such as endogenous promoters from the viral vector (e.g. the LTR of a lentiviral vector) or the well-known cytomegalovirus- or SV40 virus-early promoters. In a preferred embodiment, meganuclease genes are operably linked to a promoter that drives gene expression preferentially in the target cell (e.g., a human T cell).

The invention further provides for the introduction of an exogenous nucleic acid into the cell, such that the exogenous nucleic acid sequence is inserted into the TRC alpha constant region gene at a nuclease cleavage site. In some embodiments, the exogenous nucleic acid comprises a 5' homology arm and a 3' homology arm to promote recombination of the nucleic acid sequence into the cell genome at the nuclease cleavage site.

Exogenous nucleic acids of the invention may be introduced into the cell by any of the means previously discussed. In a particular embodiment, exogenous nucleic acids are introduced by way of a viral vector, such as a lentivirus, retrovirus, adenovirus, or preferably a recombinant AAV vector. Recombinant AAV vectors useful for introducing an exogenous nucleic acid can have any serotype that allows for transduction of the virus into the cell and insertion of the exogenous nucleic acid sequence into the cell genome. In particular embodiments, the recombinant AAV vectors have a serotype of AAV2 or AAV6. The recombinant AAV vectors can also be self-complementary such that they do not require second-strand DNA synthesis in the host cell.

In another particular embodiment, an exogenous nucleic acid can be introduced into the cell using a single-stranded DNA template. The single-stranded DNA can comprise the exogenous nucleic acid and, in preferred embodiments, can comprise 5' and 3' homology arms to promote insertion of the nucleic acid sequence into the nuclease cleavage site by homologous recombination. The single-stranded DNA can further comprise a 5' AAV inverted terminal repeat (ITR) sequence 5' upstream of the 5' homology arm, and a 3' AAV ITR sequence 3' downstream of the 3' homology arm.

In another particular embodiment, genes encoding a recombinant meganuclease of the invention and/or an exogenous nucleic acid sequence of the invention can be introduced into the cell by transfection with a linearized DNA template. In some examples, a plasmid DNA encoding a recombinant meganuclease and/or an exogenous nucleic acid sequence can be digested by one or more restriction enzymes such that the circular plasmid DNA is linearized prior to transfection into the cell.

When delivered to a cell, an exogenous nucleic acid of the invention can be operably linked to any promoter suitable for expression of the encoded polypeptide in the cell, including those mammalian promoters and inducible promoters previously discussed. An exogenous nucleic acid of the invention can also be operably linked to a synthetic promoter. Synthetic promoters can include, without limitation, the JeT promoter (WO 2002/012514).

In examples where the genetically-modified cells of the invention are human T cells, or cells derived therefrom, such cells may require activation prior to introduction of a meganuclease and/or an exogenous nucleic acid sequence. For example, T cells can be contacted with anti-CD3 and anti-CD28 antibodies that are soluble or conjugated to a support (i.e., beads) for a period of time sufficient to activate the cells.

Genetically-modified cells of the invention can be further modified to express one or more inducible suicide genes, the induction of which provokes cell death and allows for selective destruction of the cells in vitro or in vivo. In some examples, a suicide gene can encode a cytotoxic polypeptide, a polypeptide that has the ability to convert a non-toxic pro-drug into a cytotoxic drug, and/or a polypeptide that activates a cytotoxic gene pathway within the cell. That is, a suicide gene is a nucleic acid that encodes a product that causes cell death by itself or in the presence of other compounds. A representative example of such a suicide gene is one that encodes thymidine kinase of herpes simplex virus. Additional examples are genes that encode thymidine kinase of varicella zoster virus and the bacterial gene cytosine deaminase that can convert 5-fluorocytosine to the highly toxic compound 5-fluorouracil. Suicide genes also include as non-limiting examples genes that encode caspase-9, caspase-8, or cytosine deaminase. In some examples, caspase-9 can be activated using a specific chemical inducer of dimerization (CID). A suicide gene can also encode a polypeptide that is expressed at the surface of the cell that makes the cells sensitive to therapeutic and/or cytotoxic monoclonal antibodies. In further examples, a suicide gene can encode recombinant antigenic polypeptide comprising an antigenic motif recognized by the anti-CD20 mAb Rituximab and an epitope that allows for selection of cells expressing the suicide gene. See, for example, the RQR8 polypeptide described in WO2013153391, which comprises two Rituximab-binding epitopes and a QBEnd10-binding epitope. For such a gene, Rituximab can be administered to a subject to induce cell depletion when needed.

2.4 Pharmaceutical Compositions

In some embodiments, the invention provides a pharmaceutical composition comprising a genetically-modified cell of the invention, or a population of genetically-modified cells of the invention, and a pharmaceutical carrier. Such pharmaceutical compositions can be prepared in accordance with known techniques. See, e.g., Remington, *The Science And Practice of Pharmacy* ($21^{st}$ ed. 2005). In the manufacture of a pharmaceutical formulation according to the invention, cells are typically admixed with a pharmaceutically acceptable carrier and the resulting composition is administered to a subject. The carrier must, of course, be acceptable in the sense of being compatible with any other ingredients in the formulation and must not be deleterious to the subject. In some embodiments, pharmaceutical compositions of the invention can further comprise one or more additional agents useful in the treatment of a disease in the subject. In additional embodiments, where the genetically-modified cell is a genetically-modified human T cell (or a cell derived therefrom), pharmaceutical compositions of the invention can further include biological molecules, such as cytokines (e.g., IL-2, IL-7, IL-15, and/or IL-21), which promote in vivo cell proliferation and engraftment. Pharmaceutical compositions comprising genetically-modified cells of the invention can be administered in the same composition as an additional agent or biological molecule or, alternatively, can be co-administered in separate compositions.

Pharmaceutical compositions of the invention can be useful for treating any disease state that can be targeted by T cell adoptive immunotherapy. In a particular embodiment, the pharmaceutical compositions of the invention are useful in the treatment of cancer. Such cancers can include, without limitation, carcinoma, lymphoma, sarcoma, blastomas, leukemia, cancers of B-cell origin, breast cancer, gastric cancer, neuroblastoma, osteosarcoma, lung cancer, melanoma, prostate cancer, colon cancer, renal cell carcinoma, ovarian cancer, rhabdomyo sarcoma, leukemia, and Hodgkin's lymphoma. In certain embodiments, cancers of B-cell origin include, without limitation, B-lineage acute lymphoblastic leukemia, B-cell chronic lymphocytic leukemia, and B-cell non-Hodgkin's lymphoma.

2.5 Methods for Producing Recombinant AAV Vectors

In some embodiments, the invention provides recombinant AAV vectors for use in the methods of the invention. Recombinant AAV vectors are typically produced in mammalian cell lines such as HEK-293. Because the viral cap and rep genes are removed from the vector to prevent its self-replication to make room for the therapeutic gene(s) to be delivered (e.g. the endonuclease gene), it is necessary to provide these in trans in the packaging cell line. In addition, it is necessary to provide the "helper" (e.g. adenoviral) components necessary to support replication (Cots D, Bosch A, Chillon M (2013) *Curr. Gene Ther.* 13(5): 370-81). Frequently, recombinant AAV vectors are produced using a triple-transfection in which a cell line is transfected with a first plasmid encoding the "helper" components, a second plasmid comprising the cap and rep genes, and a third plasmid comprising the viral ITRs containing the intervening DNA sequence to be packaged into the virus. Viral particles comprising a genome (ITRs and intervening gene(s) of interest encased in a capsid are then isolated from cells by freeze-thaw cycles, sonication, detergent, or other means known in the art. Particles are then purified using cesium-chloride density gradient centrifugation or affinity chromatography and subsequently delivered to the gene(s) of interest to cells, tissues, or an organism such as a human patient.

Because recombinant AAV particles are typically produced (manufactured) in cells, precautions must be taken in practicing the current invention to ensure that the site-specific endonuclease is NOT expressed in the packaging cells. Because the viral genomes of the invention comprise a recognition sequence for the endonuclease, any endonuclease expressed in the packaging cell line will be capable of cleaving the viral genome before it can be packaged into viral particles. This will result in reduced packaging efficiency and/or the packaging of fragmented genomes. Several approaches can be used to prevent endonuclease expression in the packaging cells, including:

1. The endonuclease can be placed under the control of a tissue-specific promoter that is not active in the packaging cells. For example, if a viral vector is developed for delivery of (an) endonuclease gene(s) to muscle tissue, a muscle-specific promoter can be used. Examples of muscle-specific promoters include C5-12 (Liu, et al. (2004) *Hum Gene Ther.* 15:783-92), the muscle-specific creatine kinase (MCK) promoter (Yuasa, et al. (2002) *Gene Ther.* 9:1576-88), or the smooth muscle 22 (SM22) promoter (Haase, et al. (2013) *BMC Biotechnol.* 13:49-54). Examples of CNS (neuron)-specific promoters include the NSE, Synapsin, and MeCP2 promoters (Lentz, et al. (2012) *Neurobiol Dis.* 48:179-88). Examples of liver-specific promoters include albumin promoters (such as Palb), human al-antitrypsin (such as PalAT), and hemopexin (such as Phpx) (Kramer, M G et al., (2003) *Mol. Therapy* 7:375-85). Examples of eye-specific promoters include opsin, and corneal epithelium-specific K12 promoters (Martin K R G, Klein R L, and Quigley H A (2002) *Methods* (28): 267-75) (Tong Y, et al., (2007) *J Gene Med*, 9:956-66). These promoters, or other tissue-specific promoters known in the art, are not highly-active in HEK-293 cells and, thus, will not be expected to yield significant levels of endonuclease gene expression in packaging cells when incorporated into viral vectors of the present invention. Similarly, the viral vectors of the present invention contemplate the use of other cell lines with the use of incompatible tissue specific promoters (i.e., the well-known HeLa cell line (human epithelial cell) and using the liver-specific hemopexin promoter). Other examples of tissue specific promoters include: synovial sarcomas PDZD4 (cerebellum), C6 (liver), ASB5 (muscle), PPP1R12B (heart), SLC5A12 (kidney), cholesterol regulation APOM (liver), ADPRHL1 (heart), and monogenic malformation syndromes TP73L (muscle). (Jacox E, et al., (2010) *PLoS One* v.5(8):e12274).

2. Alternatively, the vector can be packaged in cells from a different species in which the endonuclease is not likely to be expressed. For example, viral particles can be produced in microbial, insect, or plant cells using mammalian promoters, such as the well-known cytomegalovirus- or SV40 virus-early promoters, which are not active in the non-mammalian packaging cells. In a preferred embodiment, viral particles are produced in insect cells using the baculovirus system as described by Gao, et al. (Gao, H., et al. (2007) *J. Biotechnol.* 131(2):138-43). An endonuclease under the control of a mammalian promoter is unlikely to be expressed in these cells (Airenne, K J, et al. (2013) *Mol. Ther.* 21(4):739-49). Moreover, insect cells utilize different mRNA splicing motifs than mammalian cells. Thus, it is possible to incorporate a mammalian intron, such as the human growth hormone (HGH) intron or the SV40 large T antigen intron, into the coding sequence of an endonuclease. Because these introns are not spliced efficiently from pre-mRNA transcripts in insect cells, insect cells will not express a functional endonuclease and will package the full-length genome. In contrast, mammalian cells to which the resulting recombinant AAV particles are delivered will properly splice the pre-mRNA and will express functional endonuclease protein. Haifeng Chen has reported the use of the HGH and SV40 large T antigen introns to attenuate expression of the toxic proteins barnase and diphtheria toxin fragment A in insect packaging cells, enabling the production of recombinant AAV vectors carrying these toxin genes (Chen, H (2012) *Mol Ther Nucleic Acids*. 1(11): e57).

3. The endonuclease gene can be operably linked to an inducible promoter such that a small-molecule inducer is required for endonuclease expression. Examples of inducible promoters include the Tet-On system (Clontech; Chen H., et al., (2015) *BMC Biotechnol.* 15(1):4)) and the RheoSwitch system (Intrexon; Sowa G., et al., (2011) *Spine*, 36(10): E623-8). Both systems, as well as similar systems known in the art, rely on ligand-inducible transcription factors (variants of the Tet Repressor and Ecdysone receptor, respectively) that activate transcription in response to a small-molecule activator (Doxycycline or Ecdysone, respectively). Practicing the current invention using such ligand-inducible transcription activators includes: 1) placing the endonuclease gene under the control of a promoter that responds to the corresponding transcription factor, the endonuclease gene having (a) binding site(s) for the transcription factor; and 2) including the gene encoding the transcription factor in the packaged viral genome The latter step is necessary because the endonuclease will not be expressed in the target cells or tissues following recombinant AAV delivery if the transcription activator is not also provided to the same cells. The transcription activator then induces endonuclease gene expression only in cells or tissues that are treated with the cognate small-molecule activator. This approach is advantageous because it enables endonuclease gene expression to be regulated in a spatio-temporal manner by selecting when and to which tissues the small-molecule inducer is delivered. However, the requirement to include the inducer in the viral genome, which has significantly limited carrying capacity, creates a drawback to this approach.

4. In another preferred embodiment, recombinant AAV particles are produced in a mammalian cell line that expresses a transcription repressor that prevents expression of the endonuclease. Transcription repressors are known in the art and include the Tet-Repressor, the Lac-Repressor, the Cro repressor, and the Lambda-repressor. Many nuclear hormone receptors such as the ecdysone receptor also act as transcription repressors in the absence of their cognate hormone ligand. To practice the current invention, packaging cells are transfected/transduced with a vector encoding a transcription repressor and the endonuclease gene in the viral genome (packaging vector) is operably linked to a promoter that is modified to comprise binding sites for the repressor such that the repressor silences the promoter. The gene encoding the transcription repressor can be placed in a variety of positions. It can be encoded on a separate vector; it can be incorporated into the packaging vector outside of the ITR sequences; it can be incorporated into the cap/rep vector or the adenoviral helper vector; or, most preferably, it can be stably integrated into the genome of the packaging cell such that it is expressed constitutively. Methods to modify common mammalian promoters to incorporate transcription repressor sites are known in the art. For example, Chang and Roninson modified the strong, constitutive CMV and RSV promoters to comprise operators for the Lac repressor and showed that gene expression from the modified promoters was greatly attenuated in cells expressing the repressor (Chang B D, and Roninson I B (1996) *Gene* 183:137-42). The use of a non-human transcription repressor ensures that transcription of the endonuclease gene will be repressed only in the packaging cells expressing the repressor and not in target cells or tissues transduced with the resulting recombinant AAV vector.

2.6 Recombinant Meganuclease Variants

Embodiments of the invention encompass the recombinant meganucleases described herein, and variants thereof. Further embodiments of the invention encompass isolated polynucleotides comprising a nucleic acid sequence encoding the recombinant meganucleases described herein, and variants of such polynucleotides.

As used herein, "variants" is intended to mean substantially similar sequences. A "variant" polypeptide is intended to mean a polypeptide derived from the "native" polypeptide by deletion or addition of one or more amino acids at one or more internal sites in the native protein and/or substitution of one or more amino acids at one or more sites in the native polypeptide. As used herein, a "native" polynucleotide or polypeptide comprises a parental sequence from which variants are derived. Variant polypeptides encompassed by the embodiments are biologically active. That is, they continue to possess the desired biological activity of the native protein; i.e., the ability to recognize and cleave recognition sequences found in the human T cell receptor alpha constant region (SEQ ID NO:1), including the TRC 1-2 recognition sequence (SEQ ID NO:3), the TRC 3-4 recognition sequence (SEQ ID NO:4), and the TRC 7-8 recognition sequence (SEQ ID NO:5). Such variants may result, for example, from human manipulation. Biologically active variants of a native polypeptide of the embodiments (e.g., SEQ ID NOs:8-32), or biologically active variants of the recognition half-site binding subunits described herein (e.g., SEQ ID NOs:33-82), will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about 99%, sequence identity to the amino acid sequence of the native polypeptide or native subunit, as determined by sequence alignment programs and parameters described elsewhere herein. A biologically active variant of a polypeptide or subunit of the embodiments may differ from that polypeptide or subunit by as few as about 1-40 amino acid residues, as few as about 1-20, as few as about 1-10, as few as about 5, as few as 4, 3, 2, or even 1 amino acid residue.

The polypeptides of the embodiments may be altered in various ways including amino acid substitutions, deletions, truncations, and insertions. Methods for such manipulations are generally known in the art. For example, amino acid sequence variants can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

A substantial number of amino acid modifications to the DNA recognition domain of the wild-type I-CreI meganuclease have previously been identified (e.g., U.S. Pat. No. 8,021,867) which, singly or in combination, result in recombinant meganucleases with specificities altered at individual bases within the DNA recognition sequence half-site, such that the resulting rationally-designed meganucleases have half-site specificities different from the wild-type enzyme. Table 4 provides potential substitutions that can be made in a recombinant meganuclease monomer or subunit to enhance specificity based on the base present at each half-site position (−1 through −9) of a recognition half-site.

TABLE 4

| Posn. | A | C | G | T | A/T | A/C | A/G | C/T | G/T | A/G/T | A/C/G/T |
|---|---|---|---|---|---|---|---|---|---|---|---|
| −1 | Y75 | R70* | K70 | Q70* | | | | T46* | | | G70 |
| | L75* | H75* | E70* | C70 | | | | | | | A70 |
| | C75* | R75* | E75* | L70 | | | | | | | S70 |
| | Y139* | H46* | E46* | Y75* | | | | | | | G46* |
| | C46* | K46* | D46* | Q75* | | | | | | | |
| | A46* | R46* | | H75* | | | | | | | |
| | | | | H139 | | | | | | | |
| | | | | Q46* | | | | | | | |
| | | | | H46* | | | | | | | |
| −2 | Q70 | E70 | H70 | Q44* | C44* | | | | | | |
| | T44* | D70 | D44* | | | | | | | | |
| | A44* | K44* | E44* | | | | | | | | |
| | V44* | R44* | | | | | | | | | |
| | I44* | | | | | | | | | | |
| | L44* | | | | | | | | | | |
| | N44* | | | | | | | | | | |
| −3 | Q68 | E68 | R68 | M68 | | H68 | | Y68 | K68 | | |
| | C24* | F68 | | C68 | | | | | | | |
| | I24* | K24* | | L68 | | | | | | | |
| | | R24* | | F68 | | | | | | | |
| −4 | A26* | E77 | R77 | S77 | S26* | | | | | | |
| | Q77 | K26* | E26* | Q26* | | | | | | | |
| −5 | | E42 | R42 | | | | K28* | C28* | | | M66 |
| | | | | | | | | Q42 | | | K66 |
| −6 | Q40 | E40 | R40 | C40 | A40 | | | | | | S40 |
| | C28* | R28* | | I40 | A79 | | | | | | S28* |
| | | | | V40 | A28* | | | | | | |
| | | | | C79 | H28* | | | | | | |
| | | | | I79 | | | | | | | |
| | | | | V79 | | | | | | | |
| | | | | Q28* | | | | | | | |
| −7 | N30* | E38 | K38 | I38 | | | | C38 | | | H38 |
| | Q38 | K30* | R38 | L38 | | | | | | | N38 |
| | | R30* | E30* | | | | | | | | Q30* |
| −8 | F33 | E33 | F33 | L33 | | R32* | R33 | | | | |
| | Y33 | D33 | H33 | V33 | | | | | | | |
| | | | | I33 | | | | | | | |
| | | | | F33 | | | | | | | |
| | | | | C33 | | | | | | | |
| −9 | E32 | R32 | L32 | | | | D32 | | | S32 | |
| | | K32 | | V32 | | | | | I32 | | N32 |
| | | | | A32 | | | | | | | H32 |
| | | | | C32 | | | | | | | Q32 |
| | | | | | | | | | | | T32 |

For polynucleotides, a "variant" comprises a deletion and/or addition of one or more nucleotides at one or more sites within the native polynucleotide. One of skill in the art will recognize that variants of the nucleic acids of the embodiments will be constructed such that the open reading frame is maintained. For polynucleotides, conservative variants include those sequences that, because of the degeneracy of the genetic code, encode the amino acid sequence of one of the polypeptides of the embodiments. Variant polynucleotides include synthetically derived polynucleotides, such as those generated, for example, by using site-directed mutagenesis but that still encode a recombinant meganuclease of the embodiments. Generally, variants of a particular polynucleotide of the embodiments will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to that particular polynucleotide as determined by sequence alignment programs and parameters described elsewhere herein. Variants of a particular polynucleotide of the embodiments (i.e., the reference polynucleotide) can also be evaluated by comparison of the percent sequence identity between the polypeptide encoded by a variant polynucleotide and the polypeptide encoded by the reference polynucleotide.

The deletions, insertions, and substitutions of the protein sequences encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by screening the polypeptide for its ability to preferentially recognize and cleave recognition sequences found within the human T cell receptor alpha constant region gene (SEQ ID NO:1).

EXAMPLES

This invention is further illustrated by the following examples, which should not be construed as limiting. Those skilled in the art will recognize, or be able to ascertain, using no more than routine experimentation, numerous equivalents to the specific substances and procedures described herein. Such equivalents are intended to be encompassed in the scope of the claims that follow the examples below.

Example 1

Characterization of Meganucleases that Recognize and Cleave TRC Recognition Sequences 1. Meganucleases that Recognize and Cleave the TRC 1-2 Recognition Sequence Recombinant meganucleases (SEQ ID NOs:8-27), collectively referred to herein as "TRC 1-2 meganucleases," were engineered to recognize and cleave the TRC 1-2 recognition sequence (SEQ ID NO:3), which is present in the human T cell receptor alpha constant region. Each TRC 1-2 recombinant meganuclease comprises an N-terminal nuclease-localization signal derived from SV40, a first meganuclease subunit, a linker sequence, and a second meganuclease subunit. A first subunit in each TRC 1-2 meganuclease binds to the TRC1 recognition half-site of SEQ ID NO:3, while a second subunit binds to the TRC2 recognition half-site (see, FIG. 1A).

Figure 3A:
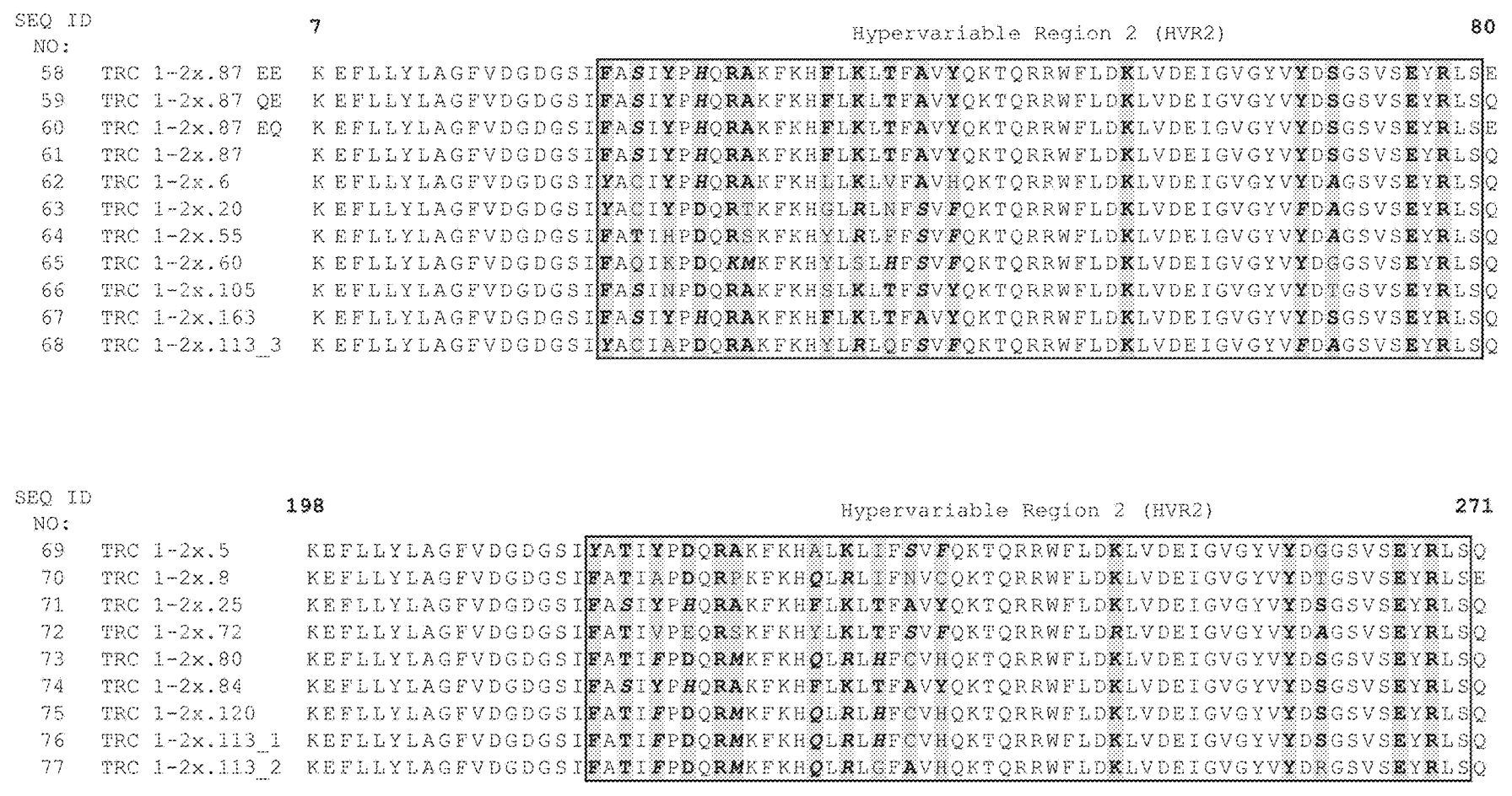

As illustrated in FIGS. 2 and 3, TRC1-binding subunits and TRC2-binding subunits each comprise a 56 base pair hypervariable region, referred to as HVR1 and HVR2, respectively. TRC1-binding subunits are identical outside of the HVR1 region except at position 80 or position 271 (comprising a Q or E residue), and are highly conserved within the HVR1 region. Similarly, TRC2-binding subunits are also identical outside of the HVR2 region except at position 80 or position 271 (comprising a Q or E residue), and at position 139 of meganucleases TRC 1-2x.87 EE, TRC 1-2x.87 QE, TRC 1-2x.87 EQ, TRC 1-2x.87, and TRC 1-2x.163, which comprise an R residue (shaded grey and underlined). Like the HVR1 region, the HVR2 region is also highly conserved.

The TRC1-binding regions of SEQ ID NOs:8-27 are illustrated in FIG. 2 and are provided as SEQ ID NOs:33-52, respectively. Each of SEQ ID NOs:33-52 share at least 90% sequence identity to SEQ ID NO:33, which is the TRC1-binding region of the meganuclease TRC 1-2x.87 EE (SEQ ID NO:8). TRC2-binding regions of SEQ ID NOs:8-27 are illustrated in FIG. 3 and are provided as SEQ ID NOs:58-77, respectively. Each of SEQ ID NOs:58-77 share at least 90% sequence identity to SEQ ID NO:58, which is the TRC2-binding region of the meganuclease TRC 1-2x.87 EE (SEQ ID NO:8).

2. Meganucleases that Recognize and Cleave the TRC 3-4 Recognition Sequence

Recombinant meganucleases (SEQ ID NOs:28 and 29), collectively referred to herein as "TRC 3-4 meganucleases," were engineered to recognize and cleave the TRC 3-4 recognition sequence (SEQ ID NO:4), which is present in the human T cell receptor alpha constant region. Each TRC 3-4 recombinant meganuclease comprises an N-terminal nuclease-localization signal derived from SV40, a first meganuclease subunit, a linker sequence, and a second meganuclease subunit. A first subunit in each TRC 3-4 meganuclease binds to the TRC3 recognition half-site of SEQ ID NO:4, while a second subunit binds to the TRC4 recognition half-site (see, FIG. 1A).

As illustrated in FIGS. 4 and 5, TRC3-binding subunits and TRC4-binding subunits each comprise a 56 base pair hypervariable region, referred to as HVR1 and HVR2, respectively. TRC3-binding subunits are identical outside of the HVR1 region except at position 80 or position 271 (comprising a Q or E residue), and are highly conserved within the HVR1 region. Similarly, TRC4-binding subunits are also identical outside of the HVR2 region except at position 80 or position 271 (comprising a Q or E residue), and are highly conserved within the HVR2 region.

The TRC3-binding regions of SEQ ID NOs:28 and 29 are illustrated in FIG. 4 and are provided as SEQ ID NOs:53 and 54, respectively. SEQ ID NOs:53 and 54 share 96.6% sequence identity. TRC4-binding regions of SEQ ID NOs:28 and 29 are illustrated in FIG. 5 and are provided as SEQ ID NOs:78 and 79, respectively. SEQ ID NOs:78 and 79 also share 96.6% sequence identity.

3. Meganucleases that Recognize and Cleave the TRC 7-8 Recognition Sequence

Recombinant meganucleases (SEQ ID NOs:30-32), collectively referred to herein as "TRC 7-8 meganucleases," were engineered to recognize and cleave the TRC 7-8 recognition sequence (SEQ ID NO:5), which is present in the human T cell receptor alpha constant region. Each TRC 7-8 recombinant meganuclease comprises an N-terminal nuclease-localization signal derived from SV40, a first meganuclease subunit, a linker sequence, and a second meganuclease subunit. A first subunit in each TRC 7-8 meganuclease binds to the TRC7 recognition half-site of SEQ ID NO:5, while a second subunit binds to the TRC8 recognition half-site (see, FIG. 1A).

As illustrated in FIGS. 6 and 7, TRC7-binding subunits and TRC8-binding subunits each comprise a 56 base pair hypervariable region, referred to as HVR1 and HVR2, respectively. TRC7-binding subunits are identical outside of the HVR1 region except at position 80 or position 271 (comprising a Q or E residue), and are highly conserved within the HVR1 region. Similarly, TRC8-binding subunits are also identical outside of the HVR2 region except at position 80 or position 271 (comprising a Q or E residue), and are highly conserved within the HVR2 region.

The TRC7-binding regions of SEQ ID NOs:30-32 are illustrated in FIG. 6 and are provided as SEQ ID NOs:55-57, respectively. Each of SEQ ID NOs:55-57 share at least 90% sequence identity to SEQ ID NO:55, which is the TRC7-binding region of the meganuclease TRC 7-8x.7 (SEQ ID NO:30). TRC8-binding regions of SEQ ID NOs:30-32 are illustrated in FIG. 7 and are provided as SEQ ID NOs:80-82, respectively. Each of SEQ ID NOs:80-82 share at least 90% sequence identity to SEQ ID NO:80, which is the TRC8-binding region of the meganuclease TRC 7-8x.7 (SEQ ID NO:30).

4. Cleavage of Human T Cell Receptor Alpha Constant Region Recognition Sequences in a CHO Cell Reporter Assay To determine whether TRC 1-2, TRC 3-4, and TRC 7-8 meganucleases could recognize and cleave their respective recognition sequences (SEQ ID NOs:3, 4, and 5, respectively), each recombinant meganuclease was evaluated using the CHO cell reporter assay previously described (see, WO/2012/167192 and FIG. 8). To perform the assays, CHO cell reporter lines were produced which carried a non-functional Green Fluorescent Protein (GFP) gene expression cassette integrated into the genome of the cells. The GFP gene in each cell line was interrupted by a pair of recognition sequences such that intracellular cleavage of either recognition sequence by a meganuclease would stimulate a homologous recombination event resulting in a functional GFP gene.

In CHO reporter cell lines developed for this study, one recognition sequence inserted into the GFP gene was the TRC 1-2 recognition sequence (SEQ ID NO:3), the TRC 3-4 recognition sequence (SEQ ID NO:4), or the TRC 7-8 recognition sequence (SEQ ID NO:5). The second recognition sequence inserted into the GFP gene was a CHO-23/24 recognition sequence, which is recognized and cleaved by a control meganuclease called "CHO-23/24". CHO reporter cells comprising the TRC 1-2 recognition sequence and the CHO-23/24 recognition sequence are referred to herein as "TRC 1-2 cells." CHO reporter cells comprising the TRC 3-4 recognition sequence and the CHO-23/24 recognition sequence are referred to herein as "TRC 3-4 cells." CHO reporter cells comprising the TRC 7-8 recognition sequence and the CHO-23/24 recognition sequence are referred to herein as "TRC 7-8 cells."

CHO reporter cells were transfected with plasmid DNA encoding their corresponding recombinant meganucleases (e.g., TRC 1-2 cells were transfected with plasmid DNA encoding TRC 1-2 meganucleases) or encoding the CHO-23/34 meganuclease. In each assay, $4e^5$ CHO reporter cells were transfected with 50 ng of plasmid DNA in a 96-well plate using Lipofectamine 2000 (ThermoFisher) according to the manufacturer's instructions. At 48 hours post-transfection, cells were evaluated by flow cytometry to determine the percentage of GFP-positive cells compared to an untransfected negative control (TRC 1-2bs). As shown in FIG. 9, all TRC 1-2, TRC 3-4, and TRC 7-8 meganucleases were found to produce GFP-positive cells in cell lines comprising their corresponding recognition sequence at frequencies significantly exceeding the negative control.

The efficacy of the TRC 1-2x.87 QE, TRC 1-2x.87 EQ, and TRC 1-2x.87 EE meganucleases was also determined in a time-dependent manner. In this study, TRC 1-2 cells ($1e^6$) were electroporated with $1e^6$ copies of meganuclease mRNA per cell using a BioRad Gene Pulser Xcell according to the manufacturer's instructions. At 1, 4, 6, 8, and 12 days post-transfection, cells were evaluated by flow cytometry to determine the percentage of GFP-positive cells. As shown in FIG. 10, each TRC 1-2 meganuclease exhibited high efficiency at 2 days post-transfection, with greater than 50% GFP-positive cells observed. This effect persisted over the 12 day period, with no evidence of cell toxicity observed.

5. Conclusions

These studies demonstrated that TRC 1-2 meganucleases, TRC 3-4 meganucleases, and TRC 7-8 meganucleases encompassed by the invention can efficiently target and cleave their respective recognition sequences in cells.

Example 2

Cleavage of TRC Recognition Sequences in T Cells and Suppression of Cell-Surface T Cell Receptor Expression 1. Cleavage of the TRC 1-2 Recognition Sequence in Jurkat Cells This study demonstrated that TRC 1-2 meganucleases encompassed by the invention could cleave the TRC 1-2 recognition sequence in Jurkat cells (an immortalized human T lymphocyte cell line). $1e^6$ Jurkat cells were electroporated with $8e^6$ copies of a given TRC 1-2 meganuclease mRNA per cell using a BioRad Gene Pulser Xcell according to the manufacturer's instructions. At 72 hours post-transfection, genomic DNA (gDNA) was harvested from cells and a T7 endonuclease I (T7E) assay was performed to estimate genetic modification at the endogenous TRC 1-2 recognition sequence (FIG. 11). In the T7E assay, the TRC 1-2 locus is amplified by PCR using primers that flank the TRC 1-2 recognition sequence. If there are indels (random insertions or deletions) within the TRC 1-2 locus, the resulting PCR product will consist of a mix of wild-type alleles and mutant alleles. The PCR product is denatured and allowed to slowly reanneal. Slow reannealing allows for the formation of heteroduplexes consisting of wild-type and mutant alleles, resulting in mismatched bases and/or bulges. The T7E1 enzyme cleaves at mismatch sites, resulting in cleavage products that can be visualized by gel electrophoresis. FIG. 11 clearly demonstrates that thirteen different versions of the TRC 1-2 meganucleases generated positive results in the T7E1 assay, indicating effective generation of indels at the endogenous TRC 1-2 recognition sequence.

To further examine the cleavage properties of TRC 1-2 meganucleases, a dose-response experiment was performed in Jurkat cells. $1e^6$ Jurkat cells were electroporated with either 3 µg or 1 µg of a given TRC 1-2 meganuclease mRNA per cell using a BioRad Gene Pulser Xcell according to the manufacturer's instructions. At 96-hours post-transfection, gDNA was harvested and the T7E1 assay was performed as described above. As seen in FIG. 12, fifteen different TRC 1-2 meganucleases showed cleavage at the endogenous TRC 1-2 recognition site, including three different versions of the TRC 1-2x.87 meganuclease. TRC 1-2x.87 EE worked especially well, generating a strong signal in the T7E1 assay with little to no toxicity in Jurkat cells.

2. Cleavage of TRC 1-2 Recognition Sequence in Human T Cells

This study demonstrated that TRC 1-2 meganucleases encompassed by the invention could cleave the TRC 1-2 recognition sequence in human T cells obtained from a donor. CD3+ T cells were stimulated with anti-CD3 and anti-CD28 antibodies for 3 days, then electroporated with mRNA encoding the TRC 1-2x.87 EE meganuclease using the Amaxa 4D-Nucleofector (Lonza) according to the manufacturer's instructions. At 3 days and 7 days post-transfection, gDNA was harvested and the T7E1 assay was performed as described above. FIG. 13A demonstrates that TRC 1-2x.87 EE effectively introduced mutations in the endogenous TRC 1-2 recognition sequence in human T cells, indicating that the meganuclease recognized and cleaved the TRC 1-2 recognition sequence. The intensity of cleavage products does not appear to change between day 3 and day 7 post-transfection, suggesting little or no toxicity due to the TRC 1-2x.87 EE meganuclease. To determine whether the mutations at the endogenous TRC 1-2 recognition sequence were sufficient to eliminate surface expression of the T cell receptor, cells were analyzed by flow cytometry using an anti-CD3 antibody. FIG. 13B shows that approximately 50% of transfected T cells stained negative for CD3, indicating knockout of the T cell receptor. The CD3 negative population did not change significantly between day 3 and day 7 post-transfection, further indicating little or no toxicity associated with the TRC 1-2x.87 EE meganuclease, or the loss of T cell receptor expression.

To verify that loss of CD3 expression was due to mutations in the TRC 1-2 recognition site, gDNA was harvested from transfected T cells and the TRC 1-2 recognition site locus was amplified by PCR. PCR products were cloned into the pCR-blunt vector using the Zero Blunt PCR cloning kit (Thermo Fisher) according to the manufacturer's instructions. Individual colonies were picked and mini-prepped plasmids were sequenced. FIG. 14 shows sequences of several representative deletions that were observed at the TRC 1-2 recognition sequence. The observed sequences are typical of deletions resulting from the non-homologous end joining repair of DNA double-strand breaks generated by endonucleases.

In addition to TRC 1-2x.87 EE, other TRC 1-2 meganucleases were able to knockout the T cell receptor in human T cells, including TRC 1-2x.55, and TRC 1-2x.72, albeit to a lesser extent than knockout previously observed for TRC 1-2x.87 EE (Tables 5 and 6). TRC 1-2x.72 Q47E carries a mutation in the active site of the meganuclease (amino acid 47) and serves as a negative control.

TABLE 5

| Meganuclease | % CD3⁻ Cells | |
|---|---|---|
| | Day 3 | Day 6 |
| TRC 1-2x.72 Q47E | 0.38 | 1.1 |
| TRC 1-2x.55 | 3.11 | 10.84 |

TABLE 6

| Meganuclease | % CD3⁻ Cells | |
|---|---|---|
| | Day 3 | Day 5 |
| TRC 1-2x.72 Q47E | 0.29 | 0.4 |
| TRC 1-2x.72 | 2.09 | 4.19 |

3. Conclusions

These studies demonstrated that TRC 1-2 meganucleases encompassed by the invention can recognize and cleave the TRC 1-2 recognition sequence in both Jurkat cells (an immortalized T lymphocyte cell line) and in T cells obtained from a human donor. Further, these studies demonstrated that NHEJ occurs at the meganuclease cleavage site, as evidenced by the appearance of indels. Moreover, TRC 1-2 meganucleases were shown to reduce cell-surface expression of the T cell receptor on human T cells obtained from a donor.

Example 3

Recombinant AAV Vectors for Introducing Exogenous Nucleic Acids into Human T Cells 1. Recombinant AAV Vectors In the present study, two recombinant AAV vectors (referred to as AAV405 and AAV406) were designed to introduce an exogenous nucleic acid sequence, comprising an EagI restriction site, into the genome of human T cells at the TRC 1-2 recognition sequence via homologous recombination. Each recombinant AAV vector was prepared using a triple-transfection protocol, wherein a cell line is transfected with a first plasmid encoding "helper" components (e.g., adenoviral) necessary to support replication, a second plasmid comprising the cap and rep genes, and a third plasmid comprising the viral inverted terminal repeats (ITRs) containing the intervening DNA sequence to be packaged into the virus (e.g., the exogenous nucleic acid sequence) (see, Cots D, Bosch A, Chillon M (2013) Curr. Gene Ther. 13(5): 370-81). FIG. 15 illustrates the general approach for using recombinant AAV vectors to introduce an exogenous nucleic acid sequence into the cell genome at the nuclease cleavage site.

AAV405 was prepared using the plasmid illustrated in FIG. 16 (SEQ ID NO:107). As shown, the AAV405 plasmid generally comprises sequences for a 5' ITR, a CMV enhancer and promoter sequence, a 5' homology arm, a nucleic acid sequence comprising the EagI restriction site, an SV40 poly(A) signal sequence, a 3' homology arm, and a 3' ITR. AAV406 was prepared using the plasmid illustrated in FIG. 17 (SEQ ID NO:108). As shown, the AAV406 plasmid comprises similar sequences to those of AAV405, but lacks the CMV enhancer and promoter sequences upstream of the 5' homology arm. The present AAV studies further included the use of an AAV vector encoding GFP (GFP-AAV), which was incorporated as a positive control for AAV transduction efficiency.

2. Introducing Exogenous Nucleic Acid Sequences into the TRC 1-2 Recognition Sequence To test whether AAV templates would be suitable for homology directed repair (HDR) following generation of a double-strand break with TRC 1-2 meganucleases, a series of experiments were performed using human T cells. In the first experiment, the timing of electroporation with TRC 1-2 RNA and transduction with recombinant AAV vectors was determined. Human CD3+ T cells were stimulated with anti-CD3 and anti-CD28 antibodies for 3 days, then electroporated with mRNA encoding the TRC 1-2x.87 EE meganuclease (1 µg) using the Amaxa 4D-Nucleofector (Lonza) according to the manufacturer's instructions. At either 2, 4, or 8 hours post-transfection, cells were transduced with GFP-AAV ($1e^5$ viral genomes per cell). Cells were analyzed by flow cytometry for GFP expression at 72 hours post-transduction. As shown in FIG. 18, the highest transduction efficiency was observed when cells were transduced at 2 hours post-transfection (88% GFP-positive cells). Transduction efficiency decreased significantly as the time between transfection and transduction increased, with 78% GFP-positive cells at 4 hours and 65% GFP-positive cells at 8 hours.

Having determined that efficient viral transduction occurred when cells were transduced 2 hours post-transfection, the AAV405 and AAV406 vectors were used as HDR templates in human T cells. CD3+ T cells were stimulated and transfected with 1 μg TRC 1-2x.87 EE mRNA as described above. At 2 hours post-transfection, cells were either transduced with AAV405 or AAV406 ($1e^5$ viral genomes per cell). As transduction-only controls, cells were mock transfected (with water) and transduced with either AAV405 or AAV406 ($1e^5$ viral genomes per cell). For a meganuclease-only control, cells were transfected with TRC 1-2x.87 EE and then mock transduced (with water) at 2 hours post-transfection.

To determine whether the AAV vectors served as HDR templates, gDNA was harvested from cells and the TRC 1-2 locus was amplified by PCR using primers that recognized sequences beyond the region of homology in the AAV vectors. PCR primers outside of the homology regions only allowed for amplification of the T cell genome, not from the AAV vectors. PCR products were purified and digested with EagI. FIG. 19 shows cleavage of the PCR products amplified from cells that were transfected with TRC 1-2x.87 EE and transduced with either AAV vector (see arrows), indicating insertion of the EagI site into the TRC 1-2 recognition sequence. The PCR products from all of the control cell populations are not cleaved by EagI, demonstrating that the insertion of the EagI site requires creation of a DNA double-strand break by a TRC 1-2 meganuclease.

To further define the insertion of the EagI site into human T cells, individual products from the bulk PCR product were examined. Undigested PCR product generated from the above experiment was cloned into the pCR-blunt vector using the Zero Blunt PCR cloning kit (Thermo Fisher) according to the manufacturer's instructions. Colony PCR was performed using M13 forward and reverse primers (pCR blunt contains M13 forward and reverse priming sites flanking the insert) and a portion of PCR products from cells transfected with TRC 1-2x.87 EE and either AAV405 or AAV406 were analyzed by gel electrophoresis (FIGS. 20A and 21A, respectively). In both cases, there are a mix of full-length PCR products (approximately 1600 bp), smaller inserts, and some empty plasmids (approximately 300 bp). In this assay, bands smaller than full-length but larger than empty plasmids are often times sequences containing large deletions within the TRC 1-2 recognition sequence. In parallel, another portion of PCR products were digested with EagI to determine the percent of clones that contain the EagI recognition site inserted into the TRC 1-2 recognition sequence. FIGS. 20B and 21B show that several PCR products were cleaved with EagI (e.g., FIG. 20B, second row, 6 lanes from the left), generating the expected fragments of approximately 700 and 800 bp. These gels allow for the estimation of EagI insertion to be approximately 25% and 6% for AAV405 and AAV406, respectively (adjusted for empty vectors).

To confirm observations from gel electrophoresis of uncut PCR products and digest with EagI, the remaining portion of each PCR product was sequenced. FIG. 22A shows sequences of several representative deletions and insertions that were observed at the TRC 1-2 recognition sequence. These sequences are typical of sequences resulting from the non-homologous end joining repair of DNA double-strand breaks generated by endonucleases. All PCR products that were cleaved with EagI contained an EagI site inserted into the TRC 1-2 recognition sequence (FIG. 22B).

3. Enhanced AAV Transduction Efficiency

In light of the observation that AAV transduction was more efficient when it was carried out 2 hours post-transfection than when it was carried out later, an experiment was performed to optimize the timing of transfection and transduction. Human CD3+ T cells were stimulated with anti-CD3 and anti-CD28 antibodies for 3 days, then electroporated with the TRC 1-2x.87 EE meganuclease (1 μg) using the Amaxa 4D-Nucleofector (Lonza) according to the manufacturer's instructions. Immediately after transfection or 2 hours post-transfection, cells were transduced with GFP-AAV ($1e^5$ viral genomes per cell). Additionally, non-stimulated cells were transduced with GFP-AAV ($1e^5$ viral genomes per cell). At 72 hours post-transduction, cells were analyzed by flow cytometry for GFP expression. FIG. 23 shows that GFP-AAV transduction performed 2 hours post-transfection resulted in 90% GFP-positive cells, but that transduction immediately after transfection resulted in 98% GFP-positive cells. Resting T cells appeared refractive to AAV transduction, with approximately 0% GFP-positive cells. Non-transduced cells also showed approximately 0% GFP-positive cells.

4. Summary

These studies demonstrate that AAV vectors can be used in conjunction with recombinant meganucleases to incorporate an exogenous nucleic acid sequence into a cleavage site in the TCR alpha constant region via homologous recombination.

Example 4

Recombinant AAV Vectors for Introducing Exogenous Nucleic Acids Encoding a Chimeric Antigen Receptor in Human T Cells 1. Recombinant AAV Vectors In the present study, two recombinant AAV vectors (referred to as AAV-CAR100 and AAV-CAR763) were designed to introduce an exogenous nucleic acid sequence, encoding a chimeric antigen receptor, into the genome of human T cells at the TRC 1-2 recognition sequence via homologous recombination. Each recombinant AAV vector was prepared using the triple-transfection protocol described previously.

AAV-CAR100 (also referred to herein as AAV408) was prepared using the plasmid illustrated in FIG. 24 (SEQ ID NO:109). As shown, the AAV-CAR100 (AAV408) is designed for producing a self-complementary AAV vector, and generally comprises sequences for a 5' ITR, a 5' homology arm, a nucleic acid sequence encoding an anti-CD19 chimeric antigen receptor, an SV40 poly(A) signal sequence, a 3' homology arm, and a 3' ITR. AAV-CAR763 (also referred to herein as AAV412) was prepared using the plasmid illustrated in FIG. 25 (SEQ ID NO:110). As shown, the AAV-CAR763 (AAV412) plasmid generally comprises the same sequences as AAV-CAR100 (AAV408), but is designed for producing a single-stranded AAV vector. Because a single-stranded AAV vector can accommodate a larger payload, the 5' homology arm and the 3' homology arm are longer in AAV-CAR763 (AAV412) than in AAV-CAR100 (AAV408). The present AAV studies will further include the use of an AAV vector encoding GFP (GFP-AAV), which will be incorporated as a positive control for AAV transduction efficiency.

2. Introducing a Chimeric Antigen Receptor Sequence into the TRC 1-2 Recognition Sequence Studies will be conducted to determine the efficiency of using recombinant AAV vectors to insert a chimeric antigen receptor sequence into the TCR alpha constant region gene while, simultaneously, knocking out cell-surface expression of the endogenous TCR receptor.

To confirm transduction efficiency, human CD3+ T cells will be obtained and stimulated with anti-CD3 and anti-CD28 antibodies for 3 days, then electroporated with mRNA encoding the TRC 1-2x.87 EE meganuclease (1 µg) using the Amaxa 4D-Nucleofector (Lonza) according to the manufacturer's instructions. Cells will be transduced with GFP-AAV ($1e^5$ viral genomes per cell) immediately after transfection as described above. Cells will be analyzed by flow cytometry for GFP expression at 72 hours post-transduction to determine transduction efficiency.

AAV-CAR100 (AAV408) and AAV-CAR763 (AAV412) vectors will then be used as HDR templates in human T cells for the insertion of the anti-CD19 chimeric antigen receptor sequence. Human CD3+ T cells will be stimulated and transfected with 1 µg TRC 1-2x.87 EE mRNA as described above. Cells will then be transduced with AAV-CAR100 (AAV408) or AAV-CAR763 (AAV412) ($1e^5$ viral genomes per cell) either immediately after transfection or within 0-8 hours of transfection. As transduction-only controls, cells will be mock transfected (with water) and transduced with either AAV-CAR100 (AAV408) or AAV-CAR763 (AAV412) ($1e^5$ viral genomes per cell). For a meganuclease-only control, cells will be transfected with mRNA encoding TRC 1-2x.87 EE and then mock transduced (with water) immediately post-transfection.

Insertion of the chimeric antigen receptor sequence will be confirmed by sequencing of the cleavage site in the TCR alpha constant region gene. Cell-surface expression of the chimeric antigen receptor will be confirmed by flow cytometry, using an anti-Fab or anti-CD19 antibody. Knockout of the endogenous T cell receptor at the cell surface will be determined by flow cytometry as previously described.

Example 5

Insertion and Expression of Chimeric Antigen Receptor

1. Insertion of Chimeric Antigen Receptor Sequence into the TRC 1-2 Recognition Sequence In the present study, we test whether AAV can provide HDR templates that can be used to insert a chimeric antigen receptor sequence into the TCR alpha constant region gene and, simultaneously, knock out cell-surface expression of the endogenous TCR receptor. In the first experiment, human CD3+ T cells ($1e^6$ cells) were stimulated and electroporated with mRNA encoding the TRC 1-2x.87 EE meganuclease (2 µg) as described above, then immediately transduced with AAV412 ($1e^5$ viral genomes/cell). As controls, cells were mock electroporated, then transduced with AAV412 or electroporated with mRNA encoding TRC 1-2x.87EE, then mock transduced. An additional control of mock electroporated, mock transduced cells was included.

A PCR-based assay was developed to determine whether the AAV HDR template was utilized to repair double-strand breaks at the TRC 1-2 recognition sequence. Three sets of primer pairs were used for PCR analysis. The first set was designed to amplify a region with the homology arms of AAV412. Since this first primer set (referred to as "Inside homolog arms/CAR region" in Table 7) lies within the homology region, it will either amplify the unmodified TRC 1-2 recognition sequence locus of the genome (349 bp), the AAV412 vector input (2603 bp), or the TRC 1-2 recognition sequence into which the CAR gene has been inserted (2603 bp). The second primer set (referred to as "Outside 5' homology arm" in Table 7) includes one primer that anneals within the CAR region of the AAV412 HDR template, one primer that anneals in the human genome, outside of the 5' homology arm of the AAV412 HDR template and will amplify an 1872 bp fragment only if the CAR gene was successfully inserted into the TRC 1-2 recognition sequence. The third primer set (referred to as "Outside 3' homology arm" in Table 7) includes one primer that anneals within the CAR region of the AAV412 HDR template, and one primer that anneals in the human genome, outside of the 3' homology arm of the AAV412 HDR template. Similarly to the second primer set, the third primer set will amplify an 1107 bp fragment only if the CAR gene was successfully inserted into the TRC 1-2 recognition sequence. Taken together, PCR products from all three primer sets will indicate whether the CAR sequence is present in cells (primer set 1), and whether it has been inserted into the TRC 1-2 recognition sequence (primer sets 2 and 3).

On day 4 post-transduction cells were analyzed using the PCR primer pairs described above. Briefly, approximately 3,000 cells were harvested, pelleted, and lysed and PCR was performed to determine whether the CAR gene was inserted into the TRC 1-2 recognition sequence. PCR products were resolved on an agarose gel, shown in FIG. 26 (lane descriptions can be found in Table 7). Lanes 1-3 are PCR products from the sample that was electroporated with mRNA encoding TRC 1-2x.87EE and mock transduced.

As expected, the first primer pair ("Inside homolog arms/CAR region") amplified the unmodified TRC 1-2 recognition sequence locus, generating a 349 bp band shown in lane 1. Lanes 2 and 3 correspond to primer pairs that only generate a product if the CAR gene has been inserted into the TRC 1-2 recognition sequence, and do not show products. Lanes 7-9 represent samples that were mock electroporated and mock transduced and show the same bands as the TRC 1-2x.87EE mRNA only control described above. Lanes 4-6 show PCR products from the sample that was electroporated with TRC 1-2x.87EE mRNA and transduced with AAV412. Lane 4 shows two bands generated by the first primer pair ("Inside homolog arms/CAR region"), indicating amplification of the unmodified TRC 1-2 recognition sequence locus of the genome (349 bp) and the AAV412 vector input (2603 bp) or the TRC 1-2 recognition sequence into which the CAR gene has been inserted (2603 bp). Lanes 5 and 6 show products generated by the primer pairs that only amplify products if the CAR nucleic acid sequence has been inserted into the TRC 1-2x.87EE recognition site. Both bands are the predicted size (1872 and 1107 bp, respectively). Lanes 10-12 represent the sample that was mock electroporated and transduced with AAV412. Lane 10 shows two bands generated by the first primer pair ("Inside homolog arms/CAR region"), indicating amplification of the unmodified TRC 1-2 recognition sequence locus of the genome (349 bp) and the AAV412 vector input (2603 bp). Lanes 11 and 12 correspond to primer pairs that only generate a product if the CAR gene has been inserted into the TRC 1-2 recognition sequence, and do not show products. The absence of bands in lanes 11 and 12 (which include primers outside of the homology arm) indicates that the 2603 bp band in lane 10 was generated from amplification of the AAV412 input.

Taken together, the PCR analysis clearly demonstrates that CAR genes are introduced into the TRC 1-2x.87EE recognition site when both TRC 1-2x.87EE mRNA and AAV412 are present in cells. Thus, we conclude that AAV412 serves to produce suitable HDR templates that can be used to insert a CAR gene into the TRC 1-2x.87EE recognition sequence.

In a second experiment, human CD3+ T cells were stimulated and electroporated with mRNA encoding the TRC 1-2x.87 EE meganuclease as described above, then immediately transduced with increasing amounts of AAV408 (0 μL, 3.125 μL, 6.25 μL, 12.5 μL, or 25 μL, which corresponds to approximately 0, $3.125e^3$, $6.250e^3$, $1.25e^4$ and $2.5e^4$ viral genomes/cell). As controls, cells were mock electroporated, then transduced with increasing amounts of AAV408. Additional controls included cells that were mock electroporated and mock transduced, as well as cells that were electroporated with TRC 1-2x.87EE mRNA then mock transduced. On day 4 post-transduction, cells were harvested and analyzed as described above, but only using the primer pairs that amplified a product only if the CAR gene has been inserted into the TRC 1-2 recognition sequence. PCR products were resolved on agarose gels, shown in FIG. 27. FIG. 27A shows the PCR products generated using the primer pair described above ("Outside 5' homology arm") which only amplifies a product on the 5' end of the TRC 1-2 recognition sequence locus if the CAR gene has been inserted into that locus. FIG. 27B shows the PCR products generated using the primer pair described above ("Outside 3' homology arm") which only amplifies a product on the 3' end of the TRC 1-2 recognition sequence locus if the CAR gene has been inserted into that locus. Lane descriptions can be found in Table 8. Lanes 1-5 in both FIGS. 27A and 27B represent the samples that were either mock electroporated or mock electroporated then mock transduced. No PCR products are visible in mock electroporated cells, indicating the HDR templates produced by AAV408 are unable to insert the CAR gene into the TRC 1-2 recognition sequence in the absence of TRC 1-2x.87EE mRNA. Lane 6 represents the sample that was electroporated with TRC 1-2x.87EE mRNA and mock transduced. No PCR products are visible, indicating that the CAR gene had not been inserted into the TRC 1-2 recognition sequence. Lanes 7-10 represent samples that were electroporated with TRC 1-2x.87EE mRNA and transduced with increasing amounts of AAV408. The appropriately sized bands for each PCR are evident, indicating that AAV408 can produce HDR donors for repair of the TRC 1-2 recognition sequence, resulting in insertion of the CAR gene.

TABLE 7

| Sample | Nucleofection | Virus (100k MOI) | PCR | Product Size |
|---|---|---|---|---|
| 1 | TRC1-2x87EE | — | Inside homolog arms/ CAR region | Genomic = 349 bp +CD19 = 2603 bp |
| 2 | TRC1-2x87EE | — | Outside 5' homology arm | 1872 bp |
| 3 | TRC1-2x87EE | — | Outside 3' homology arm | 1107 bp |
| 4 | TRC1-2x87EE | AAV412 | Inside homolog arms/ CAR region | Genomic = 349 bp +CD19 = 2603 bp |
| 5 | TRC1-2x87EE | AAV412 | Outside 5' homology arm | 1872 bp |
| 6 | TRC1-2x87EE | AAV412 | Outside 3' homology arm | 1107 bp |
| 7 | Mock (Water) | — | Inside homolog arms/ CAR region | Genomic = 349 bp +CD19 = 2603 bp |
| 8 | Mock (Water) | — | Outside 5' homology arm | 1872 bp |
| 9 | Mock (Water) | — | Outside 3' homology arm | 1107 bp |
| 10 | Mock (Water) | AAV412 | Inside homolog arms/ CAR region | Genomic = 349 bp +CD19 = 2603 bp |
| 11 | Mock (Water) | AAV412 | Outside 5' homology arm | 1872 bp |
| 12 | Mock (Water) | AAV412 | Outside 3' homology arm | 1107 bp |

TABLE 8

| Sample | Nucleofection | Virus (AAV408) μL |
|---|---|---|
| 1 | Mock (Water) | 0 |
| 2 | Mock (Water) | 3.125 |
| 3 | Mock (Water) | 6.25 |
| 4 | Mock (Water) | 12.5 |
| 5 | Mock (Water) | 25 |
| 6 | TRC1-2x87EE | 0 |
| 7 | TRC1-2x87EE | 3.125 |
| 8 | TRC1-2x87EE | 6.25 |
| 9 | TRC1-2x87EE | 12.5 |
| 10 | TRC1-2x87EE | 25 |

The PCR-based assays described above are useful in determining whether the CAR gene had been inserted into the TRC 1-2 recognition sequence, but do not give information on efficiency. To determine the efficiency of CAR insertion, we developed a digital PCR-based assay (schematic shown in FIG. 28A). In this assay, two primer sets are used. The first set amplifies an irrelevant gene sequence and serves a reference sequence to control for template number. The second set consists of one primer that anneals within the CAR gene and one primer that anneals outside of the 3' homology arm, such that a product is only amplified if the CAR gene has been inserted into the TRC 1-2 recognition sequence. A VIC-labeled probe anneals within the amplicon generated from the first primer set and FAM-labeled probe anneals within the amplicon generated by the second set of primers. By dividing the number of amplicons detected by the FAM-labeled probe to the number of reference sequence amplicons detected by the VIC-labeled probe, it is possible to accurately quantitate the percent of TRC 1-2 recognition sequence loci that were modified by insertion of the CAR gene.

FIG. 28B shows the results of the digital PCR assay for samples that were either mock electroporated then transduced, electroporated with TRC 1-2x.87EE mRNA then mock transduced, or electroporated with TRC 1-2x.87EE mRNA then transduced with increasing amounts of AAV408. Digital PCR was performed using genomic DNA isolated from cells approximately 1 week post-transduction. Consistent with the observations from the PCR described in FIG. 27, both control samples (transduction only or electroporation only) were found to have 0% CAR gene inserted into the TRC 1-2x.87EE recognition sequence. Samples that were electroporated with mRNA encoding TRC 1-2x.87EE then transduced with increasing amounts of AAV408 were found to have between approximately 1.5% and 7%. The assay was performed on two different instruments (labeled QX200 and QS3D) and showed remarkable agreement, demonstrating the sensitivity and precision of this digital PCR-based assay.

2. Expression of Anti-CD19 Chimeric Antigen Receptor on T Cells

In addition to determining whether CAR insertion occurred at the molecular level, we sought to determine the expression level of the anti-CD19 chimeric antigen receptor in cells that had the CAR gene inserted into the TRC 1-2 recognition sequence using AAV408 as the HDR template. Additionally, we examined the efficiency in which insertion of the CAR into the TRC 1-2x.87EE recognition sequence resulted in knockout of the T cell receptor. Samples described above and analyzed in FIGS. 27 and 28 were also analyzed for CAR and CD3 expression by flow cytometry. Approximately 4 days post-transduction, cells were labeled with antibodies that recognize the anti-CD19 CAR (anti-Fab-Alexa647) or CD3 (CD3⁻ BB515) and analyzed by flow cytometry. FIG. 29A shows flow cytometry plots, with anti-CAR labeling shown on the Y axis and anti-CD3 labeling shown on the X axis. Cells that were mock electroporated and mock transduced (MOI-0) were overwhelmingly CD3$^+$/CAR$^-$ (the lower right quadrant, 98.7%). Cells that were mock electroporated then transduced with increasing amounts of AAV408 looked essentially identical to the control cells, with the CD3$^+$/CAR$^-$ populations at 98.8%, 99, 99%, and 99.1%. Thus we conclude that the AAV408 virus alone is not driving detectable levels of CAR expression, nor is it capable of disrupting expression of the T cell receptor.

FIG. 29B shows flow cytometry plots for samples that were either electroporated with mRNA encoding TRC 1-2x.87EE then mock transduced or cells that were electroporated with TRC 1-2x.87EE then transduced with increasing amounts of AAV408. Cells that were electroporated then mock transduced show 47.1% CD3$^-$ cells, indicating efficient knockout of the T cell receptor complex. Background labeling with the anti-CD19 CAR was very low, with 0.6% in the CD3$^-$ population and 0.78% in the CD3$^+$ population. Samples that were electroporated with mRNA encoding TRC 1-2x.87EE then transduced with increasing amounts of AAV408 showed CAR labeling in the CD3$^-$ population, ranging from 2.09% to 5.9%. There was also a slight increase in CAR labeling in the CD3$^+$ population, ranging from 1.08% to 1.91%. We did not determine the cause of the increase in CARP cells in the CD3$^+$ population, although it is possible that the CAR was inserted into the non-expressed T cell receptor allele (only one allele of the T cell receptor alpha chain is expressed and incorporated into the T cell receptor complex).

These data correlated well with the quantitative digital PCR-based assay described above. For example, at the highest MOI of AAV408 (2.5e$^4$ viral genomes/cell), the digital PCR assay showed approximately 6% CAR insertion, and the flow cytometry assay showed 5.9% CAR$^+$/CD3$^-$ cells. If one takes into account the CAR$^+$/CD3$^+$ population, the data are still quite comparable, with the flow cytometry assay showing approximately 7.8% CARP compared to 6% by digital PCR.

Example 6

Characterization of Additional AAV Vectors

1. Insertion of a Chimeric Antigen Receptor Sequence into the TRC 1-2 Recognition Sequence Having shown that AAV vectors could provide suitable HDR templates to insert CAR genes into the TRC 1-2x.87EE recognition sequence, we sought to optimize the configuration of the AAV vector. We generated a vector that could be used to produce self-complementary AAV genomes that included the CAR gene expression cassette driven by a JeT promoter, flanked by short regions of homology to the TRC 1-2 recognition sequence locus and AAV ITRs. This vector is referred to as AAV421 (FIG. 30; SEQ ID NO:123). Short homology arms were necessary due to limited packaging capacity of self-complementary AAV. Additionally, we generated a vector that could be used to produce single-strand AAV genomes that includes the CAR gene expression cassette driven by a CMV promoter, flanked by long homology arms and AAV ITRs. This vector is referred to as AAV422 (FIG. 31; SEQ ID NO:124). Since single-strand AAV genomes have a larger cargo capacity, we were able to utilize longer homology arms than in the self-complementary vector.

To test whether AAV421 and AAV422 were useful to target insertion of the CAR gene into the TRC 1-2 recognition sequence, several experiments similar to those described above were carried out in human CD3$^+$ T cells. In a first experiment, human CD3$^+$ T cells (1e$^6$ cells) were either mock electroporated then transduced with increasing amounts of AAV421 or 422, or electroporated with TRC 1-2x.87EE mRNA (2 μg) then transduced with increasing amounts of AAV421 or AAV422. AAV422 MOIs were significantly higher than AAV421 in this experiment than in the experiments described above (approximate MOIs were 1.25e$^4$, 2.5e$^4$, 5e$^4$ and 1e$^5$ viral genomes/cell) because earlier experiments with AAV408 suggested that higher MOIs would result in more efficient CAR insertion. The AAV421 virus stock was not concentrated enough to allow for titers significantly higher than in the experiments described earlier. As controls, cells were electroporated (mock or with TRC 1-2x.87EE mRNA) then mock transduced. As an additional component to this experiment, a "large scale" condition was performed, in which 10e$^6$ cells (10 times more than a typical experiment) were electroporated with TRC 1-2x.87EE mRNA then transduced with AAV422 (2.5e$^4$ viral genomes/cell). Lastly, we also tested a second virus stock of AAV421 to compare to the primary virus stock.

Insertion of the CAR was determined by PCR as described above, using primer pairs that only amplify products if the CAR gene has been inserted into the TRC 1-2x.87EE recognition sequence. PCR was resolved by agarose gel, shown in FIGS. 32A and 32B (lane descriptions can be found in Tables 9 and 10). Sample 1 in FIG. 32A was mock electroporated then mock transduced, and samples 2-5 were mock electroporated then transduced with AAV421. The gel shows that none of these samples generated PCR products, indicating that AAV421, in the absence of TRC 1-2x.87EE mRNA, is unable to drive insertion of the CAR gene into the TRC 1-2 recognition sequence. Additionally, the control sample that was electroporated with TRC 1-2x.87EE mRNA then mock transduced (sample 6), did not show any PCR products. Samples 7-10 in FIG. 32A were electroporated with TRC 1-2x.87EE mRNA, then transduced with increasing amounts of AAV421. The gel shows PCR bands for products extending beyond both the 5' and 3' homology arm (the two bands under each sample number), demonstrating integration of the CAR gene into the TRC 1-2 recognition sequence. Lastly in FIG. 32A, lanes 11 and 12 represent samples that were electroporated with TRC 1-2x.87EE mRNA then transduced with AAV422, either starting with 1e$^6$ or 10e$^6$ cells/sample, respectively. The presence of both PCR bands (larger in the first set, because different primer was used to account for a longer homology arm) indicate successful insertion of the CAR gene into the TRC 1-2 recognition sequence.

Sample 1 in FIG. 32B was mock electroporated then mock transduced, and samples 2-5 were mock electroporated then transduced with increasing amounts of AAV422 (Table 10). The gel shows that none of these samples generated PCR products, indicating that AAV422, in the absence of TRC 1-2x.87EE mRNA, is unable to drive insertion of the CAR gene into the TRC 1-2 recognition sequence. Samples 7-10 in FIG. 32B were electroporated with TRC 1-2x.87EE mRNA, then transduced with increasing amounts of AAV422. The gel shows PCR bands for products extending beyond both the 5' and 3' homology arm, demonstrating integration of the CAR gene into the TRC 1-2 recognition sequence. Lastly, sample 11 represents the sample that was electroporated with TRC 1-2x.87EE mRNA then transduced with a AAV421 from a different virus stock than samples shown in FIG. 32A. The presence of bands indicate insertion of the CAR gene into the TRC 1-2 recognition sequence and confirms reproducibility between different virus stocks. Taken together, FIG. 32 clearly demonstrates that both AAV421 and AAV422 are capable of generating HDR templates suitable for inserting the CAR gene into the TRC 1-2 recognition sequence.

TABLE 9

| Sample | Nucleofection | AAV Virus | µl AAV | MOI (approximate) |
|---|---|---|---|---|
| 1 | Mock (Water) | 421 | 0 | 0 |
| 2 | Mock (Water) | 421 | 3.125 | 3906 |
| 3 | Mock (Water) | 421 | 6.25 | 7813 |
| 4 | Mock (Water) | 421 | 12.5 | 15625 |
| 5 | Mock (Water) | 421 | 25 | 31250 |
| 6 | TRC1-2x87EE | 421 | 0 | 0 |
| 7 | TRC1-2x87EE | 421 | 3.125 | 3906 |
| 8 | TRC1-2x87EE | 421 | 6.25 | 7813 |
| 9 | TRC1-2x87EE | 421 | 12.5 | 15625 |
| 10 | TRC1-2x87EE | 421 | 25 | 31250 |
| 11 | TRC1-2x87EE | 422 | 6.25 | 25000 |
| 12 | TRC1-2x87EE Large Scale | 422 | 62.5 | 25000 |

TABLE 10

| Sample | Nucleofection | AAV Virus | µl AAV | MOI (approximate) |
|---|---|---|---|---|
| 1 | Mock (Water) | 422 | 0 | 0 |
| 2 | Mock (Water) | 422 | 3.125 | 12500 |
| 3 | Mock (Water) | 422 | 6.25 | 25000 |
| 4 | Mock (Water) | 422 | 12.5 | 50000 |
| 5 | Mock (Water) | 422 | 25 | 100000 |
| 6 | TRC1-2x87EE | 422 | 0 | 0 |
| 7 | TRC1-2x87EE | 422 | 3.125 | 12500 |
| 8 | TRC1-2x87EE | 422 | 6.25 | 25000 |
| 9 | TRC1-2x87EE | 422 | 12.5 | 50000 |
| 10 | TRC1-2x87EE | 422 | 25 | 100000 |
| 11 | TRC1-2x87EE | 421B | 25 | 10000 |

2. Expression of Anti-CD19 Chimeric Antigen Receptor on T Cells Using AAV421

Here, we sought to determine the expression level of the anti-CD19 chimeric antigen receptor in cells that had the CAR gene inserted into the TRC 1-2 recognition sequence using AAV421. Samples described above and analyzed in FIG. 32A were also analyzed for CAR and CD3 expression by flow cytometry. Approximately 4 days post-transduction, cells were labeled with antibodies that recognize the anti-CD19 CAR or CD3 and analyzed by flow cytometry. FIG. 33A shows flow cytometry plots for cells that were mock electroporated and transduced with AAV421, along with control cells that were mock electroporated and mock transduced. Cells that were mock electroporated and mock transduced (MOI-0) were overwhelmingly CD3$^+$/CAR$^-$ (the lower right quadrant, 98.8%). Cells that were mock electroporated then transduced with increasing amounts of AAV421 looked essentially identical to the control cells, with the CD3$^+$/CAR$^-$ populations at 98.8%, 98.6%, 98.8% and 97.9%. Thus, we conclude that the AAV421 virus alone is not driving detectable levels of CAR expression, nor is it capable of disrupting expression of the T cell receptor.

FIG. 33B shows flow cytometry plots for samples that were either electroporated with TRC 1-2x.87EE mRNA then mock transduced or cells that were electroporated with TRC 1-2x.87EE then transduced with increasing amounts of AAV421. Cells that were electroporated then mock transduced show 56.7% CD3$^-$ cells, indicating efficient knockout of the T cell receptor complex. Background labeling with the anti-CD19 CAR was very low, with 0.48% in the CD3$^-$ population and 0.36% in the CD3$^+$ population. Samples that were electroporated with mRNA encoding TRC 1-2x.87EE then transduced with increasing amounts of AAV412 showed significant amounts of CAR labeling in the CD3$^-$ population, ranging from 4.99% to 13.4%. There was also a slight increase in CAR labeling in the CD3$^+$ population, ranging from 1.27% to 3.95%. As mentioned above, it is possible that the CAR gene was inserted into the non-expressed T cell receptor allele. Also in contrast to experiments with AAV408, the CARP population was much better defined, with a higher mean fluorescence intensity, suggesting that the JeT promoter drives higher expression than the eF1α core promoter.

While evaluating insertion of the CAR gene using AAV421 in conjunction with TRC 1-x.87EE, we sought to determine a method that would allow us to preferentially expand and enrich the CD3$^-$/CAR$^+$ population. From the experiment described above and shown in FIG. 33, we used cells that were electroporated with TRC 1-2x.87EE mRNA (2 µg) then transduced with AAV421 (3.13e$^4$ viral genomes/cell). Control samples were mock electroporated and mock transduced, mock electroporated and transduced with AAV421, or electroporated with TRC 1-2x.87EE and mock transduced taken from the experiment described above and shown in FIG. 33. As a control enrichment and expansion process, these cells were incubated for 6 days in complete growth medium supplemented with IL-7 and IL-15 (both at 10 ng/mL). Cells were then labeled with antibodies against the anti-CD19 CAR and CD3 and analyzed by flow cytometry (FIG. 34A). Cells that were mock electroporated and mock transduced showed low levels of background staining in the CD3$^-$/CAR$^+$ quadrant (0.13%). The CD3$^-$/CAR$^+$ population was essentially the same in samples that were either mock electroporated then transduced with AAV or electroporated with TRC 1-2x.87EE mRNA then mock transduced (0.16% and 0.55%, respectively). Cells that were electroporated with TRC 1-2x.87EE mRNA and mock transduced had a CD3$^-$/CAR$^-$ population of 53.2%, very close to the amount stained in the first part of this experiment shown in FIG. 33B (56.7%). Cells that were electroporated with TRC 1-2x.87EE and transduced with AAV showed 12.6% CD3$^-$/CAR$^+$ cells, almost identical to the original labeling of these cells shown in FIG. 33 (13.4%), demonstrating that mixture of IL-7 and IL-15 is insufficient to enrich or expand the specific CD3$^-$/CAR$^+$ cell population.

We next sought to enrich for the CD3$^-$/CAR$^+$ population in an antigen-specific manner by incubating the 4 samples described above with IM-9 cells, which present CD19 on the cell surface. IM-9 cells were inactivated by pre-treatment with mitomycin C and incubated with samples at a 1:1 ratio for 6 days in the presence of IL-7 and IL-15 (10 ng/mL). Cells were then labeled with antibodies against CD3 and the anti-CD19 CAR and analyzed by flow cytometry (FIG. 34B). Cells that were mock electroporated and mock transduced showed low levels of background staining in the CD3$^-$/CAR$^+$ quadrant (0.2%). The CD3$^-$/CAR$^+$ population was the same in samples that were mock electroporated then transduced with AAV (0.2%) and slightly higher in cells that were electroporated with TRC 1-2x.87EE and mock transduced (1.24%). The increase in CD3$^-$/CAR$^+$ cells the TRC 1-2x.87EE alone control is considered background since no CAR nucleic acid was ever introduced into the system. Cells that were electroporated with TRC 1-2x.87EE mRNA and mock transduced had a CD3$^-$/CAR$^-$ population of 42.5%, which is significantly lower than they were prior to expansion (56.7%, FIG. 33) suggesting that CD+ cells may have a growth advantage in this system. However, cells that were electroporated with TRC 1-2x.87EE and transduced with AAV showed 49.9% CD3$^-$/CAR$^+$ cells, a dramatic increase compared to the original labeling of these cells shown in FIG. 33 (13.4%), demonstrating that incubation of this sample with IM-9 cells in the presence of IL-7 and IL-15 is quite effective in enriching and expanding the CD3$^-$/CAR$^+$ population. The CD3$^+$/CAR$^+$ population was also expanded under these conditions, with the mock electroporated/AAV transduced sample and the TRC 1-2x.87EE electroporated/AV transduced sample showing 2.53% and 15.3% CD3+/CAR$^+$, respectively.

In the cells that were electroporated with TRC 1-2x.87EE then transduced with AAV421, 24.2% of the CD3$^-$ population was CARP prior to expansion (FIG. 33B). After incubation in medium supplemented with IL-7 and IL-15, that 25.3% of the CD3$^-$ cells were CARP (FIG. 34A) indicating that the ratio of gene knock-in to gene-knockout was unchanged. However, after incubation with IM-9 cells in addition to IL-7 and IL-15, over 80% (80.35%, FIG. 34B) of the CD3$^-$ cells were CARP, demonstrating that incubation with IM-9 cells resulted in antigen-specific enrichment.

Since mitocmyin C inactives cells very potently and IM-9 cells were not persisting long in the mixed culture, we reasoned that a second infusion of IM-9 cells might further increase enrichment of CD3$^-$/CAR$^+$ cells. Some of the cells described above and shown in FIG. 34B would mixed with fresh IM-9 cells (pre-treated with mitocmycin C) in medium containing IL-7 and IL-15 and were incubated another 6 days. Cells were then stained for CD3 and anti-CD19 CAR and analyzed by flow cytometry (FIG. 34C). The percentage of CD3$^-$/CAR$^+$ cells in any of the control samples were essentially unchanged compared to the first round of enrichment on IM-9 cells.

However, the cells that were electroporated with TRC 1-2x.87EE and transduced with AAV421 showed a significant enrichment of the CD3$^-$/CAR$^+$ population, increasing from 49.9% (after the first round if incubation with IM-9 cells, FIG. 34B) to 65.7% (FIG. 34C). Importantly, 93.75% of the CD3$^-$ population was CARP, indicating further antigen-specific expansion.

3. Expression of Anti-CD19 Chimeric Antigen Receptor on T Cells Using AAV422

We also examined expression of the anti-CD19 CAR from cells in which AAV422 was used to provide the HDR template (described above, PCR results shown in FIG. 32B). Approximately 4 days post-transduction, cells were labeled with antibodies that recognize the anti-CD19 CAR or CD3 and analyzed by flow cytometry. FIG. 35A shows flow cytometry plots for cells that were mock electroporated and transduced with increasing amounts of AAV422, along with control cells that were mock electroporated and mock transduced. Cells that were mock electroporated and mock transduced (MOI-0) were overwhelmingly CD3$^+$/CAR$^-$ (the lower right quadrant, 98.8%). Cells that were mock electroporated then transduced with increasing amounts of AAV422 looked essentially identical to the control cells, with the CD3$^+$/CAR$^-$ populations at 98.6%, 98.6%, 98.9% and 98.4%. Thus, the AAV422 vector alone is not driving detectable levels of CAR expression, nor is it capable of disrupting expression of the T cell receptor.

FIG. 35B shows flow cytometry plots for samples that were either electroporated with TRC 1-2x.87EE mRNA then mock transduced or cells that were electroporated with TRC 1-2x.87EE then transduced with increasing amounts of AAV422. Cells that were electroporated then mock transduced show 59.3% CD3$^-$ cells, indicating efficient knockout of the T cell receptor complex. Background labeling with the anti-CD19 CAR was very low, with 1.47% in the CD3$^-$ population and 0.52% in the CD3$^+$ population. Samples that were electroporated with mRNA encoding TRC 1-2x.87EE then transduced with increasing amounts of AAV422 showed significant amounts of CAR labeling in the CD3$^-$ population, ranging from 14.7% to 20.3%. There was also a slight increase in CAR labeling in the CD3$^+$ population, ranging from 2.3% to 2.7%.

Surprisingly, we observed a noticeable increase in T cell receptor knockout efficiency in the presence of AAV422. Overall CD3 knockout efficiency with increasing AAV422 was 71.6%, 74.9%, 77.8% and 74.4% compared to 59.3% in the TRC 1-2x.87EE electroporation alone. In contrast, overall CD3 knockout efficiency with increasing AAV421 was 56.99%, 56.62%, 57.4% and 55.4% compared to 57.18% in the TRC 1-2x.87EE electroporation alone (FIG. 33B). Thus, it appears that electroporation with TRC 1-2x.87EE in the presence of single-stranded AAV genomes, but not self-complimentary AAV genomes, results in an increase in the overall knockout efficiency of the TRC 1-2x.87EE nuclease. Because of this increase, the percent of CD3$^-$ cells that are CAR' is not significantly different between cells transduced with AAV421 and AAV422 despite the higher numbers of CD3$^-$/CAR$^+$ cells. The highest percent of CD3$^-$ cells that were CAR$^+$ using AAV421 was 24.18% (MOI=3.13e$^4$ viral genomes/cell) compared to 26.48% with AAV422 (MOI=1e$^5$ viral genomes/cell). This observation is particularly interesting considering the large difference in MOI between AAV421 and AAV422.

The concept of utilizing IM-9 cells to specifically enrich for CD3$^-$/CAR$^+$ cells was tested using cells from this experiment. Again, rather than testing the entire panel, we only attempted enrichment of either cells mock electroporated then transduced with AAV422 or electroporated with TRC 1-2x.87EE then transduced with AAV422 (2.5e$^4$ viral genomes/cell) in a new experiment. FIG. 36A shows flow cytometry plots at approximately day 4 post-transduction. Mock electroporated/transduced cells showed background staining of CD3$^-$/CAR$^+$ cells at 0.13%. In comparison, cells electroporated with TRC 1-2x.87EE the transduced with AAV422 showed 4.44% CD3$^-$/CAR$^+$ cells. Cells were incubated with IM-9 cells (pre-treated with mitomycin) in the presence of IL-7 and IL-15 for 6 days as described above, then analyzed by flow cytometry. FIG. 36B shows that incubation with IM-9 cells dramatically increased the CD3$^-$/CAR$^+$ population in AAV422 transduced cells to 35.8%. The CARP cells make up 45.2% of the total CD3$^-$ population, compared to 6.69% prior to enrichment (FIG. 36A). As above, we also further enriched by a second addition of IM-9 cells (FIG. 36C). Two rounds of incubation with IM-9 cells resulted in 65.1% CD3⁻/CAR⁺ cells. The CARP cells make up 78.25% of the total CD3⁻ population, indicating significant, antigen-dependent enrichment of CD3⁻/CAR⁺ cells.

These data, in conjunction with the data presented above, clearly demonstrate that cells that have had an anti-CD19 CAR gene inserted into the TRC 1-2 recognition sequence can be successfully enriched by incubation with IM-9 cells in the presence of IL-7 and IL-15, and can result in a CD3⁻ population that is over 90% CARP in as little as 12 days of culture.

4. Increased Knockout Efficiency Observed when Using Single-Strand AAV Vectors

In the present study, we followed up on the observation that single-stranded AAV vectors increased knockout efficiency of the TRC 1-2x.87EE nuclease. In a first experiment, cells were electroporated with TRC 1-2x.87EE (2 µg) and either mock transduced or transduced with increasing amounts of AAV412 ($6.25e^4$, $1.25e^4$, $2.5e^4$ or $5e^4$ viral genomes/cell). On day 4 post-transduction, cells were labeled with an antibody against CD3 and analyzed by flow cytometry (FIG. 37A). In the mock transduced cells, 20.7% are CD3⁻ compared to 21.6%, 23.7%, 25.5% and 25% with increasing AAV412, indicating that TRC 1-2x.87EE knockout efficiency is up to 23% higher in the presence of AAV412 (25.5% compared to 20.7%).

To determine whether this increase in knockout efficiency was nuclease specific, in an additional experiment, cells were electroporated with mRNA (2 µg) encoding a nuclease targeting the β2-microglobulin gene and either mock transduced or transduced with increasing amounts of AAV412. Cells were stained for β2-microglobulin on day 4 post-transduction and analyzed by flow cytometry (FIG. 37B). In the mock transduced cells, β2-microglobulin knockout efficiency was 64.5% and increased in the transduced cells to 68.6%, 70.7%, 77.2% and 82.5% with increasing amounts of AAV412, demonstrating an increase in knockout efficiency of up to 27.9% (82.5% compared to 64.5%).

In a parallel experiment, cells were electroporated with TRC 1-2x.87EE mRNA and either mock transduced or transduced with AAV422 (using the same MOIs as AAV412). Cells were labeled with an antibody against CD3 and cells were analyzed by flow cytometry (FIG. 37C). The mock transduced cells showed 62.2% T cell receptor knockout, and with increasing amounts of AAV, the T cell receptor knockout frequency increased to 72.6%, 75.5%, 78.3% and 75.1%. Here, the presence of AAV422 increases the knockout efficiency of TRC 1-2x.87EE by up to 25.8% (78.3% compared to 62.2%). It is striking that the increase in percent knockout efficiency is almost identical between these three experiments, using two different nucleases and two different AAV vectors. Taken together, these data strongly indicate that transduction of cells with single strand AAV vectors increase the knockout efficiency of our nucleases, irrespective of nuclease or AAV cargo.

5. Activity of T Cells Expressing Anti-CD19 Chimeric Antigen Receptor

The above experiments clearly demonstrate the generation of CAR T cells by electroporating cells with TRC 1-2x.87EE mRNA, then immediately transducing cells with AAV421, and that these cells can be enriched for a CD3⁻/CAR⁺ population by co-culture with CD19 expressing IM-9 cells. We next examined the activity of these CAR T cells against target cells. In the first experiment, the cells described above and shown in FIG. 34C were used in an IFN-gamma ELISPOT assay, in which either CD19⁺ Raji cells or CD19⁻ U937 cells were the target population. As shown in FIG. 38A, when anti-CD19 CAR T cells were incubated with U937 cells, they did not secrete IFN-gamma regardless of the target:effector ratio. Incubating CAR T cells with Raji cells, however, resulted in high levels of IFN-gamma secretion, in a dose-dependent manner, indicating that secretion of IFN-gamma is antigen-specific.

These CAR T cells were also used in a cell killing assay in which luciferase-labeled Raji cells were the target. Briefly, CAR T cells were incubated with luciferase-labeled Raji cells at a ratio of 10:1. At several time points, cells were washed and lysed to measure luciferase activity as a measure of how many cells remained. Control cells showed luciferase activity greater than 5500 arbitrary units (FIG. 38B). Co-incubation for 2, 3, 4 and 5 hours resulted in a decrease in luciferase activity to 4598, 3292, 2750 and 1932 arbitrary units, respectively. Thus, within 5 hours of co-incubation, luciferase activity was reduced approximately 65%, indicating strong cytolytic activity of the CAR T cells.

Taken together, these data demonstrate that anti-CD19 CAR T cells generated according to the methods described herein are effective at killing CD19⁺ cells.

Example 7

Linearized Plasmid DNA

1. Expression of Chimeric Antigen Receptor from Linearized Plasmid DNA

Since HDR templates produced by AAV are linear DNA molecules, we hypothesized that linear DNA from any source may be a suitable HDR template for inserting a CAR gene into the TRC 1-2 recognition sequence. To test this, we generated several plasmids that contain an anti-CD19 CAR gene flanked by homology arms that are homologous to the TRC 1-2 recognition sequence locus. Different promoters were used in some plasmids, and homology arms were either "short" (200 bp on the 5' homology arm and 180 bp on the 3' homology arm) to mimic the self-complimentary AAV vectors, or "long" (985 bp on the 5' homology arm and 763 bp on the 3' homology arm) to mimic the single strand AAV vectors. Plasmids with short homology arms are labeled "pDS" and those with long homology arms are labeled "pDI." Additionally, some plasmid contained an intron upstream of the CAR gene.

The CAR donor plasmids were linearized at a restriction site in the vector backbone and gel purified. Human CD3⁺ T cells were either electroporated with the linearized CAR donor plasmid alone (varying amounts between 500 ng and 1000 ng, depending on the concentration of the purified linearized plasmid), or co-electroporated with TRC 1-2.87EE mRNA (2 µg). As controls, cells were either mock electroporated or electroporated with TRC 1-2x.87EE alone. The graphs in FIG. 39 are labelled with descriptions for all electroporations. Approximately 4 days post-electroporation, cells were labelled with antibodies against CD3 and the anti-CD19 CAR and analyzed by flow cytometry (FIG. 39). FIG. 39A shows background CD3⁻/CAR⁺ staining of 0.15%. It should be noted that the background CD3⁺/CAR⁺ staining was unusually high at 4.31%. FIG. 39B shows cells that were electroporated with TRC 1-2x.87EE mRNA alone, demonstrating 60.8% CD3 knockout. FIGS. 39C and 39D represent samples that were co-electroporated with TRC 1-2x.87EE mRNA and either the long homology arm vector with an EF1α core promoter with an HTLV enhancer or the short homology arm vector with EF1α core promoter (with no enhancer). Interestingly, the linearized CAR donor with the EF1α core promoter alone generated a CD3⁻/CAR⁺ population of 2.38%, while the vector harboring the EF1α core promoter with the HTLV enhancer did not generate a significant percentage of CD3⁻/CAR⁺ cells. Cells that were electroporated with these two vectors in the absence of TRC 1-2x.87EE mRNA showed no significant increase in the CD3⁻/CAR⁺ population (FIGS. 39E and 39F). The increase in the CD3⁻/CAR⁺ population with the EF1α core promoter vector in the presence of TRC 1-2x.87EE suggested that a linearized plasmid could serve as an HDR template to repair double strand breaks at the TRC 1-2 recognition sequence.

FIGS. 39G and 39H show two long homology arm constructs that both contain an MND promoter driving expression of the CAR. One of these constructs, shown in FIG. 39G, also contains an intron in the 5' end of the CAR gene. Surprisingly, the long homology arm plasmid with an MND promoter and intron showed significant CAR expression (FIG. 39G, 4.14% CD3⁻/CAR⁺) while the intron-less construct (FIG. 39H) did not show detectable CAR expression when co-electroporated with TRC 1-2x.87EE mRNA. A short homology arm plasmid with the MND promoter, but with no intron, was also tested with TRC 1-2x.87EE mRNA and did not demonstrate any CAR expression (FIG. 39I). None of the MND promoter-containing constructs generated any CARP cells in the absence of TRC 1-2x.87EE mRNA (FIGS. 39J, 39K, and 39L).

Lastly in this experiment, we tested a short homology arm construct that contained a JeT promoter driving expression of the CAR and a "long" homology arm construct with a CMV promoter driving expression of the CAR. Alone, neither of these linearized plasmids resulted in significant CARP cells (FIGS. 39O and 39P). When cells were co-electroporated with TRC 1-2x.87EE mRNA, the JeT containing construct showed 2.69% CD3⁻ CAR⁺ cells and the CMV containing construct yielded 2.7% CD3⁻/CAR⁺ cells.

The flow plots shown in FIG. 39 clearly demonstrate that linearized plasmid DNA that encodes the CAR, flanked by homology arms, can serve as HDR templates to repair DNA breaks caused by TRC 1-2x.87EE, resulting in insertion of the CAR nucleic acid. It is clear that promoter strength plays a significant role in expression of the CAR, and some promoters drive more efficient expression when there is an intron in the gene. To confirm that insertion of the CAR using linearized DNA constructs was specific to the TRC 1-2 recognition sequence locus, we analyzed cells as described above using primers that sat within the CAR and outside of the homology arms (FIG. 40, Table 11). Samples 1 and 2 are PCR products from cells that were either mock electroporated or electroporated with only mRNA encoding TRC 1-2x.87EE. Consistent with results shown above, no PCR bands are present indicating the lack of CAR gene in the TRC 1-2 recognition site. Samples 3, 4 and 5 are from cells that were co-electroporated with TRC 1-2x.87EE and a linearized CAR homology plasmid (samples names in FIG. 40). Each sample shows two PCR bands of the predicted size indicating insertion of the CAR gene expression cassette into the TRC 1-2 recognition site. Samples 6, 7, and 8 are from cells that were electroporated with the same linearized CAR homology plasmids as samples 3, 4, and 5 but without TRC 1-2x.87EE mRNA. As expected, no PCR bands are present. Samples 9 and 10 are PCR products from cells that were either mock electroporated or electroporated with only mRNA encoding TRC 1-2x.87EE and show no PCR bands. Samples 11, 12, 13 and 14 are from cells that were co-electroporated with TRC 1-2x.87EE and a linearized CAR homology plasmid (samples names in FIG. 40). Each sample shows two PCR bands of the predicted size indicating insertion of the CAR gene into the TRC 1-2 recognition site. Samples 15, 16, 17, and 18 are from cells that were electroporated with the same linearized CAR homology plasmids as samples 11, 12, 13, and 14 but without TRC 1-2x.87EE mRNA. As expected, no PCR bands are present.

FIGS. 39 and 40 clearly demonstrate that co-electroporating human CD3⁺ T cells with mRNA encoding TRC 1-2x.87EE and a linearized CAR homology plasmid is an effective method to insert the CAR gene into the TRC 1-2 recognition sequence.

TABLE 11

| Sample | Nucleofection | Linearized plasmid |
|---|---|---|
| 1 | Mock (Water) | — |
| 2 | TRC1-2x87EE | — |
| 3 | TRC1-2x87EE | pDS EF1-α Core |
| 4 | TRC1-2x87EE | pDS 200 MND NC |
| 5 | TRC1-2x87EE | pDS 200 JET NC |
| 6 | Mock (Water) | pDS EF1-α Core |
| 7 | Mock (Water) | pDS 200 MND NC |
| 8 | Mock (Water) | pDS 200 JET NC |
| 9 | Mock (Water) | — |
| 10 | TRC1-2x87EE | — |
| 11 | TRC1-2x87EE | pDI EF1-α NC |
| 12 | TRC1-2x87EE | pDI MND intron NC |
| 13 | TRC1-2x87EE | pDI MND NC |
| 14 | TRC1-2x87EE | pDI CMV 985 NC 763 |
| 15 | Mock (Water) | pDI EF1-α NC |
| 16 | Mock (Water) | pDI MND intron NC |
| 17 | Mock (Water) | pDI MND NC |
| 18 | Mock (Water) | pDI CMV 985 NC 763 |
| 19 | Mock (Water) | — |
| 20 | TRC1-2x87EE | — |
| 21 | TRC1-2x87EE | pDS MCS |
| 22 | Mock (Water) | PDS MCS |

Example 8

Characterization of Additional AAV Vectors

1. Use of AAV with JeT Promoter and Long Homology Arms

Collectively, the data shown above indicate that vectors utilizing the JeT promoter drive high, consistent expression of the CAR and that longer homology arms may increase gene insertion efficiency. We designed and generated the vector shown in FIG. 41 (SEQ ID NO:125), which was used to make single-strand AAV with long homology arms, and a JeT promoter driving expression of the anti-CD19 CAR (referred to herein as AAV423). Human CD3+ T cells were electroporated with mRNA encoding TRC 1-2x.87EE and transduced with increasing amounts of AAV423. Since data shown above suggested that higher MOIs may result in increased insertion efficiency, we used titers ranging from $1.875e^4$ to $1.5e^5$. As controls, cells were either electroporated with mRNA encoding TRC 1-2x.87EE then mock transduced or mock electroporated then transduced with increasing amounts of AAV423. On day 6 post-transduction, cells were labeled with antibodies recognizing CD3 or the anti-CD19 CAR and analyzed by flow cytometry. As shown in FIG. 42, cells that were mock electroporated then transduced with increasing amounts of AAV423 are overwhelmingly CD3+/CAR− (ranging from 96.6% to 98.5%). Cells that were electroporated with mRNA encoding TRC 1-2x.87EE and mock transduced were 39% CD3− indicating efficient knockout of the T cell receptor. In these cells, background CAR staining was very low (around 2%). Cells that were electroporated with mRNA encoding TRC 1-2x.87EE then transduced with increasing amounts of AAV423 showed dramatic CAR staining in conjunction with CD3 knockout. CD3−/CAR+ populations ranged from 21.6% to 22.7%, while CD3+/CAR+ populations were around 2%. As described above, the presence of single-strand AAV increased the overall gene modification efficiency at the TRC 1-2 recognition site, with total CD3− populations increasing from 41.44% in the control cells to 57.6%, 59.2%, 58.7%, and 56.1% in cells that were electroporated then transduced with increasing amounts of AV423. The percent of CD3− cells that were CARP ranged from 37.5% to 39.9% indicating a dramatic increase in insertion efficiency compared to data described above.

To confirm that insertion of the CAR using AAV423 was specific to the TRC 1-2 recognition sequence locus, we analyzed cells as described above using primers that sat within the CAR and outside of the homology arms (FIG. 43, Table 12).

TABLE 12

| Sample | Nucleofection | AAV (μl) | MOI |
|---|---|---|---|
| 1 | Mock (Water) | — | — |
| 2 | Mock (Water) | — | — |
| 3 | Mock (Water) | pDI JET Prep A (3.125) | 18750 |
| 4 | Mock (Water) | pDI JET Prep A (6.25) | 37500 |
| 5 | Mock (Water) | pDI JET Prep A (12.5) | 7500 |
| 6 | Mock (Water) | pDI JET Prep A (25) | 150000 |
| 7 | TRC1-2x87EE | — | — |
| 8 | TRC1-2x87EE | pDI JET Prep A (3.125) | 18750 |
| 9 | TRC1-2x87EE | pDI JET Prep A (6.25) | 37500 |
| 10 | TRC1-2x87EE | pDI JET Prep A (12.5) | 7500 |
| 11 | TRC1-2x87EE | pDI JET Prep A (25) | 150000 |

Samples 1 and 2 are PCR products from cells that were mock electroporated. Consistent with results shown above, no PCR bands are present indicating the lack of CAR gene in the TRC 1-2 recognition site. Samples 3-6 are from cells that were mock electroporated then transduced with increasing amounts of AAV423. Consistent with results above, there are no PCR bands present. Sample 7 is from cells electroporated with mRNA encoding TRC 1-2x.87EE then mock transduced, and shows no PCR bands. Samples 8-11 are from cells electroporated with mRNA encoding TRC 1-2x.87EE then transduced with increasing amounts of AAV423, and show the PCR bands expected if the CAR is inserted into the TRC 1-2 recognition sequence.

Given the ability of AAV423 to insert the CAR sequence into the TRC 1-2 recognition site following cleavage, it is further envisioned that the AAV423 plasmid (FIG. 41) could be linearized by digestion with a and delivered to the cell by digestion with one or more restriction enzymes, such that the T cells could be transfected with a linearized DNA template which could integrate into the TRC 1-2 recognition site and encode an anti-CD19 CAR.

Example 9

In Vivo Efficacy of Anti-CD19 TCR-Negative CAR T Cells

1. Murine Model of Disseminated B Cell Lymphoma

The efficacy of the gene-edited anti-CD19 CAR T cells was evaluated in a murine model of disseminated B cell lymphoma. Activated T cells were electroporated with TRC 1-2x.87 EE mRNA as described above, then transduced with an AAV6 vector comprising an anti-CD19 CAR expression cassette driven by a JeT promoter and flanked by homology arms. Following 5 days of culture with IL-2 (10 ng/mL), cells were analyzed for cell-surface CD3 and anti-CD19 CAR expression by flow cytometry as previously described (FIG. 44A). CD3− cells were enriched by depleting CD3+ cells using anti-CD3 magnetic beads. Depleted cells were then cultured for 3 days in IL-15 (10 ng/mL) and IL-21 (10 ng/mL) and re-analyzed for cell-surface expression of CD3 and anti-CD19 CAR (FIG. 44B). Isolation of the CD3− population was quite efficient, yielding 99.9% purity as measured by flow cytometry following depletion of CD3+ cells (FIG. 44B). The purified CD3− population comprised 56% CD4+ and 44% CD8+ cells (FIG. 44C), and had primarily central memory/transitional memory phenotypes, determined by staining for CD62L and CD45RO (FIG. 44D).

Studies utilizing the Raji disseminated lymphoma model were conducted by Charles River Laboratories International Inc. (Morrisville, N.C., USA). CD19+ Raji cells stably expressing firefly luciferase (ffLuc)[44] were injected i.v. into 5-6 week old female NSG mice on Day 1, at a dose of $2.0 \times 10^5$ cells per mouse. On Day 4 mice were injected i.v. with PBS or PBS containing gene edited control TCR KO T cells prepared from the same healthy donor PBMC or PBS containing the indicated doses of CAR T cells prepared from the same donor. On the indicated days, live mice were injected i.p. with Luciferin substrate (150 mg/kg in saline), anesthetized, and Luciferase activity measured after 7 minutes using IVIS SpectrumCT (Perkin Elmer, Waltham, Mass.). Data was analyzed and exported using Living Image software 4.5.1 (Perkin Elmer, Waltham, Mass.). Luminescence signal intensity is represented by radiance in p/sec/cm²/sr.

2. Results

As shown in FIG. 45, growth of CD19+ Raji cells was evident in all mice at low levels by day 8, and increased significantly in untreated and TCR⁻ control groups by day 11. In control groups, significant tumor growth was observed by day 15, and by day 18 or 19 all control groups were euthanized. In contrast, all groups of mice treated with anti-CD19 CAR T cells showed no evidence of tumor growth by day 11 and, with the exception of a single mouse in the low dose group, remained tumor-free through day 29 of the study. Tumor re-growth was observed in three mice in the low dose cohort around day 36. One of the three died at day 42, though imaging revealed only low levels of tumor in this animal, so it is unlikely that death was tumor-related.

3. Conclusions

These results provide clear evidence for in vivo clearance of CD19⁺ tumor cells by gene-edited CD3⁻ CAR T cells and support further preclinical development of this platform for allogeneic CAR T cell therapy.

The invention claimed is:

1. An isolated polynucleotide comprising a nucleic acid sequence encoding an engineered meganuclease, wherein said engineered meganuclease binds and cleaves at a recognition sequence consisting of SEQ ID NO: 3, wherein said engineered meganuclease comprises a first subunit and a second subunit, wherein said first subunit binds to a first recognition half-site of said recognition sequence, and wherein said second subunit binds to a second recognition half-site of said recognition sequence, and wherein said engineered meganuclease comprises an amino acid sequence having at least 96% identity to SEQ ID NO: 8.

2. The isolated polynucleotide of claim 1, wherein said first subunit comprises an amino acid sequence having at least 96% sequence identity to residues 198-344 of SEQ ID NO:8, and wherein said second subunit comprises an amino acid sequence having at least 96% sequence identity to residues 7-153 of SEQ ID NO: 8.

3. The isolated polynucleotide of claim 1, wherein said first subunit comprises residues 198-344 of SEQ ID NO: 8.

4. The isolated polynucleotide of claim 1, wherein said second subunit comprises residues 7-153 of SEQ ID NO: 8.

5. The isolated polynucleotide of claim 1, wherein said engineered meganuclease comprises the amino acid sequence of SEQ ID NO: 8.

6. The isolated polynucleotide of claim 1, wherein said isolated polynucleotide is an mRNA.

7. A recombinant DNA construct comprising said isolated polynucleotide of claim 1.

8. A viral vector comprising said isolated polynucleotide of claim 1.

9. The viral vector of claim 8, wherein said viral vector is a recombinant adeno-associated virus vector.

* * * * *